(12) United States Patent
Glezer et al.

(10) Patent No.: US 11,359,238 B2
(45) Date of Patent: Jun. 14, 2022

(54) LINKED PAIRED STRAND SEQUENCING

(71) Applicant: SINGULAR GENOMICS SYSTEMS, INC., La Jolla, CA (US)

(72) Inventors: Eli N. Glezer, Del Mar, CA (US); Martin Maria Fabani, Encinitas, CA (US); Sabrina Shore, San Diego, CA (US); Daan Witters, San Diego, CA (US)

(73) Assignee: SINGULAR GENOMICS SYSTEMS, INC.

( * ) Notice: Subject to any disclaimer, the term of this patent is extended or adjusted under 35 U.S.C. 154(b) by 0 days.

(21) Appl. No.: 17/194,023

(22) Filed: Mar. 5, 2021

(65) Prior Publication Data

US 2021/0277461 A1    Sep. 9, 2021

Related U.S. Application Data

(60) Provisional application No. 62/986,527, filed on Mar. 6, 2020, provisional application No. 63/020,881, filed on May 6, 2020, provisional application No. 63/087,125, filed on Oct. 2, 2020.

(51) Int. Cl.
*C12Q 1/68* (2018.01)
*C12Q 1/6869* (2018.01)
*C12Q 1/6855* (2018.01)

(52) U.S. Cl.
CPC ......... *C12Q 1/6869* (2013.01); *C12Q 1/6855* (2013.01)

(58) Field of Classification Search
CPC .. C12Q 1/6869; C12Q 1/6855; C12Q 1/6806; C12Q 1/6876
See application file for complete search history.

(56) References Cited

U.S. PATENT DOCUMENTS

| | | | |
|---|---|---|---|
| 4,318,846 A | 3/1982 | Khanna et al. | |
| 5,034,506 A | 7/1991 | Summerton et al. | |
| 5,066,580 A | 11/1991 | Lee | |
| 5,188,934 A | 2/1993 | Menchen et al. | |
| 5,235,033 A | 8/1993 | Summerton et al. | |
| 5,366,860 A | 11/1994 | Bergot et al. | |
| 5,599,675 A | 2/1997 | Brenner | |
| 5,688,648 A | 11/1997 | Mathies et al. | |
| 5,750,341 A | 5/1998 | Macevicz | |
| 5,763,594 A | 6/1998 | Hiatt et al. | |
| 5,800,996 A | 9/1998 | Lee et al. | |
| 5,808,045 A | 9/1998 | Hiatt et al. | |
| 5,847,162 A | 12/1998 | Lee et al. | |
| 5,872,244 A | 2/1999 | Hiatt et al. | |
| 6,013,445 A | 1/2000 | Albrecht et al. | |
| 6,210,891 B1 | 4/2001 | Nyren et al. | |
| 6,232,465 B1 | 5/2001 | Hiatt et al. | |
| 6,255,475 B1 | 7/2001 | Kwiatkowski | |
| 6,258,568 B1 | 7/2001 | Nyren | |
| 6,274,320 B1 | 8/2001 | Rothberg et al. | |
| 6,664,079 B2 | 12/2003 | Ju et al. | |
| 7,057,026 B2 | 6/2006 | Barnes et al. | |
| 7,211,390 B2 | 5/2007 | Rothberg et al. | |
| 7,244,559 B2 | 7/2007 | Rothberg et al. | |
| 7,264,929 B2 | 9/2007 | Rothberg et al. | |
| 7,541,444 B2 | 6/2009 | Milton et al. | |
| 8,178,360 B2 | 5/2012 | Barnes et al. | |
| 8,882,980 B2 | 11/2014 | Ling et al. | |
| 8,883,990 B2 | 11/2014 | Mikawa | |
| 9,416,409 B2 | 8/2016 | Hayden | |
| 9,970,054 B2 | 5/2018 | Otwinowski et al. | |
| 10,370,701 B2 | 8/2019 | Wilson | |
| 10,738,072 B1 | 8/2020 | Graham et al. | |
| 2003/0148344 A1 | 8/2003 | Rothberg et al. | |
| 2009/0118128 A1 | 5/2009 | Liu et al. | |
| 2012/0316086 A1* | 12/2012 | Lin | C12Q 1/6806 506/26 |
| 2013/0012399 A1 | 1/2013 | Myers et al. | |
| 2014/0134610 A1* | 5/2014 | Pham | C12P 19/34 435/6.1 |
| 2018/0258472 A1 | 9/2018 | Glezer | |
| 2018/0274024 A1 | 9/2018 | Ju et al. | |
| 2019/0093160 A1 | 3/2019 | Schmitt et al. | |
| 2019/0177776 A1 | 6/2019 | Coll Mulet et al. | |
| 2019/0360043 A1* | 11/2019 | Pham | C12Q 1/6813 |
| 2021/0002711 A1 | 1/2021 | Otwinowski et al. | |
| 2021/0371924 A1* | 12/2021 | Salk | C12Q 1/6869 |
| 2022/0033895 A1 | 2/2022 | Glezer et al. | |

FOREIGN PATENT DOCUMENTS

| | | |
|---|---|---|
| WO | WO-89/10977 A1 | 11/1989 |
| WO | WO-96/07669 A1 | 3/1996 |
| WO | WO-2004/018497 A2 | 3/2004 |

(Continued)

OTHER PUBLICATIONS

Bains, W. et al. (Dec. 7, 1988). "A novel method for nucleic acid sequence determination," *J Theor Biol* 135(3):303-307.
Beattie, W.G. et al. (Dec. 1995). "Hybridization of DNA targets to glass-tethered oligonucleotide probes," *Mol Biotechnol* 4(3):213-225.
Beck, T.N. et al. (Jun. 19, 2019). "Circulating tumor cell and cell-free RNA capture and expression analysis identify platelet-associated genes in metastatic lung cancer," *BMC Cancer* 19(1):603.
Benayed, R. et al. (Aug. 1, 2019, e-published Apr. 26, 2019). "High Yield of RNA Sequencing for Targetable Kinase Fusions in Lung Adenocarcinomas with No Mitogenic Driver Alteration Detected by DNA Sequencing and Low Tumor Mutation Burden," *Clin Cancer Res* 25(15):4712-4722.
Bentley, D.R. et al. (Nov. 6, 2008). "Accurate whole human genome sequencing using reversible terminator chemistry," *Nature* 456(7218):53-59.

(Continued)

*Primary Examiner* — Jezia Riley
(74) *Attorney, Agent, or Firm* — Mintz, Levin, Cohn, Ferris, Glovsky and Popeo, P.D.

(57) ABSTRACT

Provided herein are methods for sequencing both strands of a double stranded nucleic acid fragment that improves fidelity and accuracy of a sequence determination compared to traditional next generation sequencing methods. Compositions and kits for use in the methods are also provided.

30 Claims, 25 Drawing Sheets

Specification includes a Sequence Listing.

(56) References Cited

FOREIGN PATENT DOCUMENTS

| WO | WO-2004/018497 A3 | 3/2004 |
|---|---|---|
| WO | WO-2017/205336 A1 | 11/2017 |
| WO | WO-2018/148723 A1 | 8/2018 |
| WO | WO-2019/183640 A1 | 9/2019 |
| WO | WO-2020/056044 A1 | 3/2020 |
| WO | WO-2021/022237 A1 | 2/2021 |
| WO | WO-2021/178893 A2 | 9/2021 |
| WO | WO-2021/178893 A3 | 9/2021 |

OTHER PUBLICATIONS

Bergen, K. et al. (Jun. 17, 2013, e-published Jun. 3, 2013). "Structures of KOD and 9°N DNA polymerases complexed with primer template duplex," Chembiochem 14(9):1058-1062.

Campbell, M.A. et al. (Dec. 2006). "Comprehensive analysis of alternative splicing in rice and comparative analyses with Arabidopsis," BMC Genomics 7:327.

Chen, F. et al. (Feb. 2013, e-published Jan. 23, 2013). "The history and advances of reversible terminators used in new generations of sequencing technology," Genomics Proteomics Bioinformatics 11(1):34-40.

Chen L, et al. (2016). "DNA Damage is a Major Cause of Sequencing Errors, Directly Confounding Variant Identification," bioRxiv 30 pages.

Columbus, L. et al. (Jun. 2002). "A new spin on protein dynamics," Trends Biochem 27(6):288-295.

Costello, M. et al. (Apr. 1, 2013, e-published Jan. 8, 2013). "Discovery and characterization of artifactual mutations in deep coverage targeted capture sequencing data due to oxidative DNA damage during sample preparation," Nucleic Acids Res 41(6):e67.

Do, H. et al. (Jan. 2015, e-published Nov. 24, 2014). "Sequence artifacts in DNA from formalin-fixed tissues: causes and strategies for minimization," Clin Chem 61(1):64-71.

Drmanac, S. et al. (Jan. 1998). "Accurate sequencing by hybridization for DNA diagnostics and individual genomics," Nat Biotechnol 16(1):54-58.

Dubrovina A.S. et al. (2013, e-published Dec. 26, 2012). "The role of canonical and noncanonical pre-mRNA splicing in plant stress responses," Biomed. Res. Int. 2013:264314.

Ehrlich, M. et al. (2013). "DNA hypomethylation and hemimethylation in cancer," Adv Exp Med Biol 754:31-56.

Fodor, S.P. et al. (Feb. 15, 1991). "Light-directed, spatially addressable parallel chemical synthesis," Science 251(4995):767-773.

Frommer, M. et al. (Mar. 1, 1992). "A genomic sequencing protocol that yields a positive display of 5-methylcytosine residues in individual DNA strands," PNAS USA 89(5):1827-1831.

Fuller, C.W. et al. (May 10, 2016, e-published Apr. 18, 2016). "Real-time single-molecule electronic DNA sequencing by synthesis using polymer-tagged nucleotides on a nanopore array," PNAS USA 113(19):5233-5238.

Greenberg, M.V.C. et al. (Oct. 2019, e-published Aug. 9, 2019). "The diverse roles of DNA methylation in mammalian development and disease," Nat Rev Mol Cell Biol 20(10):590-607.

Grunau, C. et al. (Jul. 1, 2001). "Bisulfite genomic sequencing: systematic investigation of critical experimental parameters," Nucleic Acids Res 29(13):E65-5.

Guilliam, T.A. et al. (Aug. 18, 2015, e-published Jun. 24, 2015). "Primase-polymerases are a functionally diverse superfamily of replication and repair enzymes," Nucleic Acids Res 43(14):6651-6664.

Guo, J. et al. (Jul. 8, 2008, e-published Jun. 30, 2008). "Four-color DNA sequencing with 3'-O-modified nucleotide reversible terminators and chemically cleavable fluorescent dideoxynucleotides," PNAS USA 105(27):9145-9150.

Haque, I.S. et al. (2017). "Challenges in Using ctDNA to Achieve Early Detection of Cancer," bioRxiv, 20 pages.

Hu, H. et al. (Feb. 7, 2020). "Analysis of Alternative Splicing and Alternative Polyadenylation in Populus alba var. pyramidalis by Single-Molecular Long-Read Sequencing," Front. Genet. 11:48.

Kaur, M. et al. (Mar. 15, 2003). "Novel amplification of DNA in a hairpin structure: towards a radical elimination of PCR errors from amplified DNA," Nucleic Acids Res 31(6):e26.

Kringel, D. et al. (Sep. 19, 2018). "Development of an AmpliSeq TM Panel for Next-Generation Sequencing of a Set of Genetic Predictors of Persisting Pain," Front Pharmacol 9:1008.

Kumar, S. et al. (2012, e-published Sep. 21, 2012). "PEG-labeled nucleotides and nanopore detection for single molecule DNA sequencing by synthesis," Sci Rep 2:684.

Li, Y. et al. (Apr. 2017, e-published Feb. 11, 2017). "Global identification of alternative splicing via comparative analysis of SMRT- and Illumina-based RNA-seq in strawberry," The Plant J. 90(1):164-176.

Liao, X et al. (2019). "Current challenges and solutions of de novo assembly," Quant. Biol. 7(2):90-109.

Liao, Y.C. et al. (Sep. 4, 2019). "Completing Circular Bacterial Genomes With Assembly Complexity by Using a Sampling Strategy From a Single MinION Run With Barcoding," Front. Microbiol. 10:2068.

Liu, Y. et al. (Apr. 2019, e-published Feb. 25, 2019). "Bisulfite-free direct detection of 5-methylcytosine and 5-hydroxymethylcytosine at base resolution," Nat Biotechnol 37(4):424-429.

Lizardi, P.M. et al. (Jul. 1998). "Mutation detection and single-molecule counting using isothermal rolling-circle amplification," Nat. Genet. 19(3):225-232.

Newman, J.A. et al. (Dec. 1, 2015). "Structure of the Helicase Domain of DNA Polymerase Theta Reveals a Possible Role in the Microhomology-Mediated End-Joining Pathway," Structure 23(12):2319-2330.

Nilsson, M. et al. (Sep. 1994). "Padlock probes: circularizing oligonucleotides for localized DNA detection," Science 265(5181):2085-2088.

Olek, A. et al. (Dec. 15, 1996). "A modified and improved method for bisulphite based cytosine methylation analysis," Nucleic Acids Res 24(24):5064-5066.

Pietrasz, D. et al. (Jan. 2017, e-published Dec. 19, 2016). "Plasma Circulating Tumor DNA in Pancreatic Cancer Patients is a Prognostic Marker," Clin Cancer Res 23(1):116-123.

Quail, M.A. et al. (Dec. 2008). "A large genome center's improvements to the Illumina sequencing system," Nat Methods 5(12):1005-1010.

Rehm, H.L. (Apr. 2013, e-published Mar. 12, 2013). "Disease-targeted sequencing: a cornerstone in the clinic," Nat Rev Genet 14(4):295-300.

Robertson, K.D. (Aug. 2005). "DNA methylation and human disease," Nat Rev Genet 6(8):597-610.

Ronaghi, M. et al. (Nov. 1, 1996). "Real-time DNA sequencing using detection of pyrophosphate release," Anal Biochem 242(1):84-89.

Ronaghi, M. et al. (Jul. 17, 1998). "A sequencing method based on real-time pyrophosphate," Science 281 (5375):363-365.

Ronaghi, M. (Jan. 2001). "Pyrosequencing sheds light on DNA sequencing," Genome Res 11(1):3-11.

Shen, L. et al. (2014). "Mechanism and function of oxidative reversal of DNA and RNA methylation," Annu Rev Biochem 83:585-614.

Shendure, J. et al. (Sep. 9, 2005, e-published Aug. 4, 2005). "Accurate multiplex polony sequencing of an evolved bacterial genome," Science 309(5741):1728-1732.

Shiraishi, M. et al. (Dec. 31, 2004). "High-speed conversion of cytosine to uracil in bisulfite genomic sequencing analysis of DNA methylation," DNA Res 11(6):409-415.

Simen, B.B. et al. (Apr. 2015, e-published Oct. 30, 2014). "Validation of a next-generation-sequencing cancer panel for use in the clinical laboratory," Arch Pathol Lab Med 139(4):508-517.

Singh, R.R. et al. (Sep. 2013, e-published Jun. 26, 2013). "Clinical validation of a next-generation sequencing screen for mutational hotspots in 46 cancer-related genes," J Mol Diagn 15(5):607-622.

(56) References Cited

OTHER PUBLICATIONS

Song, C-X. et al. (Oct. 2017, e-published Aug. 18, 2017). "5-Hydroxymethylcytosine signatures in cell-free DNA provide information about tumor types and stages," *Cell Res* 27(10):1231-1242.
Sorber, L. et al. (Mar. 30, 2019). "Circulating Cell-Free DNA and RNA Analysis as Liquid Biopsy: Optimal Centrifugation Protocol," *Cancers* 11(4):458.
Southworth, M.W. et al. (May 28, 1996). "Cloning of thermostable DNA polymerases from hyperthermophilic marine Archaea with emphasis on *Thermococcus* sp. 9°N-7 and mutations affecting 3'-5' exonuclease activity," *PNAS USA* 93(11):5281-5285.
Valentine, C.C. et al. (Dec. 29, 2020, e-published Dec. 14, 2020). "Direct quantification of in vivo mutagenesis and carcinogenesis using duplex sequencing," PNAS USA 117(52):33414-33425.
Vogelstein, B. et al. (Mar. 29, 2013). "Cancer genome landscapes," *Science* 339(6127).
Wahl, M.C. et al. (Feb. 20, 2009). "The spliceosome: design principles of a dynamic RNP machine," *Cell* 136(4):701-718.
Wang, Q. et al. (Aug. 28, 2018, e-published Aug. 13, 2018). "JUM is a computational method for comprehensive annotation-free analysis of alternative pre-mRNA splicing patterns," *PNAS USA.* 115(35):E8181-E8190.
Yi, S. et al. (Dec. 19, 2017). "An optimized rapid bisulfite conversion method with high recovery of cell-free DNA," *BMC Mol Biol* 18(1):24.
Yohe, S. et al. (Feb. 2015). "Clinical validation of targeted next-generation sequencing for inherited disorders," *Arch Pathol Lab Med* 139(2):204-210.
Zhang, L. et al. (Nov. 23, 2018, e-published Sep. 13, 2018). "Somatic Mutagenesis in Mammals and Its Implications for Human Disease and Aging," *Annu Rev Genet* 52:397-419.
Zhao, L. et al. (Aug. 2014, e-published May 16, 2014). "The dynamics of DNA methylation fidelity during mouse embryonic stem cell self-renewal and differentiation," *Genome Res* 24(8):1296-1307.
Zhao, S. et al. (Mar. 19, 2018). "Evaluation of two main RNA-seq approaches for gene quantification in clinical RNA sequencing: polyA+ selection versus rRNA depletion," *Scientific Reports* 8(1): 4781.
U.S. Appl. No. 17/392,180.
U.S. Appl. No. 17/392,203.
International Search Report dated Aug. 31, 2021, for PCT Application No. PCT/US2021/021208, filed Mar. 5, 2021, 7 pages.
Written Opinion dated Aug. 31, 2021, for PCT Application No. PCT/US2021/021208, filed Mar. 5, 2021, 14 pages.

\* cited by examiner

LINKED PAIRED STRAND SEQUENCING

CROSS-REFERENCES TO RELATED APPLICATIONS

This application claims the benefit of U.S. Provisional Application No. 62/986,527, filed Mar. 6, 2020; U.S. Provisional Application No. 63/020,881, filed May 6, 2020; and U.S. Provisional Application No. 63/087,125, filed Oct. 2, 2020; which are incorporated herein by reference in their entirety and for all purposes.

SEQUENCE LISTING

The instant application contains a Sequence Listing which has been submitted electronically in ASCII format and is hereby incorporated by reference in its entirety. Said ASCII copy, created on Mar. 4, 2021, is named 051385-523001US_SL_ST25.txt and is 5,134 bytes in size.

BACKGROUND

DNA sequencing is a fundamental tool in biological and medical research; it is an essential technology for the paradigm of personalized precision medicine. Sanger sequencing, where the sequence of a nucleic acid is determined by selective incorporation and detection of dideoxynucleotides, enabled the mapping of the first human reference genome. While this methodology is still useful for validating newer sequencing technologies, efforts to sequence and assemble genomes using the Sanger method are an expensive and laborious undertaking, requiring specialized equipment and expertise. Next generation sequencing (NGS) methodologies make use of simultaneously sequencing millions of fragments of nucleic acids in a single run. However, traditional NGS struggles with distinguishing rare sequence variants from errors introduced during sample preparation, amplification, and/or sequencing.

SUMMARY

In view of the foregoing, innovative approaches to address issues with existing sequencing technologies are needed. Disclosed herein are solutions to these and other problems in the art which, in embodiments, increase the fidelity and accuracy of high throughput sequencing methods. In certain embodiments, the compositions and methods provided herein reduce the amount of nucleic acid manipulation and duplication required by traditional next generation sequencing techniques. In embodiments, the sequencing methods described herein permit greater accuracy of a sequence determination compared to traditional next generation sequencing methods without requiring additional sequencing depth.

In some aspects, presented herein is a method of sequencing a double stranded nucleic acid. In embodiments, the method comprises (a) ligating a first adapter to a first end of the double stranded nucleic acid, and ligating a second adapter to a second end of the double stranded nucleic acid, wherein the second adapter is a hairpin adapter, thereby forming a nucleic acid template; (b) annealing a first primer to the nucleic acid template, wherein the first primer comprises a sequence that is complementary to a portion of the first adapter, or a complement thereof; (c) sequencing a first portion of the nucleic acid template by extending the first primer, thereby generating a first read (and generating an extended sequencing primer) comprising a first nucleic acid sequence of at least a first portion of the double stranded nucleic acid; (d) annealing a second primer to the nucleic acid template, wherein the second primer comprises a sequence that is complementary to a sequence within a loop or stem of the hairpin adapter, or a complement thereof; and (e) sequencing a second portion of the nucleic acid template by extending the second primer, thereby generating a second read (and generating an extended sequencing primer) comprising a nucleic acid sequence of at least a second portion of the double stranded nucleic acid. In some embodiments, the double stranded nucleic acid comprises a forward strand and a reverse strand.

In some embodiments, the first adapter is a Y-adapter. In some embodiments, the Y-adapter comprises (i) a first strand having a 5'-arm and a 3'-portion, and (ii) a second strand having a 5'-portion and a 3'-arm, wherein the 3'-portion of the first strand is substantially complementary to the 5'-portion of the second strand, and the 5'-arm of the first strand is not substantially complementary to the 3'-arm of the second strand. In some embodiments, the ligating of the first adapter comprises ligating a 3'-end of the first strand of the Y-adapter to a 5'-end of the forward strand of the double stranded nucleic acid, and ligating a 5'-end of the second strand of the Y-adapter to a 3'-end of the reverse strand of the double stranded nucleic acid. In some embodiments, the first primer anneals to the second strand of the Y-adapter. In some embodiments, the 5'-arm of the first strand or the 3'-arm of the second strand of the Y-adapter comprises a GC content of greater than 50%. In some embodiments, the 5'-arm of the first strand or the 3'-arm of the second strand of the Y-adapter comprises a melting temperature (Tm) in a range of 60-85° C. In certain embodiments, the 5'-arm of the first strand or the 3'-arm of the second strand of the Y-adapter comprises modified nucleotides (e.g., locked nucleotides (i.e., LNAs) or diamino purine nucleotides). In some embodiments, the 3'-portion of the first strand or the 5'-portion of second strand of the Y-adapter comprises a Tm in a range of about 40-50° C. In some embodiments, a duplex comprising the 3'-portion of the first strand and the 5'-portion of second strand of the Y-adapter comprise a Tm of less than 40° C. In some embodiments, a duplex comprising the 3'-portion of the first strand and the 5'-portion of second strand of the Y-adapter comprise a Tm of about 30° C., 32° C., 34° C., 36° C., 38° C., or 40° C. In some embodiments, a duplex comprising the 3'-portion of the first strand and the 5'-portion of second strand of the Y-adapter comprise a Tm in a range of 40-50° C. In some embodiments, the 3'-end or 3'-arm of the second strand of the Y-adapter comprises a binding motif or a nucleic acid sequence complementary to a capture nucleic acid. In some embodiments, the 5'-end or 5'-arm of the first strand of the Y-adapter comprises a binding motif or a nucleic acid sequence substantially identical to a capture nucleic acid. In some embodiments, a nucleic acid template generated by a method herein comprises sequences of the first strand of a Y-adapter, a forward strand of a double stranded nucleic acid, a second adapter, a reverse strand of the double stranded nucleic acid and a second strand of the Y-adapter arranged in a 5' to 3' direction. In some embodiments, a first primer anneals to a 5'-portion of the second strand of the Y-adapter. In embodiments, about 6, 8, 10, 12, or 14 nucleotides of the 3'-portion of the first strand and the 5'-portion of the second strand are substantially complementary. In embodiments, about 10 to 12 nucleotides of the 3'-portion of the first strand and the 5'-portion of the second strand are substantially complementary.

In some embodiments, a first adapter is a hairpin adapter. In some embodiments, a first primer anneals to a sequence within a loop of the first adapter.

In some embodiments, the first read comprises a nucleic acid sequence of the reverse strand of the double stranded nucleic acid, or a portion thereof, and the second read comprises a nucleic acid sequence of the forward strand of the double stranded nucleic acid, or a portion thereof. In some embodiments, the first read comprises a nucleic acid sequence of the forward strand of the double stranded nucleic acid, or a portion thereof, and the second read comprises a nucleic acid sequence of the reverse strand of the double stranded nucleic acid, or a portion thereof.

In some embodiments, the second adapter is a hairpin adapter comprising a nucleic acid having a 5'-end, a 5'-portion, a loop, a 3'-portion and a 3'-end, and the 5'-portion of the second adapter is substantially complementary to the 3'-portion of the second adapter. In some embodiments, ligating of the second adapter comprises ligating the 5'-end of the second adapter to a 3'-end of the forward strand of a double stranded nucleic acid and ligating the 3'-end of the second adapter to a 5'-end of the reverse strand of the double stranded nucleic acid. In some embodiments, a duplex comprising the 5'-portion and the 3'-portion of the second adapter comprise a Tm in a range of 40-50° C. In some embodiments, a duplex comprising the 5'-portion and the 3'-portion of the second adapter comprise a Tm in a range of about 40-50° C. In some embodiments, a duplex comprising the 5'-portion and the 3'-portion of the second adapter comprise a Tm of less than 40° C. In some embodiments, a duplex comprising the 5'-portion and the 3'-portion of the second adapter comprise a Tm of about 30° C., 32° C., 34° C., 36° C., 38° C., or 40° C.

In some embodiments, the first end of the double stranded nucleic acid comprises a blunt end, a 5' overhang, or a 3' overhang. In some embodiments, the second end of the double stranded nucleic acid comprises a blunt end, a 5' overhang, or a 3' overhang.

In some embodiments, the method comprises generating amplicons of a nucleic acid template described herein (e.g., the nucleic acid ligated to a first and second adapter, as described herein). In some embodiments, the method of generating amplicons of the nucleic acid template comprises a polymerase chain reaction. In some embodiments, a polymerase chain reaction comprises a bridge amplification method. In some embodiments, generating of amplicons comprises attaching the nucleic acid template to a substrate. In some embodiments, a substrate comprises a chip, a wafer, a bead, or a flow cell. In embodiments a substrate comprises a first capture nucleic acid comprising a nucleic acid sequence complementary to at least a portion of the second strand of the Y-adapter, or a complement thereof. In some embodiments, attaching of the nucleic acid template to the substrate comprises annealing the nucleic acid template to the first capture nucleic acid. In some embodiments, a substrate comprises a second capture nucleic acid comprising a nucleic acid sequence complementary to at least a portion of the first strand of the Y-adapter, or complement thereof. In some embodiments, amplicons comprise a first copy of the nucleic acid template having a nucleic acid sequence that is substantially identical to the nucleic acid sequence of the nucleic acid template, or a portion thereof, and a second copy of the template comprises a nucleic acid sequence that is substantially complementary to the nucleic acid sequence of the nucleic acid template. In some embodiments, after generating the amplicons of the nucleic acid template, the first or the second copy of the nucleic acid template is removed from the substrate. In some embodiments, the amplicons that are attached to the substrate are attached at addressable locations on the substrate.

In embodiments where the first adapter is a hairpin adapter and the second adapter is a hairpin adapter, the generating of amplicons may comprise a rolling circle amplification. In some embodiments, a method of sequencing a template comprises a process comprising sequencing by synthesis. In some embodiments, a first adapter and/or a second adapter comprise one or more of a sample barcode sequence, a molecular identifier sequence, or both.

In some aspects, presented herein is a composition for sequencing a double stranded nucleic acid. In embodiments, the kit comprises a forward strand and a reverse strand, the composition comprising: (i) a template nucleic acid comprising sequences of a first strand of a Y-adapter, the forward strand of the double stranded nucleic acid, a hairpin adapter, the reverse strand of the double stranded nucleic acid and a second strand of the Y-adapter arranged in a 5' to 3' direction; and (ii) a primer hybridized to a loop of the hairpin adapter; wherein the template is attached to a substrate.

In some aspects, presented herein is a kit for sequencing a double stranded nucleic acid. In embodiments, the kit comprises: (i) a first adapter, wherein the first adapter comprises a double-stranded portion and at least one single-stranded portion; (ii) a second adapter, wherein the second adapter is a hairpin adapter comprising a nucleic acid having a 5'-end, a 5'-portion, a loop, a 3'-portion and a 3'-end, and the 5'-portion of the hairpin adapter is substantially complementary to the 3'-portion of the hairpin adapter; (iii) a first primer having a nucleic acid sequence complementary to a portion of the first adapter, or a complement thereof and (iv) a second primer having a nucleic acid sequence complementary to the loop of the hairpin adapter, or a complement thereof. In some embodiments, the first adapter is a Y-adapter, where the Y-adapter comprises (i) a first strand having a 5'-arm and a 3'-portion, and (ii) a second strand having a 5'-portion and a 3'-arm, wherein the 3'-portion of the first strand is substantially complementary to the 5'-portion of the second strand, and the 5'-arm is not substantially complementary to the 3'-arm. In some embodiments, the first adapter is a hairpin adapter.

In some aspects, presented herein is a method of selectively sequencing a double-stranded nucleic acid. In embodiments, the method comprises (a) ligating a first adapter to a first end of the double-stranded nucleic acid, and ligating a second adapter to a second end of the double-stranded nucleic acid, wherein the second adapter is a hairpin adapter; (b) displacing at least a portion of one strand of the double-stranded nucleic acid from step (a); (c) hybridizing a probe oligonucleotide to the displaced portion of the double-stranded nucleic acid; (d) separating the probe-hybridized double-stranded nucleic acid from nucleic acids not hybridized to a probe; and (e) sequencing the probe-hybridized double-stranded nucleic acid of step (d).

BRIEF DESCRIPTION OF THE DRAWINGS

FIG. 1A shows an embodiment of an adapter-target-adapter template comprising a double stranded nucleic acid of interest annealed to a Y-adapter and a hairpin adapter. FIG. 1B shows an embodiment of an adapter ligation process where a hairpin adapter may comprise an optional UMI (unique molecular identifier; barcode). FIG. 1C shows an embodiment of an adapter-target-adapter template where a double stranded nucleic acid of interest is annealed to a first hairpin adapter (hairpin adapter 1) and a second, non-identical, hairpin adapter (hairpin adapter 2). FIG. 1D shows an embodiment of an adapter ligation process.

FIG. 2A shows an embodiment of a Y adapter. FIG. 2B shows an embodiment of a hairpin adapter comprising a 5'-end, a 5' portion, a loop, a 3' portion and a 3'-end. In this embodiment, a duplex region of the adapter comprises a Tm (melting temperature) of about 40-45° C. and a length of about 10-16 bases. In embodiments, the duplex region of the adapter comprises a Tm (melting temperature) of about 35-45° C. or 30-45° C. and a length of about 12 bases.

FIG. 6A shows a Y-template-hairpin construct hybridizing to an immobilized P2 primer. In the presence of a polymerase, a copy of the original template is made; this copy then hybridizes to an immobilized P1 primer. FIG. 6B depicts annealing, extending, denaturing, re-annealing, and extending steps common to one embodiment of an amplification method described herein.

FIG. 7A shows a process where a template bound to an immobilized P1 is optionally cleaved at X and removed. The P2-anchored strands are terminated using a suitable technique (e.g., depicted is a dideoxynucleotide (dd), however any suitable terminating process is contemplated herein). FIG. 7B shows sequencing up with a strand displacing polymerase (left), following by priming at the P3 priming site and sequencing down with a strand displacing polymerase (right).

FIG. 15A shows a Y-template-hairpin construct containing methylated cytosines undergoing cytosine conversion. Cytosines lacking a methyl group are converted to uracil. Following bisulfite conversion, adapter-target-adapter constructs may be amplified prior to clustering. FIG. 15B shows a cytosine-converted Y-template-hairpin construct hybridizing to an immobilized P2 primer. In the presence of a polymerase, a copy of the original template is made; this copy then hybridizes to an immobilized P1 primer. The uracil is copied as an adenine, while the Me-C are copied as guanines. FIG. 15C depicts annealing, extending, denaturing, re-annealing, and extending steps common to one embodiment of an amplification method for a cytosine-converted construct. FIG. 15D shows an amplified, cytosine-converted Y-template-hairpin construct hybridizing to an immobilized P2 primer. As this was amplified prior to hybridization, the uracil has now been replaced with a thymine. In the presence of a polymerase, a copy of the original template is made; this copy then hybridizes to an immobilized P1 primer as shown in FIG. 15C.

FIG. 17A Illustrates an embodiment of the Y-template adapter containing a bisulfite conversion control region consisting of one or more unmethylated cytosine bases. Following bisulfite treatment, the efficiency of bisulfite conversion may be estimated via the fraction of cytosine bases within this region that are read as thymine. An optional methylcytosine UMI region is located adjacent to the bisulfite conversion control region. This element consists of a plurality of cytosine bases designed to be methylated with approximately 50% probability, such that bisulfite conversion gives rise to a low complexity UMI consisting of the resultant combination of methylation protected (unconverted) and bisulfite converted bases. Optionally, the double stranded stem region of the adapter may be designed to contain one or more unmethylated cytosines, which reduce self-complementarity of the construct following bisulfite conversion. In embodiments, the one or more unmethylated cytosines are not present in the sequence that is complementary to a sequencing primer. FIG. 17B Illustrates an embodiment of the hairpin adapter containing an optional bisulfite conversion control region, an optional methylcytosine UMI region, and optionally including unmethylated cytosines within the stem region to reduce self-complementarity following bisulfite conversion.

FIG. 18A shows a Y-template-hairpin construct attached to the solid support. A primer anneals to the loop of the hairpin (identified as P3 in FIG. 18A) and is extended with a strand displacing enzyme (depicted as a gray ellipse). A sequencing primer hybridizes to the liberated end of the construct and is extended in the presence of a sequencing enzyme to generate a first sequencing read, as shown in FIG. 18B. The hairpin may include a cleavable site, depicted as an 'X', and may optionally be cleaved and removed. A second sequencing primer is then annealed to the 3' end of the immobilized single-stranded template, and is sequenced in the presence of a sequencing enzyme to generate a second sequencing read.

FIG. 19A shows an 8-oxo-dG-containing Y-template-hairpin construct hybridizing to an immobilized P2 primer. In the presence of a polymerase, a copy of the original template is made; this copy then hybridizes to an immobilized P1 primer. The 8-oxo-dG is copied as an adenine, resulting in an A-G mismatch. FIG. 19B depicts annealing, extending, denaturing, re-annealing, and extending steps common to one embodiment of an amplification method for an oxidative damage-induced construct. Boxes have been drawn to highlight mismatches. FIG. 19C shows a Y-template-hairpin construct containing an 8-oxo-dG base undergoing amplification. Following amplification, the damaged base is replaced with a thymine. FIG. 19D shows hybridization of the amplified Y-template-hairpin construct of FIG. 19C to an immobilized P2 primer. In the presence of a polymerase, a copy of the template is made; this copy then hybridizes to an immobilized P1 primer as shown in FIG. 19B.

DETAILED DESCRIPTION

I. Definitions

Figure 1A:
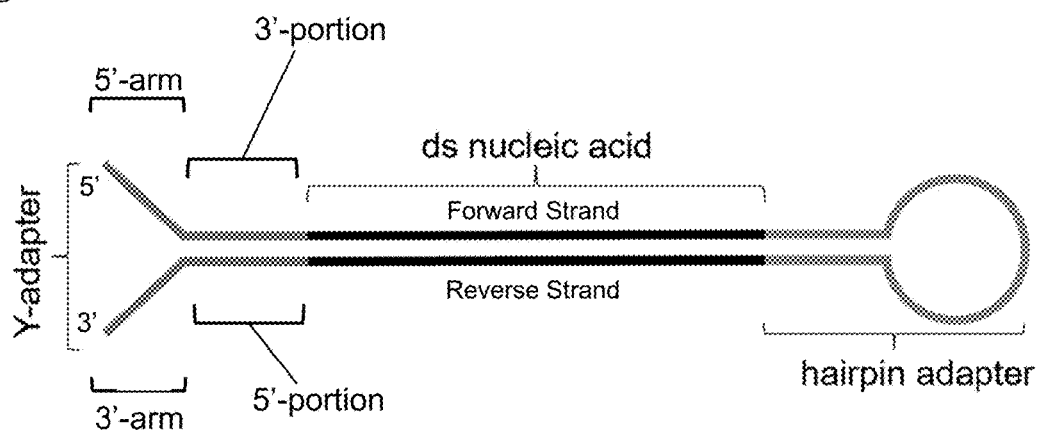
FIGS. 1A-1D.

The practice of the technology described herein will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Examples of such techniques are available in the literature. Methods, devices and materials similar or equivalent to those described herein can be used in the practice of embodiments of the present invention.

All patents, patent applications, articles and publications mentioned herein, both supra and infra, are hereby expressly incorporated herein by reference in their entireties.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art. The following definitions are provided to facilitate understanding of certain terms used frequently herein and are not meant to limit the scope of the present disclosure.

As used herein, the singular terms "a", "an", and "the" include the plural reference unless the context clearly indicates otherwise. Reference throughout this specification to, for example, "one embodiment", "an embodiment", "another embodiment", "some embodiments", "a particular embodiment", "a related embodiment", "a certain embodiment", "an additional embodiment", or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

As used herein, the term "control" or "control experiment" is used in accordance with its plain and ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

As used herein, the term "complement" is used in accordance with its plain and ordinary meaning and refers to a nucleotide (e.g., RNA nucleotide or DNA nucleotide) or a sequence of nucleotides capable of base pairing with a complementary nucleotide or sequence of nucleotides (e.g., Watson-Crick base pairing). As described herein and commonly known in the art the complementary (matching) nucleotide of adenosine is thymidine and the complementary (matching) nucleotide of guanosine is cytosine. Thus, a complement may include a sequence of nucleotides that base paired with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence.

As described herein, the complementarity of sequences may be partial, in which only some of the nucleic acids match according to base pairing, or complete, where all the nucleic acids match according to base pairing. Thus, two sequences that are complementary to each other, may have a specified percentage of nucleotides that complement one another (e.g., about 60%, preferably 65%, 70%, 75%, 80%, 85%, 90%, 91%, 92%, 93%, 94%, 95%, 96%, 97%, 98%, 99%, or higher complementarity over a specified region). In embodiments, two sequences are complementary when they are completely complementary, having 100% complementarity. In embodiments, sequences in a pair of complementary sequences form portions of a single polynucleotide with non-base-pairing nucleotides (e.g., as in a hairpin or loop structure, with or without an overhang) or portions of separate polynucleotides. In embodiments, one or both sequences in a pair of complementary sequences form portions of longer polynucleotides, which may or may not include additional regions of complementarity.

As used herein, the term "contacting" is used in accordance with its plain ordinary meaning and refers to the process of allowing at least two distinct species (e.g. chemical compounds including biomolecules or cells) to become sufficiently proximal to react, interact or physically touch. However, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound, a protein or enzyme (e.g., a DNA polymerase).

As may be used herein, the terms "nucleic acid," "nucleic acid molecule," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences. As may be used herein, the terms "nucleic acid oligomer" and "oligonucleotide" are used interchangeably and are intended to include, but are not limited to, nucleic acids having a length of 200 nucleotides or less. In some embodiments, an oligonucleotide is a nucleic acid having a length of 2 to 200 nucleotides, 2 to 150 nucleotides, 5 to 150 nucleotides or 5 to 100 nucleotides. In some embodiments, an oligonucleotide is a primer configured for extension by a polymerase when the primer is annealed completely or partially to a complementary nucleic acid template. A primer is often a single stranded nucleic acid. In certain embodiments, a primer, or portion thereof, is substantially complementary to a portion of an adapter. In some embodiments, a primer has a length of 200 nucleotides or less. In certain embodiments, a primer has a length of 10 to 150 nucleotides, 15 to 150 nucleotides, 5 to 100 nucleotides, 5 to 50 nucleotides or 10 to 50 nucleotides.

As used herein, the terms "polynucleotide primer" and "primer" refers to any polynucleotide molecule that may hybridize to a polynucleotide template, be bound by a polymerase, and be extended in a template-directed process for nucleic acid synthesis. The primer may be a separate polynucleotide from the polynucleotide template, or both may be portions of the same polynucleotide (e.g., as in a hairpin structure having a 3' end that is extended along another portion of the polynucleotide to extend a double-stranded portion of the hairpin). Primers (e.g., forward or reverse primers) may be attached to a solid support. A primer can be of any length depending on the particular technique it will be used for. For example, PCR primers are generally between 10 and 40 nucleotides in length. The length and complexity of the nucleic acid fixed onto the nucleic acid template may vary. In some embodiments, a primer has a length of 200 nucleotides or less. In certain embodiments, a primer has a length of 10 to 150 nucleotides, 15 to 150 nucleotides, 5 to 100 nucleotides, 5 to 50 nucleotides or 10 to 50 nucleotides. One of skill can adjust these factors to provide optimum hybridization and signal production for a given hybridization procedure. The primer permits the addition of a nucleotide residue thereto, or oligonucleotide or polynucleotide synthesis therefrom, under suitable conditions. In an embodiment the primer is a DNA primer, i.e., a primer consisting of, or largely consisting of, deoxyribonucleotide residues. The primers are designed to have a sequence that is the complement of a region of template/target DNA to which the primer hybridizes. The addition of a nucleotide residue to the 3' end of a primer by formation of a phosphodiester bond results in a DNA extension product. The addition of a nucleotide residue to the 3' end of the DNA extension product by formation of a phosphodiester bond results in a further DNA extension product. In another embodiment the primer is an RNA primer. In embodiments, a primer is hybridized to a target polynucleotide. A "primer" is complementary to a polynucleotide template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

In some embodiments, a nucleic acid comprises a capture nucleic acid. A capture nucleic acid refers to a nucleic acid that is attached to a substrate. In some embodiments, a capture nucleic acid comprises a primer. In some embodiments, a capture nucleic acid is a nucleic acid configured to specifically hybridize to a portion of one or more nucleic acid templates (e.g., a template of a library). In some embodiments a capture nucleic acid configured to specifically hybridize to a portion of one or more nucleic acid templates is substantially complementary to a suitable portion of a nucleic acid template, or an amplicon thereof. In some embodiments a capture nucleic acid is configured to specifically hybridize to a portion of an adapter, or a portion thereof. In some embodiments a capture nucleic acid, or portion thereof, is substantially complementary to a portion of an adapter, or a complement thereof. In embodiments, a capture nucleic acid is a probe oligonucleotide. Typically, a probe oligonucleotide is complementary to a target polynucleotide or portion thereof, and further comprises a label (such as a binding moiety) or is attached to a surface, such that hybridization to the probe oligonucleotide permits the selective isolation of probe-bound polynucleotides from unbound polynucleotides in a population. A probe oligonucleotide may or may not also be used as a primer.

Nucleic acids, including e.g., nucleic acids with a phosphorothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

As used herein, the terms "analogue" and "analog", in reference to a chemical compound, refers to compound having a structure similar to that of another one, but differing from it in respect of one or more different atoms, functional groups, or substructures that are replaced with one or more other atoms, functional groups, or substructures. In the context of a nucleotide, a nucleotide analog refers to a compound that, like the nucleotide of which it is an analog, can be incorporated into a nucleic acid molecule (e.g., an extension product) by a suitable polymerase, for example, a DNA polymerase in the context of a nucleotide analogue. The terms also encompass nucleic acids containing known nucleotide analogs or modified backbone residues or linkages, which are synthetic, naturally occurring, or non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphorothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see, e.g., see Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, CARBO- HYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

As used herein, a "native" nucleotide is used in accordance with its plain and ordinary meaning and refers to a naturally occurring nucleotide that does not include an exogenous label (e.g., a fluorescent dye, or other label) or chemical modification such as may characterize a nucleotide analog. Examples of native nucleotides useful for carrying out procedures described herein include: dATP (2'-deoxyadenosine-5'-triphosphate); dGTP (2'-deoxyguanosine-5'-triphosphate); dCTP (2'-deoxycytidine-5'-triphosphate); dTTP (2'-deoxythymidine-5'-triphosphate); and dUTP (2'-deoxyuridine-5'-triphosphate).

In embodiments, the nucleotides of the present disclosure use a cleavable linker to attach the label to the nucleotide. The use of a cleavable linker ensures that the label can, if required, be removed after detection, avoiding any interfering signal with any labelled nucleotide incorporated subsequently. The use of the term "cleavable linker" is not meant to imply that the whole linker is required to be removed from the nucleotide base. The cleavage site can be located at a position on the linker that ensures that part of the linker remains attached to the nucleotide base after cleavage. The linker can be attached at any position on the nucleotide base provided that Watson-Crick base pairing can still be carried out. In the context of purine bases, it is preferred if the linker is attached via the 7-position of the purine or the preferred deazapurine analogue, via an 8-modified purine, via an N-6 modified adenosine or an N-2 modified guanine. For pyrimidines, attachment is preferably via the 5-position on cytidine, thymidine or uracil and the N-4 position on cytosine. The term "cleavable linker" or "cleavable moiety" as used herein refers to a divalent or monovalent, respectively, moiety which is capable of being separated (e.g., detached, split, disconnected, hydrolyzed, a stable bond within the moiety is broken) into distinct entities. A cleavable linker is cleavable (e.g., specifically cleavable) in response to external stimuli (e.g., enzymes, nucleophilic/basic reagents, reducing agents, photo-irradiation, electrophilic/acidic reagents, organometallic and metal reagents, or oxidizing reagents). A chemically cleavable linker refers to a linker which is capable of being split in response to the presence of a chemical (e.g., acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), or hydrazine ($N_2H_4$)). A chemically cleavable linker is non-enzymatically cleavable. In embodiments, the cleavable linker is cleaved by contacting the cleavable linker with a cleaving agent. In embodiments, the cleaving agent is a phosphine containing reagent (e.g., TCEP or THPP), sodium dithionite ($Na_2S_2O_4$), weak acid, hydrazine ($N_2H_4$), Pd(0), or light-irradiation (e.g., ultraviolet radiation).

As used herein, the term "modified nucleotide" refers to nucleotide modified in some manner. Typically, a nucleotide contains a single 5-carbon sugar moiety, a single nitrogenous base moiety and 1 to three phosphate moieties. In embodiments, a nucleotide can include a blocking moiety and/or a label moiety. A blocking moiety on a nucleotide prevents formation of a covalent bond between the 3' hydroxyl moiety of the nucleotide and the 5' phosphate of another nucleotide. A blocking moiety on a nucleotide can be reversible, whereby the blocking moiety can be removed or modified to allow the 3' hydroxyl to form a covalent bond with the 5' phosphate of another nucleotide. A blocking moiety can be effectively irreversible under particular conditions used in a method set forth herein. In embodiments, the blocking moiety is attached to the 3' oxygen of the nucleotide and is independently —$NH_2$, —CN, —$CH_3$, $C_2$-$C_6$ allyl (e.g., —$CH_2$—CH=$CH_2$), methoxyalkyl (e.g., —$CH_2$—O—$CH_3$), or —$CH_2N_3$. In embodiments, the blocking moiety is attached to the 3' oxygen of the nucleotide and is independently

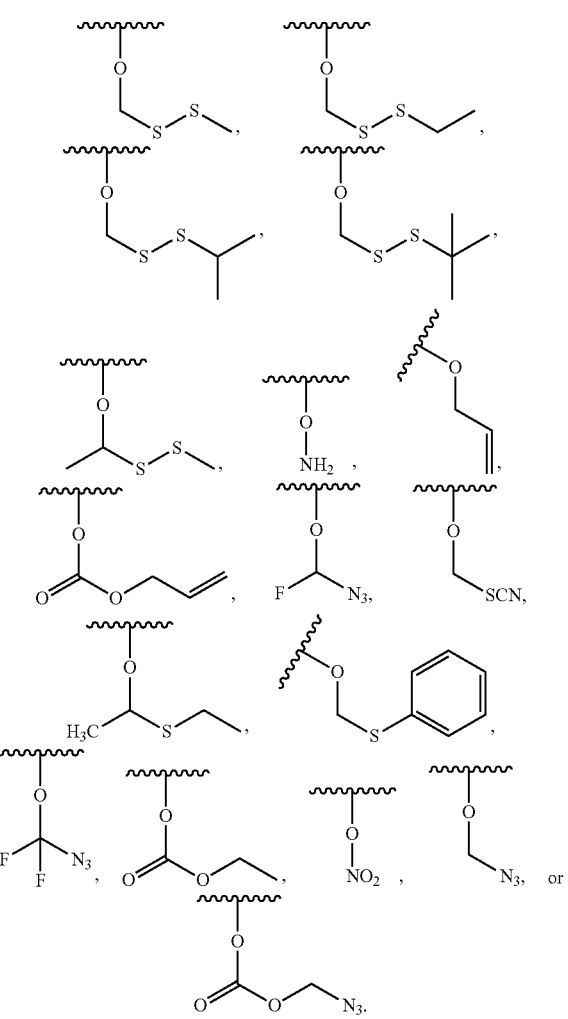

A label moiety of a nucleotide can be any moiety that allows the nucleotide to be detected, for example, using a spectroscopic method. Exemplary label moieties are fluorescent labels, mass labels, chemiluminescent labels, electrochemical labels, detectable labels and the like. One or more of the above moieties can be absent from a nucleotide used in the methods and compositions set forth herein. For example, a nucleotide can lack a label moiety or a blocking moiety or both. Examples of nucleotide analogues include, without limitation, 7-deaza-adenine, 7-deaza-guanine, the analogues of deoxynucleotides shown herein, analogues in which a label is attached through a cleavable linker to the 5-position of cytosine or thymine or to the 7-position of deaza-adenine or deaza-guanine, and analogues in which a small chemical moiety is used to cap the OH group at the 3'-position of deoxyribose. Nucleotide analogues and DNA polymerase-based DNA sequencing are also described in U.S. Pat. No. 6,664,079, which is incorporated herein by reference in its entirety for all purposes.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the complement of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

As used herein, the term "removable" group, e.g., a label or a blocking group or protecting group, is used in accordance with its plain and ordinary meaning and refers to a chemical group that can be removed from a nucleotide analogue such that a DNA polymerase can extend the nucleic acid (e.g., a primer or extension product) by the incorporation of at least one additional nucleotide. Removal may be by any suitable method, including enzymatic, chemical, or photolytic cleavage. Removal of a removable group, e.g., a blocking group, does not require that the entire removable group be removed, only that a sufficient portion of it be removed such that a DNA polymerase can extend a nucleic acid by incorporation of at least one additional nucleotide using a nucleotide or nucleotide analogue. In general, the conditions under which a removable group is removed are compatible with a process employing the removable group (e.g., an amplification process or sequencing process).

As used herein, the terms "blocking moiety," "reversible blocking group," "reversible terminator" and "reversible terminator moiety" are used in accordance with their plain and ordinary meanings and refer to a cleavable moiety which does not interfere with incorporation of a nucleotide comprising it by a polymerase (e.g., DNA polymerase, modified DNA polymerase), but prevents further strand extension until removed ("unblocked"). For example, a reversible terminator may refer to a blocking moiety located, for example, at the 3' position of the nucleotide and may be a chemically cleavable moiety such as an allyl group, an azidomethyl group or a methoxymethyl group, or may be an enzymatically cleavable group such as a phosphate ester. Suitable nucleotide blocking moieties are described in applications WO 2004/018497, U.S. Pat. Nos. 7,057,026, 7,541, 444, WO 96/07669, U.S. Pat. Nos. 5,763,594, 5,808,045, 5,872,244 and 6,232,465 the contents of which are incorporated herein by reference in their entirety. The nucleotides may be labelled or unlabeled. They may be modified with reversible terminators useful in methods provided herein and may be 3'-O-blocked reversible or 3'-unblocked reversible terminators. In nucleotides with 3'-O-blocked reversible terminators, the blocking group may be represented as —OR [reversible terminating (capping) group], wherein O is the oxygen atom of the 3'-OH of the pentose and R is the blocking group, while the label is linked to the base, which acts as a reporter and can be cleaved. The 3'-O-blocked reversible terminators are known in the art, and may be, for instance, a 3'-$ONH_2$ reversible terminator, a 3'-O-allyl reversible terminator, or a 3'-O-azidomethyl reversible terminator.

In some embodiments, a nucleic acid (e.g., an adapter or a primer) comprises a molecular identifier or a molecular barcode. As used herein, the term "molecular barcode" (which may be referred to as a "tag", a "barcode", a "molecular identifier", an "identifier sequence" or a "unique molecular identifier" (UMI)) refers to any material (e.g., a nucleotide sequence, a nucleic acid molecule feature) that is capable of distinguishing an individual molecule in a large heterogeneous population of molecules. In embodiments, a barcode is unique in a pool of barcodes that differ from one another in sequence, or is uniquely associated with a particular sample polynucleotide in a pool of sample polynucleotides. In embodiments, every barcode in a pool of adapters is unique, such that sequencing reads comprising the barcode can be identified as originating from a single sample polynucleotide molecule on the basis of the barcode alone. In other embodiments, individual barcode sequences may be used more than once, but adapters comprising the duplicate barcodes are associated with different sequences and/or in different combinations of barcoded adaptors, such that sequence reads may still be uniquely distinguished as originating from a single sample polynucleotide molecule on the basis of a barcode and adjacent sequence information (e.g., sample polynucleotide sequence, and/or one or more adjacent barcodes). In embodiments, barcodes are about or at least about 5, 6, 7, 8, 9, 10, 15, 20, 25, 30, 40, 50, 75 or more nucleotides in length. In embodiments, barcodes are shorter than 20, 15, 10, 9, 8, 7, 6, or 5 nucleotides in length. In embodiments, barcodes are about 10 to about 50 nucleotides in length, such as about 15 to about 40 or about 20 to about 30 nucleotides in length. In a pool of different barcodes, barcodes may have the same or different lengths. In general, barcodes are of sufficient length and include sequences that are sufficiently different to allow the identification of sequencing reads that originate from the same sample polynucleotide molecule. In embodiments, each barcode in a plurality of barcodes differs from every other barcode in the plurality by at least three nucleotide positions, such as at least 3, 4, 5, 6, 7, 8, 9, 10, or more nucleotide positions. In some embodiments, substantially degenerate barcodes may be known as random. In some embodiments, a barcode may include a nucleic acid sequence from within a pool of known sequences. In some embodiments, the barcodes may be pre-defined.

In embodiments, a nucleic acid (e.g., an adapter or primer) comprises a sample barcode. In general, a "sample barcode" is a nucleotide sequence that is sufficiently different from other sample barcode to allow the identification of the sample source based on sample barcode sequence(s) with which they are associated. In embodiments, a plurality of nucleotides (e.g., all nucleotides from a particular sample source, or sub-sample thereof) are joined to a first sample barcode, while a different plurality of nucleotides (e.g., all nucleotides from a different sample source, or different subsample) are joined to a second sample barcode, thereby associating each plurality of polynucleotides with a different sample barcode indicative of sample source. In embodiments, each sample barcode in a plurality of sample barcodes differs from every other sample barcode in the plurality by at least three nucleotide positions, such as at least 3, 4, 5, 6, 7, 8, 9, 10, or more nucleotide positions. In some embodiments, substantially degenerate sample barcodes may be known as random. In some embodiments, a sample barcode may include a nucleic acid sequence from within a pool of known sequences. In some embodiments, the sample barcodes may be pre-defined. In embodiments, the sample barcode includes about 1 to about 10 nucleotides. In embodiments, the sample barcode includes about 3, 4, 5, 6, 7, 8, 9, or about 10 nucleotides. In embodiments, the sample barcode includes about 3 nucleotides. In embodiments, the sample barcode includes about 5 nucleotides. In embodiments, the sample barcode includes about 7 nucleotides. In embodiments, the sample barcode includes about 10 nucleotides. In embodiments, the sample barcode includes about 6 to about 10 nucleotides.

In some embodiments, a nucleic acid comprises a label. As used herein, the term "label" or "labels" is used in accordance with their plain and ordinary meanings and refer to molecules that can directly or indirectly produce or result in a detectable signal either by themselves or upon interaction with another molecule. Non-limiting examples of detectable labels include fluorescent dyes, biotin, digoxin, haptens, and epitopes. In general, a dye is a molecule, compound, or substance that can provide an optically detectable signal, such as a colorimetric, luminescent, bioluminescent, chemiluminescent, phosphorescent, or fluorescent signal. In embodiments, the label is a dye. In embodiments, the dye is a fluorescent dye. Non-limiting examples of dyes, some of which are commercially available, include CF dyes (Biotium, Inc.), Alexa Fluor dyes (Thermo Fisher), DyLight dyes (Thermo Fisher), Cy dyes (GE Healthscience), IRDyes (Li-Cor Biosciences, Inc.), and HiLyte dyes (Anaspec, Inc.). In embodiments, a particular nucleotide type is associated with a particular label, such that identifying the label identifies the nucleotide with which it is associated. In embodiments, the label is luciferin that reacts with luciferase to produce a detectable signal in response to one or more bases being incorporated into an elongated complementary strand, such as in pyrosequencing. In embodiment, a nucleotide comprises a label (such as a dye). In embodiments, the label is not associated with any particular nucleotide, but detection of the label identifies whether one or more nucleotides having a known identity were added during an extension step (such as in the case of pyrosequencing).

As used herein, the term "DNA polymerase" and "nucleic acid polymerase" are used in accordance with their plain ordinary meanings and refer to enzymes capable of synthesizing nucleic acid molecules from nucleotides (e.g., deoxyribonucleotides). Exemplary types of polymerases that may be used in the compositions and methods of the present disclosure include the nucleic acid polymerases such as DNA polymerase, DNA- or RNA-dependent RNA polymerase, and reverse transcriptase. In some cases, the DNA polymerase is 9° N polymerase or a variant thereof, E. coli DNA polymerase I, Bacteriophage T4 DNA polymerase, Sequenase, Taq DNA polymerase, DNA polymerase from Bacillus stearothermophilus, Bst 2.0 DNA polymerase, 9° N polymerase (exo-)A485L/Y409V, Phi29 DNA Polymerase (φ29 DNA Polymerase), T7 DNA polymerase, DNA polymerase II, DNA polymerase III holoenzyme, DNA polymerase IV, DNA polymerase V, VentR DNA polymerase, Therminator™ II DNA Polymerase, Therminator™ III DNA Polymerase, or Therminator™ IX DNA Polymerase. In embodiments, the polymerase is a protein polymerase. Typically, a DNA polymerase adds nucleotides to the 3'-end of a DNA strand, one nucleotide at a time. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ, DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol υ DNA polymerase, or a thermophilic nucleic acid polymerase (e.g. Therminator γ, 9° N polymerase (exo-), Therminator II, Therminator III, or Therminator IX). In embodiments, the DNA polymerase is a modified archaeal DNA polymerase. In embodiments, the polymerase is a reverse transcriptase. In embodiments, the polymerase is a mutant P. abyssi polymerase (e.g., such as a mutant P. abyssi polymerase described in WO 2018/148723 or WO 2020/056044).

As used herein, the term "thermophilic nucleic acid polymerase" refers to a family of DNA polymerases (e.g., 9° N™) and mutants thereof derived from the DNA polymerase originally isolated from the hyperthermophilic archaea, Thermococcus sp. 9 degrees N-7, found in hydrothermal vents at that latitude (East Pacific Rise) (Southworth M W, et al. PNAS. 1996; 93(11):5281-5285). A thermophilic nucleic acid polymerase is a member of the family B DNA polymerases. Site-directed mutagenesis of the 3'-5' exo motif I (Asp-Ile-Glu or DIE) to AIA, AIE, EIE, EID or DIA yielded polymerase with no detectable 3' exonuclease activity. Mutation to Asp-Ile-Asp (DID) resulted in reduction of 3'-5' exonuclease specific activity to <1% of wild type, while maintaining other properties of the polymerase including its high strand displacement activity. The sequence AIA (D141A, E143A) was chosen for reducing exonuclease. Subsequent mutagenesis of key amino acids results in an increased ability of the enzyme to incorporate dideoxynucleotides, ribonucleotides and acyclonucleotides (e.g., Therminator II enzyme from New England Biolabs with D141A/E143A/Y409V/A485L mutations); 3'-amino-dNTPs, 3'-azido-dNTPs and other 3'-modified nucleotides (e.g., NEB Therminator III DNA Polymerase with D141A/E143A/L408S/Y409A/P410V mutations, NEB Therminator IX DNA polymerase), or γ-phosphate labeled nucleotides (e.g., Therminator γ: D141A/E143A/W355A/L408W/R460A/Q4615/K464E/D480V/R484W/A485L). Typically, these enzymes do not have 5'-3' exonuclease activity. Additional information about thermophilic nucleic acid polymerases may be found in (Southworth M W, et al. PNAS. 1996; 93(11):5281-5285; Bergen K, et al. ChemBioChem. 2013; 14(9):1058-1062; Kumar S, et al. Scientific Reports. 2012; 2:684; Fuller C W, et al. 2016; 113(19):5233-5238; Guo J, et al. Proceedings of the National Academy of Sciences of the United States of America. 2008; 105(27): 9145-9150), which are incorporated herein in their entirety for all purposes.

As used herein, the term "exonuclease activity" is used in accordance with its ordinary meaning in the art, and refers to the removal of a nucleotide from a nucleic acid by a DNA polymerase. For example, during polymerization, nucleotides are added to the 3' end of the primer strand. Occasionally a DNA polymerase incorporates an incorrect nucleotide to the 3'-OH terminus of the primer strand, wherein the incorrect nucleotide cannot form a hydrogen bond to the corresponding base in the template strand. Such a nucleotide, added in error, is removed from the primer as a result of the 3' to 5' exonuclease activity of the DNA polymerase. In embodiments, exonuclease activity may be referred to as "proofreading." When referring to 3'-5' exonuclease activity, it is understood that the DNA polymerase facilitates a hydrolyzing reaction that breaks phosphodiester bonds at either the 3' end of a polynucleotide chain to excise the nucleotide. In embodiments, 3'-5' exonuclease activity refers to the successive removal of nucleotides in single-stranded DNA in a 3'→5' direction, releasing deoxyribonucleoside 5'-monophosphates one after another. Methods for quantifying exonuclease activity are known in the art, see for example Southworth et al, PNAS Vol 93, 8281-8285 (1996).

As used herein, the term "incorporating" or "chemically incorporating," when used in reference to a primer and cognate nucleotide, refers to the process of joining the cognate nucleotide to the primer or extension product thereof by formation of a phosphodiester bond.

As used herein, the term "selective" or "selectivity" or the like of a compound refers to the compound's ability to discriminate between molecular targets. For example, a chemical reagent may selectively modify one nucleotide type in that it reacts with one nucleotide type (e.g., cytosines) and not other nucleotide types (e.g., adenine, thymine, or guanine). When used in the context of sequencing, such as in "selectively sequencing," this term refers to sequencing one or more target polynucleotides from an original starting population of polynucleotides, and not sequencing non-target polynucleotides from the starting population. Typically, selectively sequencing one or more target polynucleotides involves differentially manipulating the target polynucleotides based on known sequence. For example, target polynucleotides may be hybridized to a probe oligonucleotide that may be labeled (such as with a member of a binding pair) or bound to a surface. In embodiments, hybridizing a target polynucleotide to a probe oligonucleotide includes the step of displacing one strand of a double-stranded nucleic acid. Probe-hybridized target polynucleotides may then be separated from non-hybridized polynucleotides, such as by removing probe-bound polynucleotides from the starting population or by washing away polynucleotides that are not bound to a probe. The result is a selected subset of the starting population of polynucleotides, which is then subjected to sequencing, thereby selectively sequencing the one or more target polynucleotides.

As used herein, the term "template polynucleotide" refers to any polynucleotide molecule that may be bound by a polymerase and utilized as a template for nucleic acid synthesis. A template polynucleotide may be a target polynucleotide. In general, the term "target polynucleotide" refers to a nucleic acid molecule or polynucleotide in a starting population of nucleic acid molecules having a target sequence whose presence, amount, and/or nucleotide sequence, or changes in one or more of these, are desired to be determined. The target sequence may be a portion of a gene, a regulatory sequence, genomic DNA, cDNA, RNA including mRNA, miRNA, rRNA, or others. The target sequence may be a target sequence from a sample or a secondary target such as a product of an amplification reaction. A target polynucleotide is not necessarily any single molecule or sequence. For example, a target polynucleotide may be any one of a plurality of target polynucleotides in a reaction, or all polynucleotides in a given reaction, depending on the reaction conditions. For example, in a nucleic acid amplification reaction with random primers, all polynucleotides in a reaction may be amplified. As a further example, a collection of targets may be simultaneously assayed using polynucleotide primers directed to a plurality of targets in a single reaction. As yet another example, all or a subset of polynucleotides in a sample may be modified by the addition of a primer-binding sequence (such as by the ligation of adapters containing the primer binding sequence), rendering each modified polynucleotide a target polynucleotide in a reaction with the corresponding primer polynucleotide(s). In the context of selective sequencing, "target polynucleotide(s)" refers to the subset of polynucleotide(s) to be sequenced from within a starting population of polynucleotides.

In embodiments, a target polynucleotide is a cell-free polynucleotide. In general, the terms "cell-free," "circulating," and "extracellular" as applied to polynucleotides (e.g. "cell-free DNA" (cfDNA) and "cell-free RNA" (cfRNA)) are used interchangeably to refer to polynucleotides present in a sample from a subject or portion thereof that can be isolated or otherwise manipulated without applying a lysis step to the sample as originally collected (e.g., as in extraction from cells or viruses). Cell-free polynucleotides are thus unencapsulated or "free" from the cells or viruses from which they originate, even before a sample of the subject is collected. Cell-free polynucleotides may be produced as a byproduct of cell death (e.g. apoptosis or necrosis) or cell shedding, releasing polynucleotides into surrounding body fluids or into circulation. Accordingly, cell-free polynucleotides may be isolated from a non-cellular fraction of blood (e.g. serum or plasma), from other bodily fluids (e.g. urine), or from non-cellular fractions of other types of samples As used herein, the terms "specific", "specifically", "specificity", or the like of a compound refers to the compound's ability to cause a particular action, such as binding, to a particular molecular target with minimal or no action to other proteins in the cell.

As used herein, the terms "bind" and "bound" are used in accordance with their plain and ordinary meanings and refer to an association between atoms or molecules. The association can be direct or indirect. For example, bound atoms or molecules may be directly bound to one another, e.g., by a covalent bond or non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). As a further example, two molecules may be bound indirectly to one another by way of direct binding to one or more intermediate molecules, thereby forming a complex.

As used herein, the terms "sequencing", "sequence determination", "determining a nucleotide sequence", and the like include determination of a partial or complete sequence information (e.g., a sequence) of a polynucleotide being sequenced, and particularly physical processes for generating such sequence information. That is, the term includes sequence comparisons, consensus sequence determination, contig assembly, fingerprinting, and like levels of information about a target polynucleotide, as well as the express identification and ordering of nucleotides in a target polynucleotide. The term also includes the determination of the identification, ordering, and locations of one, two, or three of the four types of nucleotides within a target polynucleotide. In some embodiments, a sequencing process described herein comprises contacting a template and an annealed primer with a suitable polymerase under conditions suitable for polymerase extension and/or sequencing. The sequencing methods are preferably carried out with the target polynucleotide arrayed on a solid substrate. Multiple target polynucleotides can be immobilized on the solid support through linker molecules, or can be attached to particles, e.g., microspheres, which can also be attached to a solid substrate. In embodiments, the solid substrate is in the form of a chip, a bead, a well, a capillary tube, a slide, a wafer, a filter, a fiber, a porous media, or a column. In embodiments, the solid substrate is gold, quartz, silica, plastic, glass, diamond, silver, metal, or polypropylene. In embodiments, the solid substrate is porous.

As used herein, the terms "solid support" and "substrate" and "solid surface" refers to discrete solid or semi-solid surfaces to which a plurality of primers may be attached. A solid support may encompass any type of solid, porous, or hollow sphere, ball, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. Solid supports in the form of discrete particles may be referred to herein as "beads," which alone does not imply or require any particular shape. A bead can be non-spherical in shape. A solid support may further comprise a polymer or hydrogel on the surface to which the primers are attached (e.g., the splint primers are covalently attached to the polymer, wherein the polymer is in direct contact with the solid support). Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefin copolymers, polyimides etc.), nylon, ceramics, resins, Zeonor, silica or silica-based materials including silicon and modified silicon, carbon, metals, inorganic glasses, optical fiber bundles, photopatternable dry film resists, UV-cured adhesives and polymers. The solid supports for some embodiments have at least one surface located within a flow cell. The solid support, or regions thereof, can be substantially flat. The solid support can have surface features such as wells, pits, channels, ridges, raised regions, pegs, posts or the like. The term solid support is encompassing of a substrate (e.g., a flow cell) having a surface comprising a polymer coating covalently attached thereto. In embodiments, the solid support is a flow cell. The term "flow cell" as used herein refers to a chamber including a solid surface across which one or more fluid reagents can be flowed. Examples of flow cells and related fluidic systems and detection platforms that can be readily used in the methods of the present disclosure are described, for example, in Bentley et al., Nature 456:53-59 (2008).

As used herein, the term "sequencing reaction mixture" is used in accordance with its plain and ordinary meaning and refers to an aqueous mixture that contains the reagents necessary to allow dNTP or dNTP analogue to add a nucleotide to a DNA strand by a DNA polymerase. In embodiments, the sequencing reaction mixture includes a buffer. In embodiments, the buffer includes an acetate buffer, 3-(N-morpholino)propanesulfonic acid (MOPS) buffer, N-(2-Acetamido)-2-aminoethanesulfonic acid (ACES) buffer, phosphate-buffered saline (PBS) buffer, 4-(2-hydroxyethyl)-1-piperazineethanesulfonic acid (HEPES) buffer, N-(1,1-Dimethyl-2-hydroxyethyl)-3-amino-2-hydroxypropanesulfonic acid (AMPSO) buffer, borate buffer (e.g., borate buffered saline, sodium borate buffer, boric acid buffer), 2-Amino-2-methyl-1,3-propanediol (AMPD) buffer, N-cyclohexyl-2-hydroxyl-3-aminopropanesulfonic acid (CAPSO) buffer, 2-Amino-2-methyl-1-propanol (AMP) buffer, 4-(Cyclohexylamino)-1-butanesulfonic acid (CABS) buffer, glycine-NaOH buffer, N-Cyclohexyl-2-aminoethanesulfonic acid (CHES) buffer, tris(hydroxymethyl)aminomethane (Tris) buffer, or a N-cyclohexyl-3-aminopropanesulfonic acid (CAPS) buffer. In embodiments, the buffer is a borate buffer. In embodiments, the buffer is a CHES buffer. In embodiments, the sequencing reaction mixture includes nucleotides, wherein the nucleotides include a reversible terminating moiety and a label covalently linked to the nucleotide via a cleavable linker. In embodiments, the sequencing reaction mixture includes a buffer, DNA polymerase, detergent (e.g., Triton X), a chelator (e.g., EDTA), and/or salts (e.g., ammonium sulfate, magnesium chloride, sodium chloride, or potassium chloride).

As used herein, the term "sequencing cycle" is used in accordance with its plain and ordinary meaning and refers to incorporating one or more nucleotides (e.g., nucleotide analogues) to the 3' end of a polynucleotide with a polymerase, and detecting one or more labels that identify the one or more nucleotides incorporated. The sequencing may be accomplished by, for example, sequencing by synthesis, pyrosequencing, and the like. In embodiments, a sequencing cycle includes extending a complementary polynucleotide by incorporating a first nucleotide using a polymerase, wherein the polynucleotide is hybridized to a template nucleic acid, detecting the first nucleotide, and identifying the first nucleotide. In embodiments, to begin a sequencing cycle, one or more differently labeled nucleotides and a DNA polymerase can be introduced. Following nucleotide addition, signals produced (e.g., via excitation and emission of a detectable label) can be detected to determine the identity of the incorporated nucleotide (based on the labels on the nucleotides). Reagents can then be added to remove the 3' reversible terminator and to remove labels from each incorporated base. Reagents, enzymes and other substances can be removed between steps by washing. Cycles may include repeating these steps, and the sequence of each cluster is read over the multiple repetitions.

As used herein, the term "extension" or "elongation" is used in accordance with their plain and ordinary meanings and refer to synthesis by a polymerase of a new polynucleotide strand complementary to a template strand by adding free nucleotides (e.g., dNTPs) from a reaction mixture that are complementary to the template in the 5'-to-3' direction. Extension includes condensing the 5'-phosphate group of the dNTPs with the 3'-hydroxy group at the end of the nascent (elongating) DNA strand.

As used herein, the term "sequencing read" is used in accordance with its plain and ordinary meaning and refers to an inferred sequence of nucleotide bases (or nucleotide base probabilities) corresponding to all or part of a single polynucleotide fragment. A sequencing read may include 10, 20, 30, 40, 50, 60, 70, 80, 90, 100, 150, 200, 250, or more nucleotide bases. In embodiments, a sequencing read includes reading a barcode and a template nucleotide sequence. In embodiments, a sequencing read includes reading a template nucleotide sequence. In embodiments, a sequencing read includes reading a barcode and not a template nucleotide sequence.

Complementary single stranded nucleic acids and/or substantially complementary single stranded nucleic acids can hybridize to each other under hybridization conditions, thereby forming a nucleic acid that is partially or fully double stranded. All or a portion of a nucleic acid sequence may be substantially complementary to another nucleic acid sequence, in some embodiments. As referred to herein, "substantially complementary" refers to nucleotide sequences that can hybridize with each other under suitable hybridization conditions. Hybridization conditions can be altered to tolerate varying amounts of sequence mismatch within complementary nucleic acids that are substantially complementary. Substantially complementary portions of nucleic acids that can hybridize to each other can be 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more complementary to each other. In some embodiments substantially complementary portions of nucleic acids that can hybridize to each other are 100% complementary. Nucleic acids, or portions thereof, that are configured to hybridize to each other often comprise nucleic acid sequences that are substantially complementary to each other.

"Hybridize" shall mean the annealing of a nucleic acid sequence to another nucleic acid sequence (e.g., one single-stranded nucleic acid (such as a primer) to another nucleic acid) based on the well-understood principle of sequence complementarity. In an embodiment the other nucleic acid is a single-stranded nucleic acid. In some embodiments, one portion of a nucleic acid hybridizes to itself, such as in the formation of a hairpin structure. The propensity for hybridization between nucleic acids depends on the temperature and ionic strength of their milieu, the length of the nucleic acids and the degree of complementarity. The effect of these parameters on hybridization is described in, for example, Sambrook J., Fritsch E. F., Maniatis T., Molecular cloning: a laboratory manual, Cold Spring Harbor Laboratory Press, New York (1989). As used herein, hybridization of a primer, or of a DNA extension product, respectively, is extendable by creation of a phosphodiester bond with an available nucleotide or nucleotide analogue capable of forming a phosphodiester bond, therewith. For example, hybridization can be performed at a temperature ranging from 15° C. to 95° C. In some embodiments, the hybridization is performed at a temperature of about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., or about 95° C. In other embodiments, the stringency of the hybridization can be further altered by the addition or removal of components of the buffered solution.

As used herein, "specifically hybridizes" refers to preferential hybridization under hybridization conditions where two nucleic acids, or portions thereof, that are substantially complementary, hybridize to each other and not to other nucleic acids that are not substantially complementary to either of the two nucleic acid. For example, specific hybridization includes the hybridization of a primer or capture nucleic acid to a portion of a target nucleic acid (e.g., a template, or adapter portion of a template) that is substantially complementary to the primer or capture nucleic acid. In some embodiments nucleic acids, or portions thereof, that are configured to specifically hybridize are often about 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more or 100% complementary to each other over a contiguous portion of nucleic acid sequence. A specific hybridization discriminates over non-specific hybridization interactions (e.g., two nucleic acids that a not configured to specifically hybridize, e.g., two nucleic acids that are 80% or less, 70% or less, 60% or less or 50% or less complementary) by about 2-fold or more, often about 10-fold or more, and sometimes about 100-fold or more, 1000-fold or more, 10,000-fold or more, 100,000-fold or more, or 1,000,000-fold or more. Two nucleic acid strands that are hybridized to each other can form a duplex which comprises a double stranded portion of nucleic acid.

A nucleic acid can be amplified by a suitable method. The term "amplified" as used herein refers to subjecting a target nucleic acid in a sample to a process that linearly or exponentially generates amplicon nucleic acids having the same or substantially the same (e.g., substantially identical) nucleotide sequence as the target nucleic acid, or segment thereof, and/or a complement thereof. In some embodiments an amplification reaction comprises a suitable thermal stable polymerase. Thermal stable polymerases are known in the art and are stable for prolonged periods of time, at temperature greater than 80° C. when compared to common polymerases found in most mammals. In certain embodiments the term "amplified" refers to a method that comprises a polymerase chain reaction (PCR). Conditions conducive to amplification (i.e., amplification conditions) are well known and often comprise at least a suitable polymerase, a suitable template, a suitable primer or set of primers, suitable nucleotides (e.g., dNTPs), a suitable buffer, and application of suitable annealing, hybridization and/or extension times and temperatures. In certain embodiments an amplified product (e.g., an amplicon) can contain one or more additional and/or different nucleotides than the template sequence, or portion thereof, from which the amplicon was generated (e.g., a primer can contain "extra" nucleotides (such as a 5' portion that does not hybridize to the template), or one or more mismatched bases within a hybridizing portion of the primer).

As used herein, the term "rolling circle amplification (RCA)" refers to a nucleic acid amplification reaction that amplifies a circular nucleic acid template (e.g., single-stranded DNA circles) via a rolling circle mechanism. Rolling circle amplification reaction is initiated by the hybridization of a primer to a circular, often single-stranded, nucleic acid template. The nucleic acid polymerase then extends the primer that is hybridized to the circular nucleic acid template by continuously progressing around the circular nucleic acid template to replicate the sequence of the nucleic acid template over and over again (rolling circle mechanism). The rolling circle amplification typically produces concatemers comprising tandem repeat units of the circular nucleic acid template sequence. The rolling circle amplification may be a linear RCA (LRCA), exhibiting linear amplification kinetics (e.g., RCA using a single specific primer), or may be an exponential RCA (ERCA) exhibiting exponential amplification kinetics. Rolling circle amplification may also be performed using multiple primers (multiply primed rolling circle amplification or MPRCA) leading to hyper-branched concatemers. For example, in a double-primed RCA, one primer may be complementary, as in the linear RCA, to the circular nucleic acid template, whereas the other may be complementary to the tandem repeat unit nucleic acid sequences of the RCA product. Consequently, the double-primed RCA may proceed as a chain reaction with exponential (geometric) amplification kinetics featuring a ramifying cascade of multiple-hybridization, primer-extension, and strand-displacement events involving both the primers. This often generates a discrete set of concatemeric, double-stranded nucleic acid amplification products. The rolling circle amplification may be performed in-vitro under isothermal conditions using a suitable nucleic acid polymerase such as Phi29 DNA polymerase. RCA may be performed by using any of the DNA polymerases that are known in the art (e.g., a Phi29 DNA polymerase, a Bst DNA polymerase, or SD polymerase).

A nucleic acid can be amplified by a thermocycling method or by an isothermal amplification method. In some embodiments a rolling circle amplification method is used. In some embodiments amplification takes place on a solid support (e.g., within a flow cell) where a nucleic acid, nucleic acid library or portion thereof is immobilized. In certain sequencing methods, a nucleic acid library is added to a flow cell and immobilized by hybridization to anchors under suitable conditions. This type of nucleic acid amplification is often referred to as solid phase amplification. In some embodiments of solid phase amplification, all or a portion of the amplified products are synthesized by an extension initiating from an immobilized primer. Solid phase amplification reactions are analogous to standard solution phase amplifications except that at least one of the amplification oligonucleotides (e.g., primers) is immobilized on a solid support.

In some embodiments solid phase amplification comprises a nucleic acid amplification reaction comprising only one species of oligonucleotide primer immobilized to a surface or substrate. In certain embodiments solid phase amplification comprises a plurality of different immobilized oligonucleotide primer species. In some embodiments solid phase amplification may comprise a nucleic acid amplification reaction comprising one species of oligonucleotide primer immobilized on a solid surface and a second different oligonucleotide primer species in solution. Multiple different species of immobilized or solution based primers can be used. Non-limiting examples of solid phase nucleic acid amplification reactions include interfacial amplification, bridge PCR amplification, emulsion PCR, WildFire amplification (e.g., US patent publication US20130012399), the like or combinations thereof.

In certain embodiments, a nucleic acid template comprising a complementary forward and reverse stand of a double stranded nucleic acid, a hairpin adapter on one end, and a Y adapter on the other end, is amplified by bridge PCR amplification. The bridge PCR amplification process of a nucleic acid template comprising such a configuration is mechanistically distinct from a bridge amplification that takes place for a single stranded nucleic acid template containing no internal complementary regions. For example, after a denaturation step in bridge PCR of a nucleic acid template comprising such a configuration, amplicons can preferentially form an intramolecular double-stranded region as opposed to staying double-stranded at an intermolecular scale. This enables a free 3' end at the Y-adapter end, which is available for re-priming with additional solid-phase primers.

In some embodiments, a nucleic acid, adapter, oligonucleotide probe, template and/or substrate comprises a binding motif. In some embodiments a binding motif is one member of a binding pair where each member of the binding pair can bind to each other specifically and with relatively high affinity. For example, typical binding pairs bind to each other with a Kd of less than about 10 µM, 5 µM, 1 µM, 500 nM, 250 nM, 100 nM, 75 nM, 50 nM, 25 nM, 15 nM, 10 nM, 5 nM, 1 nM, or less than about 0.1 nM. In some embodiments a binding pair comprises at least two members (e.g., molecules) that bind non-covalently to (e.g., associate with) each other. Members of a binding pair often bind specifically to each other. In certain embodiments, members of a binding pair bind reversibly to each other, for example where the association of two members of a binding pair can be dissociated by a suitable method. Non-limiting examples of a binding pair include antibody/antigen, antibody/antibody, antibody/antibody fragment, antibody/antibody receptor, antibody/protein A, antibody/protein G, hapten/anti-hapten, biotin/avidin, biotin/streptavidin, folic acid/folate binding protein, receptor/ligand, vitamin B12/intrinsic factor, analogues thereof, derivatives thereof, binding portions thereof, the like or combinations thereof. Non-limiting examples of a binding motif or a member of a binding pair include an antibody, antibody fragment, reduced antibody, chemically modified antibody, antibody receptor, Fab, Fab', F(ab')2, Fv fragment, single-chain Fv (scFv), diabody (Dab), synbody, TandAbs, nanobodies, BiTEs, SMIPs, DARPins, DNLs, affibodies, Duocalins, adnectins, fynomers, Kunitz Domains AlbudAbs, DARTs, DVD-IG, Covx-bodies, peptibodies, scFv-Igs, SVD-Igs, dAb-Igs, Knob-in-Holes, triomAbs, an antigen, hapten, anti-hapten, aptamer, receptor, ligand, metal ion, avidin, streptavidin, neutravidin, biotin, B12, intrinsic factor, analogues thereof, derivatives thereof, binding portions thereof, the like or combinations thereof.

In some embodiments a nucleic acid is directly or indirectly bound (e.g., covalently or non-covalently bound) to a suitable substrate. In certain embodiments a substrate comprises a surface (e.g., a surface of a flow cell, a surface of a tube, a surface of a chip), for example a metal surface (e.g. steel, gold, silver, aluminum, silicon and copper). In some embodiments a substrate (e.g., a substrate surface) is coated and/or comprises functional groups and/or inert materials. In certain embodiments a substrate comprises a bead, a chip, a capillary, a plate, a membrane, a wafer (e.g., silicon wafers), a comb, or a pin for example. In some embodiments a substrate comprises a bead and/or a nanoparticle. A substrate can be made of a suitable material, non-limiting examples of which include a plastic or a suitable polymer (e.g., polycarbonate, poly(vinyl alcohol), poly(divinylbenzene), polystyrene, polyamide, polyester, polyvinylidene difluoride (PVDF), polyethylene, polyurethane, polypropylene, and the like), borosilicate, glass, nylon, Wang resin, Merrifield resin, metal (e.g., iron, a metal alloy, sepharose, agarose, polyacrylamide, dextran, cellulose and the like or combinations thereof. In some embodiments a substrate comprises a magnetic material (e.g., iron, nickel, cobalt, platinum, aluminum, and the like). In certain embodiments a substrate comprises a magnetic bead (e.g., DYNABEADS®, hematite, AMPure XP. Magnets can be used to purify and/or capture nucleic acids bound to certain substrates (e.g., substrates comprising a metal or magnetic material).

Provided herein are methods and compositions for analyzing a sample (e.g., sequencing nucleic acids within a sample). A sample (e.g., a sample comprising nucleic acid) can be obtained from a suitable subject. A sample can be isolated or obtained directly from a subject or part thereof. In some embodiments, a sample is obtained indirectly from an individual or medical professional. A sample can be any specimen that is isolated or obtained from a subject or part thereof. A sample can be any specimen that is isolated or obtained from multiple subjects. Non-limiting examples of specimens include fluid or tissue from a subject, including, without limitation, blood or a blood product (e.g., serum, plasma, platelets, buffy coats, or the like), umbilical cord blood, chorionic villi, amniotic fluid, cerebrospinal fluid, spinal fluid, lavage fluid (e.g., lung, gastric, peritoneal, ductal, ear, arthroscopic), a biopsy sample, celocentesis sample, cells (blood cells, lymphocytes, placental cells, stem cells, bone marrow derived cells, embryo or fetal cells) or parts thereof (e.g., mitochondrial, nucleus, extracts, or the like), urine, feces, sputum, saliva, nasal mucous, prostate fluid, lavage, semen, lymphatic fluid, bile, tears, sweat, breast milk, breast fluid, the like or combinations thereof. A fluid or tissue sample from which nucleic acid is extracted may be acellular (e.g., cell-free). Non-limiting examples of tissues include organ tissues (e.g., liver, kidney, lung, thymus, adrenals, skin, bladder, reproductive organs, intestine, colon, spleen, brain, the like or parts thereof), epithelial tissue, hair, hair follicles, ducts, canals, bone, eye, nose, mouth, throat, ear, nails, the like, parts thereof or combinations thereof. A sample may comprise cells or tissues that are normal, healthy, diseased (e.g., infected), and/or cancerous (e.g., cancer cells). A sample obtained from a subject may comprise cells or cellular material (e.g., nucleic acids) of multiple organisms (e.g., virus nucleic acid, fetal nucleic acid, bacterial nucleic acid, parasite nucleic acid).

In some embodiments, a sample comprises nucleic acid, or fragments thereof. A sample can comprise nucleic acids obtained from one or more subjects. In some embodiments a sample comprises nucleic acid obtained from a single subject. In some embodiments, a sample comprises a mixture of nucleic acids. A mixture of nucleic acids can comprise two or more nucleic acid species having different nucleotide sequences, different fragment lengths, different origins (e.g., genomic origins, cell or tissue origins, subject origins, the like or combinations thereof), or combinations thereof. A sample may comprise synthetic nucleic acid.

A subject can be any living or non-living organism, including but not limited to a human, non-human animal, plant, bacterium, fungus, virus or protist. A subject may be any age (e.g., an embryo, a fetus, infant, child, adult). A subject can be of any sex (e.g., male, female, or combination thereof). A subject may be pregnant. In some embodiments, a subject is a mammal. In some embodiments, a subject is a human subject. A subject can be a patient (e.g., a human patient). In some embodiments a subject is suspected of having a genetic variation or a disease or condition associated with a genetic variation.

Where a range of values is provided, it is understood that each intervening value, to the tenth of the unit of the lower limit unless the context clearly indicates otherwise, between the upper and lower limit of that range, and any other stated or unstated intervening value in, or smaller range of values within, that stated range is encompassed within the invention. The upper and lower limits of any such smaller range (within a more broadly recited range) may independently be included in the smaller ranges, or as particular values themselves, and are also encompassed within the invention, subject to any specifically excluded limit in the stated range. Where the stated range includes one or both of the limits, ranges excluding either or both of those included limits are also included in the invention.

The methods and kits of the present disclosure may be applied, mutatis mutandis, to the sequencing of RNA, or to determining the identity of a ribonucleotide.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., packaging, buffers, written instructions for performing a method, etc.) from one location to another. For example, kits include one or more enclosures (e.g., boxes) containing the relevant reaction reagents and/or supporting materials. As used herein, the term "fragmented kit" refers to a delivery system comprising two or more separate containers that each contain a subportion of the total kit components. The containers may be delivered to the intended recipient together or separately. For example, a first container may contain an enzyme for use in an assay, while a second container contains oligonucleotides. In contrast, a "combined kit" refers to a delivery system containing all of the components of a reaction assay in a single container (e.g., in a single box housing each of the desired components). The term "kit" includes both fragmented and combined kits.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

II. Methods of Amplifying and Sequencing

Provided herein is a method of sequencing both strands of a double stranded nucleic acid. In some embodiments, a method comprises sequencing both strands of a plurality of double stranded nucleic acids. In some embodiments, a double stranded nucleic acid is a native or endogenous nucleic acid obtained from a subject or sample. In some embodiments, a double stranded nucleic acid is a sequencing library insert. In some embodiments, a double stranded nucleic acid is a target nucleic acid that one desires to obtain a sequence of. For example, in some embodiments, a double stranded nucleic acid is fragment of genomic DNA, RNA or cDNA that one desires to obtain a sequence of A double stranded nucleic acid may be obtained from a subject and/or sample using a suitable method. In embodiments, the double-stranded nucleic acid includes a first DNA strand hybridized to a second DNA strand. In embodiments, the double-stranded nucleic acid includes a DNA strand hybridized to a RNA strand.

In some embodiments, a double stranded nucleic comprises two complementary nucleic acid strands. In certain embodiments, a double stranded nucleic acid comprises a first strand and a second strand which are complementary or substantially complementary to each other. A first strand of a double stranded nucleic acid is sometimes referred to herein as a forward strand and a second strand of the double stranded nucleic acid is sometime referred to herein as a reverse strand. In some embodiments, a double stranded nucleic acid comprises two opposing ends. Accordingly, a double stranded nucleic acid often comprises a first end and a second end. An end of a double stranded nucleic acid may comprise a 5'-overhang, a 3'-overhang or a blunt end. In some embodiments, one or both ends of a double stranded nucleic acid are blunt ends. In certain embodiments, one or both ends of a double stranded nucleic acid are manipulated to include a 5'-overhang, a 3'-overhang or a blunt end using a suitable method. In some embodiments, one or both ends of a double stranded nucleic acid are manipulated during library preparation such that one or both ends of the double stranded nucleic acid are configured for ligation to an adapter using a suitable method. For example, one or both ends of a double stranded nucleic acid may be digested by a restriction enzyme, polished, end-repaired, filled in, phosphorylated (e.g., by adding a 5'-phosphate), dT-tailed, dA-tailed, the like or a combination thereof.

In embodiments, the double stranded nucleic acid, alternatively referred to as a library insert or target polynucleotide, is at least 50, 100, 150, 200, 250, or 300 nucleotides in length. In embodiments, the double stranded nucleic acid, alternatively referred to as a library insert, is at least 150, 200, 250, 300, 350, or 400 nucleotides in length. In embodiments, the double stranded nucleic acid, alternatively referred to as a library insert, is at least 450, 500, 650, 700, 750, or 800 nucleotides in length. In embodiments, the double stranded nucleic acid, alternatively referred to as a library insert, is at least 850, 900, 950, 1000, 1050, or 1100 nucleotides in length.

In embodiments, the double stranded nucleic acid, alternatively referred to as a library insert, is about 50, 100, 150, 200, 250, or 300 nucleotides in length. In embodiments, the double stranded nucleic acid, alternatively referred to as a library insert, is about 150, 200, 250, 300, 350, or 400 nucleotides in length. In embodiments, the double stranded nucleic acid, alternatively referred to as a library insert, is about 450, 500, 650, 700, 750, or 800 nucleotides in length. In embodiments, the double stranded nucleic acid, alternatively referred to as a library insert, is about 850, 900, 950, 1000, 1050, or 1100 nucleotides in length. In embodiments, the double stranded nucleic acid, alternatively referred to as a library insert, is about 500-1500 nucleotides in length. In embodiments, the double stranded nucleic acid, alternatively referred to as a library insert, is about 750-1500 nucleotides in length. In embodiments, the double stranded nucleic acid, alternatively referred to as a library insert, is about 1-2 kilobases (kb) in length. In embodiments, the double stranded nucleic acid, alternatively referred to as a library insert, is about 300, 400, 600, or 800 nucleotides in length. In embodiments, the double stranded nucleic acid, alternatively referred to as a library insert, is about 250 to 600 nucleotides in length.

In embodiments, the double stranded nucleic acid is about 100, 125, 150, 175, or 200 nucleotides in length. In embodiments, the double stranded nucleic acid is about 200, 225, 250, 275, or 300 nucleotides in length. In embodiments, the double stranded nucleic acid is less than 150 nucleotides in length. In embodiments, the double stranded nucleic acid is less than 100 nucleotides in length. In embodiments, the double stranded nucleic acid is less than 75 nucleotides in length. In embodiments, the double stranded nucleic acid is about 150 nucleotides in length. In embodiments, the double stranded nucleic acid is about 100 nucleotides in length. In embodiments, the double stranded nucleic acid is about 75 nucleotides in length. In embodiments, the method provides sequencing both strands of a double stranded nucleic acid such that there is overlap in the sequencing reads of the first and second strand. For example, if the double stranded nucleic acid is short (e.g., 150-200 nucleotides) it is possible to sequence the first strand and a complementary region of the second strand (e.g., in the same read).

In embodiments, the double stranded nucleic acid is greater than 150 nucleotides in length. In embodiments, the double stranded nucleic acid is greater than 200 nucleotides in length. In embodiments, the double stranded nucleic acid is greater than 250 nucleotides in length. In embodiments, the double stranded nucleic acid is greater than 300 nucleotides in length. In embodiments, the double stranded nucleic acid is greater than 500 nucleotides in length. In embodiments, the double stranded nucleic acid is greater than 700 nucleotides in length. In embodiments, the double stranded nucleic acid is greater than 900 nucleotides in length. In embodiments, the double stranded nucleic acid is greater than 1,000 nucleotides in length (i.e., greater than 1 kb). In embodiments, the method provides sequencing both strands of a double stranded nucleic acid such that there is no overlap in the sequencing reads of the first and second strand, rather a portion of the first strand and portion of the second strand.

In some embodiments, a method herein comprises ligating one or more adapters to a double stranded nucleic acid. In some embodiments, a method herein comprises ligating one or more adapters to a plurality of double stranded nucleic acids. In some embodiments, a method herein comprises ligating a first adapter to a first end of a double stranded nucleic acid, and ligating a second adapter to a second end of a double stranded nucleic acid. In some embodiments, the first adapter and the second adapter are different. For example, in certain embodiments, the first adapter and the second adapter may comprise different nucleic acid sequences or different structures. In some embodiments, the first adapter is a Y-adapter and the second adapter is a hairpin adapter. In some embodiments, the first adapter is a hairpin adapter and a second adapter is a hairpin adapter. In certain embodiments, the first adapter and the second adapter may comprise different primer binding sites, different structures, and/or different capture sequences (e.g., a sequence complementary to a capture nucleic acid). In some embodiments, some, all or substantially all of the nucleic acid sequence of a first adapter and a second adapter are the same. In some embodiments, some, all or substantially all of the nucleic acid sequence of a first adapter and a second adapter are substantially different.

In embodiments, the method comprises (a) ligating a first adapter to a first end of the double stranded nucleic acid, and ligating a second adapter to a second end of the double stranded nucleic acid, wherein the second adapter is a hairpin adapter, thereby forming a nucleic acid template; (b) annealing a first primer to the nucleic acid template, wherein the first primer comprises a sequence that is complementary to a portion of the first adapter, or a complement thereof; (c) sequencing a first portion and a second portion of the nucleic acid template by extending the first primer, thereby generating a first read comprising a first nucleic acid sequence of at least a first portion of the double stranded nucleic acid, and a second read comprising a nucleic acid sequence of at least a second portion of the double stranded nucleic acid. In embodiments, the method comprises (a) ligating a first adapter to a first end of the double stranded nucleic acid, and ligating a second adapter to a second end of the double stranded nucleic acid, wherein the second adapter is a hairpin adapter, thereby forming a nucleic acid template; (b) annealing a first primer to the nucleic acid template, wherein the first primer comprises a sequence that is complementary to a portion of the first adapter, or a complement thereof; (c) sequencing a first portion of the nucleic acid template by extending the first primer, thereby generating a first read comprising a first nucleic acid sequence of at least a first portion of the double stranded nucleic acid; (d) annealing a second primer to the nucleic acid template, wherein the second primer comprises a sequence that is complementary to a sequence within a loop or stem of the hairpin adapter, or a complement thereof; and (e) sequencing a second portion of the nucleic acid template by extending the second primer, thereby generating a second read comprising a nucleic acid sequence of at least a second portion of the double stranded nucleic acid. In some embodiments, the double stranded nucleic acid comprises a forward strand and a reverse strand. In embodiments, the method comprises ligating a first adapter to a first end of the double stranded nucleic acid, and ligating a second adapter to a second end of the double stranded nucleic acid, wherein the second adapter is a hairpin adapter, thereby forming a nucleic acid template in solution. Following ligation, in embodiments the nucleic acid templates are captured with a biotinylated-oligonucleotide complementary to the loop region. The resulting biotin-captured complexes can then be captured and purified via methods of purifications based on avidin, streptavidin, or neutravidin, and amplified. For example, the captured constructs may be amplified (e.g., amplified using a polymerase chain reaction) and immobilized on a solid support. Additional solid phase amplification techniques (e.g., bridge PCR amplification) may be performed to generate clusters of nucleic acids.

In some embodiments, an adapter is a Y-adapter. In some embodiments, a Y-adapter comprises a first strand and a second strand where a portion of the first strand (e.g., FIG. 1A (3'-portion)) is complementary, or substantially complementary, to a portion (e.g., FIG. 1A (5'-portion)) of the second strand. In some embodiments, a Y-adapter comprises a first strand and a second strand where a 3'-portion of the first strand is hybridized to a 5'-portion of the second strand. In certain embodiments, the 3'-portion of the first strand that is substantially complementary to the 5'-portion of the second strand forms a duplex comprising double stranded nucleic acid. Accordingly, a Y-adapter often comprises a first end comprising a duplex region comprising double stranded nucleic acid, and a second end comprising a forked region comprising a 5'-arm (FIG. 1A (5'-arm)) and a 3'-arm (FIG. 1A (3'-arm)). In some embodiments, a 5'-portion of the first stand (e.g., 5'-arm) and a 3'-portion of the second strand (3'-arm) are not complementary. In certain embodiments, the first and second strands of a Y-adapter are not covalently attached to each other. In some embodiments, a Y-adapter comprises (i) a first strand having a 5'-arm and a 3'-portion, and (ii) a second strand having a 3'-arm and a 5'-portion, wherein the 3'-portion of the first strand is substantially complementary to the 5'-portion of the second strand, and the 5'-arm of the first strand is not substantially complementary to the 3'-arm of the second strand. In some embodiments, a Y-adapter comprises a structure shown in any one of FIGS. 1A, 1B, 2A, and 3. In some embodiments, the first adapter includes a sample barcode sequence, a molecular identifier sequence, or both a sample barcode sequence and a molecular identifier sequence. In some embodiments, the first adapter includes a sample barcode sequence (e.g., a 6-10 nucleotide sequence).

In embodiments, ligating includes ligating both the 3' end and the 5' end of the duplex region of the first adapter to the double stranded nucleic acid. In embodiments, ligating includes ligating either the 3' end or the 5' end of the duplex region of the first adapter to the double stranded nucleic acid. In embodiments, ligating includes ligating the 5' end of the duplex region of the first adapter to the double stranded nucleic acid and not the 3' end of the duplex region. In embodiments, the method includes ligating a first adapter to a first end of the double stranded nucleic acid wherein both strands of the double stranded nucleic acid are ligated to the first adapter. In embodiments, the method includes ligating a first adapter to a first end of the double stranded nucleic acid wherein one strand of the double stranded nucleic acid is ligated to the first adapter.

In some embodiments, each strand of a Y-adapter, each of the non-complementary arms of a Y-adapter, or a duplex portion of a Y-adapter has a length independently selected from at least 5, at least 10, at least 15, at least 25, and at least 40 nucleotides. In some embodiments, each strand of a Y-adapter, each of the non-complementary arms of a Y-adapter, or a duplex portion of a Y-adapter has a length in a range independently selected from 15 to 500 nucleotides, 15-250 nucleotides, 15 to 200 nucleotides, 15 to 150 nucleotides, 20 to 100 nucleotides, 20 to 50 nucleotides and 10-50 nucleotides. In embodiments, one or both non-complementary arms of the Y-adapter is about or at least about 10, 15, 20, 25, 30, 35, 40, 45, 50, or more nucleotides in length. In embodiments, one or both non-complementary arms of the Y-adapter is about or at least about 20 nucleotides in length. In embodiments, one or both non-complementary arms of the Y-adapter is about or at least about 30 nucleotides in length. In embodiments, one or both non-complementary arms of the Y-adapter is about or at least about 40 nucleotides in length. In embodiments, the duplex portion of a Y-adapter is about or at least about 5, 10, 15, 20, 25, 30, or more nucleotides in length. In embodiments, the duplex portion of a Y-adapter is about 5-50, 5-25, or 10-15 nucleotides in length. In embodiments, the duplex portion of a Y-adapter is about or at least about 10 nucleotides in length. In embodiments, the duplex portion of a Y-adapter is about or at least about 15 nucleotides in length. In embodiments, the duplex portion of a Y-adapter is about or at least about 12 nucleotides in length. In embodiments, the duplex portion of a Y-adapter is about or at least about 20 nucleotides in length.

In some embodiments, a Y-adapter comprises a first end comprising a duplex region comprising double stranded nucleic acid, and a second end comprising a forked region, where the first end is configured for ligation to an end of double stranded nucleic acid (e.g., a nucleic acid fragment, e.g., a library insert). In embodiments, a duplex end of a Y-adapter comprises a 5'-overhang or a 3'-overhang that is complementary to a 3'-overhang or a 5'-overhang of an end of a double stranded nucleic acid. In some embodiments, a duplex end of a Y-adapter comprises a blunt end that can be ligated to a blunt end of a double stranded nucleic acid. In certain embodiment, a duplex end of a Y-adapter comprises a 5'-end that is phosphorylated.

In some embodiments, the first and/or second adapter (e.g., one or both strands of a Y-adapter) comprise one or more of a primer binding site, a capture nucleic acid binding site (e.g., a nucleic acid sequence complementary to a capture nucleic acid), a UMI, a sample barcode, a sequencing adapter, a label, a binding motif, the like or combinations thereof. In some embodiments, a non-complementary portion (e.g., 5'-arm and/or 3'-arm) of a Y-adapter comprises one or more of a primer binding site, a capture nucleic acid binding site (e.g., a nucleic acid sequence complementary to a capture nucleic acid), a UMI, a sample barcode, a sequencing adapter, a label, a binding motif, the like or combinations thereof. In certain embodiments, a non-complementary portion of a Y-adapter comprises a primer binding site. In certain embodiments, a non-complementary portion of a Y-adapter comprises a binding site for a capture nucleic acid. In certain embodiments, a non-complementary portion of a Y-adapter comprises a primer binding site and a UMI. In certain embodiments, a non-complementary portion of a Y-adapter comprises a binding motif. In embodiments, the first and/or second adapter (e.g., one or both strands of a Y-adapter) does not comprise a UMI or sample barcode.

In certain embodiments, a complementary strand (e.g., a 3'-portion or 5'-portion) of a Y-adapter comprises a primer binding site. In certain embodiments, a complementary strand (e.g., a 3'-portion or 5'-portion) of a Y-adapter comprises a binding site for a capture nucleic acid. In certain embodiments, a complementary strand (e.g., a 3'-portion or 5'-portion) of a Y-adapter comprises a primer binding site and a UMI. In certain embodiments, a complementary strand (e.g., a 3'-portion or 5'-portion) of a Y-adapter comprises a binding motif.

In some embodiments, each of the non-complementary portions (i.e., arms) of a Y-adapter independently have a predicted, calculated, mean, average or absolute melting temperature (Tm) that is greater than 50° C., greater than 55° C., greater than 60° C., greater than 65° C., greater than 70° C. or greater than 75° C. In some embodiments, each of the non-complementary portions of a Y-adapter independently have a predicted, estimated, calculated, mean, average or absolute melting temperature (Tm) that is in a range of 50-100° C., 55-100° C., 60-100° C., 65-100° C., 70-100° C., 55-95° C., 65-95° C., 70-95° C., 55-90° C., 65-90° C., 70-90° C., or 60-85° C. In embodiments, the Tm is about or at least about 70° C. In embodiments, the Tm is about or at least about 75° C. In embodiments, the Tm is about or at least about 80° C. In embodiments, the Tm is a calculated Tm. Tm's are routinely calculated by those skilled in the art, such as by commercial providers of custom oligonucleotides. In embodiments, the Tm for a given sequence is determined based on that sequence as an independent oligo. In embodiments, Tm is calculated using web-based algorithms, such as Primer3 and Primer3Plus (www.bioinformatics.nl/cgi-bin/primer3plus/primer3plus.cgi) using default parameters. The Tm of a non-complementary portion of a Y-adapter can be changed (e.g., increased) to a desired Tm using a suitable method, for example by changing (e.g., increasing) GC content, changing (e.g., increasing) length and/or by the inclusion of modified nucleotides, nucleotide analogues and/or modified nucleotides bonds, non-limiting examples of which include locked nucleic acids (LNAs, e.g., bicyclic nucleic acids), bridged nucleic acids (BNAs, e.g., constrained nucleic acids), CS-modified pyrimidine bases (for example, 5-methyl-dC, propynyl pyrimidines, among others) and alternate backbone chemistries, for example peptide nucleic acids (PNAs), morpholinos, the like or combinations thereof. Accordingly, in some embodiments, each of the non-complementary portion of a Y-adapter independently comprise one or more modified nucleotides, nucleotide analogues and/or modified nucleotides bonds.

In some embodiments, each of the non-complementary portions of a Y-adapter independently comprise a GC content of greater than 40%, greater than 50%, greater than 55%, greater than 60% greater than 65% or greater than 70%. In certain embodiments, each of the non-complementary portions of a Y-adapter independently comprise a GC content in a range of 40-100%, 50-100%, 60-100% or 70-100%. In embodiments, one or both non-complementary portions of a Y-adapter have a GC content of about or more than about 40%. In embodiments, one or both non-complementary portions of a Y-adapter have a GC content of about or more than about 50%. In embodiments, one or both non-complementary portions of a Y-adapter have a GC content of about or more than about 60%. Non-base modifiers can also be incorporated into a non-complementary portion of a Y-adapter to increase Tm, non-limiting examples of which include a minor grove binder (MGB), spermine, G-clamp, a Uaq anthraquinone cap, the like or combinations thereof.

In certain embodiments, a duplex region of a Y-adapter comprises a predicted, estimated, calculated, mean, average or absolute Tm in a range of 30-70° C., 35-65° C., 35-60° C., 40-65° C., 40-60° C., 35-55° C., 40-55° C., 45-50° C. or 40-50° C. In embodiments, the Tm of a duplex region of the Y-adapter is about or more than about 30° C. In embodiments, the Tm of a duplex region of the Y-adapter is about or more than about 35° C. In embodiments, the Tm of a duplex region of the Y-adapter is about or more than about 40° C. In embodiments, the Tm of a duplex region of the Y-adapter is about or more than about 45° C. In embodiments, the Tm of a duplex region of the Y-adapter is about or more than about 50° C.

In some embodiments, an adapter is hairpin adapter. In some embodiments, a hairpin adapter comprises a single nucleic acid strand comprising a stem-loop structure. A hairpin adapter can be any suitable length. In some embodiments, a hairpin adapter is at least 40, at least 50, or at least 100 nucleotides in length. In some embodiments, a hairpin adapter has a length in a range of 45 to 500 nucleotides, 75-500 nucleotides, 45 to 250 nucleotides, 60 to 250 nucleotides or 45 to 150 nucleotides. In some embodiments, a hairpin adapter comprises a nucleic acid having a 5'-end, a 5'-portion, a loop, a 3'-portion and a 3'-end (e.g., arranged in a 5' to 3' orientation). In some embodiments, the 5' portion of a hairpin adapter is annealed and/or hybridized to the 3' portion of the hairpin adapter, thereby forming a stem portion of the hairpin adapter. In some embodiments, the 5' portion of a hairpin adapter is substantially complementary to the 3' portion of the hairpin adapter. In certain embodiments, a hairpin adapter comprises a stem portion (i.e., stem) and a loop, wherein the stem portion is substantially double stranded thereby forming a duplex. In some embodiments, the loop of a hairpin adapter comprises a nucleic acid strand that is not complementary (e.g., not substantially complementary) to itself or to any other portion of the hairpin adapter. In some embodiments, a hairpin adapter comprises a structure shown in any one of FIGS. 1, 2B, 4 and 5. In some embodiments, the second adapter includes a sample barcode sequence, a molecular identifier sequence, or both a sample barcode sequence and a molecular identifier sequence. In some embodiments, the second adapter includes a sample barcode sequence.

In some embodiments, a duplex region or stem portion of a hairpin adapter comprises an end that is configured for ligation to an end of double stranded nucleic acid (e.g., a nucleic acid fragment, e.g., a library insert). In embodiments, an end of a duplex region or stem portion of a hairpin adapter comprises a 5'-overhang or a 3'-overhang that is complementary to a 3'-overhang or a 5'-overhang of one end of a double stranded nucleic acid. In some embodiments, an end of a duplex region or stem portion of a hairpin adapter comprises a blunt end that can be ligated to a blunt end of a double stranded nucleic acid. In certain embodiment, an end of a duplex region or stem portion of a hairpin adapter comprises a 5'-end that is phosphorylated. In some embodiments, a stem portion of a hairpin adapter is at least 15, at least 25, or at least 40 nucleotides in length. In some embodiments, a stem portion of a hairpin adapter has a length in a range of 15 to 500 nucleotides, 15-250 nucleotides, 15 to 200 nucleotides, 15 to 150 nucleotides, 20 to 100 nucleotides or 20 to 50 nucleotides.

In embodiments, ligating includes ligating both the 3' end and the 5' end of the duplex region of the second adapter to the double stranded nucleic acid. In embodiments, ligating includes ligating either the 3' end or the 5' end of the duplex region of the second adapter to the double stranded nucleic acid. In embodiments, ligating includes ligating the 5' end of the duplex region of the second adapter to the double stranded nucleic acid and not the 3' end of the duplex region.

In some embodiments, a loop of a hairpin adapter comprise one or more of a primer binding site, a capture nucleic acid binding site (e.g., a nucleic acid sequence complementary to a capture nucleic acid), a UMI, a sample barcode, a sequencing adapter, a label, the like or combinations thereof. In certain embodiments, a loop of a hairpin adapter comprises a primer binding site. In certain embodiments, a loop of a hairpin adapter comprises a primer binding site and a UMI. In certain embodiments, a loop of a hairpin adapter comprises a binding motif.

In some embodiments, a loop of a hairpin adapter has a predicted, calculated, mean, average or absolute melting temperature (Tm) that is greater than 50° C., greater than 55° C., greater than 60° C., greater than 65° C., greater than 70° C. or greater than 75° C. In some embodiments, a loop of a hairpin adapter has a predicted, estimated, calculated, mean, average or absolute melting temperature (Tm) that is in a range of 50-100° C., 55-100° C., 60-100° C., 65-100° C., 70-100° C., 55-95° C., 65-95° C., 70-95° C., 55-90° C., 65-90° C., 70-90° C., or 60-85° C. In embodiments, the Tm of the loop is about 65° C. In embodiments, the Tm of the loop is about 75° C. In embodiments, the Tm of the loop is about 85° C. The Tm of a loop of a hairpin adapter can be changed (e.g., increased) to a desired Tm using a suitable method, for example by changing (e.g., increasing GC content), changing (e.g., increasing) length and/or by the inclusion of modified nucleotides, nucleotide analogues and/or modified nucleotides bonds, non-limiting examples of which include locked nucleic acids (LNAs, e.g., bicyclic nucleic acids), bridged nucleic acids (BNAs, e.g., constrained nucleic acids), CS-modified pyrimidine bases (for example, 5-methyl-dC, propynyl pyrimidines, among others) and alternate backbone chemistries, for example peptide nucleic acids (PNAs), morpholinos, the like or combinations thereof. Accordingly, in some embodiments, a loop of a hairpin adapter comprises one or more modified nucleotides, nucleotide analogues and/or modified nucleotides bonds.

In some embodiments, a loop of a hairpin adapter independently comprises a GC content of greater than 40%, greater than 50%, greater than 55%, greater than 60% greater than 65% or greater than 70%. In certain embodiments, a loop of a hairpin adapter independently comprises a GC content in a range of 40-100%, 50-100%, 60-100% or 70-100%. In embodiments, the loops has a GC content of about or more than about 40%. In embodiments, the loops has a GC content of about or more than about 50%. In embodiments, the loops has a GC content of about or more than about 60%. Non-base modifiers can also be incorporated into a loop of a hairpin adapter to increase Tm, non-limiting examples of which include a minor grove binder (MGB), spermine, G-clamp, a Uaq anthraquinone cap, the like or combinations thereof. A loop of a hairpin adapter can be any suitable length. In some embodiments, a loop of a hairpin adapter is at least 15, at least 25, or at least 40 nucleotides in length. In some embodiments, a hairpin adapter has a length in a range of 15 to 500 nucleotides, 15-250 nucleotides, 20 to 200 nucleotides, 30 to 150 nucleotides or 50 to 100 nucleotides.

In certain embodiments, a duplex region or stem region of a hairpin adapter comprises a predicted, estimated, calculated, mean, average or absolute Tm in a range of 30-70° C., 35-65° C., 35-60° C., 40-65° C., 40-60° C., 35-55° C., 40-55° C., 45-50° C. or 40-50° C. In embodiments, the Tm of the stem region is about or more than about 35° C. In embodiments, the Tm of the stem region is about or more than about 40° C. In embodiments, the Tm of the stem region is about or more than about 45° C. In embodiments, the Tm of the stem region is about or more than about 50° C.

In some embodiments, a method comprises ligating a first adapter to a first end of a double stranded nucleic acid, and ligating a second adapter to a second end of the double stranded nucleic acid, wherein the second adapter is a hairpin adapter, thereby forming a nucleic acid template. The first adapter can be a Y-adapter or a hairpin adapter. In some embodiments, the first adapter is a Y-adapter. Accordingly, in some embodiments, a nucleic acid template comprises a first adapter, a double stranded nucleic acid (e.g., a library insert), and a hairpin adapter. In some embodiments, a nucleic acid template is a single strand of a nucleic acid comprising single-stranded non-complementary portions and complementary portions that are capable of forming double-stranded regions. In certain embodiments, a nucleic acid template comprises a structure shown in FIG. 1A or 1C. For example, when the first adapter is a Y-adapter, a nucleic acid template comprises a first strand of the Y-adapter, a first strand (e.g., forward strand) of a double stranded nucleic acid (e.g., a library insert), a hairpin adapter, a second strand (e.g., reverse strand) of the double stranded nucleic acid, and a second strand of the Y-adapter arranged in a 5'-3' direction. The phrases "forward strand" and "reverse strand" as used herein, when referring to the double stranded nucleic acid, do not imply a direction of transcription or that either of the strands comprises a coding region, but simply indicate that the two strands are different and are complementary to each other.

In embodiments, a hairpin structure is formed by joining the ends of a Y-adapter after ligation to a double-stranded nucleic acid. For example, in embodiments disclosed herein relating to ligation to a hairpin adapter, ligation may instead be to a Y-adapter, followed by ligation of the unpaired ends of the adapter to each other. For example, the two unpaired arms may be hybridized to a splint oligonucleotide that brings the ends of the unpaired arms in proximity, which are then ligated with a ligase.

In embodiments, the Y-adaptor portion of a Y-adaptor-ligated double-stranded nucleic acid is formed from cleavage in the loop of a hairpin adapter (e.g., one or more adapters as described in U.S. Pat. No. 8,883,990, which is incorporated herein by reference for all purposes). For example, in embodiments disclosed herein relating to ligation to a Y-adapter, ligation may instead be to a hairpin adapter, followed by cleavage within the loop of the hairpin adapter to release two unpaired ends. In embodiments, a hairpin adapter comprises one or more uracil nucleotide(s) in the loop, and cleavage in the loop may be accomplished by the combined activities of Uracil DNA glycosylase (UDG) and the DNA glycosylase-lyase Endonuclease VIII, or suitable cleavage conditions known in the art. UDG cleaves the glycosidic bond between the deoxyribose of the DNA sugar-phosphate backbone and the uracil base, and Endonuclease VIII cleaves the AP site, effectively cleaving the loop. In embodiments, the hairpin adapter includes a recognition sequence for a compatible restriction enzyme. In embodiments, the hairpin adapter includes one or more ribonucleotides and cleavage in the loop is accomplished by RNase H. In embodiments, the loop of the hairpin adapter includes a cleavable linkage that is positioned between two non-complementary regions of the loop. In embodiments, the non-complementary region that is 5' of the cleavable linkage comprises a primer binding site that is in the range of 8 to 100 nucleotides in length. In embodiments, the first adapter is a hairpin adapter, wherein the hairpin adapter comprises a cleavable site in the loop. In embodiments, the first adapter is a first hairpin adapter and the second adapter is a hairpin adapter, wherein only the first hairpin adapter comprises a cleavable site in the loop.

In some embodiments, a method comprises sequencing a template described herein. In some embodiments, the sequencing comprises contacting the template with a suitable polymerase. In certain embodiments, the polymerase is in an aqueous phase. In certain embodiments, the polymerase is soluble in an aqueous solution. In some embodiments, the polymerase is not attached to a substrate. In some embodiments, the polymerase is attached to a substrate. In embodiments, the polymerase is a mutant polymerase capable of incorporating modified nucleotides.

In certain embodiments, a method comprises annealing a first primer to a 3'-portion of a template described herein, or to a 3'-end of a complementary sequence of a template described herein (e.g., a 3' end of an amplicon of a template). In certain embodiments, a method comprises annealing a first primer to a 3'-portion of a template described herein, where the 3'-portion of the template comprises a portion of an adapter (e.g., a first adapter). In certain embodiments, a method comprises annealing a first primer to a 3'-portion of a template described herein, where the 3'-portion of the template comprises a portion of a Y-adapter. In certain embodiments, a method comprises annealing a first primer to a 3'-arm of a Y-adapter of a template described herein, where the 3'-arm of the adapter comprises a primer binding site for the first primer. In certain embodiments, a method comprises annealing a first primer to a 5'-portion of a second strand of a Y-adapter of a template described herein, where the 5'-portion of the adapter comprises a primer binding site for the first primer.

Figure 1B:
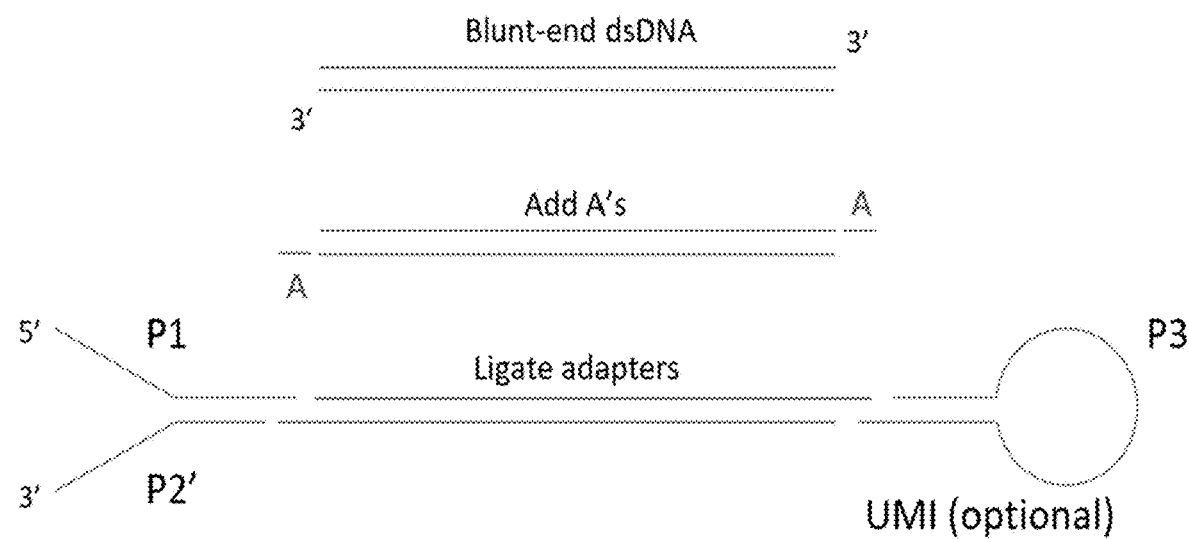
Figure 1C:
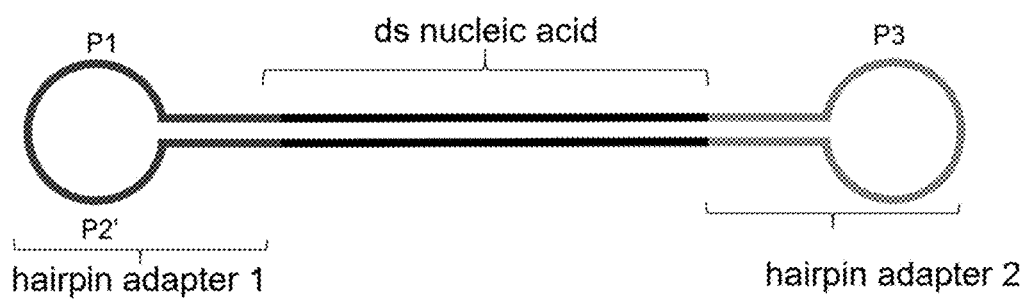
Figure 1D:
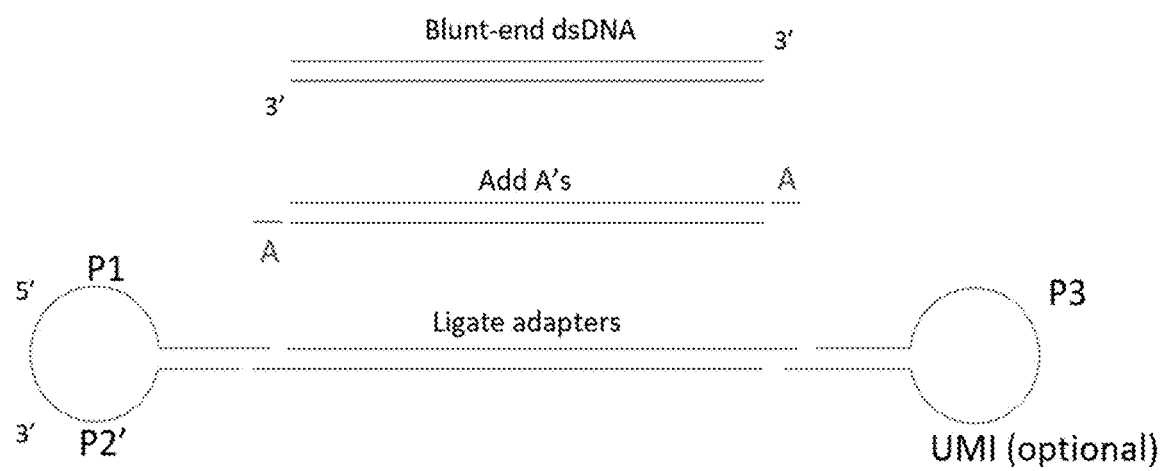
Figure 8:
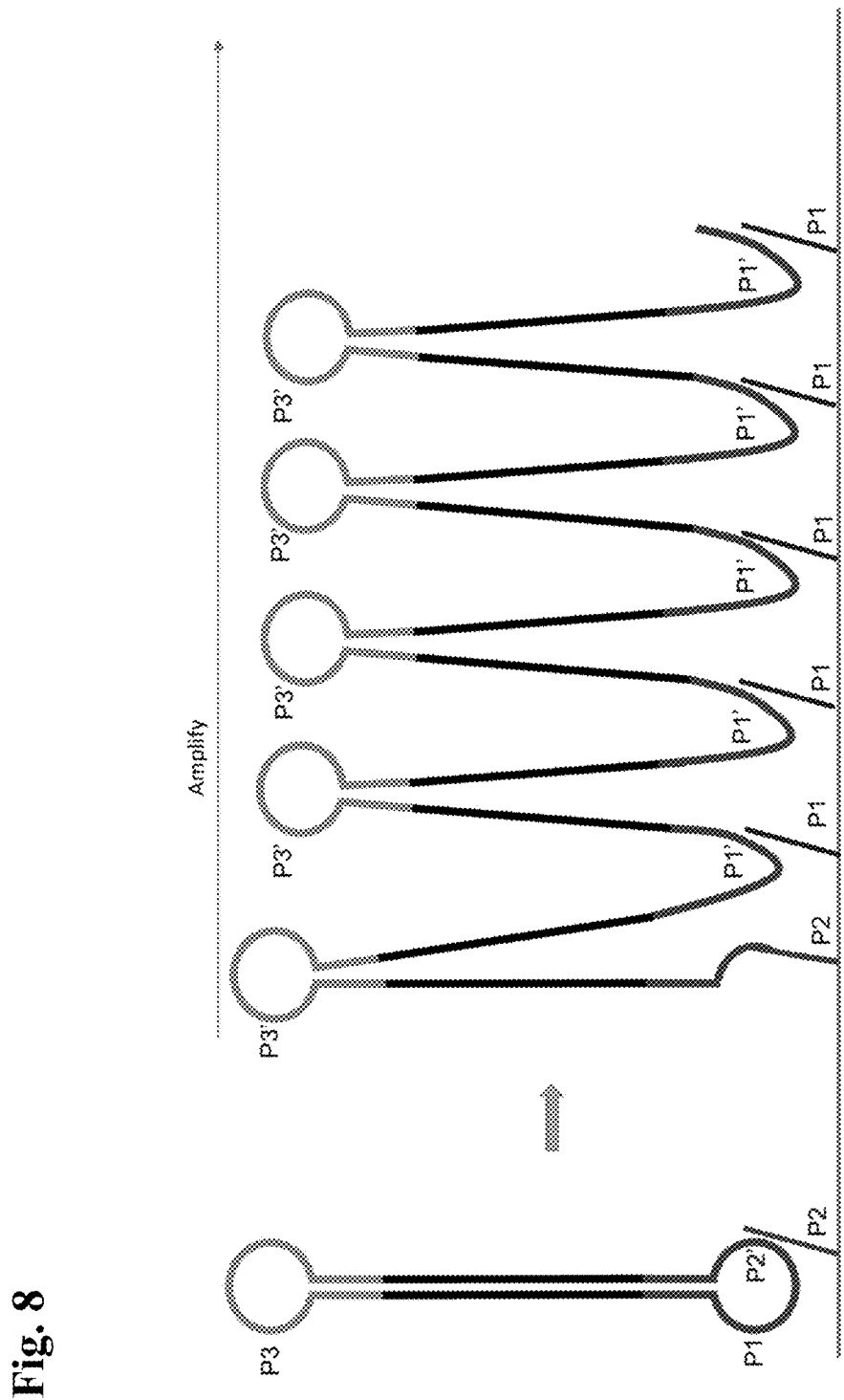
FIG. 8 shows an overview of an embodiment of a seeding and amplification process, wherein the amplification method includes rolling circle amplification (RCA), exponential rolling circle amplification (eRCA), or a method of amplification which includes PCR and RCA or PCR and eRCA.

In embodiments where a template comprises two hairpin adapters located on opposing sides of a double stranded nucleic acid, a method comprises annealing a first primer to a portion of a first adapter of a template described herein (e.g., see FIGS. 1C, 1D and 8). In certain embodiments, a method comprises annealing a first primer to a loop of a first hairpin adapter of a template described herein, where the loop of the adapter comprises a first primer binding site for the first primer. In some embodiments, a method comprises annealing a first primer to a stem of a first hairpin adapter of a template described herein, where the stem of the adapter comprises a first primer binding site for the first primer.

In certain embodiments, a method comprises sequencing a first portion of a nucleic acid template by extending a first primer, thereby generating a first read comprising a first nucleic acid sequence of at least a first portion of the double stranded nucleic acid. In some embodiments, a method comprises sequencing a reverse strand (e.g., see FIG. 1A) of a nucleic acid template by extending a first primer, thereby generating a first read comprising a nucleic acid sequence of at least a portion of the reverse strand of a double stranded nucleic acid.

In certain embodiments, a method comprises sequencing a second portion of a nucleic acid template by extending a second primer, thereby generating a second read comprising a second nucleic acid sequence of at least a second portion of the double stranded nucleic acid. In some embodiments, a method comprises sequencing a forward strand (e.g., see FIG. 1A) of a nucleic acid template by extending a second primer, thereby generating a second read comprising a nucleic acid sequence of at least a portion of the forward strand of a double stranded nucleic acid. In some embodiments, a method comprises annealing a second primer to the nucleic acid template, wherein the second primer comprises a sequence that is complementary to a primer binding sequence located within a loop of the hairpin adapter (i.e., second adapter). In certain embodiments, a second primer is annealed to a loop of the hairpin adapter (i.e., second adapter) and a second portion of the nucleic acid template (e.g., the forward strand) is sequenced by extending the second primer, thereby generating a second read of the nucleic acid template.

In some embodiments, a method comprises (i) hybridizing a first primer to a 3'-portion of a template where the 3' portion of the template comprises a portion of a Y-adapter, (ii) sequencing a portion of a first strand of a double-stranded nucleic acid, (iii) hybridizing a second primer to a loop or stem of a hairpin adapter of the template, and (iv) sequencing a portion of a second strand of the double-stranded nucleic acid. In some embodiments, the methods herein can be applied to an amplicon or copy of a template (or complement thereof), as well as to the original template.

In some embodiments, the step of sequencing a first portion of a nucleic acid template as described herein is conducted before, after and/or during the step of sequencing a second portion of a nucleic acid template as described herein. For example, in certain embodiments, a second primer is annealed to a loop or stem region of a hairpin adapter and a first portion of a double stranded nucleic acid insert is sequenced by extending the second primer, followed by annealing a first primer to a 3'-end of the template comprising a portion of a Y-adapter, and sequencing a second portion of the double stranded nucleic acid insert by extending the first primer.

In certain embodiments, a method comprises generating amplicons of the nucleic acid template (e.g., the nucleic acid ligated to a first and second adapter, as described herein). Amplicons may be generated using a suitable amplification method. In certain embodiments, amplicons of a template are generated using a polymerase chain reaction or a rolling circle amplification method, or a combination thereof. In certain embodiments, amplicons are generated using a polymerase chain reaction. In certain embodiments, amplicons are generated using a bridge PCR amplification method. In embodiments, amplicons are generated using thermal bridge polymerase chain reaction (t-bPCR) amplification. In embodiments, amplicons are generated using a chemical bridge polymerase chain reaction (c-bPCR) amplification. Chemical bridge polymerase chain reactions include fluidically cycling a denaturant (e.g., formamide) and maintaining the temperature within a narrow temperature range (e.g., +/−5° C.). In contrast, thermal bridge polymerase chain reactions include thermally cycling between high temperatures (e.g., 85° C.-95° C.) and low temperatures (e.g., 60° C.-70° C.). Thermal bridge polymerase chain reactions may also include a denaturant, typically at a much lower concentration than traditional chemical bridge polymerase chain reactions. In embodiments, generating amplicons includes a thermal bridge polymerase chain reaction (t-bPCR) amplification. In embodiments, the plurality of cycles includes thermally cycling between (i) about 85° C. for about 15-30 sec for denaturation, and (ii) about 65° C. for about 1 minute for annealing/extension of the primer. In embodiments, the plurality of cycles includes thermally cycling between (i) about 85° C. for about 15-30 sec for denaturation, and (ii) about 65° C. for about 30 seconds for annealing/extension of the primer.

Provided herein in an aspect is a method of amplifying a double-stranded nucleic acid template. In embodiments, the method includes (a) ligating a first adapter to a first end of the double stranded nucleic acid, and ligating a second adapter to a second end of the double stranded nucleic acid, wherein the second adapter is a hairpin adapter, thereby forming a nucleic acid template; (b) annealing a first primer to the nucleic acid template, wherein the first primer comprises a sequence that is complementary to a portion of the first adapter, or a complement thereof, and is not substantially complementary to a portion of the second adapter; (c) generating amplicons using a suitable amplification method. In embodiments, the method provides a copy of the nucleic acid template as a single-stranded molecule of DNA, and, advantageously, contains both forward and reverse strands of the original double-stranded DNA molecule. In embodiments, the method further includes sequencing the amplicons using a method known in the art or described herein.

In embodiments, the method includes amplifying a double stranded nucleic acid including a first strand and a second strand, the method including: (a) ligating a first adapter to a first end of the double stranded nucleic acid wherein the first adapter is a Y adapter including (i) a first strand having a 5'-arm and a 3'-portion, and (ii) a second strand having a 5'-portion and a 3'-arm, wherein the 3'-portion of the first strand is substantially complementary to the 5'-portion of the second strand, and the 5'-arm of the first strand is not substantially complementary to the 3'-arm of the second strand, and ligating a second adapter to a second end of the double stranded nucleic acid, wherein the second adapter is a hairpin adapter, thereby forming a nucleic acid template; (b) annealing a primer to the nucleic acid template, wherein the first primer includes a sequence that is complementary to a portion of the first adapter, or a complement thereof, and is not substantially complementary to a portion of the second adapter, or a complement thereof; and (c) amplifying the nucleic acid template by extending the primer using a strand-displacing polymerase, thereby generating an amplicon (e.g., a single-stranded amplicon) including a complement of the first and second strand of the double stranded nucleic acid. In embodiments, the amplicon is a contiguous strand of DNA that contains the first and second strand of the double-stranded nucleic acid. In embodiments, the amplicon is a continuous strand lacking free 5' and 3' ends. In embodiments, the amplicon is a single-stranded amplicon. In embodiments, after step (a) the method includes amplifying the nucleic acid template to generate a plurality of nucleic acid templates using a polymerase chain reaction.

In embodiments, amplifying the nucleic acid template is on a solid support including a plurality of primers attached to the solid support, wherein the plurality of primers include a plurality of forward primers with complementarity to a complement of the first strand of the Y adapter (e.g., the 5' arm portion) and a plurality of reverse primers with complementarity to the second strand of the Y adapter (e.g., the 3' arm portion), and the amplifying includes a plurality of cycles of strand denaturation, primer hybridization, and primer extension, thereby generating a plurality of forward amplicons and a plurality of reverse amplicons.

In embodiments, the plurality of forward primers are covalently attached to the solid support via a first linker and the reverse primers are covalently attached to the solid support via a second linker. The linker tethering the polynucleotide strands may be any linker capable of localizing nucleic acids to arrays. The linkers may be the same, or the linkers may be different. Solid-supported molecular arrays have been generated previously in a variety of ways, for example, the attachment of biomolecules (e.g., proteins and nucleic acids) to a variety of substrates (e.g., glass, plastics, or metals) underpins modern microarray and biosensor technologies employed for genotyping, gene expression analysis and biological detection. Silica-based substrates are often employed as supports on which molecular arrays are constructed, and functionalized silanes are commonly used to modify glass to permit a click-chemistry enabled linker to tether the biomolecule.

In embodiments, the method further includes removing the plurality of reverse amplicons, annealing a primer to the amplicon (e.g., the first amplicon), wherein the first primer includes a sequence that is complementary to a portion of the amplicon, or a complement thereof, and sequencing a portion of the first amplicon by extending the primer, thereby generating a sequencing read including a first nucleic acid sequence of at least a first portion of the double stranded nucleic acid. In embodiments, the method further includes removing the plurality of forward amplicons, annealing a primer to the amplicon (e.g., the first amplicon), wherein the first primer includes a sequence that is complementary to a portion of the first amplicon, or a complement thereof, and sequencing a portion of the first amplicon by extending the primer, thereby generating a sequencing read including a first nucleic acid sequence of at least a first portion of the double stranded nucleic acid.

In embodiments, amplifying includes incubation in a denaturant. In embodiments, the denaturant is acetic acid, ethylene glycol, hydrochloric acid, nitric acid, formamide, guanidine, sodium salicylate, sodium hydroxide, dimethyl sulfoxide (DMSO), propylene glycol, urea, or a mixture thereof. In embodiments, the denaturant is an additive that lowers a DNA denaturation temperature. In embodiments, the denaturant is betaine, dimethyl sulfoxide (DMSO), ethylene glycol, formamide, glycerol, guanidine thiocyanate, 4-methylmorpholine 4-oxide (NMO), or a mixture thereof. In embodiments, the denaturant is betaine, dimethyl sulfoxide (DMSO), ethylene glycol, formamide, glycerol, guanidine thiocyanate, or 4-methylmorpholine 4-oxide (NMO).

In embodiments, amplifying includes a plurality of cycles of strand denaturation, primer hybridization, and primer extension. Although each cycle will include each of these three events (denaturation, hybridization, and extension), events within a cycle may or may not be discrete. For example, each step may have different reagents and/or reaction conditions (e.g., temperatures). Alternatively, some steps may proceed without a change in reaction conditions. For example, extension may proceed under the same conditions (e.g., same temperature) as hybridization. After extension, the conditions are changed to start a new cycle with a new denaturation step, thereby amplifying the amplicons. Primer extension products from an earlier cycle may serve as templates for a later amplification cycle. In embodiments, the plurality of cycles is about 5 to about 50 cycles. In embodiments, the plurality of cycles is about 10 to about 45 cycles. In embodiments, the plurality of cycles is about 10 to about 20 cycles. In embodiments, the plurality of cycles is about 20 to about 30 cycles. In embodiments, the plurality of cycles is 10 to 45 cycles. In embodiments, the plurality of cycles is 10 to 20 cycles. In embodiments, the plurality of cycles is 20 to 30 cycles. In embodiments, the plurality of cycles is about 10 to about 45 cycles. In embodiments, the plurality of cycles is about 20 to about 30 cycles.

In some embodiments, an amplification method comprises attaching a nucleic acid template described herein to a substrate. In certain embodiments, attaching a nucleic acid template to a substrate comprises annealing a capture nucleic acid to a template. In some embodiments, a capture nucleic acid anneals to a complementary sequence that is present on an adapter portion of a template (e.g., a Y-adapter or hairpin adapter). In certain embodiments, a capture nucleic acid anneals to a primer binding site located on a Y-adapter portion of a template described herein. A capture nucleic acid may anneal to a portion of a Y-adapter on or near the 3'-end or 3'-side of a template. In some embodiments, a capture nucleic acid anneals to a 3'-arm of a Y-adapter on a template.

Figure 6A:
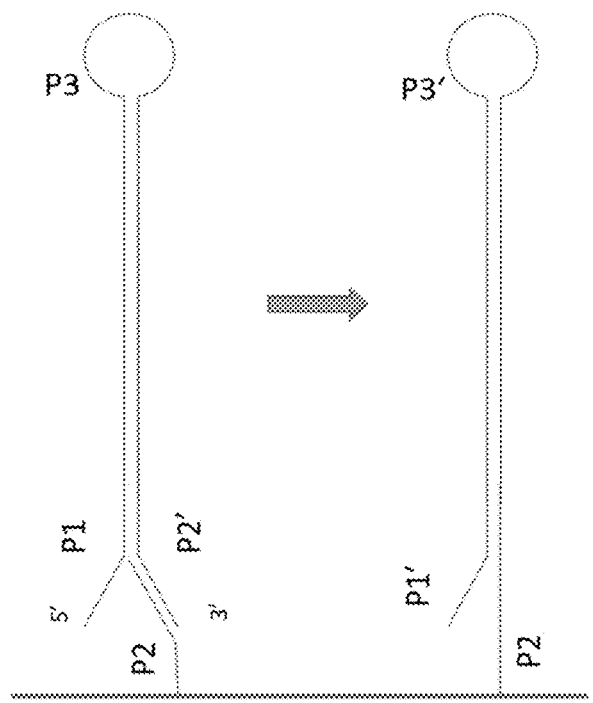
FIGS. 6A-6B show an overview of an embodiment of an amplification method.
Figure 6B:
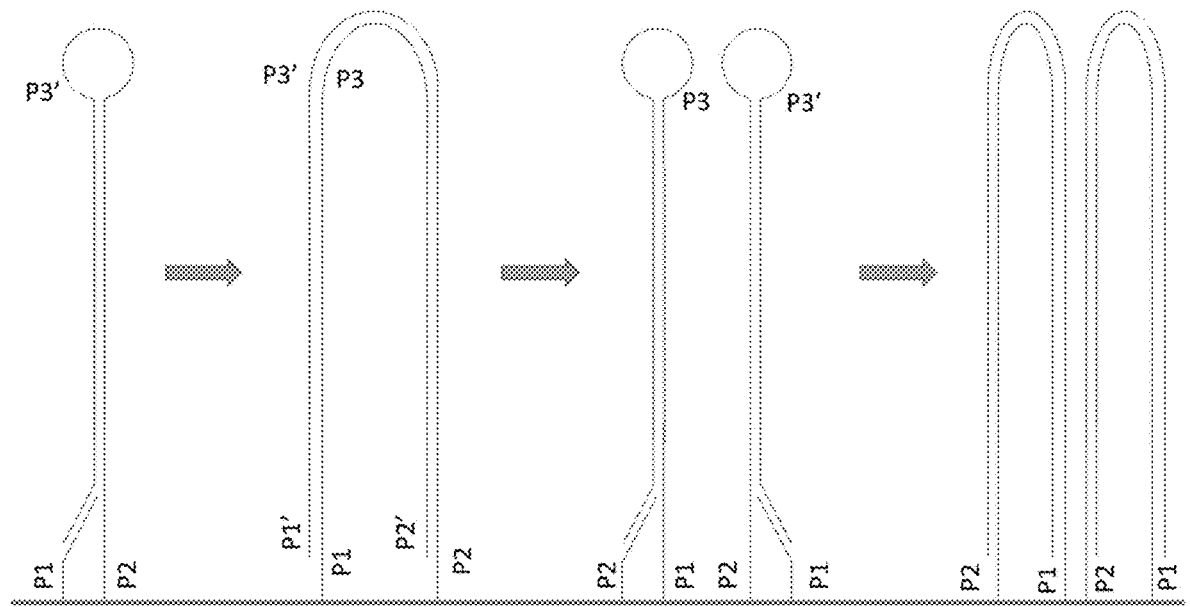

In embodiments, the nucleic acid template is provided in a clustered array. In embodiments, the clustered array includes a plurality of amplicons localized to discrete sites on a solid support. In embodiments, the solid support is a bead. In embodiments, the solid support is substantially planar. In embodiments, the solid support is contained within a flow cell. Flow cells provide a convenient format for housing an array of clusters produced by the methods described herein, in particular when subjected to an SBS or other detection technique that involves repeated delivery of reagents in cycles. For example, to initiate a first SBS cycle, one or more labeled nucleotides and a DNA polymerase in a buffer, can be flowed into/through a flow cell that houses an array of clusters. The clusters of an array where primer extension causes a labeled nucleotide to be incorporated can then be detected. Optionally, the nucleotides can further include a reversible termination moiety that temporarily halts further primer extension once a nucleotide has been added to a primer. For example, a nucleotide analog having a reversible terminator moiety can be added to a primer such that subsequent extension cannot occur until a deblocking agent (e.g., a reducing agent) is delivered to remove the moiety. Thus, for embodiments that use reversible termination, a deblocking reagent (e.g., a reducing agent) can be delivered to the flow cell (before, during, or after detection occurs). Washes can be carried out between the various delivery steps as needed. The cycle can then be repeated N times to extend the primer by N nucleotides, thereby detecting a sequence of length N. Example SBS procedures, fluidic systems and detection platforms that can be readily adapted for use with an array produced by methods of the present disclosure are described, for example, in Bentley et al., Nature 456:53-59 (2008), US Patent Publication 2018/0274024, WO 2017/205336, US Patent Publication 2018/0258472, each of which are incorporated herein in their entirety for all purposes In some embodiments, an amplification method comprises annealing a primer or capture nucleic acid to a portion of a Y-adapter on or near a 3'-end of a template, and extending the primer using a polymerase, thereby generating a first amplicon (first copy) of the template. In certain embodiments, a 3'-end of the first amplicon is annealed to another primer or capture nucleic acid, which is then extended to generate a second amplicon. The amplification process continues until a plurality of first amplicons (e.g., a set of first amplicons) and a plurality of second amplicons (e.g., a set of second amplicons) are generated. An exemplary bridge amplification process is shown in FIGS. 6A and 6B. In embodiments, a bridge PCR amplification method produces a first set of amplicons that are complementary to an original template, and a second set of amplicons that have nucleic acid sequences substantially identical to the original template, where both the first and second sets of amplicons are attached to a substrate (e.g., a substrate of a flow cell). After bridge amplification, in certain embodiments, the first set of amplicons, or alternatively the second set of amplicons, are removed from a surface or substrate using a suitable method, usually by restriction enzyme cleavage (e.g., see FIG. 7A where the X indicates a restriction enzyme cleavage site). Cleaving one strand may be referred to as linearization. Suitable methods for linearization are known, and described in more detail in U.S. Patent Publication No. 2009/0118128, which is incorporated herein by reference in its entirety. For example, the first strand may be cleaved by exposing the first strand to a mixture containing a glycosylase and one or more suitable endonucleases. In embodiments, cleaving includes chemically cleaving one strand at a cleavable site. In embodiments, the cleavable site includes a diol linker, disulfide linker, photocleavable linker, abasic site, deoxyuracil triphosphate (dUTP), deoxy-8-Oxo-guanine triphosphate (d-8-oxoG), methylated nucleotide, ribonucleotide, or a sequence containing a modified or unmodified nucleotide that is specifically recognized by a cleaving agent.

Any suitable enzymatic, chemical, or photochemical cleavage reaction may be used to cleave the cleavage site. The cleavage reaction may result in removal of a part or the whole of the strand being cleaved. Suitable cleavage means include, for example, restriction enzyme digestion, in which case the cleavage site is an appropriate restriction site for the enzyme which directs cleavage of one or both strands of a duplex template; RNase digestion or chemical cleavage of a bond between a deoxyribonucleotide and a ribonucleotide, in which case the cleavage site may include one or more ribonucleotides; chemical reduction of a disulfide linkage with a reducing agent (e.g., THPP or TCEP), in which case the cleavage site should include an appropriate disulfide linkage; chemical cleavage of a diol linkage with periodate, in which case the cleavage site should include a diol linkage; generation of an abasic site and subsequent hydrolysis, etc. In embodiments, the cleavage site is included in the surface immobilized primer (e.g., within the polynucleotide sequence of the primer). In embodiments, one strand of the double-stranded amplification product (or the surface immobilized primer) may include a diol linkage which permits cleavage by treatment with periodate (e.g., sodium periodate). It will be appreciated that more than one diol can be included at the cleavage site. One or more diol units may be incorporated into a polynucleotide using standard methods for automated chemical DNA synthesis. Polynucleotide primers including one or more diol linkers can be conveniently prepared by chemical synthesis. The diol linker is cleaved by treatment with any substance which promotes cleavage of the diol (e.g., a diol-cleaving agent). In embodiments, the diol-cleaving agent is periodate, e.g., aqueous sodium periodate (NaIO4). Following treatment with the diol-cleaving agent (e.g., periodate) to cleave the diol, the cleaved product may be treated with a "capping agent" in order to neutralize reactive species generated in the cleavage reaction. Suitable capping agents for this purpose include amines, e.g., ethanolamine or propanolamine.

Figure 18A:
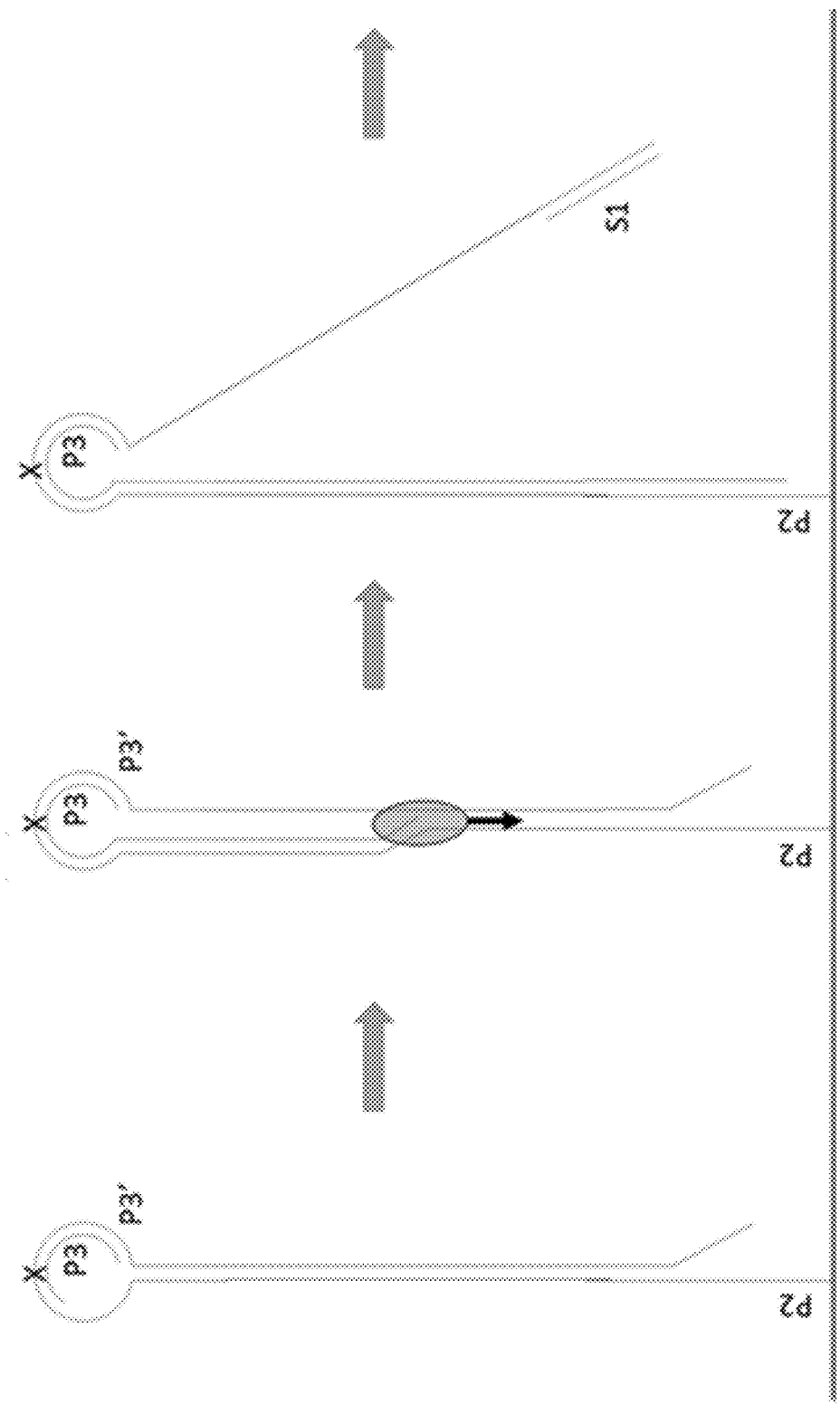
FIGS. 18A-18B. An illustration depicting generating a blocking strand to allow for sequencing two strands of a template nucleic acid.
Figure 18B:
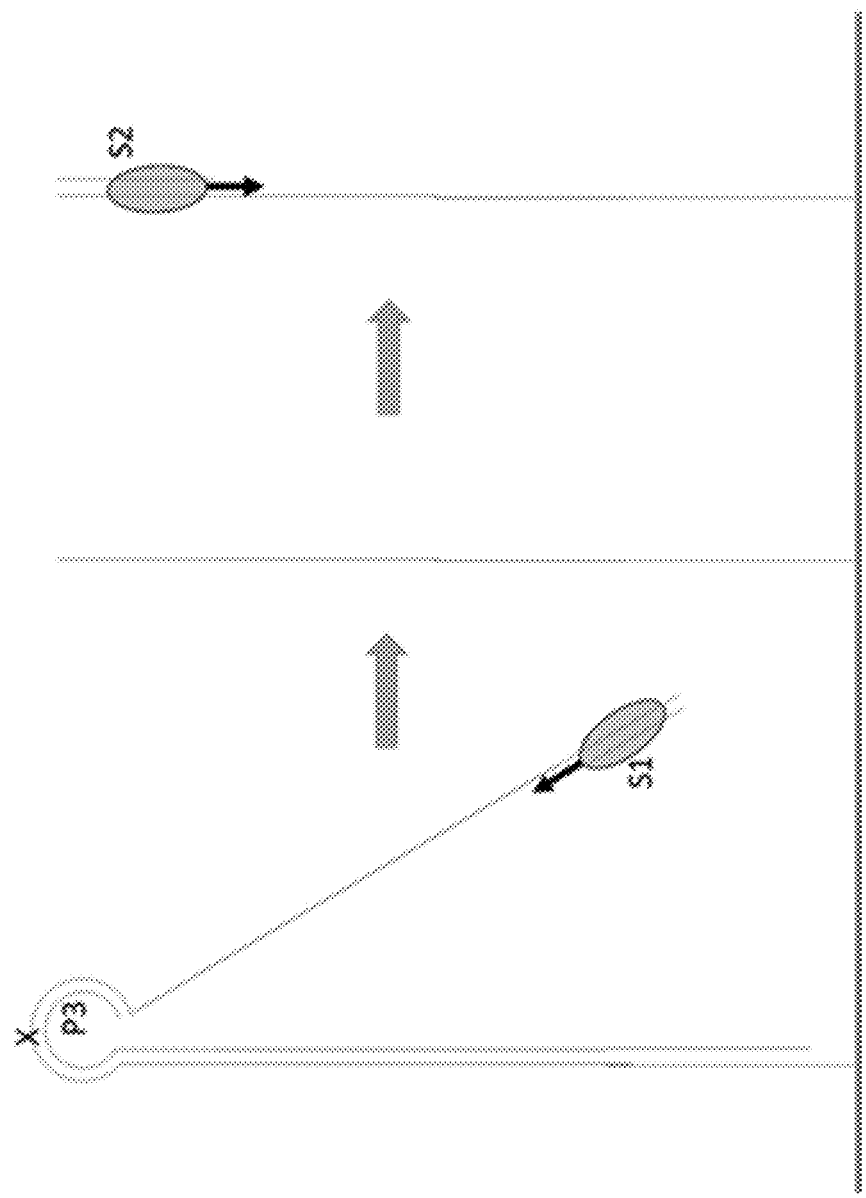
Figure 19A:
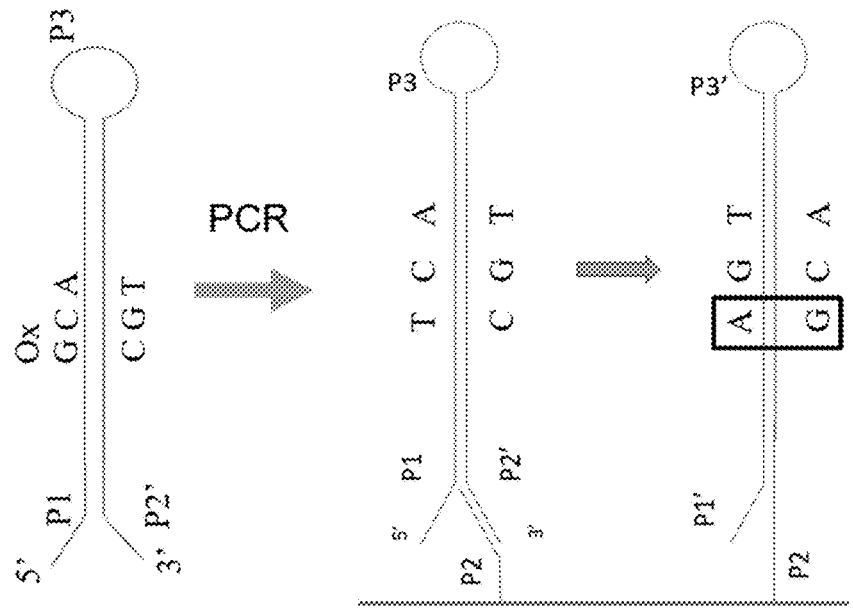
FIGS. 19A-19D show an overview of an embodiment of an amplification method for true somatic variant detection of an oxidative damage-containing (e.g., 8-oxo-dG) adapter-target-adapter construct.
Figure 19B:
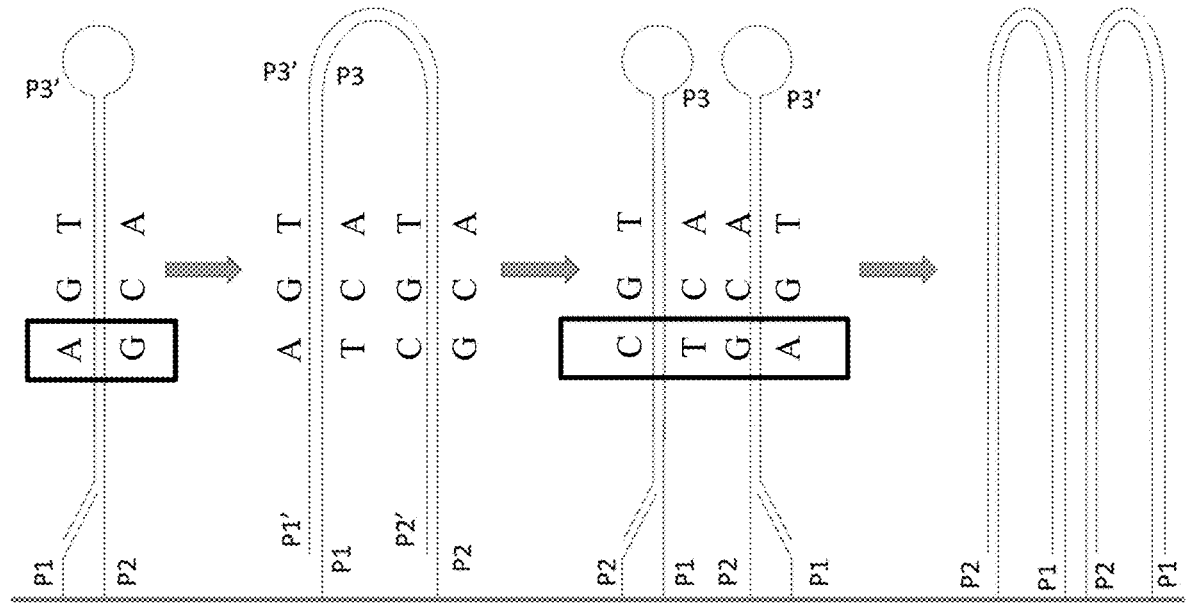
Figure 19C:
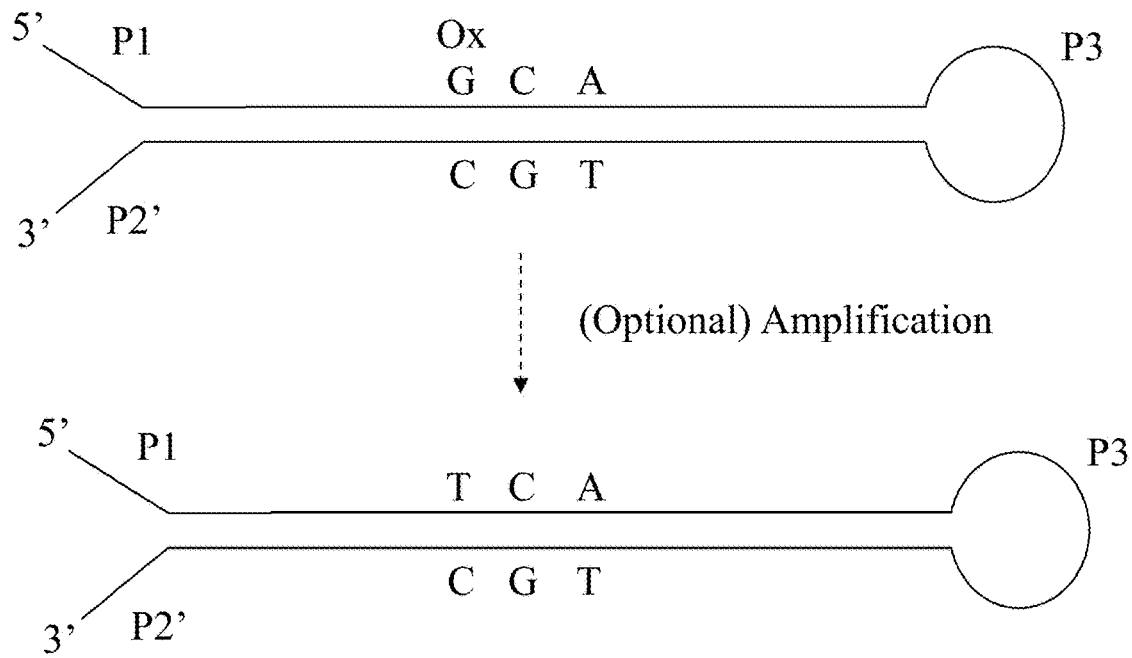
Figure 19D:
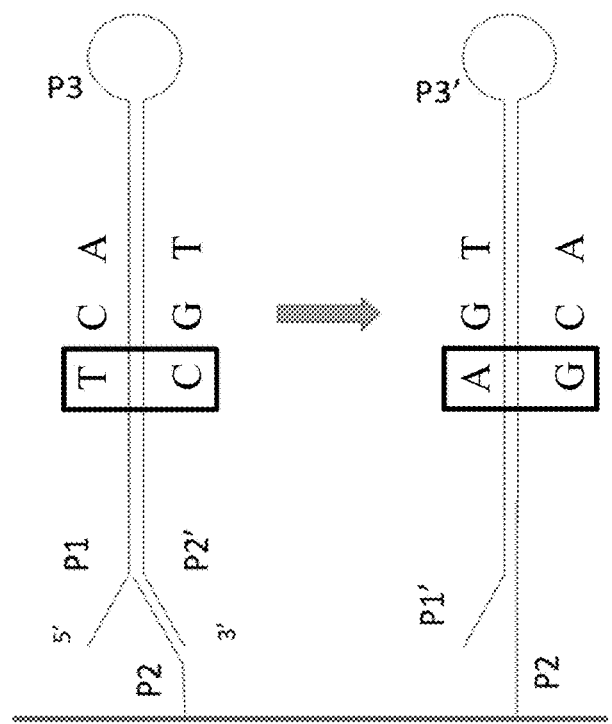

In another aspect is provided a method of sequencing a first portion and a second portion of a double-stranded nucleic acid, the method including (a) ligating a first adapter to a first end of the double stranded nucleic acid, and ligating a second adapter to a second end of the double stranded nucleic acid, wherein the second adapter is a hairpin adapter, thereby forming a nucleic acid template; (b) displacing at least a portion of one strand of the nucleic acid template by annealing a blocking primer to the nucleic acid template and extending the blocking primer to generate a blocking strand, wherein the blocking primer comprises a sequence within a loop of the hairpin adapter, or a complement thereof; (c) annealing a first sequencing primer to the nucleic acid template and sequencing a first portion of the nucleic acid template by extending the first sequencing primer, thereby generating a first read comprising a first nucleic acid sequence of at least a first portion of the double stranded nucleic acid, wherein the first sequencing primer comprises a sequence that is complementary to a portion of the first adapter; and (d) annealing a second sequencing primer to the nucleic acid template and sequencing a second portion of the nucleic acid template by extending the second sequencing primer, thereby generating a second read comprising a second nucleic acid sequence of at least a second portion of the double stranded nucleic acid, wherein the second sequencing primer comprises a sequence that is complementary to a sequence within a loop of the hairpin adapter, or a complement thereof. See FIGS. 18A-18B for an overview of the process. In embodiments, the second adapter includes a cleavable site. In embodiments, the blocking strand is removed prior to step d). In embodiments, the extended sequencing primer from step c) is removed prior to step d). The blocking strand may remain during the first sequencing read, and may be removed prior to starting the second sequencing read. In embodiments, following step a) the nucleic acid template is amplified. In embodiments, the method further includes amplifying the nucleic acid template. In embodiments, step c) includes annealing a second primer to the nucleic acid template, wherein the second primer includes a sequence that is complementary to a sequence within a loop of the hairpin adapter, or a complement thereof. In embodiments, sequencing the first portion and a second portion of a double-stranded nucleic acid is on a solid support (e.g., a polymer coated solid support). In embodiments, sequencing the first portion and a second portion of a double-stranded nucleic acid is on a solid support including a plurality of primers attached to said solid support, wherein the plurality of primers include a plurality of forward primers with complementarity to a complement of the first strand of the Y adapter and a plurality of reverse primers with complementarity to the second strand of the Y adapter In embodiments, the method includes removing immobilized primers that do not contain a first or second strand of the nucleic acid template (i.e., unused primers) on a solid support. Methods of removing immobilized primers can include digestion using an enzyme with exonuclease activity. Removing unused primers may serve to increase the free volume and allow for greater accessibility. Removal of unused primers may also prevent opportunities for the newly released first strand to rehybridize to an available surface primer, producing a priming site off the available surface primer, thereby facilitating the "reblocking" of the released first strand.

In embodiments, generating the blocking strand includes a plurality of blocking primer extension cycles. In embodiments, generating the blocking strand includes extending the blocking primer by incorporating one or more nucleotides (e.g., dNTPs) using Bst large fragment (Bst LF) polymerase, Bst2.0 polymerase, Bsu polymerase, SD polymerase, Vent exo-polymerase, Phi29 polymerase, or a mutant thereof.

After removal of one of the sets of amplicons from the substrate, the other remaining set of substrate-attached amplicons is subjected to sequencing by annealing a first sequencing primer at the 3'-end (3'-region) of each of the amplicons (formerly a portion of the Y-adapter), and extending the first primer to obtain a sequence read of a 3' portion of each of the amplicons, which comprises a sequence of a first strand of the original double stranded insert. Before, during or after obtaining a sequence read of the 3'-portion of the amplicons, a second primer is annealed to the loop of each of the set of amplicons (i.e., the loop portion of the hairpin adapter used to make the template) and the second primer is used to obtain a second sequence read of a second portion of the amplicon, which comprises a sequence of the opposite strand of the original doubled stranded insert. The process described above obtains a sequence read of both strands of the original double stranded nucleic acid insert from a single set of substantially identical amplicons. In some embodiments, sequencing method is complete at this stage and does not require another amplification step. Traditional methods of paired-end sequencing that utilize bridge amplification require a first amplification to obtain a first read of one strand of an insert followed by a second amplification to obtain a second read of the other strand of an insert. The required second amplification step of traditional method introduces a substantial amount of error in the sequencing reads obtained after the second amplification. The methods described herein, in certain embodiments, do not require a second amplification step and therefore provide for less error in the sequence reads obtained. Accordingly, in some embodiments, a method of sequencing both strands of a double stranded nucleic acid, as described herein, comprises, or consists essentially of, generating a first read and a second read from the same template. In some embodiments, a method of sequencing both strands of a double stranded nucleic acid, as described herein, comprises, or consists essentially of, generating a first read and a second read from a set of amplicons that are substantially complementary to a nucleic acid template. In some embodiments, a method of sequencing both strands of a double stranded nucleic acid, as described herein, comprises, or consists essentially of, generating a first read and a second read from a set of amplicons that are substantially identical to a nucleic acid template.

In certain embodiments, a sequencing method provided herein comprises sequencing both strands of a double stranded nucleic acid with an error rate of $5 \times 10^{-5}$ or less, $1 \times 10^{-5}$ or less, $5 \times 10^{-6}$ or less, $1 \times 10^{-6}$ or less, $5 \times 10^{-7}$ or less, $1 \times 10^{-7}$ or less, $5 \times 10^{-8}$ or less, or $1 \times 10^{-8}$ or less. In certain embodiments, a sequencing method provided herein comprises sequencing both strands of a double stranded nucleic acid with an error rate of $5 \times 10^{-5}$ to $1 \times 10^{-8}$, $1 \times 10^{-5}$ to $1 \times 10^{-8}$, $5 \times 10^{-5}$ to $1 \times 10^{-7}$, $1 \times 10^{-5}$ to $1 \times 10^{-7}$, $5 \times 10^{-6}$ to $1 \times 10^{-8}$, or $1 \times 10^{-6}$ to $1 \times 10^{-8}$. In certain embodiments, a sequencing method provided herein comprises sequencing both strands of a double stranded nucleic acid with an error rate of or $1 \times 10^{-6}$ to $1 \times 10^{-8}$. In certain embodiments, a sequencing method provided herein comprises sequencing both strands of a double stranded nucleic acid with an error rate of $1 \times 10^{-4}$ to $1 \times 10^{-6}$. In certain embodiments, a sequencing method provided herein comprises sequencing both strands of a double stranded nucleic acid with an error rate of $1 \times 10^{-3}$ or less. In embodiments, a sequencing method provided herein comprises sequencing both strands of a double stranded nucleic acid with an error rate of $1 \times 10^{-4}$ or less. In embodiments, a sequencing method provided herein comprises sequencing both strands of a double stranded nucleic acid with an error rate of $1 \times 10^{-5}$ or less. In embodiments, a sequencing method provided herein comprises sequencing both strands of a double stranded nucleic acid with an error rate of $1 \times 10^{-6}$ or less. In embodiments, a sequencing method provided herein comprises sequencing both strands of a double stranded nucleic acid with an error rate of $1 \times 10^{-7}$ or less. In embodiments, a sequencing method provided herein comprises sequencing both strands of a double stranded nucleic acid with an error rate of $1 \times 10^{-8}$ or less.

Optionally, after obtaining sequences of both the first strand and second strand of the original double stranded insert from a single set of substantially identical amplicons (e.g., the first set of amplicons) attached to the substrate, a copy of each of the amplicons is generated by a process comprising annealing the free 3'-end of each amplicon to a surface-bound capture nucleic acid, extending the capture nucleic acid with a polymerase to generate third set of amplicons, removing the first set of amplicons from the substrate, and sequencing the third set of amplicons. In certain embodiments, the novel methods provided herein do not require this second amplification step which introduces additional error into the sequence reads obtained from the third set of amplicons.

In certain embodiments, templates or amplicons described herein are attached to addressable locations on a substrate using a suitable method known in the art or described herein.

In embodiments where a template is generated using two hairpin adapters, a template can be amplified using a rolling circle amplification method (e.g., see FIG. 8 for an overview of an embodiment of a seeding and amplification process). In such embodiments, a template can be captured to a substrate and/or amplified using one or more capture nucleic acids that anneal to a loop region of one of the hairpin adapters. Captured templates or amplicons can be further sequenced by a method described herein.

In some embodiments, methods provided herein comprise sequencing a template nucleic acid or amplicon described herein. The methods of template preparation and nucleic acid sequencing described herein can be incorporated into a suitable sequencing technique, non-limiting examples of which include SMRT (single-molecule real-time sequencing), ion semiconductor, pyrosequencing, sequencing by synthesis, combinatorial probe anchor synthesis, and SOLiD sequencing (sequencing by ligation). Non-limiting sequencing platforms include those provided by Illumina® (e.g., the MiniSeq™, MiSeq™, NextSeq™, and/or NovaSeq™ sequencing systems); Ion Torrent™ (e.g., the Ion PGM™, Ion S5™, and/or Ion Proton™ sequencing systems); Pacific Biosciences (e.g., the PACBIO RS II and/or Sequel II System sequencing system); ThermoFisher (e.g., a SOLID® sequencing system); or BGI Genomics (e.g., DNBSeq™ sequencing systems). See, for example U.S. Pat. Nos. 7,211, 390; 7,244,559; 7,264,929; 6,255,475; 6,013,445; 8,882, 980; 6,664,079; and 9,416,409. In some embodiments, a sequencing method described herein does not comprise the use of SMRT sequencing or single-molecule sequencing.

In embodiments, the method includes sequencing the first and the second strand of a double-stranded template and/or amplification product by extending a sequencing primer hybridized thereto. A variety of sequencing methodologies can be used such as sequencing-by-synthesis (SBS), pyrosequencing, sequencing by ligation (SBL), or sequencing by hybridization (SBH). Pyrosequencing detects the release of inorganic pyrophosphate (PPi) as particular nucleotides are incorporated into a nascent nucleic acid strand (Ronaghi, et al., Analytical Biochemistry 242(1), 84-9 (1996); Ronaghi, Genome Res. 11(1), 3-11 (2001); Ronaghi et al. Science 281(5375), 363 (1998); U.S. Pat. Nos. 6,210,891; 6,258,568; and 6,274,320, each of which is incorporated herein by reference in its entirety). In pyrosequencing, released PPi can be detected by being converted to adenosine triphosphate (ATP) by ATP sulfurylase, and the level of ATP generated can be detected via light produced by luciferase. In this manner, the sequencing reaction can be monitored via a luminescence detection system. In both SBL and SBH methods, target nucleic acids, and amplicons thereof, that are present at features of an array are subjected to repeated cycles of oligonucleotide delivery and detection. SBL methods, include those described in Shendure et al. Science 309:1728-1732 (2005); U.S. Pat. Nos. 5,599,675; and 5,750, 341, each of which is incorporated herein by reference in its entirety; and the SBH methodologies are as described in Bains et al., Journal of Theoretical Biology 135(3), 303-7 (1988); Drmanac et al., Nature Biotechnology 16, 54-58 (1998); Fodor et al., Science 251(4995), 767-773 (1995); and WO 1989/10977, each of which is incorporated herein by reference in its entirety.

In SBS, extension of a nucleic acid primer along a nucleic acid template is monitored to determine the sequence of nucleotides in the template. The underlying chemical process can be catalyzed by a polymerase, wherein fluorescently labeled nucleotides are added to a primer (thereby extending the primer) in a template dependent fashion such that detection of the order and type of nucleotides added to the primer can be used to determine the sequence of the template. A plurality of different nucleic acid fragments that have been attached at different locations of an array can be subjected to an SBS technique under conditions where events occurring for different templates can be distinguished due to their location in the array. In embodiments, the sequencing step includes annealing and extending a sequencing primer to incorporate a detectable label that indicates the identity of a nucleotide in the target polynucleotide, detecting the detectable label, and repeating the extending and detecting steps. In embodiments, the methods include sequencing one or more bases of a target nucleic acid by extending a sequencing primer hybridized to a target nucleic acid (e.g., an amplification product produced by the amplification methods described herein). In embodiments, the sequencing step may be accomplished by a sequencing-by-synthesis (SBS) process. In embodiments, sequencing comprises a sequencing by synthesis process, where individual nucleotides are identified iteratively, as they are polymerized to form a growing complementary strand. In embodiments, nucleotides added to a growing complementary strand include both a label and a reversible chain terminator that prevents further extension, such that the nucleotide may be identified by the label before removing the terminator to add and identify a further nucleotide. Such reversible chain terminators include removable 3' blocking groups, for example as described in U.S. Pat. No. 10,738, 072 and Chen et al, Proteomics & Bioinformatics, V. 11, Issue 1, 2013, Pages 34-40, each of which are incorporated herein by reference. Once such a modified nucleotide has been incorporated into the growing polynucleotide chain complementary to the region of the template being sequenced, there is no free 3'-OH group available to direct further sequence extension and therefore the polymerase cannot add further nucleotides. Once the identity of the base incorporated into the growing chain has been determined, the 3' block may be removed to allow addition of the next successive nucleotide. By ordering the products derived using these modified nucleotides it is possible to deduce the DNA sequence of the DNA template. Non-limiting examples of suitable labels are described in U.S. Pat. Nos. 8,178,360, 5,188,934 (4,7-dichlorofluorscein dyes); U.S. Pat. No. 5,366,860 (spectrally resolvable rhodamine dyes); U.S. Pat. No. 5,847,162 (4,7-dichlororhodamine dyes); U.S. Pat. No. 4,318,846 (ether-substituted fluorescein dyes); U.S. Pat. No. 5,800,996 (energy transfer dyes); U.S. Pat. No. 5,066,580 (xanthene dyes): U.S. Pat. No. 5,688,648 (energy transfer dyes); and the like.

Sequencing includes, for example, detecting a sequence of signals. Examples of sequencing include, but are not limited to, sequencing by synthesis (SBS) processes in which reversibly terminated nucleotides carrying fluorescent dyes are incorporated into a growing strand, complementary to the target strand being sequenced. In embodiments, the nucleotides are labeled with up to four unique fluorescent dyes. In embodiments, the nucleotides are labeled with at least two unique fluorescent dyes. In embodiments, the readout is accomplished by epifluorescence imaging. A variety of sequencing chemistries are available, non-limiting examples of which are described herein.

III. Methods of Selectively Capturing and Methods of Selectively Sequencing

In an aspect is provided a method of selectively capturing a double-stranded nucleic acid. In embodiments, the method comprises (a) ligating a first adapter to a first end of the double-stranded nucleic acid, and ligating a second adapter to a second end of the double-stranded nucleic acid, wherein the second adapter is a hairpin adapter; (b) displacing at least a portion of one strand of the double-stranded nucleic acid from step (a); (c) hybridizing a probe oligonucleotide to the displaced portion of the double-stranded nucleic acid; (d) separating the probe-hybridized double-stranded nucleic acid from nucleic acids not hybridized to a probe. In embodiments, the method further includes amplifying double-stranded nucleic acid of step (d). The double-stranded nucleic acid of step (d) may be amplified by a suitable method to generate amplicons. For example, amplicons may be generated in solution. In some embodiments, amplifying includes solid phase nucleic acid amplification. In embodiments, the method of generating amplicons of the nucleic acid template includes a polymerase chain reaction. In embodiments, the polymerase chain reaction includes a bridge PCR or isothermal amplification method. In embodiments, the method further includes sequencing the amplicons.

In an aspect is provided a method of preparing a double-stranded nucleic acid for capture and/or sequencing. In embodiments, the method comprises (a) ligating a first adapter to a first end of the double-stranded nucleic acid, and ligating a second adapter to a second end of the double-stranded nucleic acid, wherein the second adapter is a hairpin adapter; (b) hybridizing a probe oligonucleotide to a loop of the hairpin adapter; and (c) extending the probe oligonucleotide with a polymerase.

In an aspect is provided a method of selectively capturing and enriching a region of a double-stranded nucleic acid. In embodiments, the method comprises (a) ligating a first adapter to a first end of the double-stranded nucleic acid, and ligating a second adapter to a second end of the double-stranded nucleic acid, wherein the second adapter is a hairpin adapter; (b) hybridizing a probe oligonucleotide to a loop of the hairpin adapter; (c) separating the probe-hybridized double-stranded nucleic acid from nucleic acids not hybridized to a probe; (d) amplifying probe-hybridized double-stranded nucleic acid of step (c) to generate double-stranded amplification products. In embodiments, the method further includes immobilizing the double-stranded amplification products on a solid support. In embodiments, the method includes providing a solid support including a plurality of immobilized oligonucleotide primers attached to the solid support via a linker, wherein the plurality of oligonucleotide primers include a plurality of forward primers and a plurality of reverse primers, amplifying the double-stranded amplification products of step (d) by using the oligonucleotide primers attached to the solid support to generate a plurality of double-stranded amplification products. In embodiments, generating a double-stranded amplification product includes bridge polymerase chain reaction (bPCR) amplification, solid-phase rolling circle amplification (RCA), solid-phase exponential rolling circle amplification (eRCA), solid-phase recombinase polymerase amplification (RPA), solid-phase helicase dependent amplification (HDA), template walking amplification, or emulsion PCR on particles, or combinations of the methods. In embodiments, generating a double-stranded amplification product includes a bridge polymerase chain reaction amplification. In embodiments, generating a double-stranded amplification product includes a thermal bridge polymerase chain reaction (t-bPCR) amplification. In embodiments, generating a double-stranded amplification product includes a chemical bridge polymerase chain reaction (c-bPCR) amplification. Chemical bridge polymerase chain reactions include fluidically cycling a denaturant (e.g., formamide) and maintaining the temperature within a narrow temperature range (e.g., +/−5° C.). In contrast, thermal bridge polymerase chain reactions include thermally cycling between high temperatures (e.g., 85° C.-95° C.) and low temperatures (e.g., 60° C.-70° C.). Thermal bridge polymerase chain reactions may also include a denaturant, typically at a much lower concentration than traditional chemical bridge polymerase chain reactions.

In embodiments, generating a double-stranded amplification product includes amplifying the template polynucleotide or complement thereof on a solid support including a plurality of primers attached to the solid support, wherein the plurality of primers include a plurality of forward primers with complementarity to the template polynucleotide and a plurality of reverse primers with complementarity to a complement of the template polynucleotide, and the amplifying includes a plurality of cycles of strand denaturation, primer hybridization, and primer extension.

In an aspect is provided a method of selectively capturing and enriching a region of a double-stranded nucleic acid. In embodiments, the method comprises (a) ligating a first adapter to a first end of the double-stranded nucleic acid, and ligating a second adapter to a second end of the double-stranded nucleic acid, wherein the second adapter is a hairpin adapter; (b) displacing at least a portion of one strand of the double-stranded nucleic acid from step (a); (c) hybridizing a probe oligonucleotide to the displaced portion of the double-stranded nucleic acid; (d) extending the probe oligonucleotide with a polymerase. In embodiments, the probe oligonucleotide acts as a primer. In embodiments, both the first and second adapter are hairpin adapters and extending the primer with a polymerase includes rolling circle amplification (RCA) (see, e.g., Lizardi et al., Nat. Genet. 19:225-232 (1998), which is incorporated herein by reference in its entirety). Several suitable RCA methods are known in the art. For example, RCA amplifies circular DNA by polymerase extension of an amplification primer complementary to a portion of the template polynucleotide. This process generates copies of the circular DNA template such that multiple copies of a DNA sequence arranged end to end in tandem are generated (i.e., a concatemer). In embodiments, extending the primer with a polymerase includes exponential rolling circle amplification (eRCA). Exponential RCA is similar to the linear process except that it uses a second primer of identical sequence to the DNA circle (Lizardi et al. Nat. Genet. 19:225 (1998)). This two-primer system achieves isothermal, exponential amplification. Exponential RCA has been applied to the amplification of non-circular DNA through the use of a linear probe that binds at both of its ends to contiguous regions of a target DNA followed by circularization using DNA ligase (Nilsson et al. Science 265(5181):208 5 (1994)). In embodiments, the probe oligonucleotide hybridizes within a loop of the first hairpin adapter. In embodiments, the probe oligonucleotide hybridizes within a loop of the second hairpin adapter.

In embodiments, the probe oligonucleotide contains a sequence capable of hybridizing to a mutated sequence (i.e., a hotspot sequence) as identified in Catalogue of Somatic Mutations In Cancer (COSMIC), full-length genes, copy number genes, single nucleotide polymorphisms (SNPs), or inter- and intragenic gene fusions. In embodiments, the probe oligonucleotide contains a sequence capable of hybridizing to a region of interest, such as a gene associated with cancer (e.g., lung, colon, breast, ovarian, melanoma, or prostate cancer) see for example Simen B B, Arch Pathol Lab Med; 139(4):508-517 (2015) or Singh R R, J Mol Diagn. September; 15(5):607-22 (2013); a gene associated with a disease (e.g., retinopathy, epilepsy, immunodeficiency, cardiomyopathy, hearing loss, muscular dystrophy, aneuploidy), see for example S. Yohe et al. Vol. 139, No. 2, pp. 204-210 (2015) or Rehm H L. Nat Rev Genet. 14(4): 295-300 (2013); or a gene associated with persisting pain (see for example Kringel et al. Front. Pharmacol. V9 Art. 1008 2018).

In embodiments, the probe oligonucleotide includes a sequence capable of hybridizing to an oncogene and/or tumor suppressor gene sequence, or a portion thereof. Non-limiting examples of oncogenes and tumor suppressor genes include the ABL1 gene, AKT1 gene, ALK gene, APC gene, ATM gene, BRAF gene, BRCA gene, CDH1 gene, CDKN2A gene, CSF1R gene, CTNNB1 gene, EGFR gene, ERBB2 gene, ERBB4 gene, EZH2 gene, FBXW7 gene, FGFR1 gene, FGFR2 gene, FGFR3 gene, FLT3 gene, GNA11 gene, GNAQ gene, GNAS gene, HNF1A gene, HRAS gene, IDH1 gene, IDH2 gene, JAK2 gene, JAK3 gene, KDR gene, KIT gene, KRAS gene, MET gene, MLH1 gene, MPL gene, NOTCH1 gene, NPM1 gene, NRAS gene, PDGFRA gene, PIK3CA gene, PTEN gene, PTPN11 gene, RB1 gene, RET gene, SMAD4 gene, SMARCB1 gene, SMO gene, SRC gene, STK11 gene, TP53 gene, VHL gene, or a portion thereof.

In embodiments, the method comprises (a) ligating a first adapter to a first end of the double-stranded nucleic acid, and ligating a second adapter to a second end of the double-stranded nucleic acid, wherein the second adapter is a hairpin adapter; (b) displacing at least a portion of one strand of the double-stranded nucleic acid from step (a); (c) hybridizing a probe oligonucleotide to the displaced portion of the double-stranded nucleic acid; (d) separating the probe-hybridized double-stranded nucleic acid from nucleic acids not hybridized to a probe; and (e) sequencing the probe-hybridized double-stranded nucleic acid of step (d).

In some embodiments, a double stranded nucleic comprises two complementary nucleic acid strands. In certain embodiments, a double stranded nucleic acid comprises a first strand and a second strand which are complementary or substantially complementary to each other. A first strand of a double stranded nucleic acid is sometimes referred to herein as a forward strand and a second strand of the double stranded nucleic acid is sometime referred to herein as a reverse strand. In some embodiments, a double stranded nucleic acid comprises two opposing ends. Accordingly, a double stranded nucleic acid often comprises a first end and a second end. An end of a double stranded nucleic acid may comprise a 5'-overhang, a 3'-overhang or a blunt end. In some embodiments, one or both ends of a double stranded nucleic acid are blunt ends. In certain embodiments, one or both ends of a double stranded nucleic acid are manipulated to include a 5'-overhang, a 3'-overhang or a blunt end using a suitable method. In some embodiments, one or both ends of a double stranded nucleic acid are manipulated during library preparation such that one or both ends of the double stranded nucleic acid are configured for ligation to an adapter using a suitable method. For example, one or both ends of a double stranded nucleic acid may be digested by a restriction enzyme, polished, end-repaired, filled in, phosphorylated (e.g., by adding a 5'-phosphate), dT-tailed, dA-tailed, the like or a combination thereof.

In some embodiments, a method herein comprises ligating one or more adapters to a double stranded nucleic acid. In some embodiments, a method herein comprises ligating one or more adapters to a plurality of double stranded nucleic acids. In some embodiments, a method herein comprises ligating a first adapter to a first end of a double stranded nucleic acid, and ligating a second adapter to a second end of a double stranded nucleic acid. In some embodiments, the first adapter and the second adapter are different. For example, in certain embodiments, the first adapter and the second adapter may comprise different nucleic acid sequences or different structures. In some embodiments, the first adapter is a Y-adapter and the second adapter is a hairpin adapter. In some embodiments, the first adapter is a hairpin adapter and a second adapter is a hairpin adapter. In certain embodiments, the first adapter and the second adapter may comprise different primer binding sites, different structures, and/or different capture sequences (e.g., a sequence complementary to a capture nucleic acid). In some embodiments, some, all or substantially all of the nucleic acid sequence of a first adapter and a second adapter are the same. In some embodiments, some, all or substantially all of the nucleic acid sequence of a first adapter and a second adapter are substantially different.

In embodiments, the first adapter is a first adapter as described with respect to other aspects disclosed herein, including with respect to methods of sequencing described above (such as a Y-adapter or a hairpin adapter described above).

In embodiments, the second adapter is a second adapter as described with respect to other aspects disclosed herein, including with respect to methods of sequencing described above (such as a hairpin adapter described above).

In embodiments, a hairpin structure is formed by joining the ends of a Y-adapter after ligation to a double-stranded nucleic acid. For example, in embodiments disclosed herein relating to ligation to a hairpin adapter, ligation may instead be to a Y-adapter, followed by ligation of the unpaired ends of the adapter to each other. For example, the two unpaired arms may be hybridized to a splint oligonucleotide that brings the ends of the unpaired arms in proximity, which are then ligated with a ligase.

In embodiments, the Y-adaptor portion of a Y-adaptor-ligated double-stranded nucleic acid is formed from cleavage in the loop of a hairpin adapter. For example, in embodiments disclosed herein relating to ligation to a Y-adapter, ligation may instead be to a hairpin adapter, followed by cleavage within the loop of the hairpin adapter to release two unpaired ends. In embodiments, a hairpin adapter comprises one or more uracil nucleotide(s) in the loop, and cleavage in the loop may be accomplished by the combined activities of Uracil DNA glycosylase (UDG) and the DNA glycosylase-lyase Endonuclease VIII. UDG cleaves the glycosidic bond between the deoxyribose of the DNA sugar-phosphate backbone and the uracil base, and Endonuclease VIII cleaves the AP site, effectively cleaving the loop. In embodiments, the hairpin adapter includes a recognition sequence for a compatible restriction enzyme. In embodiments, the hairpin adapter includes one or more ribonucleotides and cleavage in the loop is accomplished by RNase H.

In embodiments, the first adapter is a Y-adapter, and the displacing at least a portion of one strand of the double-stranded nucleic acid comprises: (i) hybridizing a primer to a single-stranded portion of the Y-adapter, and (ii) in a primer extension reaction, extending the primer with a strand-displacing polymerase that terminates extension within a loop of the hairpin adapter at a terminating nucleotide.

In embodiments, the first adapter is a hairpin adapter, and the displacing at least a portion of one strand of the double-stranded nucleic acid comprises: (i) hybridizing a primer within a loop of the first hairpin adapter, and (ii) in a primer extension reaction, extending the primer with a strand-displacing polymerase that terminates extension within a loop of the second hairpin adapter at a terminating nucleotide.

In embodiments, the terminating nucleotide comprises a removable group that blocks progression of the strand-displacing polymerase, and further wherein the terminating nucleotide is treated to release the removable group prior to sequencing. Any of a variety of suitable modifications capable of terminating strand extensions may be used. In general, the terminating nucleotide is the nucleotide position that is modified to inhibit strand extension. The terminating nucleotide may or may not be a nucleotide analogue. Thus, a terminating nucleotide is not necessarily chemically modified. For example, a terminating nucleotide may be a naturally occurring nucleotide, but is bound by another factor that inhibits strand extension (such as a sequence-specific binding protein). Any of a variety of suitable chemical modifications and blocking groups may be used. In embodiments, the terminating nucleotide is a nucleotide analog. Non-limiting examples include C3'-modifications, C2'-modifications, and phosphorodithioates.

In embodiments, the removable group is a polymer or a protein joined to the terminating nucleotide by a cleavable linker. In embodiments, the removable group is a polymer, such as a dendrimer. Non-limiting examples of polymers include PEG, polyethyleneimine, and poly(amidoamine). In embodiments, the protein is a bovine serum albumin (BSA).

In embodiments, the removable group is a protein that is non-covalently complexed to the terminating nucleotide, and further wherein releasing the protein comprises a change in reaction conditions to disrupt the complex. The nature of the change in reaction conditions will depend on the nature of the protein complexed to the terminating nucleotide. In embodiments, the change in reaction conditions includes a change in temperature. In embodiments, the change in reaction conditions includes a change in buffer conditions, such as an increase in salt concentration. In embodiments, the change in reactions conditions includes the addition of another agent that competes with, inhibits, or degrades the protein.

In embodiments, the protein is a first member of a binding pair complexed with a second member of the binding pair that is linked to the terminating nucleotide. In embodiments, the protein is a single-stranded binding protein that recognizes a sequence within the loop of the hairpin adapter. In embodiments, the binding pair is a binding pair as described with respect to other aspects disclosed herein, including with respect to methods of sequencing described above.

In embodiments, the terminating nucleotide is a first nucleotide analog that base pairs with a second nucleotide analog, and the second nucleotide analog is not present in the primer extension reaction, such that primer extension terminates.

In embodiments, the terminating nucleotide is an RNA nucleotide.

In embodiments, the first adapter is a Y-adapter, and the displacing at least a portion of one strand of the double-stranded nucleic acid comprises: (i) hybridizing a primer within a loop of the hairpin adapter, and (ii) in a primer extension reaction, extending the primer with a strand-displacing polymerase to generate a blocking strand. With the formation of a double-stranded product, that is, wherein one strand is hybridized to a blocking strand, the other strand is single stranded and available for capture (e.g., hybridizing to a surface-bound complementary oligonucleotide) and/or sequencing. For example, see FIG. 18 for an overview of an illustrative process.

In embodiments, generating the blocking strand includes extending the invasion primer by incorporating one or more nucleotides (e.g., dNTPs) using Bst large fragment (Bst LF) polymerase, Bst2.0 polymerase, Bsu polymerase, SD polymerase, Vent exo-polymerase, Phi29 polymerase, or a mutant thereof. In embodiments, the primer is about 10 to 100 nucleotides in length. In embodiments, the primer is about 15 to about 75 nucleotides in length. In embodiments, the primer is about 25 to about 75 nucleotides in length. In embodiments, the primer is about 15 to about 50 nucleotides in length. In embodiments, the primer is about 10 to about 20 nucleotides in length.

In embodiments, the reaction conditions for the extension cycles include incubation in a denaturant. In embodiments, the denaturant is a buffered solution including betaine, dimethyl sulfoxide (DMSO), ethylene glycol, formamide, glycerol, guanidine thiocyanate, 4-methylmorpholine 4-oxide (NMO), or a mixture thereof. In embodiments, the denaturant is a buffered solution including betaine, dimethyl sulfoxide (DMSO), ethylene glycol, formamide, or a mixture thereof. In embodiments, the denaturant is a buffered solution including about 0% to about 50% dimethyl sulfoxide (DMSO); about 0% to about 50% ethylene glycol; about 0% to about 20% formamide; or about 0 to about 3M betaine, or a mixture thereof. In embodiments, the reaction conditions include incubation in a denaturant, wherein the denaturant is a buffered solution including about 15% to about 50% dimethyl sulfoxide (DMSO); about 15% to about 50% ethylene glycol; about 10% to about 20% formamide; or about 0 to about 3M betaine, or a mixture thereof.

In embodiments, the first adapter is a hairpin adapter, and the displacing at least a portion of one strand of the double-stranded nucleic acid comprises: (i) hybridizing a primer within a loop of the hairpin adapter, and (ii) in a primer extension reaction, extending the primer with a strand-displacing polymerase. In embodiments, the first adapter hairpin is the same as the second adapter hairpin. In embodiments, the first adapter hairpin is different from the second adapter hairpin.

In embodiments, the displacing at least a portion of one strand of the double-stranded nucleic acid comprises (i) forming a complex comprising a portion of the double-stranded nucleic acid, a primer, and a homologous recombination complex comprising a recombinase, (ii) releasing the recombinase, and (iii) in a primer extension reaction, extending the primer with a strand-displacing polymerase. In embodiments, the complex comprises a helicase-polymerase fusion protein, such as DNA polymerase theta.

Non-limiting examples are described by Newman et al., Structure, 2015, Dec. 1, 23(12), 2319-2330; and Guilliam et al., Nucleic Acids Res., 2015, Aug. 18, 43(14), 6651-64; which are incorporated herein by reference.

In embodiments, the displacing at least a portion of one strand of the double-stranded nucleic acid comprises forming a complex comprising a portion of the double-stranded nucleic acid, the probe oligonucleotide, and a homologous recombination complex comprising a recombinase, and the step of hybridizing the probe oligonucleotide comprises releasing the recombinase.

In embodiments, the homologous recombination complex further comprises a loading factor, a single-stranded binding (SSB) protein, or both. In embodiments, the recombinase reaction further includes a crowding factor, such as a dextran and PET, and ATP. In embodiments, the crowding factor includes poly(ethylene glycol) (PEG), polyvinylpyrrolidone (PVP), bovine serum albumin (BSA), dextran, Ficoll (e.g., Ficoll 70 or Ficoll 400), glycerol, or a combination thereof. In embodiments, the crowding agent is poly(ethylene glycol) (e.g., PEG 200, PEG 600, PEG 800, PEG 2,050, PEG 4,600, PEG 6,000, PEG 8,000, PEG 10,000, PEG 20,000, or PEG 35,000), dextran sulfate, bovine pancreatic trypsin inhibitor (BPTI), ribonuclease A, lysozyme, β-lactoglobulin, hemoglobin, bovine serum albumin (BSA), or poly(sodium 4-styrene sulfonate) (PSS). In embodiments, the crowding agent is PEG 200, PEG 600, PEG 800, PEG 2,050, PEG 4,600, PEG 6,000, PEG 8,000, PEG 10,000, PEG 20,000, or PEG 35,000. In embodiments, the crowding agent is PEG 10,000, PEG 20,000, or PEG 35,000

In embodiments, the recombinase is a T4 UvsX, RecA, or Rad51 protein. In embodiments, the recombinase is a T4 UvsX protein. In embodiments, the recombinase is a RecA protein. In embodiments, the recombinase is a Rad51 protein. In embodiments, the homologous recombination complex further includes a loading factor, a single-stranded binding (SSB) protein, or both. In embodiments, the homologous recombination complex includes a single-stranded binding (SSB) protein. In embodiments, the SSB protein is T4 gp32 protein, SSB protein, Extreme Thermostable Single-Stranded DNA Binding Protein (ET-SSB), T7 gene 2.5 SSB protein, *Thermococcus kodakarensis* (KOD) SSB, *Thermus thermophilus* (TTH) SSB, *Sulfolobus solfataricus* (SSO) SSB, or phi29 SSB protein In embodiments, the loading factor comprises a T4 UvsY protein.

In embodiments, the displacing at least a portion of one strand of the double-stranded nucleic acid includes exposing the double-stranded nucleic acid to denaturing conditions. Non-limiting examples of denaturing conditions include increasing the temperature, changing the pH, adding chemical denaturants (e.g., NaOH). Suitable denaturing conditions, for example sodium hydroxide solution, formamide solution or heat, will be apparent to the skilled reader with reference to standard molecular biology protocols (Sambrook et al., 2001, Molecular Cloning, A Laboratory Manual, 3rd Ed, Cold Spring Harbor Laboratory Press, Cold Spring Harbor Laboratory Press, NY; Current Protocols, eds Ausubel et al.). In embodiments, the displacing at least a portion of one strand of the double-stranded nucleic acid includes incubation with a single-stranded binding (SSB) protein. In embodiments, the SSB is T4 gp32 protein, SSB protein, T7 gene 2.5 SSB protein, or phi29 SSB protein, *Thermococcus kodakarensis* (KOD) SSB, *Thermus thermophilus* (TTH) SSB, *Sulfolobus solfataricus* (SSO) SSB, or Extreme Thermostable Single-Stranded DNA Binding Protein (ET-SSB). In embodiments, the SSB is active (i.e., has measurable activity) at temperatures less than about 72° C. In embodiments, the SSB is active (i.e., has measurable activity) at temperatures about 72° C. In embodiments, the SSB is active (i.e., has measurable activity) at temperatures greater than about 72° C.

In embodiments, the probe oligonucleotide is covalently attached to a solid substrate. In embodiments, the solid substrate is in the form of a chip, a bead, a well, a capillary tube, a slide, a wafer, a filter, a fiber, a porous media, or a column. In embodiments, the solid substrate is gold, quartz, silica, plastic, glass, diamond, silver, metal, or polypropylene. In embodiments, the solid substrate is porous. In embodiments, the probe oligonucleotide is covalently attached to a bead.

In embodiments, the probe oligonucleotide is labeled with a first member of a binding pair, and the step of separating the probe-hybridized double-stranded nucleic acid comprises capturing the probe with a second member of the binding pair. In embodiments, the binding pair is a binding pair as described with respect to other aspects disclosed herein, including with respect to methods of sequencing described above.

In embodiments, the first member of the binding pair is biotin and the second member of the binding pair is avidin or streptavidin, or the second member of the binding pair is biotin and the first member of the binding pair is avidin or streptavidin. In embodiments, the first member of the binding pair is biotin and the second member of the binding pair is avidin or streptavidin. In embodiments, the second member of the binding is biotin and the first member of the binding pair is avidin or streptavidin. In embodiments, a member of the binding pair is avidin. In embodiments, a member of the binding pair is streptavidin.

In embodiments, the probe is complementary to 10, 15, 20, 25, 50, 75, 120, or more consecutive nucleotides of the displaced portion of the double-stranded nucleic acid. In embodiments, the probe is complementary to 10 consecutive nucleotides of the displaced portion of the double-stranded nucleic acid. In embodiments, the probe is complementary to 10, or more consecutive nucleotides of the displaced portion of the double-stranded nucleic acid. In embodiments, the probe is complementary to 15 consecutive nucleotides of the displaced portion of the double-stranded nucleic acid. In embodiments, the probe is complementary to 15, or more consecutive nucleotides of the displaced portion of the double-stranded nucleic acid. In embodiments, the probe is complementary to 20 consecutive nucleotides of the displaced portion of the double-stranded nucleic acid. In embodiments, the probe is complementary to 20, or more consecutive nucleotides of the displaced portion of the double-stranded nucleic acid. In embodiments, the probe is complementary to 25 consecutive nucleotides of the displaced portion of the double-stranded nucleic acid. In embodiments, the probe is complementary to 25, or more consecutive nucleotides of the displaced portion of the double-stranded nucleic acid. In embodiments, the probe is complementary to 50 consecutive nucleotides of the displaced portion of the double-stranded nucleic acid. In embodiments, the probe is complementary to 50, or more consecutive nucleotides of the displaced portion of the double-stranded nucleic acid. In embodiments, the probe is complementary to 75 consecutive nucleotides of the displaced portion of the double-stranded nucleic acid. In embodiments, the probe is complementary to 75, or more consecutive nucleotides of the displaced portion of the double-stranded nucleic acid. In embodiments, the probe is complementary to 120 consecutive nucleotides of the displaced portion of the double-stranded nucleic acid. In embodiments, the probe is complementary to 120, or more consecutive nucleotides of the displaced portion of the double-stranded nucleic acid.

In embodiments, the probe is complementary to about 15 to about 60 consecutive nucleotides of the displaced portion of the double-stranded nucleic acid. In embodiments, the probe is complementary to about 20 to about 50 consecutive nucleotides of the displaced portion of the double-stranded nucleic acid. In embodiments, the probe is complementary to about 30 to about 40 consecutive nucleotides of the displaced portion of the double-stranded nucleic acid.

In certain embodiments, where the first strand of the complex is available to rehybridize to the second strand of the complex (such as in certain embodiments where strand displacement relies on denaturing conditions), longer probes may be preferred, such as probes that are complementary to 100, 120, or more consecutive nucleotides of the displaced portion of the double-stranded nucleic acid.

In embodiments, the double-stranded nucleic acid is a cell-free DNA (cfDNA) or circulating tumor DNA (ctDNA). In embodiments, the double-stranded nucleic acid is a cell-free DNA (cfDNA). In embodiments, the double-stranded nucleic acid is a circulating tumor DNA (ctDNA). In embodiments, the double-stranded nucleic acid is from a FFPE sample. In embodiments, the double-stranded nucleic acid is extracted from plasma or from peripheral blood mononuclear cells (PBMCs). In embodiments, the double-stranded nucleic acid is 50 to 100 bp in length. In embodiments, the double-stranded nucleic acid includes genomic DNA, complementary DNA (cDNA), cell-free DNA (cfDNA), messenger RNA (mRNA), transfer RNA (tRNA), ribosomal RNA (rRNA), cell-free RNA (cfRNA), or non-coding RNA (ncRNA).

In embodiments, a plurality of different probe oligonucleotides are utilized during the hybridizing step, such that multiple target polynucleotides having different sequences are processed simultaneously.

In embodiments, the sequencing comprises sequencing according to any of the aspects described herein, including with respect to methods of sequencing described above.

IV. Compositions and Kits

In certain embodiments, presented herein are compositions for conducting a method described herein, and including one or more elements thereof. In some embodiments, a composition comprises (i) a template nucleic acid comprising sequences of a first strand of a Y-adapter, a forward strand (e.g., a first strand) of the double stranded nucleic acid, a hairpin adapter, a reverse strand (e.g., second strand) of the double stranded nucleic acid and a second strand of the Y-adapter arranged in a 5' to 3' direction; wherein the template is attached to a substrate. In embodiments, the composition includes (ii) a primer hybridized to a loop of the hairpin adapter; wherein the template is attached to a substrate. In some embodiments, the substrate is a surface of a flow cell. In some embodiments, the substrate is a polymer coated surface of a flow cell. In embodiments, the composition includes the complement of the template nucleic acid comprising sequences of a first strand of a Y-adapter, a forward strand (e.g., a first strand) of the double stranded nucleic acid, a hairpin adapter, a reverse strand (e.g., second strand) of the double stranded nucleic acid and a second strand of the Y-adapter arranged in a 5' to 3' direction wherein the complement of the template is attached to a substrate. In embodiments, the substrate includes a glass surface including a polymer coating. In embodiments, the substrate is glass or quartz, such as a microscope slide, having a surface that is uniformly silanized. This may be accomplished using conventional protocols, such as those described in Beattie et a (1995), Molecular Biotechnology, 4: 213. Such a surface is readily treated to permit end-attachment of oligonucleotides (e.g., forward and reverse primers) prior to amplification. In embodiments the substrate surface further includes a polymer coating, which contains functional groups capable of immobilizing primers. In some embodiments, the substrate includes a patterned surface suitable for immobilization of primers in an ordered pattern. A patterned surface refers to an arrangement of different regions in or on an exposed layer of a substrate. For example, one or more of the regions can be features where one or more primers are present. The features can be separated by interstitial regions where capture primers are not present. In some embodiments, the pattern can be an x-y format of features that are in rows and columns. In some embodiments, the pattern can be a repeating arrangement of features and/or interstitial regions. In some embodiments, the pattern can be a random arrangement of features and/or interstitial regions. In some embodiments, the primers are randomly distributed upon the substrate. In some embodiments, the primers are distributed on a patterned surface.

In certain embodiments, presented herein is a kit for sequencing double stranded nucleic acid, in accordance with any of the methods described herein, and including one or more elements thereof. In embodiments, the kit comprises: (i) a first adapter, wherein the first adapter comprises a double-stranded portion and at least one single-stranded portion; (ii) a second adapter, wherein the second adapter is a hairpin adapter comprising a nucleic acid having a 5'-end, a 5'-portion, a loop, a 3'-portion and a 3'-end, and the 5'-portion of the hairpin adapter is substantially complementary to the 3'-portion of the hairpin adapter; (iii) a first primer having a nucleic acid sequence complementary to a portion of the first adapter, or a complement thereof; and (iv) a second primer having a nucleic acid sequence complementary to the loop of the hairpin adapter, or a complement thereof. In certain embodiments, the first adapter is a Y-adapter, where the Y-adapter comprises (i) a first strand having a 5'-portion and a 3'-portion, and (ii) a second strand having a 5'-portion and a 3'-portion, and the 3'-portion of the first strand is substantially complementary to the 5'-portion of the second strand, and the 5'-portion of the first strand is not substantially complementary to the 3'-portion of the second strand.

In embodiments, the kit includes at least a supply of a Y adapter as defined herein, a hairpin adapter, and a supply of at least one amplification primer which is capable of annealing to the Y adapter and priming synthesis of an extension product, and a supply of at least one amplification primer which is capable of annealing to the hairpin adapter and priming synthesis of an extension product.

The structure and properties of amplification primers will be well known to those skilled in the art. Suitable primers of appropriate nucleotide sequence for use with the adapters included in the kit can be readily prepared using standard automated nucleic acid synthesis equipment and reagents in routine use in the art. The kit may include as supply of one single type of primer or separate supplies (e.g., a mixture) of two different primers, for example a pair of PCR primers suitable for PCR amplification of templates modified with the adapters (e.g., Y adapter, hairpin adapter, or both adapters) in solution phase and/or on a suitable solid support (i.e. solid-phase PCR).

Adapters and/or primers may be supplied in the kits ready for use, or more preferably as concentrates-requiring dilution before use, or even in a lyophilized or dried form requiring reconstitution prior to use. If required, the kits may further include a supply of a suitable diluent for dilution or reconstitution of the primers. Optionally, the kits may further comprise supplies of reagents, buffers, enzymes, and dNTPs for use in carrying out nucleic acid amplification. Further components which may optionally be supplied in the kit include sequencing primers suitable for sequencing templates prepared using the methods described herein. In embodiments, the kit further includes instructions.

In an aspect is provided an isolated nucleic acid comprising a nucleic acid template. In embodiments, the nucleic acid template comprises a double stranded nucleic acid (e.g., cfDNA molecule), a first adapter ligated to a first end of the double stranded nucleic acid, and a second adapter ligated to a second end of the double stranded nucleic acid, wherein the second adapter is a hairpin adapter. In embodiments, less than 50%, 60%, 70%, 80%, or 90% of the cytosines in the first or second adapter are methylated cytosines. In embodiments, about 50% of the cytosines in the first or second adapter are methylated cytosines. In embodiments, less than 50%, 60%, 70%, 80%, or 90% of the cytosines in the first adapter are methylated cytosines. In embodiments, about 50% of the cytosines in the first adapter are methylated cytosines. In embodiments, less than 50%, 60%, 70%, 80%, or 90% of the cytosines in the hairpin adapter are methylated cytosines. In embodiments, about 50% of the cytosines in the hairpin adapter are methylated cytosines. In embodiments, the first adapter includes a bisulfite conversion control region. In embodiments, the first adapter includes one or more unmethylated cytosines. In embodiments, the second adapter includes a bisulfite conversion control region. In embodiments, the second adapter includes one or more unmethylated cytosines. In embodiments, the first adapter includes one or more consecutive unmethylated cytosines. In embodiments, the second adapter includes one or more consecutive unmethylated cytosines.

V. Methods for Methylation and Mutational Analyses

In an aspect is provided a method of detecting methylation of a cytosine in a nucleic acid. In embodiments, the method includes sequencing a double stranded nucleic acid including one or more methylated cytosines, the method including: (a) ligating a first adapter to a first end of the double stranded nucleic acid, and ligating a second adapter to a second end of the double stranded nucleic acid, wherein the second adapter is a hairpin adapter, thereby forming a nucleic acid template; (b) converting one or more cytosines (e.g., a methylated cytosine or a non-methylated cytosine) to uracil; (c) annealing a first primer to the nucleic acid template, wherein the first primer includes a sequence that is complementary to a portion of the first adapter, or a complement thereof; (d) sequencing a first portion of the nucleic acid template by extending the first primer, thereby generating a first read including a first nucleic acid sequence of at least a first portion of the double stranded nucleic acid; (e) annealing a second primer to the nucleic acid template, wherein the second primer includes a sequence that is complementary to a sequence within a loop or stem of the hairpin adapter, or a complement thereof; and (f) sequencing a second portion of the nucleic acid template by extending the second primer, thereby generating a second read including a nucleic acid sequence of at least a second portion of the double stranded nucleic acid. In embodiments, converting one or more cytosines includes converting one or more methylated-cytosines. In embodiments, converting one or more cytosines includes converting one or more methylated-cytosines using TET-assisted pyridine borane methods known in the art and/or described herein. In embodiments, converting one or more cytosines includes converting one or more nonmethylated-cytosines using bisulfate conversion or enzymatic conversion methods known in the art and/or described herein.

In embodiments, the first adapter includes one or more methylated cytosines. In embodiments, the second adapter includes one or more methylated cytosines. In embodiments, the first adapter includes a consecutive sequence of methylated cytosines. In embodiments, the second adapter includes a consecutive sequence of methylated cytosines.

In embodiments, the method includes converting one or more cytosines to uracil. In embodiments, converting the one or more cytosines to uracil includes chemical or enzymatic conversion. Chemical reagents that can be used to distinguish between methylated and non-methylated CpG dinucleotide sequences include for example, hydrazine, which cleaves the nucleic acid, and bisulfite treatment. Bisulfite treatment followed by alkaline hydrolysis specifically converts non-methylated cytosine to uracil, leaving 5-methylcytosine unmodified. In embodiments, the method includes converting the one or more cytosines to uracil by contacting the nucleic acid template with sodium bisulfite. Cytosine reacts with the bisulfite ion to form a sulfonated cytosine reaction intermediate which is susceptible to deamination, giving rise to a sulfonated uracil. The sulfonate group can be removed under alkaline conditions, resulting in the formation of uracil. Alternatively, conversion may be accomplished using restriction enzymes, such as HpaII and MspI, which recognize the sequence CCGG.

A method for bisulfite-free direct detection of 5-methylcytosine (5mC) and 5-hydroxymethylcytosine (5hmC) has been described (Liu Y et al. Nat. Biotechnol. 2019, 37(4) 424-429, which is incorporated herein by reference), which combines ten-eleven translocation (TET) enzymatic oxidation of 5mC and 5hmC to 5-carboxylcytosine (5caC) with pyridine borane reduction of 5caC to dihydrouracil (DHU). Another bisulfite-free approach for methylation analysis is the NEBNext® Enzymatic Methyl-seq product, which first protects 5mC and 5hmC from deamination by TET2 and an oxidation enhancer, followed by APOBEC deamination of unprotected cytosines to uracils.

In another aspect is provided a method of sequencing a single-stranded nucleic acid including one or more methylated cytosines, the method including: (a) ligating the 5' end of a hairpin adapter to a first end of the single-stranded nucleic acid; and extending the 3' end of the hairpin adapter with one or more polymerases in an amplification reaction mixture including a plurality of conversion-resistant cytosine analogue, to create a complementary strand hybridized to the single-stranded nucleic acid; (b) ligating a second adapter to the to a second end of the single-stranded nucleic acid, thereby forming a nucleic acid template; (c) converting one or more cytosines to uracil; (d) annealing a first primer to the nucleic acid template, wherein the first primer includes a sequence that is complementary to a portion of the second adapter, or a complement thereof; (e) sequencing a first portion of the nucleic acid template by extending the first primer, thereby generating a first read including a first nucleic acid sequence of at least a first portion of the single-stranded nucleic acid; (f) annealing a second primer to the nucleic acid template, wherein the second primer includes a sequence that is complementary to a sequence within a loop or stem of the hairpin adapter, or a complement thereof; and (g) sequencing a second portion of the nucleic acid template by extending the second primer, thereby generating a second read including a nucleic acid sequence of at least a portion of the complementary strand of the single-stranded nucleic acid. In embodiments, the conversion-resistant cytosine analogue is selected from the group consisting of: 5-hydroxymethylcytosine, 5-formylcytosine (5fC), 5-ethyl dCTP, 5-methyl dCTP, 5-fluoro dCTP, 5-bromo dCTP, 5-iodo dCTP, 5-chloro dCTP, 5-trifluoromethyl dCTP, and 5-aza dCTP.

In another aspect is a method of detecting a single-nucleotide polymorphism (SNP) or a single-nucleotide variant (SNV) in a double-stranded nucleic acid. One unresolved problem with bisulfite conversion is that it is often difficult to distinguish between SNPs or unmethylated cytosine in the same double stranded nucleic acid. This is especially difficult for C>T SNPs, which is the most common substitution (>60%) in human population. Often this requires very high sequencing depth to discern simultaneous SNVs, SNPs, and methylation profiles. For example, computational methods have been developed to predict germline SNPs in bulk sequencing and suggest that at least 30× genomic coverage is required to identify 96% of SNPs from bisulfite converted DNA. Using methods described herein, e.g., generating the Y-template-hairpin constructs, and obtaining sequencing information from both strands permits identification of a SNP and a methylation profile. In embodiments, the methods described herein reduce sequencing overhead with higher accuracy for ctDNA. Methods described herein also differentiate SNV and methylation simultaneously, at low sequencing depths for germline mutations.

In embodiments, the method includes detecting SNVs and methylation status from a double stranded nucleic acid. Although SNVs can determine if a mutation occurred, it cannot reveal tissue of origin. Methylation is highly tissue specific and can be used to predict tissue of origin of cfDNA. Current studies have shown common methylation CpG sites that are differentially methylated depending on tissue. By searching for these different methylation signals within ctDNA, one could determine if there are elevated levels of certain tissue signals within the plasma.

In an aspect is provided a method of detecting a disease in a subject. In embodiments, the method includes obtaining a sample that includes a double-stranded nucleic acid from the subject; identifying whether a disease is present in the sample by sequencing the sample according to the methods described herein, and detecting a disease in a subject when the presence of a disease is identified in the sample. In another aspect is provided a method of diagnosing a subject with a disease. In embodiments, the method includes obtaining a sample that includes a double-stranded nucleic acid from the subject; identifying whether a disease is present in the sample by sequencing the sample according to the methods described herein, and diagnosing a subject with a disease when the presence of a disease is identified in the sample. In some embodiments, the disease is an autoimmune disease, hereditary disease, or cancer.

In embodiments, the disease is an autoimmune disease. In embodiments, the autoimmune disease is arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, autoimmune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, or atopic dermatitis. In embodiments, the autoimmune disease is Achalasia, Addison's disease, Adult Still's disease, Agammaglobulinemia, Alopecia areata, Amyloidosis, Ankylosing spondylitis, Anti-GBM/Anti-TBM nephritis, Antiphospholipid syndrome, Autoimmune angioedema, Autoimmune dysautonomia, Autoimmune encephalomyelitis, Autoimmune hepatitis, Autoimmune inner ear disease (AIED), Autoimmune myocarditis, Autoimmune oophoritis, Autoimmune orchitis, Autoimmune pancreatitis, Autoimmune retinopathy, Autoimmune urticaria, Axonal & neuronal neuropathy (AMAN), Baló disease, Behcet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss Syndrome (CSS) or Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hidradenitis Suppurativa (HS) (Acne Inversa), Hypogammalglobulinemia, IgA Nephropathy, IgG4-related sclerosing disease, Immune thrombocytopenic purpura (ITP), Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonage-Turner syndrome, Pemphigus, Peripheral neuropathy, Perivenous encephalomyelitis, Pernicious anemia (PA), POEMS syndrome, *Polyarteritis nodosa*, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Thyroid eye disease (TED), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, or Vogt-Koyanagi-Harada Disease.

In embodiments the disease is a hereditary disease. In embodiments, the hereditary disease is cystic fibrosis, alpha-thalassemia, beta-thalassemia, sickle cell anemia (sickle cell disease), Marfan syndrome, fragile X syndrome, Huntington's disease, or hemochromatosis.

In embodiments the disease is a cancer. As used herein, the term "cancer" refers to all types of cancer, neoplasm or malignant tumors found in mammals (e.g., humans), including leukemia, carcinomas and sarcomas. Exemplary cancers that may be treated with a compound or method provided herein include brain cancer, glioma, glioblastoma, neuroblastoma, prostate cancer, colorectal cancer, pancreatic cancer, cervical cancer, gastric cancer, ovarian cancer, lung cancer, and cancer of the head. Exemplary cancers that may be treated with a compound or method provided herein include cancer of the thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer. In embodiments, the cancer is breast cancer, lung cancer, prostate cancer, colorectal cancer, renal cancer, uterine cancer, pancreatic cancer, cancer of the esophagus, a lymphoma, head/neck cancer, ovarian cancer, a hepatobiliary cancer, a melanoma, cervical cancer, multiple myeloma, leukemia, thyroid cancer, bladder cancer, gastric cancer, or a combination thereof. In embodiments, the cancer is a predefined stage of a breast cancer, a predefined stage of a lung cancer, a predefined stage of a prostate cancer, a predefined stage of a colorectal cancer, a predefined stage of a renal cancer, a predefined stage of a uterine cancer, a predefined stage of a pancreatic cancer, a predefined stage of a cancer of the esophagus, a predefined stage of a lymphoma, a predefined stage of a head/neck cancer, a predefined stage of a ovarian cancer, a predefined stage of a hepatobiliary cancer, a predefined stage of a melanoma, a predefined stage of a cervical cancer, a predefined stage of a multiple myeloma, a predefined stage of a leukemia, a predefined stage of a thyroid cancer, a predefined stage of a bladder cancer, or a predefined stage of a gastric cancer. In some embodiments, the cancer is a predefined subtype of a cancer. In certain instances, the cancer is early stage cancer. In other instances, the cancer is late stage cancer.

In embodiments, the subject is suspected of having a genetic variation or a disease or condition associated with a genetic variation (e.g., an oncogene). In embodiments, the sample, and/or the oncogene includes one or more mutations in one or more of the genes TP53, PIK3CA, PTEN, APC, VHL, KRAS, MLL3, MLL2, ARID1A, PBRM1, NAV3, EGFR, NF1, PIK3R1, CDKN2A, GATA3, RB1, NOTCH1, FBXW7, CTNNB1, DNMT3A, MAP3K1, FLT3, MALAT1, TSHZ3, KEAP1, CDH1, ARHGAP35, CTCF, NFE2L2, SETBP1, BAP1, NPM1, RUNX1, NRAS, IDH1, TBX3, MAP2K4, RPL22, STK11, CRIPAK, CEBPA, KDM6A, EPHA3, AKT1, STAG2, BRAF, AR, AJUBA, EPPK1, TSHZ2, PIK3CG, SOX9, ATM, CDKN1B, WT1, HGF, KDM5C, PRX, ERBB4, MTOR, TLR4, U2AF1, ARID5B, TET2, ATRX, MLL4, ELF3, BRCA1, LRRK2, POLQ, FOXA1, IDH2, CHEK2, KIT, HIST1H1C, SETD2, PDGFRA, EP300, FGFR2, CCND1, EPHB6, SMAD4, FOXA2, USP9X, BRCA2, NFE2L3, FGFR3, ASXL1, TGFBR2, SOX17, CDKN1A, B4GALT3, SF3B1, TAF1, PPP2R1A, CBFB, ATR, SIN3A, VEZF1, HIST1H2BD, EIF4A2, CDK12, PHF6, SMC1A, PTPN11, ACVR1B, MAPK8IP1, H3F3C, NSD1, TBL1XR1, EGR3, ACVR2A, MECOM, LIFR, SMC3, NCOR1, RPL5, SMAD2, SPOP, AXIN2, MIR142, RAD21, ERCC2, CDKN2C, EZH2, or PCBP1. In embodiments, the cancer is lung cancer, colorectal cancer, skin cancer, colon cancer, pancreatic cancer, breast cancer, cervical cancer, lymphoma, leukemia, or a cancer associated with aberrant K-Ras, aberrant APC, aberrant Smad4, aberrant p53, or aberrant TGFβ. In embodiments, the cancer cell includes a ERBB2, KRAS, TP53, PIK3CA, or FGFR2 gene.

EXAMPLES

Example 1: Linked Paired Strand Sequencing

Commercially available next-generation sequencing (NGS) technologies typically require library preparation, whereby a pair of specific adapter sequences are ligated to the ends of DNA fragments in order to enable sequencing by the instrument. Typically, preparation of a nucleic acid library involves 5 steps: DNA fragmentation, polishing, adapter ligation, size selection, and library amplification.

Fragmentation of DNA can be achieved by enzymatic digestion or physical methods (e.g., sonication, nebulization, or hydrodynamic shearing). Enzymatic digestion produces DNA ends that can be efficiently polished and ligated to adapter sequences. However, it is difficult to control the enzymatic reaction and produce fragments of predictable length. In addition, enzymatic fragmentation is frequently base-specific thus introducing representation bias into the sequence analysis. Alternatively, physical methods to fragment DNA are random and DNA size distribution can be more easily controlled, but DNA ends produced by physical fragmentation are often damaged and a conventional polishing reaction may be insufficient to generate ample ligation-compatible ends. Typical polishing mixtures contain T4 DNA polymerase and T4 polynucleotide kinase. These enzymes excise 3' overhangs, fill in 3' recessed ends, and remove any potentially damaged nucleotides thereby generating blunt ends on the nucleic acid fragments. The T4 polynucleotide kinase used in the polishing mix adds a phosphate to the 5' ends of DNA fragments that can be lacking such, thus making them ligation-compatible to NGS adapters.

Prior to ligation, adenylation of repaired nucleic acids using a polymerase which lacks 3'-5' exonuclease activity is often performed in order to minimize chimera formation and adapter-adapter (dimer) ligation products. In these methods, single 3' A-overhang DNA fragments are ligated to single 5' T-overhang adapters, whereas A-overhang fragments and T-overhang adapters have incompatible cohesive ends for self-ligation. During size selection, fragments of undesired size are eliminated from the library using gel or bead-based selection in order to optimize the library insert size for the desired sequencing read length. This often maximizes sequence data output by minimizing overlap of paired end sequencing that occurs from short DNA library inserts. Amplifying libraries prior to NGS analysis is typically a beneficial step to ensure there is a sufficient quantity of material to be sequenced.

Linked Duplex Sequencing: Ligating Adaptors

In some aspects of a method herein, an adapter-target-adapter nucleic acid template (FIG. 1A and FIG. 1C) is provided where two non-identical adapters are ligated to each respective end of a polynucleotide duplex. A general overview is provided in FIG. 1B and FIG. 1D. Embodiments of adapters contemplated herein include those shown in FIGS. 2A-2B and FIG. 4. A polynucleotide duplex refers to a double-stranded portion of a polynucleotide, for example a polynucleotide desired to be sequenced.

As depicted in FIG. 1B, a first adapter is a Y adapter (alternatively, this may be referred to as a mismatched adapter or a forked adapter) that is ligated to one end of a polynucleotide duplex. The adapter is formed by annealing two single-stranded oligonucleotides, herein referred to as P1 and P2'. P1 and P2' may be prepared by a suitable automated oligonucleotide synthesis technique. The oligonucleotides are partially complementary such that a 3' end and/or a 3' portion of P1 is complementary to the 5' end and/or a 5' portion of P2'. A 5' end and/or a 5' portion of P1 and a 3' end and/or a 3' portion of P2' are not complementary to each other, in certain embodiments. When the two strands are annealed, the resulting Y adapter is double-stranded at one end (the double-stranded region) and single-stranded at the other end (the unmatched region), and resembles a 'Y' shape.

Figure 2A:
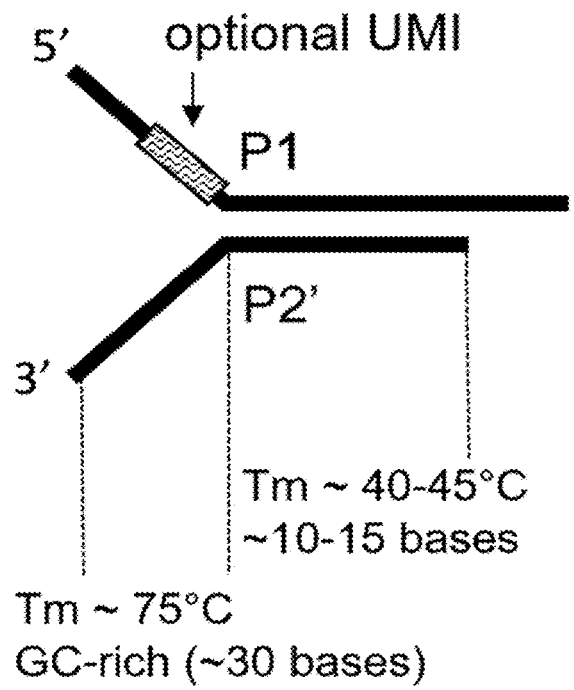
FIGS. 2A-2B show embodiments of an adapter.
Figure 2B:
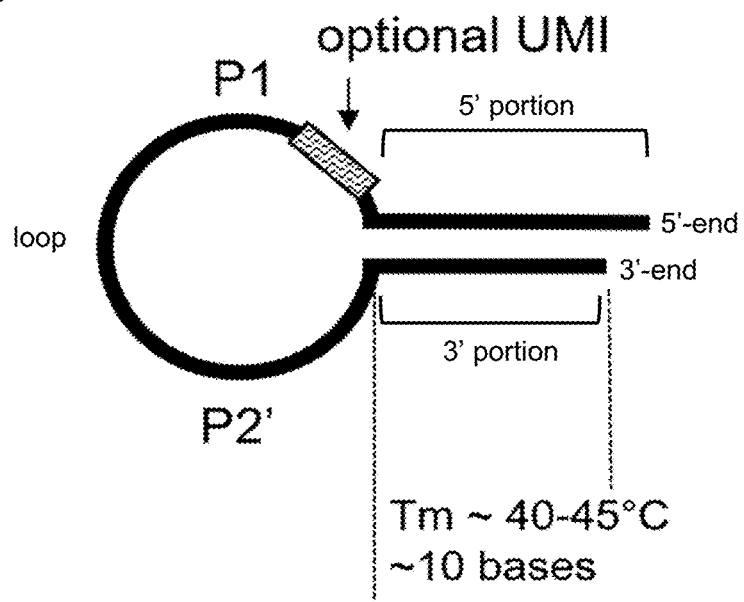

The single-stranded portions (the unmatched regions) of both P1 and P2' have an elevated melting temperature ($T_m$) (e.g., about 75° C.) relative to their respective complements to enable efficient binding of surface primers and stable binding of sequencing primers. To achieve an elevated $T_m$ in a reasonable length primer, the GC content is often >50% (e.g., approximately 60-75% GC content). In contrast to the single-stranded portions, a double-stranded region, in certain embodiments, has a moderate $T_m$ (e.g., 40-45° C.) so that it is stable during ligation. In embodiments, a double-stranded region has an elevated $T_m$ (e.g., 60-70° C.). In embodiments, the GC content of the double-stranded region is >50% (e.g., approximately 60-75% GC content). The unmatched region of P1 and P2', in certain embodiments, are about 25-35 nucleotides (e.g., 30 nucleotides), whereas the double-stranded region is shorter, ranging about 10-20 nucleotides (e.g., 13 nucleotides) in total. For example, P2' may be a total of 43 nucleotides in length, as shown in FIG. 2A. In embodiments, the P1 region of the Y adapter has the sequence S1 sequence (SEQ ID NO:1) and the P2' region of the Y adapter has the S2 (SEQ ID NO:3) sequence, as described in Table 1 below. In embodiments, the P1 region of the Y adapter has the sequence S4 sequence (SEQ ID NO:2) and the P2' region of the Y adapter has the S5 (SEQ ID NO:4) sequence, as described in Table 1 below.

TABLE 1

Sequences for the Y adapters. Note, the '*' is indicative of an optional phosphorothioate linkage. Phosphorothioate linkages assist in protecting the oligonucleotide against exonuclease degradation from certain polymerases (e.g., phi29).

| P1 regions of the Y adapter | |
|---|---|
| S1 (SEQ ID NO: 1) | ACAAAGGCAGCCACGCACTCCTTCCCT GAAGGCCGGAATC*T |
| S4 (SEQ ID NO: 2) | GCTGCCGCCACTAGCCATCTTACTGCT GAGGACTCTTCGC*T |

| P2' regions of the Y adapter | |
|---|---|
| S2 (SEQ ID NO: 3) | /5Phos/GATTCCGGCCTTGTGGTTGGTGA GGGTCATCTCGCTGGAG |
| S5 (SEQ ID NO: 4) | /5Phos/GCGAAGAGTCCTGGAGTGCCGC CAATGTATGCGAGGGTGA |

Figure 3:
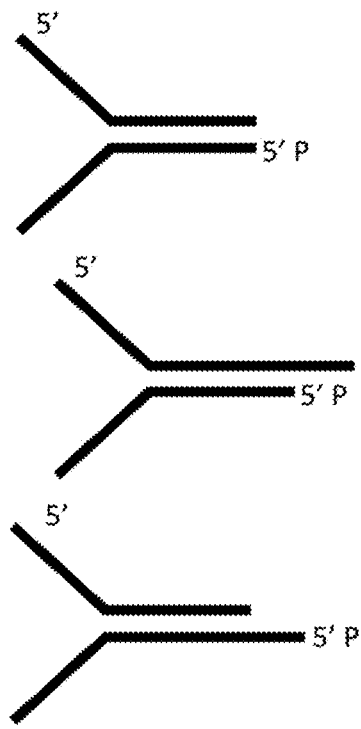
FIG. 3 shows embodiments of a Y adapter. In some embodiments, a Y adapter is double stranded at one end (the double-stranded region) and single stranded at the other end (the unmatched region), wherein 5'P refers to a phosphorylated 5' end. The double-stranded region of a Y adapter (alternatively referred to as a forked adapter) may be blunt-ended (top), have a 3' overhang (middle), or a 5' overhang (bottom). An overhang may comprise a single nucleotide or more than one nucleotide.

As shown in FIG. 3, the double-stranded region of the forked adapter may be blunt-ended (top), it may have a 3' overhang (middle), or a 5' overhang (bottom). The overhang may comprise a single nucleotide or more than one nucleotide. The 5' end of the double-stranded part of the forked adapter is phosphorylated, i.e. the 5' end of P2'. The presence of the 5' phosphate group (referred to as 5'P in FIG. 3) allows the adapter to ligate to the polynucleotide duplex. The 5' end of P1 may be biotinylated or have a functional group at the end, thus enabling it to be immobilized on a surface (e.g., a planar solid support).

Alternatively, as depicted in FIG. 1D, the first adapter is a hairpin adapter (e.g., the hairpin adapter of FIG. 2B) and it is ligated to one end of a polynucleotide duplex.

Figure 4:
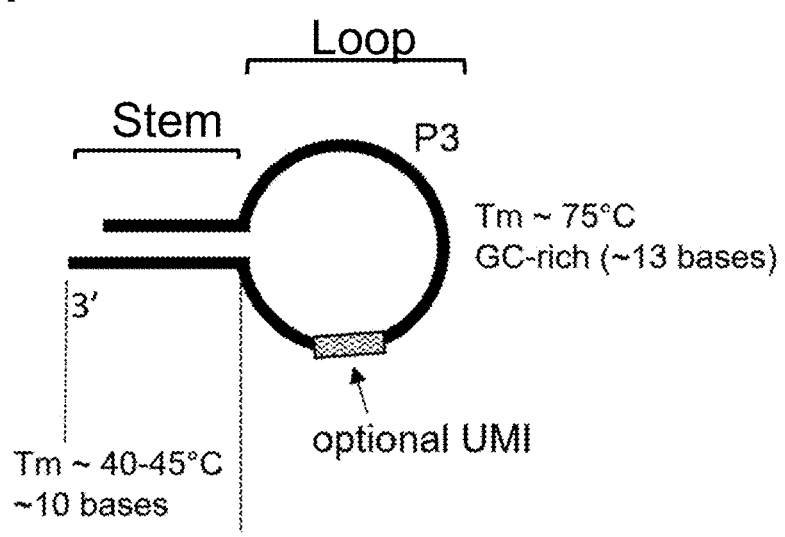
FIG. 4 shows an embodiment of a hairpin adapter, which includes a double stranded (stem) region and a loop region. Within the loop region is a priming site (P3) and optionally a unique molecular identifier.

The second adapter is a hairpin adapter (alternatively, it may be referred to as a stem-loop adapter, barbell, or hairpin loop adapter) and it is ligated to one end of a polynucleotide duplex, depicted as containing a P3 priming site in FIG. 1C and FIG. 4. The hairpin adapter comprises a double-stranded region which has a moderate T. (e.g., 40-45° C.) so that it is stable during ligation, and comprises at least 10 nucleotides. The hairpin adapter also comprises a loop region which has a primer sequence and has an elevated T. (e.g., 75° C.) relative to the double stranded region to enable stable binding of a complementary sequencing primer. The loop region or the stem region of the hairpin may further comprise a barcode or Unique Molecular Identifier (UMI) using degenerate sequences. The UMI consists of 3-5 degenerate nucleotides.

TABLE 2

Sequences for the hairpin adapter. Note, the '*' is
indicative of an optional phosphorothioate linkage.
Phosphorothioate linkages assist in protecting the
oligonucleotide against exonuclease degradation
from certain polymerases (e.g., phi29).

```
B1 (SEQ ID NO: 5)      /5Phos/ GCGCGCG TTT TTT TT
                       GCTTGCGTCTCCTGCCAGCCATATCCGGTCTACGTGATC
                       C TTT TTT TT CGCGCGC*T B2 (SEQ ID NO: 6)      /5Phos/GCGCGCGTTT TTT TTT TTT TT
                       GCTTGCGTCTCCTGCCAGCCATATCCGGTCTACGTGATC
                       C TTT TTT TTT TTT TT CGCGCGC*T B3 (SEQ ID NO: 7)      /5Phos/GGATCACGTAGATTTTGCTTGCGTCTCCTGCCAG
                       CCATATCCGGTTTTTCTACGTGATTCC*T B4 (SEQ ID NO: 8)      /5Phos/GCGAAGAGTCCT
S4S5'_in_loop_0Ts      GGAGTGCCGCCAATGTATGCGAGGGTGA
                       GCTGCCGCCACTAGCCATCTTACTGCTG
                       AGGACTCTTCGC*T B5 (SEQ ID NO: 9)      /5Phos/GCGAAGAGTCCT TTT TTT
S4S5'_in loop_6Ts      GGAGTGCCGCCAATGTATGCGAGGGTGA
                       GCTGCCGCCACTAGCCATCTTACTGCTG TTT TTT
                       AGGACTCTTCGC*T B6 (SEQ ID NO: 10)     /5Phos/GCGAAGAGTCCT TTT TTT
S4S5'_in loop_6+8Ts    GGAGTGCCGCCAATGTATGCGAGGGTGA TTT TTT T
                       GCTGCCGCCACTAGCCATCTTACTGCTG TTT TTT
                       AGGACTCTTCGC*T B7 (SEQ ID NO: 11)     /5Phos/GATTCCGGCCTT
S1S2'_in loop_0Ts      GTGGTTGGTGAGGGTCATCTCGCTGGAGACAAAGGCAG
                       CCACGCACTCCTTCCCTGAAGGCCGGAATC*T B8 (SEQ ID NO: 12)     /5Phos/GATTCCGGCCTT TTT TTT
S1S2'_in loop_6Ts      GTGGTTGGTGAGGGTCATCTCGCTGGAGACAAAGGCAG
                       CCACGCACTCCTTCCCTGTTTTTTAAGGCCGGAATC*T B9 (SEQ ID NO:13)      /5Phos/GATTCCGGCCTT TTT TTT
S1S2'_in loop_6+7Ts    GTGGTTGGTGAGGGTCATCTCGCTGGAGTTT TTT
                       TACAAAGGCAGCCACGCACTCCTTCCCTG TTT TTT
                       AAGGCCGGAATC*T B10 (SEQ ID NO: 14)    /5Phos/GGATCACGTAGATTTTGCTTGCGTCTCCTGCCAG
                       CCATATCCGGTTTTTCTACGTGATCC*T B11 (SEQ ID NO: 15)    5Phos/
                       GG ATC ACG TAG ATT TTT TTT TTT TGC TTG CGT
B10+12T                CTC CTG CCA GCC ATA TCC GGT TTT TTT TTT TTT CTA
                       CGT GAT CC*T B12 (SEQ ID NO: 16)    5Phos/
                       GG ATC ACG TAG ATT TTT TTT TTT TTT TTT
B10+24T                TTT TGC TTG CGT CTC CTG CCA GCC ATA TCC GGT
                       TTT TTT TTT TTT TTT TTT TTT TTT CTA CGT GAT CC*T B13 (SEQ ID NO: 17)    5Phos/
                       GG ATC ACG TAG ATT TTT TTT TTT TTT TTT
B10+40-10T             TTT TTT TTT TTT TTT TTT TTG CTT GCG TCT CCT GCC
                       AGC CAT ATC CGG TTT TTT TTT TTC TAC GTG ATC C*T B14 (SEQ ID NO: 18)    /5Phos/GGA TCA CGT AGA TTT TAG ATC TGC TTG CGT
B10 + clv              CTC CTG CCA GCC ATA TCC GGT TTT TCT ACG TGA
                       TCC* T B15 (SEQ ID NO: 19)    /5Phos/GGA TCA CGT AGA TTTTTTTTTTT AGA TCT
B11 + clv              GCT TGC GTC TCC TGC CAG CCA TAT CCG
                       GTTTTTTTTTTTC TAC GTG ATC C*T
```

In embodiments, a hairpin adapter comprises a sequence selected from SEQ ID NOs:5-17. In embodiments, the hairpin adapter has the B1 (SEQ ID NO:5) sequence described in Table 2. In embodiments, the hairpin adapter has the B2 (SEQ ID NO:6) sequence described in Table 2. In embodiments, the hairpin adapter has the B3 (SEQ ID NO:7) sequence described in Table 2. In embodiments, the hairpin adapter has the B4 (SEQ ID NO: 8) sequence described in Table 2. In embodiments, the hairpin adapter has the B5 (SEQ ID NO:9) sequence described in Table 2. In embodiments, the hairpin adapter has the B6 (SEQ ID NO:10) sequence described in Table 2. In embodiments, the hairpin adapter has the B7 (SEQ ID NO:11) sequence described in Table 2. In embodiments, the hairpin adapter has the B8 (SEQ ID NO:12) sequence described in Table 2. In embodiments, the hairpin adapter has the B9 (SEQ ID NO:13) sequence described in Table 2. In embodiments, the hairpin adapter has the B10 (SEQ ID NO:14) sequence described in Table 2. In embodiments, the hairpin adapter has the B11 (SEQ ID NO:15) sequence described in Table 2. In embodiments, the hairpin adapter has the B12 (SEQ ID NO:16) sequence described in Table 2. In embodiments, the hairpin adapter has the B13 (SEQ ID NO:17) sequence described in Table 2. In embodiments, the hairpin adapter has the B13 (SEQ ID NO:18) sequence described in Table 2. In embodiments, the hairpin adapter has the B13 (SEQ ID NO:19) sequence described in Table 2.

Figure 5:
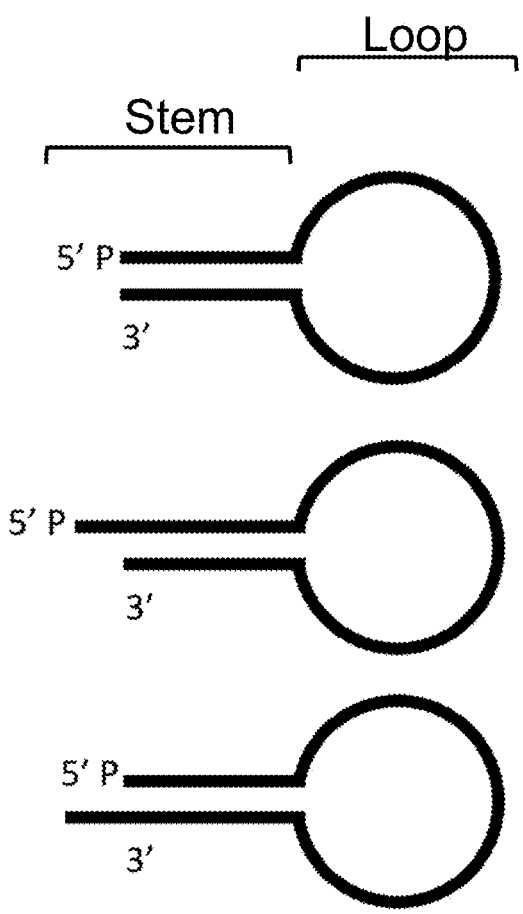
FIG. 5 shows embodiments of hairpin adapters, each comprising a 5'-end and a 3'-end. In some embodiments, a hairpin adapter comprises a double stranded portion (a double-stranded "stem" region) and a loop, where 5'P refers to a phosphorylated 5' end. A double-stranded stem region of a hairpin adapter may be blunt-ended (top), it may have a 5' overhang (middle), or a 3' overhang (bottom). An overhang may comprise a single nucleotide or more than one nucleotide.

As shown in FIG. 5, the double-stranded region of the hairpin adapter may be blunt-ended (top), it may have a 5' overhang (middle), or a 3' overhang (bottom). The overhang may comprise a single nucleotide or more than one nucleotide. The 5' end of the double-stranded part of the hairpin adapter is phosphorylated. The presence of the 5' phosphate group allows the adapter to ligate to the polynucleotide duplex.

The order of ligation events is not relevant, however for the purposes of discussion the terms 'first' and 'second' are used in reference to the sequence in which the adapter is ligated to the polynucleotide duplex. It is understood that the ligation of the Y adapter or the hairpin adapter may occur first, such that the resulting adapter-target-adapter constructs contain non-identical adapters.

Note, during this step it is possible to form adapter dimers (i.e., two adapters ligate together with no intervening template nucleic acid). There are several ways to reduce adapter dimer formation in the adapter ligation NGS library preparation described herein, including i) a stringent purification step (e.g., SPRI) after 3' adapter ligation to remove non-ligated 3' adapter molecules, prior to the second ligation of the 5' adapter; ii) the use of A-tailed DNA and T-overhang adapters; iii) or utilizing alkaline phosphatase treatment after 3' adapter ligation, before any SPRI cleanup, to remove 5' phosphate group from the 3' adapter to render any carryover 3' adapter to be ligation incompatible and inert in the 5' adapter ligation step.

Methods

Fragmented DNA may be made blunt-ended by a number of methods known to those skilled in the art. In embodiments, the ends of the fragmented DNA are end repaired with T4 DNA polymerase and Klenow polymerase, a procedure well known to those skilled in the art, and then phosphorylated with a polynucleotide kinase enzyme. A single 'A' deoxynucleotide is then added to both 3' ends of the DNA molecules using Taq polymerase enzyme, producing a one-base 3' overhang that is complementary to the one-base T overhang on the double-stranded end of the Y adapter and hairpin adapter. For example, in the presence of a T4 DNA ligase, an A overhang is created on both strands at the 3' hydroxyl end of a target duplex polynucleotide. For example, using Blunt/TA Ligase Master Mix (NEB #M0367) includes a T4 DNA ligase in a reaction buffer and ligation enhancers to ensure efficient A tailing. It is preferable to polish or use a filling reaction to ensure the ends of the target duplex polynucleotide are blunt before adding the A overhang. Examples of ends that need polishing or filling include inserts generated by shearing or sonication. A number of DNA polymerases will remove DNA overhangs and/or can be used to fill in missing bases if there is a 3' hydroxyl available for priming. Polymerases for such reactions include, but are not limited to, a T4 DNA polymerase, PFU, and the Klenow Fragment of DNA polymerase I.

A ligation reaction between the Y adapter, the hairpin adapter, and the DNA fragments is then performed using a suitable ligase enzyme (e.g. T4 DNA ligase) which joins one hairpin adapter and one Y adapter to each DNA fragment, one at either end, to form adapter-target-adapter constructs that somewhat resemble a bobby pin hair fastener (see FIG. 1A). Alternatively, a ligation reaction between a first hairpin adapter (e.g., FIG. 2B), and a different second hairpin adapter (e.g., FIG. 4), and the DNA fragments is then performed using a suitable ligase enzyme (e.g. T4 DNA ligase) which joins the first hairpin adapter and the second hairpin adapter to each DNA fragment, one at either end, to form adapter-target-adapter constructs (see FIG. 1D).

The products of this reaction can be purified from leftover unligated adapters that by a number of means (e.g., Nucleo-Mag NGS Clean-up and Size Select kit, Solid Phase Reversible Immobilization (SPRI) bead methods such as AMPureXP beads, PCRclean-dx kit, Axygen AxyPrep FragmentSelect-I Kit), including size-inclusion chromatography, preferably by electrophoresis through an agarose gel slab followed by excision of a portion of the agarose that contains the DNA greater in size that the size of the adapter.

Linked Duplex Sequencing: Clustering Amplification.

Once formed, the library of adapter-target-adapter templates prepared according to the methods described above can be used for solid-phase nucleic acid amplification.

Thus, in another aspect is provided a method of nucleic acid amplification of template polynucleotide molecules which includes preparing a library of template polynucleotide molecules (e.g., adapter-target-adapter templates) and performing an amplification reaction (e.g., a solid-phase nucleic acid amplification reaction) wherein the template polynucleotide molecules are amplified. In embodiments, the method includes providing a plurality of primers (e.g., P1 and P2) that are immobilized on a solid substrate. Note, however, for clarity only a few immobilized primers are depicted in FIG. 6A.

An adapter-target-adapter construct (i.e., the denatured single strand, reading from 5' to 3' having the formula P1-template-P3-template-P2' generated according to the methods described herein) is hybridized to a complementary primer (e.g., the complement to P2', referred to as P2) that is immobilized on a solid substrate. In the presence of a polymerase (wherein the polymerase is not shown in FIG. 6A) the P2 strand is extended to generate a complementary copy, wherein the denatured single strand, reading from the 5' to the 3' has the formula P1'-template-P3'-template-P2. The original adapter-target-adapter may be removed. Because of the self-folding of the adapter-target-adapter construct, initially seeding on the solid surface could be done without additional denaturation steps (e.g., as long as the products are in the hairpin state).

Next, the complementary copy is annealed to a P1 primer that is immobilized on the solid substrate, which in the presence of a DNA polymerase (again, the polymerase is not shown in FIG. 6B) extends P1 primer to reform the original adapter-target-adapter construct (i.e., the denatured single strand having the formula P1-template-P3-template-P2') which then hybridizes with an immobilized P2 primer. The products of the extension reaction (i.e. the P1-template-P3-template-P2' hybridized to an immobilized P2, and P1'-template-P3'-template-P2 hybridized to P1) may be subjected to standard denaturing conditions in order to separate the extension products from strands of the adapter-target constructs. The adapter-target-adapter constructs may then anneal to a complementary immobilized primer and may be extended in the presence of a polymerase. These steps, depicted in FIGS. 6A-6B, may be repeated one or more times, through rounds of primer annealing, extension and denaturation, in order to form multiple copies of the same extension products containing adapter-target-adapter constructs, or the complements thereof. Note, this bridging amplification is typically more efficient than amplifying linear strands, because the adapter-target-adapter products self-fold, thus leaving the primer site accessible.

The term "solid-phase amplification" as used herein refers to any nucleic acid amplification reaction carried out on or in association with a solid support such that all or a portion of the amplified products are immobilized on the solid support as they are formed. The term encompasses solid-phase polymerase chain reaction (solid-phase PCR), which is a reaction analogous to standard solution phase PCR, except that both of the forward and reverse amplification primers (referred to herein as P1 and P2) are immobilized on the solid support. In practice, there will be a "plurality" of identical forward primers and/or a "plurality" of identical reverse primers immobilized on the solid support, since the PCR process requires an excess of primers to sustain amplification.

In embodiments, amplification primers for solid-phase amplification are preferably immobilized by covalent attachment to the solid support at or near the 5' end of the primer, leaving the template-specific portion of the primer free for annealing to the cognate template and the 3' hydroxyl group free for primer extension. Any suitable covalent attachment means known in the art may be used for this purpose. The primer itself may include a moiety, which may be a non-nucleotide chemical modification, to facilitate attachment. In embodiments, the primer may include a sulfur-containing nucleophile (e.g., phosphorothioate or thiophosphate) at the 5' end.

In embodiments, the adapter-target-adapter templates prepared according to the methods described above can be used to prepare clustered arrays of nucleic acid colonies by solid-phase PCR amplification. The terms "cluster" and "colony" are used interchangeably herein to refer to a discrete site on a solid support comprised of a plurality of immobilized nucleic acid strands and a plurality of immobilized complementary nucleic acid strands. The term "clustered array" refers to an array formed from such clusters or colonies. In this context the term "array" is not to be understood as requiring an ordered arrangement of clusters.

Linked Duplex Sequencing: Use in Sequencing

In another aspect is provided methods of sequencing amplified nucleic acids, optionally generated by the amplification methods described herein. The method includes optionally removing all or a portion of one immobilized strand in a "bridged" double-stranded nucleic acid structure (i.e. linearizing) and sequencing.

The products of solid-phase amplification reactions described herein wherein both P1 and P2 primers are covalently immobilized on the solid surface are may be referred to as "bridged structures" formed by annealing of pairs of immobilized polynucleotide strands and immobilized complementary strands, both strands being attached to the solid support at the 5' end.

Arrays comprised of such bridged structures provide inefficient templates for nucleic acid sequencing, since hybridization of a conventional sequencing primer to one of the immobilized strands is not preferred compared to annealing of this strand to its immobilized complementary strand under standard conditions for hybridization. In order to provide more suitable templates for nucleic acid sequencing it is preferred to remove substantially all or at least a portion of one of the immobilized strands in the "bridged" structure in order to generate a template which is at least partially single-stranded. The portion of the template which is single-stranded will thus be available for hybridization to a sequencing primer. The process of removing all or a portion of one immobilized strand in a "bridged" double-stranded nucleic acid structure may be referred to herein as "linearization". Bridged template structures may be linearized by cleavage of one or both strands with a restriction endonuclease or by cleavage of one strand with a nicking endonuclease. Other methods of cleavage can be used as an alternative to restriction enzymes or nicking enzymes, including chemical cleavage (e.g. cleavage of a diol linkage with periodate), cleavage of abasic sites by cleavage with endonuclease, or by exposure to heat or alkali, cleavage of ribonucleotides incorporated into amplification products otherwise comprised of deoxyribonucleotides, photochemical cleavage or cleavage of a peptide linker. Alternatively, the primers may be attached to the solid surface with a cleavable linker, such that upon exposure to a cleaving agent, all or a portion of the primer is removed from the surface.

Figure 7A:
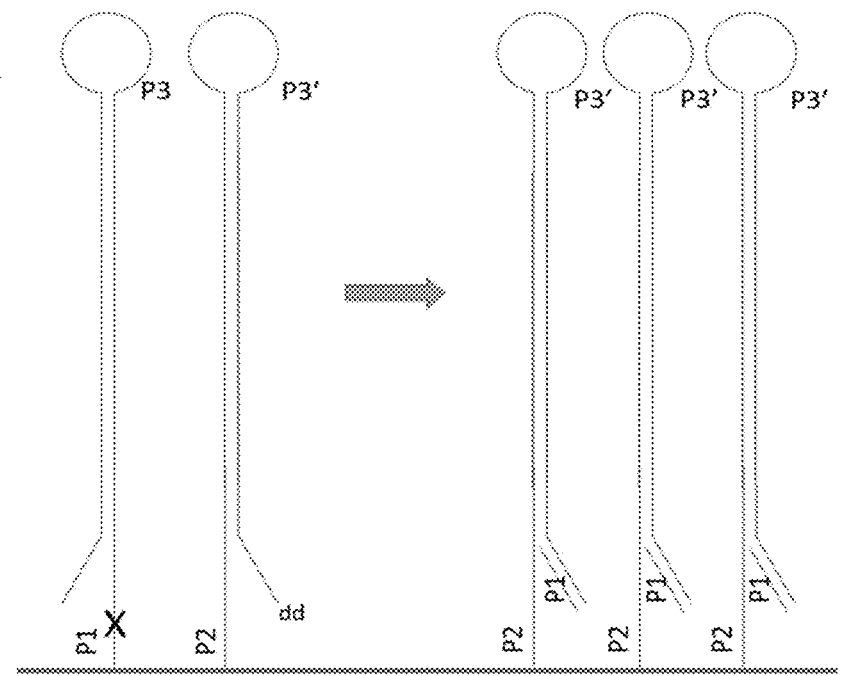
FIGS. 7A-7B show an overview of an embodiment of a linked duplex sequencing process; the gray ellipse represents a polymerase.

Linearization: To a solid surface having a plurality of extension products generated according to the methods described above, the method includes optionally cleaving one of the immobilized primers (e.g., P1). To the remaining extended primers (e.g., P2), the strands are terminated using dideoxy nucleotides, as shown in FIG. 7A.

Figure 7B:
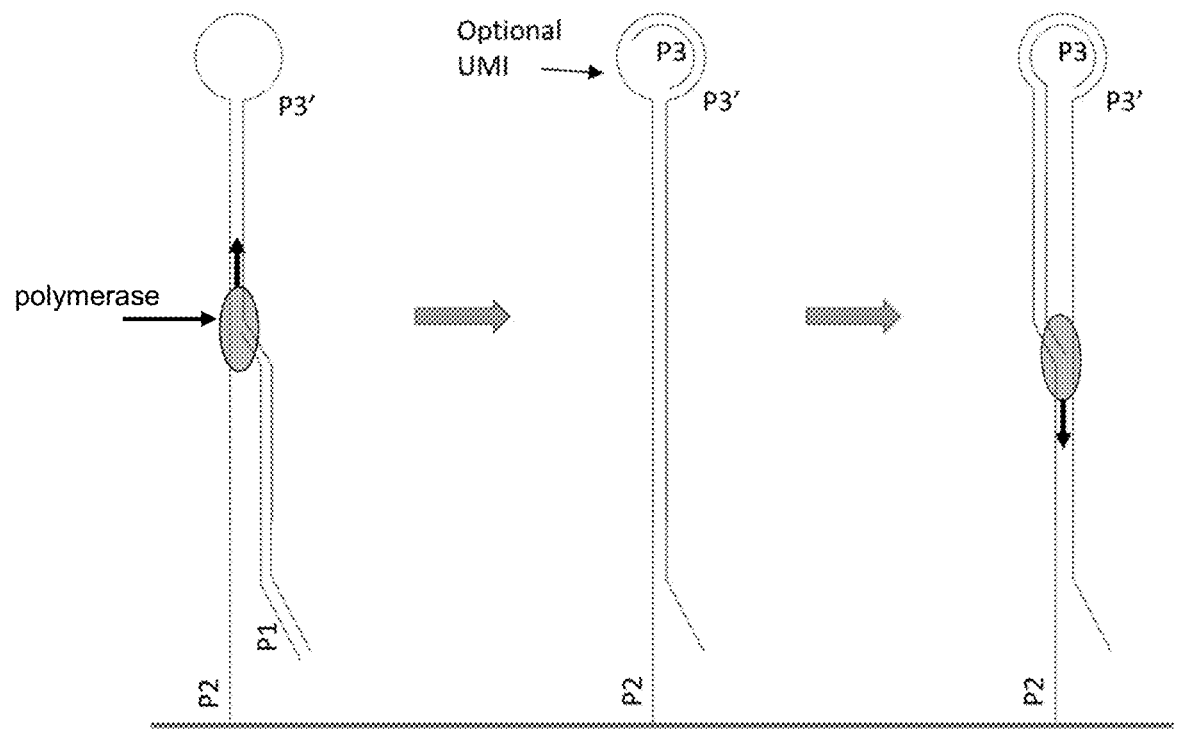

Sequencing reactions: The initiation point for the first sequencing reaction is provided by annealing of a sequencing primer complementary to one of the strands in the Y adapter (e.g., P1), also shown in FIG. 7A. FIG. 7B depicts the sequencing steps. In the presence of a strand displacing polymerase, nucleotides (e.g., labeled nucleotides) are incorporated and detected such that the identity of the incorporated nucleotides allow for the identification of the first template strand. Thus, the first sequencing reaction may include hybridizing a sequencing primer to a region of a linearized amplification product, sequentially incorporating one or more nucleotides into a polynucleotide strand complementary to the region of amplified template strand to be sequenced, identifying the base present in one or more of the incorporated nucleotide(s) and thereby determining the sequence of a region of the template strand. Note, the first sequenced strand (i.e., the first primer extension product) may be i) removed; 2) terminated (e.g., introducing dideoxy nucleotides); or iii) extended and ligated to the hairpin adapter.

Next, a second sequencing reaction is initiated by annealing a sequencing primer complementary to a region in the hairpin (e.g., P3), and in the presence of a strand displacing polymerase, nucleotides (e.g., labeled nucleotides) are incorporated and detected such that the identity of the incorporated nucleotides allows for the identification of the second template strand. Thus, the second sequencing reaction may include hybridizing a sequencing primer to a region of a linearized amplification product, sequentially incorporating one or more nucleotides into a polynucleotide strand complementary to the region of amplified template strand to be sequenced, identifying the base present in one or more of the incorporated nucleotide(s) and thereby determining the sequence of a region of the template strand.

Sequencing can be carried out using any suitable sequencing-by-synthesis technique, wherein nucleotides are added successively to a free 3' hydroxyl group, resulting in synthesis of a polynucleotide chain in the 5' to 3' direction. In embodiments, the identity of the nucleotide added is determined after each nucleotide addition.

In embodiments, the sequencing method relies on the use of modified nucleotides that can act as reversible reaction terminators. Once the modified nucleotide has been incorporated into the growing polynucleotide chain complementary to the region of the template being sequenced there is no free 3'-OH group available to direct further sequence extension and therefore the polymerase cannot add further nucleotides. Once the identity of the base incorporated into the growing chain has been determined, the 3' reversible terminator may be removed to allow addition of the next successive nucleotide. Such reactions can be done in a single experiment if each of the modified nucleotides has a different label attached thereto, known to correspond to the particular base, to facilitate discrimination between the bases added at each incorporation step. Alternatively, a separate reaction may be carried out containing each of the modified nucleotides separately.

The modified nucleotides may carry a label (e.g., a fluorescent label) to facilitate their detection. Each nucleotide type may carry a different fluorescent label. However, the detectable label need not be a fluorescent label. For example, the detectable label can be a paramagnetic spin label such as nitroxide, and detected by electron paramagnetic resonance and related techniques. Exemplary spin labels and techniques for their detection are described in Hubbell et al. Trends Biochem Sci. 27:288-95 (2002), which is incorporated herein by reference in its entirety. Any label can be used which allows the detection of an incorporated nucleotide. One method for detecting fluorescently labeled nucleotides includes using laser light of a wavelength specific for the labeled nucleotides, or the use of other suitable sources of illumination. The fluorescence from the label on the nucleotide may be detected by a detection apparatus (e.g., by a CCD camera or other suitable detection means).

Use of the sequencing method outlined above is a non-limiting example, as essentially any sequencing methodology which relies on successive incorporation of nucleotides into a polynucleotide chain can be used. Suitable alternative techniques include, for example, pyrosequencing methods, FISSEQ (fluorescent in situ sequencing), MPSS (massively parallel signature sequencing), or sequencing by ligation-based methods.

Example 2: Cell-Free DNA

It is a major challenge to distinguish true variants from background noise for rare variant discovery. Typically, large amounts of sequencing data (high sequencing depth) are required to differentiate a true variant from an amplification and/or sequencing error using previous methods. In addition, the heterogeneity of mutations within populations of rare cells in liquid biopsy samples, such as plasma or saliva, make it difficult to distinguish between sequencing-related errors and true somatic mutations originating from tumors. Methods and constructs provided herein do not necessarily require such large sequencing depths, thereby dramatically reducing the costs associated with sequencing.

Studying cell-free DNA (cfDNA) proves to be a useful test case for testing the capabilities of the linked duplex sequencing methods described herein, for recovering sequencing depth and for detecting rare mutations in a clinical application. Nucleic acids, e.g., cfDNA, are released into the bloodstream and other body fluids as part of natural cell apoptosis, necrosis, and secretion, and comprises both single- and double-stranded DNA fragments that are relatively short (overwhelmingly less than 200 base-pairs) and are normally at a low concentration (e.g. 1-100 ng/mL in plasma). It is known that the concentration of cfDNA and ctDNA in plasma correlates with tumor size and stage. For example, patients having stage I cancer types had fewer than 10 copies per 5 ml of tumor mutations in plasma. In contrast, the copy number increased 10 to 100 times among late-stage patients (Hague et al. bioRxiv. 2017; 237578). Thus, ctDNA assays used for early cancer diagnosis should be highly sensitive. Commercial solutions require UMIs on both strands of the double-stranded template, followed by low-error sequencing. To determine a true variant using previous commercial solutions, large amounts of sequencing data (high sequencing depth) is required to generate a consensus sequencing read to confidently ascertain a single nucleotide change.

Recent cancer genome sequencing studies have shown that virtually all cancers harbor somatic genetic alterations. These alterations include insertions, deletions, single-base substitutions, and translocations (Vogelstein et al Science. 2013 Mar. 29; 339(6127): 1546-1558). In cancer, a proportion of cfDNA circulating in plasma can come from the tumor, with the relative contribution of cfDNA coming from the tumor increases with cancer severity. The rate of these chromosomal changes in cancer cells is elevated and mutations can be challenging to detect accurately (Pietrasz et al Clin Cancer Res. 2017 Jan. 1; 23(1):116-123). While typical commercial sequencing instruments have a sequencing error rate that varies from about 0.05-1% (Quail et al Nat Methods. 2008 December; 5(12):1005-10), and can reveal comprehensive genomic alterations, it remains a challenge to distinguish variants at such low fraction from background errors of sequencing. Nonetheless, identifying cfDNA harboring these genetic alterations serves as valuable biomarkers and accurately detecting these variants will significantly improve current methods of cancer diagnosis, cancer progression monitoring, therapy effectiveness, and early-stage detection.

To address these issues, we designed a protocol described herein for ligating two different adapters at each end of a double stranded template nucleic acid. High accuracy sequencing reads would be particularly useful for rare variant detection in cfDNA. DNA variants cannot be statistically distinguished from sample prep and/or sequencing errors when they are present within a sample at a frequency below the error rate of the sequencing method (typically between 0.05-1%). By linking the parent DNA strands together with a hairpin adapter as described herein, and sequencing both strands of the double stranded template nucleic acid, sample prep and sequencing errors can be distinguished from true variants by identifying discordant base calls between the complementary sequencing reads. True genetic variants will be observed as mutations on both strands, whereas errors will only be observed as mutations on a single strand. The sequencing method described herein allows for very high accuracy results by identifying and correcting for errors within the data which in turn increases the sensitivity for rare variant detection. In general, since two independent sequencing measurements are made for the same base, that is, one for each strand, the accuracy of the consensus base call is the product of the error rate for each individual base call. For example if the single-pass error rate is $10^{-3}$ (Q30), then pairwise sequencing using the methods described allows for a double pass rate to be at least double the single-pass rate, i.e., $10^{-6}$ (Q60).

Blood samples (4-6 ml) are collected from patients into EDTA tubes during routine phlebotomy. Plasma is separated by centrifugation with Ficoll solution at 2,000 rpm for 15 min and transferred into micro-centrifuge tubes. Then, the plasma is further centrifuged at 13,000 rpm for 10 min to remove cell debris. The supernatant is stored at −80° C. before extraction.

The cfDNA is extracted from 1 mL aliquots of plasma using the QIAamp circulating nucleic acid kit (Qiagen). Typically, cfDNA is approximately 160-180 bp, and additional fragmentation is not necessary. Depending on the average sizes of the cfDNA, the cfDNA sample may be optionally fragmented to an average size of approximately 160-200 bp by enzymatic fragmentation, or other fragmentation/sizing method known in the art. The extracted DNA is then end repaired, dA-tailed using known methods in the art, and ligated using the two classes of adapters (e.g., S1 and S4 sequences comprise the Y adapter as described in Table 1; and the B1, B10, or B14 hairpin adapter as described in Table 2) as described herein to yield adapter-target-adapter nucleic acids. The resulting adapter-target-adapters may then be amplified and sequenced as described herein.

An example workflow is provided herein that was used to sequence samples of cfDNA. Linked-paired strand libraries were prepared in triplicate with 100 ng of cfDNA (Horizon catalog #HD780) with wild type or a 1% allelic frequency. Pre-fragmented cfDNA was end repaired, dA tailed, and Phosphorylated using the NEBNext® End Repair Module (E6050S) at 20° C. for 30 minutes, 65° C. for 3 minutes followed by bead purification. 0.8 uM adapters (S1 (SEQ ID NO:1), S2 (SEQ ID NO:3), and B14 (SEQ ID NO: 18)) were then ligated onto the DNA molecules using 16 U/uL T4 DNA Ligase, 1×T4 DNA Ligase buffer at 25° C. for 15 min followed by a bead purification step. Next, the B14 hairpin adapter loop region was captured to isolate desired constructs containing a hairpin from unwanted side products (e.g., S1/S2 adapter library contaminants and/or adapter dimers). 5 pmoles of a biotinylated probe was hybridized to the library at 45° C. for 15 minutes. 50 ug of My1C1 streptavidin beads were incubated with biotinylated probe bound-library molecules in a buffer rotating at room temperature for about 30 minutes. Unbound components were washed away using a wash buffer and products were eluted/denatured off of capture probe using 0.1 M NaOH and then quenched with 200 mM Tris-HCl pH 7.0. The eluent was split into two PCR reactions amplified with 0.5 uM S1, S2 primers (i.e., primers complementary to a portion of S1 and S2, respectively), 0.5 mM dNTPs, 1×SD polymerase buffer, salts, and 10 Units SD Polymerase. PCR thermocycling was performed (e.g., cycling parameters included an initial denaturation at greater than 90° C. for at least 1 min, followed by thermally cycling between 95° C.-68° C. followed by maintaining the temperature at about 70-75° C. for about 5 minutes. Finally, a bead purification step was performed to isolate the amplified molecules.

Figure 20:
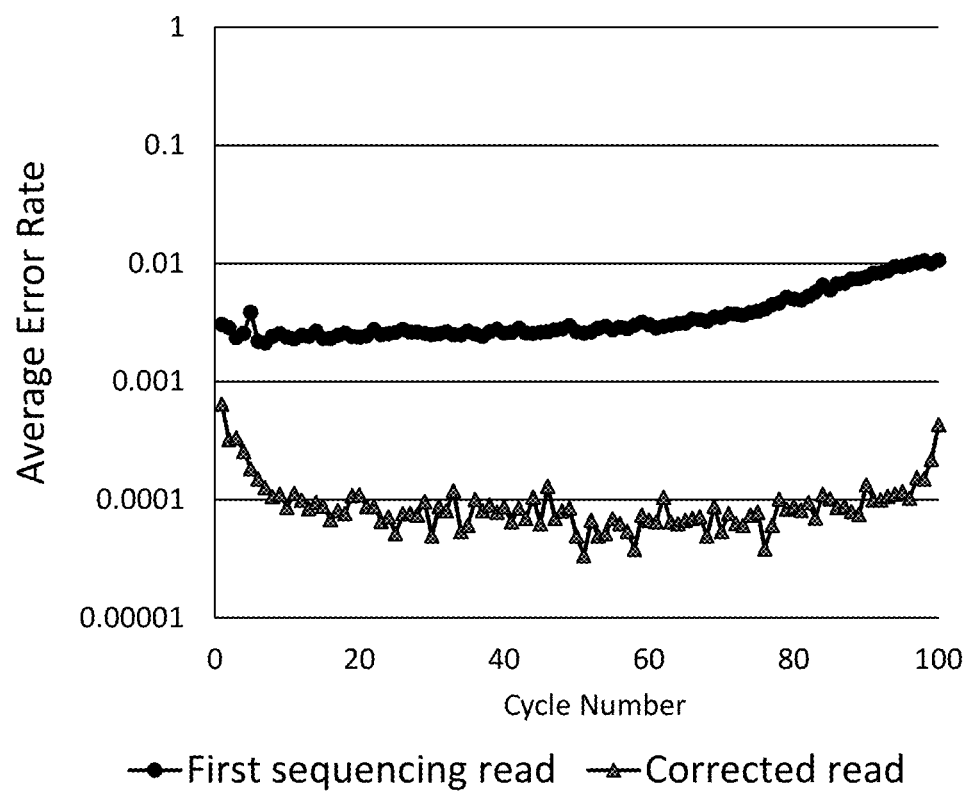
FIG. 20. A plot showing an example average error rate (Error Rate=1−Accuracy) per sequencing cycle. The first sequencing read (circles, top plot) shows the sequencing error as a function of cycle number from the first strand (Read 1). The corrected read (triangles, bottom plot) shows the sequencing error when read 1 reads are bioinformatically corrected based on the combined weight of the second strand (Read 2) sequencing reads. Base calling accuracy, measured by the Phred quality score (Q score), is the most common metric used to assess the accuracy of a sequencing platform. It indicates the probability that a given base is called incorrectly by the sequencer. For example, if the base calling algorithm assigns a Q score of 30 (Q30) to a base, this is equivalent to the probability of an incorrect base call 1 in 1000 times. This means that the base call accuracy (i.e., the probability of a correct base call) is 99.9%. In some embodiments, methods described herein permit a double pass rate to be at least double the single-pass rate, i.e., $10^{-6}$ (Q60).

Affinity Capture: 500 ng of linked-paired strand library molecules were opened up by denaturing, then hybridizing a 5' phosphorylated primer (one for each hairpin complement) in the hairpin loop and extending with a strand displacing polymerase, 0.5 mM dNTPs, 10 Units SD polymerase, 1×SD polymerase buffer, 60 pmoles of each primer. The reaction was heated to 92° C. for about 1 minute followed by cooling to less than 60° C. for about 15 minutes and then purified with bead purification. An affinity capture was performed with the XGen Pan-Cancer Panel v1.5 (IDT #1056205) and the protocol was followed per manufacturers recommendations with a few modifications, such as eliminating the heat step during hybridization. Hybridization was performed for about 16 hours at 65° C. and custom blockers were used that were appropriate for the adapters. After capture, digestion of the previously extended "blocker" strand is done with Lambda Exonuclease [1×SD buffer, 3 mM Mg, 5 Units Lambda Exonuclease] and then PCR amplification and bead size selection purification was performed. Clustering: A 4 lane flow cell containing immobilized primers (referred to as S1 and S2, having complementarity to S1 (SEQ ID NO:1), S2 (SEQ ID NO:3), or complements thereof) 28 bp in length was used for clustering. 2 pM of Y-template-hairpin (e.g., having the general structure depicted in FIG. 1A) libraries with cfDNA (wild type or 1% allelic frequency) were mixed with an aqueous solution containing ethylene glycol and a buffer and loaded onto the flow cell which was placed at 85° C. The temperature was slowly reduced to 45° C. for template seeding. First, extension was performed at 60° C. for at least 20 minutes to copy the template onto the anchored primers, followed by removal of the non-anchored template strand with 0.1 M NaOH. The anchored templates were amplified via a solid-phase nucleic acid amplification reaction for 45 cycles (bridge PCR amplification) using a strand displacing polymerase (e.g., Bst large fragment (Bst LF) polymerase, Bst2.0 polymerase, Bsu polymerase, SD polymerase, Vent exo-polymerase, Phi29 polymerase, or a mutant thereof)) 0.2 mM dNTPs and a combination of denaturants (e.g., betaine, dimethyl sulfoxide (DMSO), ethylene glycol, formamide, glycerol, guanidine thiocyanate, 4-methylmorpholine 4-oxide (NMO), or a mixture thereof). One of anchored strands was cleaved from the surface with enzymes able to cleave Uracil, thereby leaving the forward or the reverse complement of the construct on the surface. Surface primers and free 3' ends were blocked using terminal transferase and dideoxy (ddNTPs) for 30 minutes. A primer complementary to a portion of the hairpin loop was hybridized and extended using a strand displacing polymerase to free up one arm of the construct for sequencing. 1 uM of a sequencing primer complementary to the 51' foot region on the construct was hybridized. Sequencing Read 1: 105 cycles of sequencing were performed. Preparation of the construct for Read 2: The extended "blocking" strand was removed with 0.1M NaOH. 1 uM of an oligo complementary to a portion of the hairpin loop adapter and a Bgl II restriction site was hybridized and cleaved with Bgl II restriction endonuclease. These sequences were removed with NaOH 0.1M. 1 uM of a second sequencing primer complementary to the remaining adapter was hybridized and ready for sequencing. Sequencing Read 2: 155 cycles of sequencing was performed. Bioinformatically combining the results from sequencing read 1 and sequencing read 2 results in a consensus read. Since two independent sequencing measurements (i.e., sequencing read 1 and sequencing read 2) are made for the same base, that is, one for each strand, the accuracy of the consensus base call is the product of the error rate for each individual base call. For the first sequencing read, the average error rate is 0.01-0.001, that is $10^{-3}$ (Q30). Following the generation of a consensus read, then pairwise sequencing using the methods described allows for a double pass rate to be double the single-pass rate, i.e., $10^{-6}$ (Q60). In embodiments, the accuracy is 99.99%. In embodiments, the accuracy is 99.999%. In embodiments, the accuracy is 99.9999%. In embodiments, the accuracy is between about 99.9999% to 100%. In embodiments, the accuracy is between about 99.999% to 100%. In embodiments, the accuracy is between about 99.99% to 100%. See for example, the accuracy per sequencing cycle by sequencing the constructs and generating a consensus read according to the methods described herein in FIG. 20.

Following sequencing of cfDNA and acquiring the resulting reads, overlapping bases for each read pair are identified, and bases where the sequence for the first read (i.e., Read 1) varies from the expected corresponding complementary base in the second sequencing read (i.e., Read 2) are either marked as a no-call (called "N" in sequence) or the most likely base is chosen based on base quality scores. These reads are mapped to a reference genome. The process of mapping identifies the genomic origin of each fragment on the basis of a sequence comparison. For example, it is possible to determine if a given fragment of cfDNA was originally part of a specific region of chromosome 18.

The methods described herein are typically in reference to cfDNA and/or ctDNA, however they may equally apply, mutatis mutandis, to cfRNA. Technological advances are developing that enable the capture and isolation of cfRNA and ctRNA, see for example Beck, et al. BMC Cancer 19, 603 (2019) and Sorber, et al. Cancers, 11(4), 458 (2019), and Benayed et al. Clin Cancer Res. 2019(15):4712-4722, each of which is incorporated herein by reference.

Example 3: FFPE Samples

Formalin fixation and paraffin embedding (FFPE) has been the standard sample preparation method for pathologists, however the quality of the nucleic acid (e.g., DNA or RNA) extracted from FFPE blocks is highly variable due to nucleic acid damage introduced by the fixation process. Formalin fixation results in hydrolysis of the phosphodiester bonds, leading to varying degrees of fragmentation. Furthermore, formalin is capable of interacting (i.e. crosslinking) with cytosine nucleotides on either strand, which can result in mutations during amplification.

The methods described herein permit sequencing of two distinct regions, one at each end of the complementary strands of a target polynucleotide duplex. Sequencing the complementary original strands of dsDNA would aid in differentiating between true variants and errors due to DNA damage caused by FFPE storage. The protocol as described in the application, consists of ligating two different classes of adapters at each end of a double stranded template nucleic acid. Additional protocols and reaction conditions may be found in, for example, Kau and Makrigiorgos Nucleic Acids Research, 2003, Vol. 31, No. 6 e26.

Extraction of nucleic acids from FFPE samples is accomplished utilizing commercial solutions, such as the Nucleic Acid Isolation Kit for FFPE (Cat. No. AM1975) or Invitrogen™ MagMAX™ FFPE DNA Isolation Kit (Cat. No. 4463578). Both procedures perform proteolytic digestions followed by purification with solid-phase extraction. Typically, FFPE DNA may not require additional fragmentation (e.g., badly damaged FFPE DNA), however the sample may optionally be fragmented to an average size of approximately 160-200 bp enzymatic fragmentation, or other fragmentation/sizing method known in the art. The fragments are then end repaired, dA-tailed using known methods in the art, and ligated using the two classes of adapters (e.g., S2 and S5 sequences comprise the Y adapter as described in Table 1; and the B2, B10, or B14 hairpin adapter as described in Table 2) as described herein to yield adapter-target-adapter nucleic acids. The resulting adapter-target-adapters may then be amplified and sequenced as described herein.

Example 4: AML Rare Mutation Detection

Typically, the conventional technology for measuring cellular mutations and heterogeneity for complex diseases includes bulk sequencing, which provide average variant allele frequencies. However, using averages to resolve mutational co-occurrences across cell lines is difficult and further, relying on averages may miss rare cancer mutations. Moving beyond averages helps deliver on the promise of precision medicine.

Traditional sequencing paradigms struggle to characterize instances of AML (acute myeloid leukemia). AML is a cancer of the myeloid line of blood cells, which results in impaired hematopoiesis and bone marrow failure. Two or more driver mutations are frequently observed in one or multiple genes in AML. The most common gene mutation is found in the tumor suppressor and DNA repair gene TP53, however specific mutations in genes such as FLT3, SF3B1, NPM1, and KIT may influence the outcome of the disease. For example, TP53 possesses a c.722 C>G mutation and SF3B1 may have a c.2098 A>G mutation. A major challenge has been the unambiguous identification of potentially rare and genetically heterogeneous neoplastic cell populations, however using the methods described herein will address these and other problems known in the art. The sequencing method described herein will allow for very high accuracy results; for example if the single-pass error rate is $10^{-3}$ (Q30), then pairwise sequencing using these methods would allow for a double pass rate to be 10' (Q60).

To do so, a collection of cells (e.g., peripheral blood mononuclear cells (PBMCs) from AML patients and a control population of cells) are lysed and treated using known techniques in the art to extract DNA from histones and other DNA-binding proteins. The DNA-lysates may be blunt-ended or polished prior to ligating adapters.

The resulting DNA-lysates are ligated to two different adapters, wherein one adapter is a UMI containing adapter (e.g., a Y adapter as depicted in FIG. 2A, a hairpin adapter in FIG. 2B, or a hairpin adapter shown in FIG. 4) wherein the UMI is used to uniquely identify the origin of the DNA. The resulting adapter-target-adapters are then amplified (e.g., as depicted in FIG. 8) and sequenced as described herein. Following sequencing and acquiring the resulting reads, these reads are mapped to a control genome permitting the detection of gene mutations.

Example 5: Selective Sequencing

For some samples, only a subset of polynucleotides in a sample are relevant to a particular assay. In such cases, it can be faster, more efficient, and even more sensitive to sequence only that subset. Selectively enriching a population of polynucleotides by probe hybridization is simpler when the target polynucleotides are linear, as the strands can be denatured from one another by distances that allow for easier competition with probe oligonucleotides. However, when two strands of a target polynucleotide are joined by one or more loops (e.g., when ligated to a hairpin adapter on one or both ends), the two strands remain in close proximity when denatured, and more easily re-hybridize with one another. This ease of re-hybridization increases competition with probe oligonucleotides for binding their respective target sequence and can decrease recovery of target sequences. Example methods for displacing a strand of a target polynucleotide ligated to at least one hairpin adapter to increase probe capture efficiency are provided herein.

Figure 9:
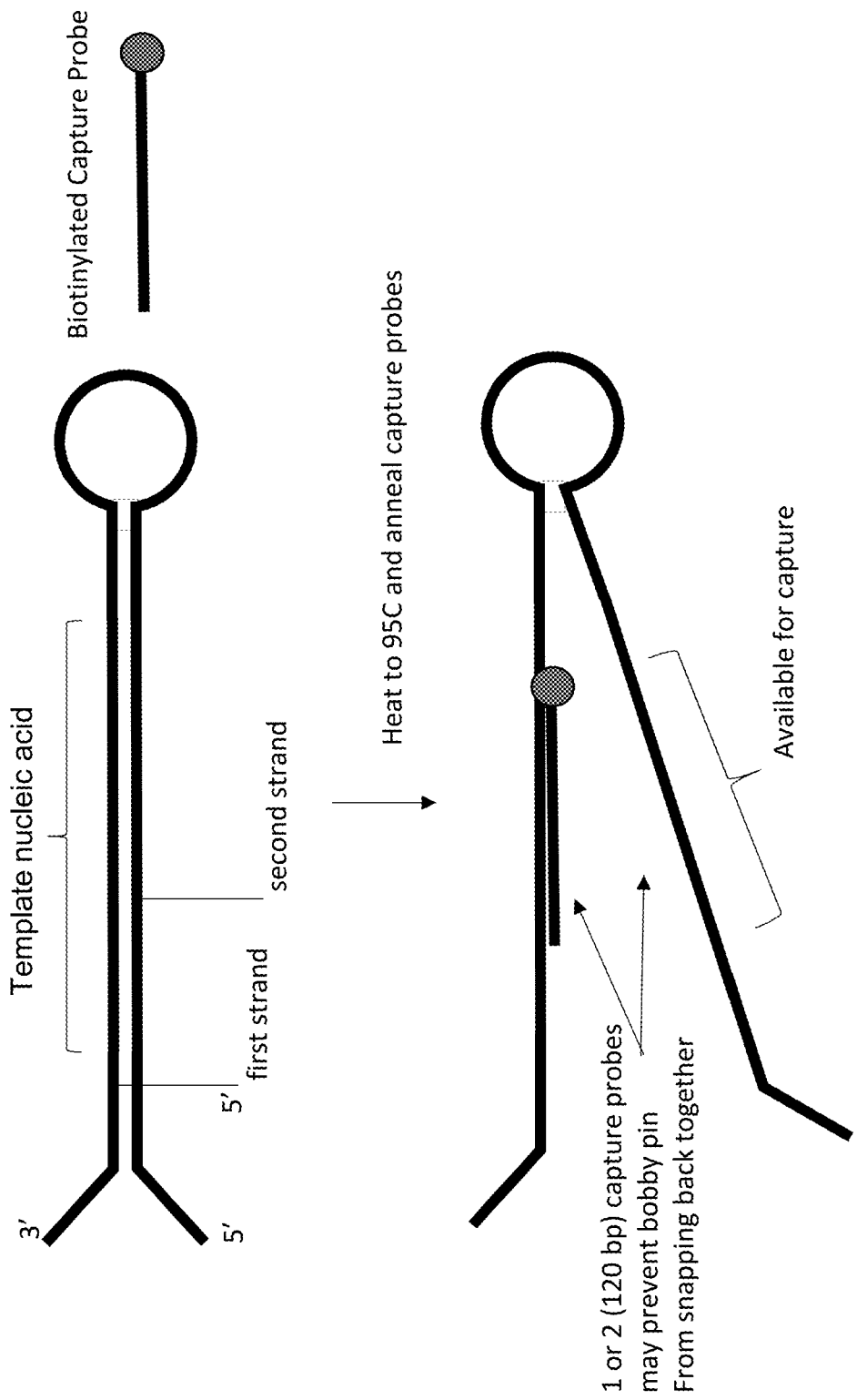
FIG. 9 shows an overview of an embodiment of an affinity capture process of a Y-template-hairpin construct by hybridization with a capture probe, wherein the capture probe is a biotinylated capture probe.

A first method is the use of one or more biotinylated single stranded probe oligonucleotides, or "biotinylated capture probes", which are annealed to specific regions of polynucleotide duplexes comprising a double stranded nucleic acid of interest annealed to a Y-adapter and a hairpin adapter, therefore labeling said polynucleotide duplexes. In this method, an initial step of denaturation (i.e. strand dissociation) is used to allow the biotinylated probes, to bind to the first strand and/or second strand of the target nucleic acid. The resulting biotin-labeled complexes can then be purified via methods of purifications based on avidin, streptavidin, or neutravidin, or can be captured via the available regions of the previously double stranded template nucleic acid, now single stranded. FIG. 9 presents an example of such a method of labeling a polynucleotide duplex of interest, via the use of a biotinylated probe complementary to a region of the first strand of the polynucleotide duplex (the template nucleic acid), a step of heat induced denaturation at 95° C., and a following step of annealing of the probe to its target region in the first strand of the template nucleic acid, therefore labeling it.

Figure 10:
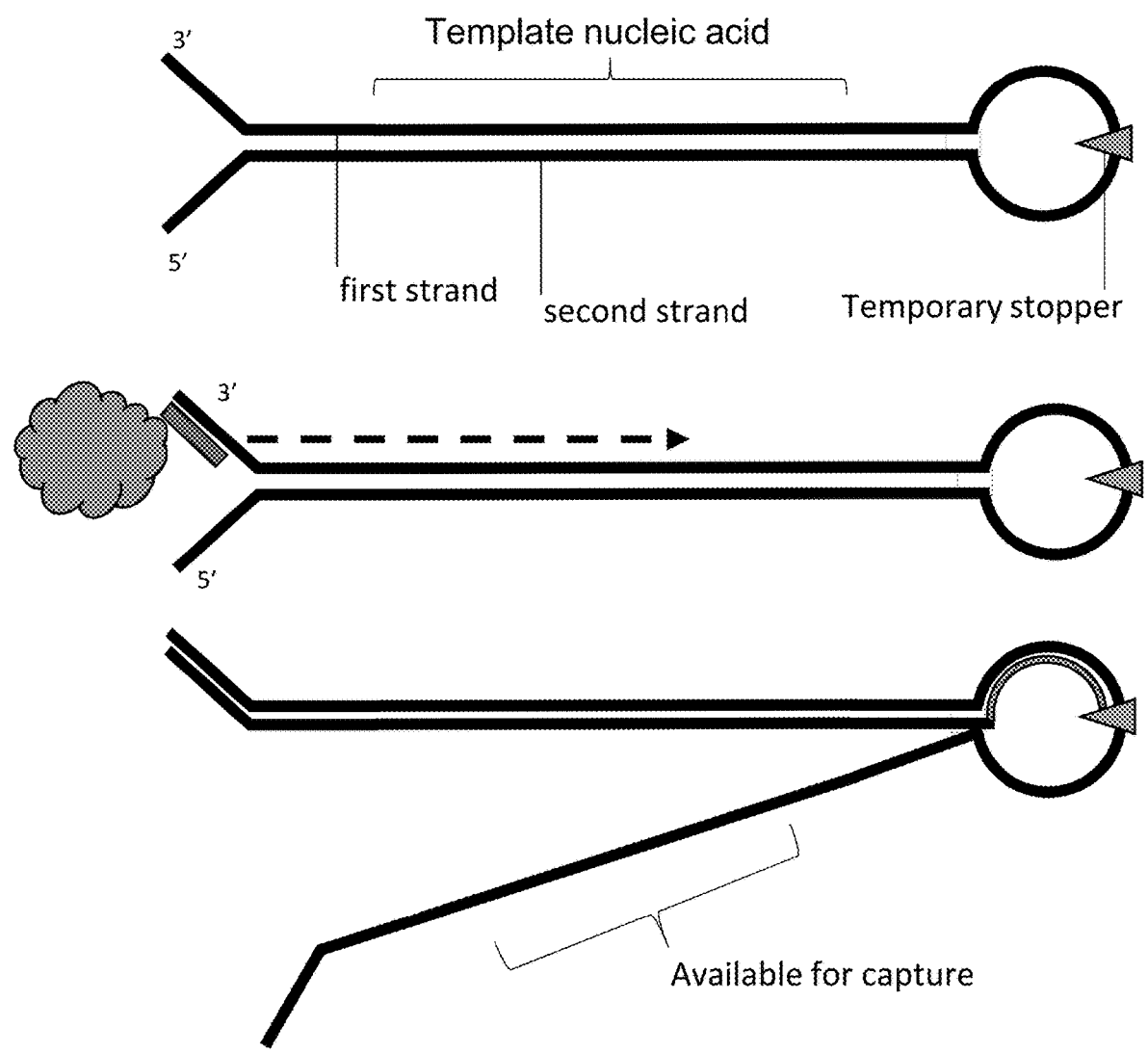
FIG. 10 shows an overview of an embodiment of an affinity capture process for a Y-template-hairpin construct comprising a modification within the loop region that prevents further elongation (the "temporary stopper," also referred to herein as a "terminating nucleotide"), thereby rendering the second strand of the construct available for capture.

Another method is the use of modified nucleotides in the hairpin loop of a polynucleotide duplex including a double-stranded nucleic acid of interest ligated to a Y-adapter and a hairpin adapter. In this method, the modified nucleotides are selected to create a "temporary stop," which stops polymerase extension of a primer complementary to the single-stranded 3' end of the Y-adapter. The result of this method is the formation of a double-stranded product, in which the second strand of the polynucleotide duplex is single-stranded and available for capture (e.g. by a surface-bound primer, complementary to a specific region of the second strand of the polynucleotide duplex). Following capture, the temporary stopper can be removed. FIG. 10 presents an example of such method.

In one example implementation of a temporary stopper, a polymerase (e.g., phi-29) can be used to extend a primer complementary to the single stranded 3' end of the Y-adapter, up to the temporary stopper containing one or more modified nucleotides. After capture of the polynucleotide duplex, another enzyme that is capable of extending the product of the first polymerase beyond the temporary stopper (e.g. Pfu) can be used for subsequent steps. In another example implementation, the temporary stopper is composed of one or more modified nucleotides with a cleavable linker (e.g., 5', 3', or a base) containing PEG, thereby blocking the extension of a primer complementary to the single stranded 3' end of the Y-adapter, up to the temporary stopper. After capture of the polynucleotide duplex, the linker(s) can be cleaved so as to remove the PEG. In another example implementation, the temporary stopper is composed of one or more modified nucleotides linked to biotin, to which a protein (e.g., streptavidin) can be bound, thereby blocking polymerase extension. After capture of the polynucleotide duplex, the reaction conditions can be modified (e.g., increased salt concentration, and/or, increased temperature) so as to release the protein, or proteins, bound to the one or more modified nucleotides. In another example implementation, the temporary stopper is a modified nucleotide, such as iso dGTP or iso dCTP, which are complementary to each other. In a reaction of polymerization lacking the complementary modified nucleotides, the extension of a primer complementary to the single-stranded 3' end of the Y-adapter is therefore only possible up to the temporary stopper. After capture of the polynucleotide duplex, the corresponding complementary modified nucleotide (iso dGTP in the case of iso dCTP in the loop) can be added to the solution, therefore allowing the polymerization process to proceed. In another example implementation, the temporary stopper comprises one or more sequences which is recognized and bound by one or more single-stranded DNA-binding proteins, thereby blocking polymerase extension at the bound site. After capture of the polynucleotide duplex, the reaction conditions can be modified (e.g., increased salt concentration, and/or, increased temperature) so as to release the protein(s), therefore allowing polymerization to proceed. In another example implementation, the temporary stopper comprises one or more sequences which are recognized and bound by one or more short RNA or PNA oligos, thereby blocking the extension by a strand displacing DNA polymerase that cannot strand displace RNA or PNA. For example, after capture of the polynucleotide duplex, RNase H can be then used to digest the RNA oligos, therefore allowing the polymerization process to proceed. In embodiments, after capture of the polynucleotide duplex, the PNA is subjected to denaturing conditions (e.g., increasing the temperature to release the PNA); RNase H can be then used to digest the oligos, therefore allowing the polymerization process to proceed.

Figure 11:
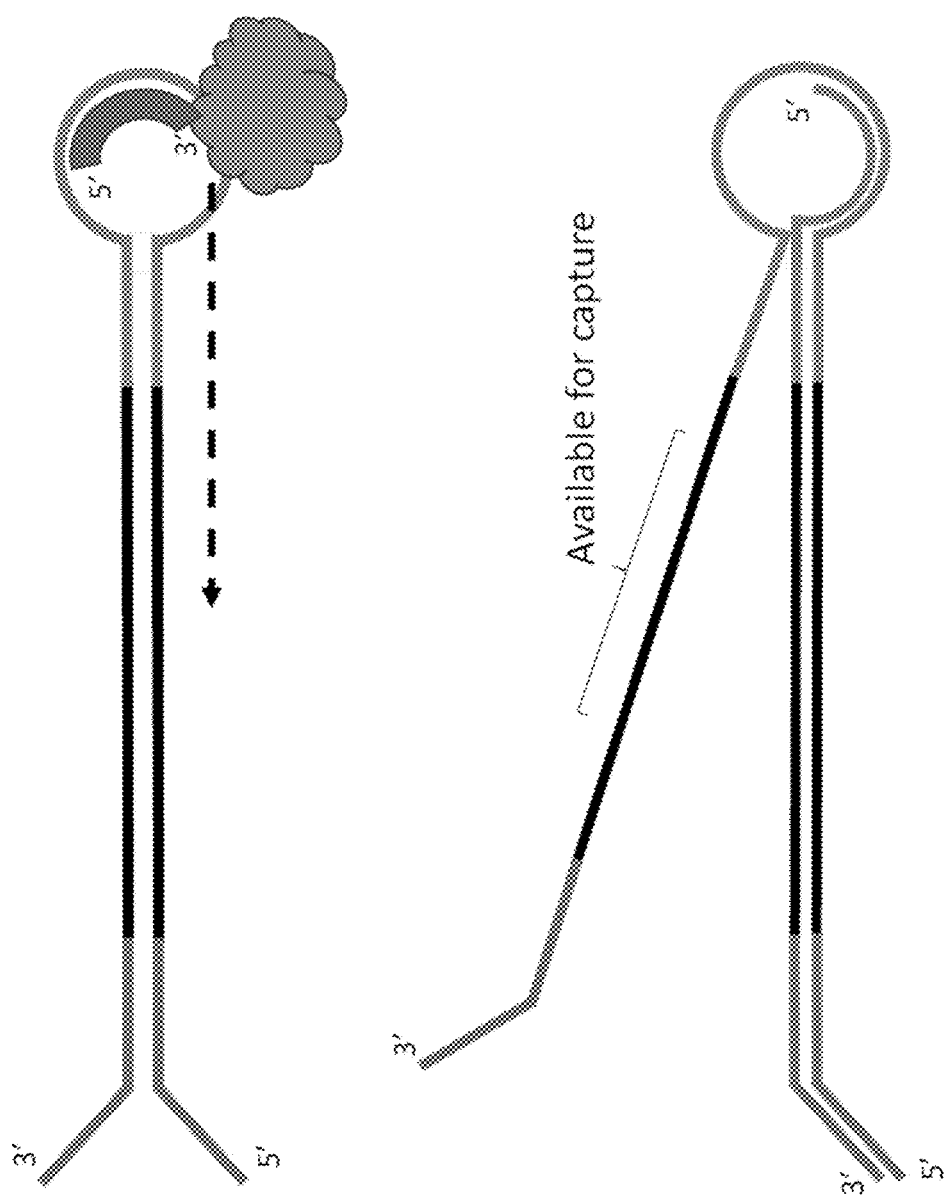
FIG. 11 shows an overview of an embodiment of an affinity capture process for a Y-hairpin construct in which a primer is complementary to a region within the loop of the hairpin adapter of the construct. The result of primer elongation is a double stranded second strand of the Y-hairpin construct, and a single stranded first strand which remains available for capture.

Another method is the use of a primer complementary to the hairpin loop or stem of a hairpin adapter, within a polynucleotide duplex including a double stranded nucleic acid of interest ligated to a Y-adapter and the hairpin adapter. In this method, a primer hybridizes to a complementary region within the hairpin loop, and a strand-displacing enzyme extends from the primer to form a double-stranded product. With the formation of a double-stranded product, the first strand is single stranded and available for capture (e.g., a surface-bound complementary oligonucleotide). FIG. 11 presents an example of such method.

Figure 12:
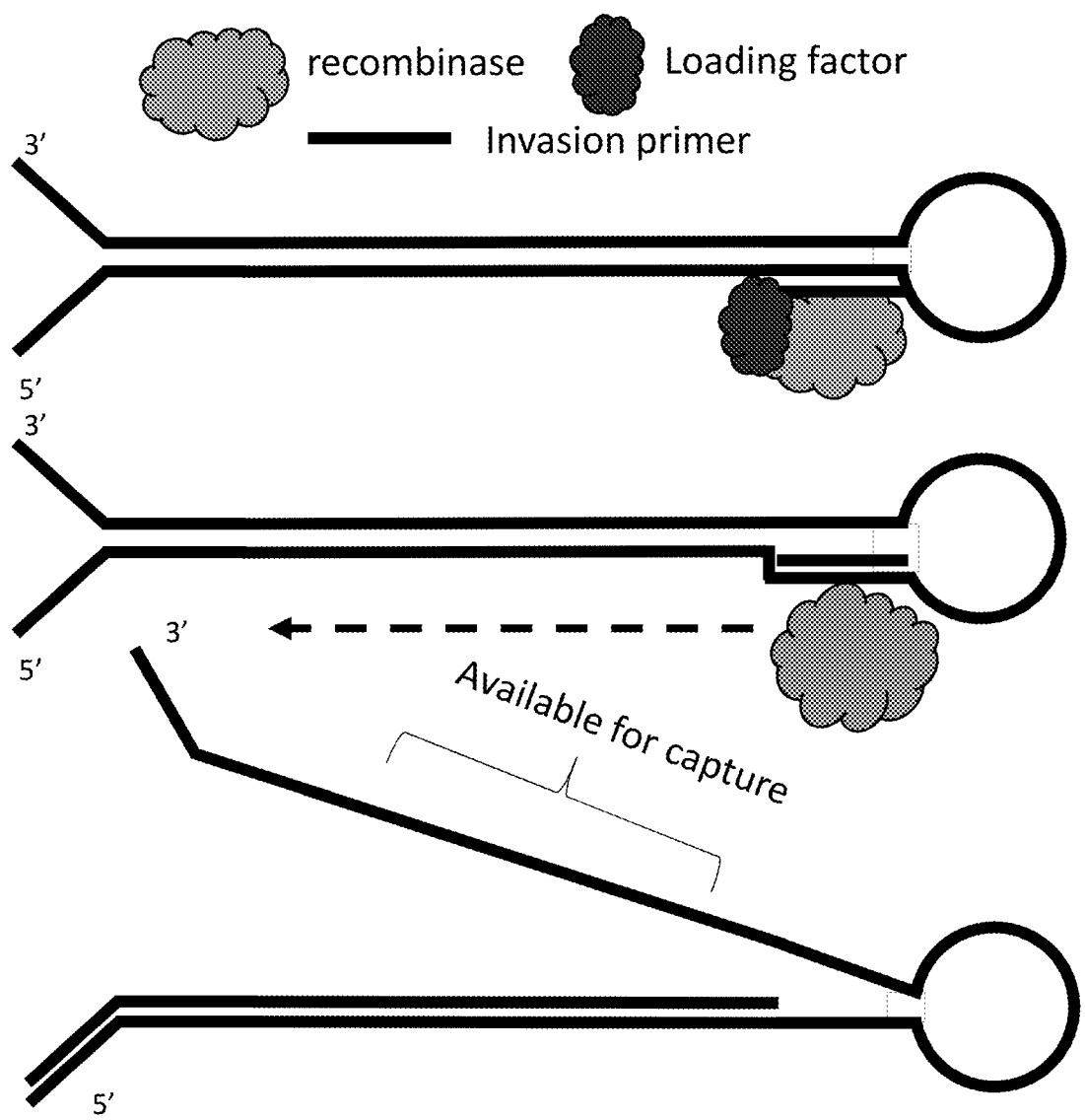
FIG. 12 shows an overview of an embodiment of an affinity capture process of a Y-hairpin construct in which a primer invades the double stranded region of the hairpin adapter of the construct upstream of the second strand of the construct, via the use of a recombinase and of a loading factor. Elongation of the primer results in a double stranded second strand, and a single stranded first strand which remains available for capture.

Another method is the use of an insertion primer complementary to a portion of the 5' region of the double stranded portion of a hairpin adapter (an "invasion primer"), within a polynucleotide duplex including a double stranded nucleic acid of interest ligated to a Y-adapter and the hairpin adapter. In this method, a recombinase (e.g., T4 UvsX protein), assisted by a loading factor (e.g., T4 UvsY), and the insertion primer, form a nucleoprotein complex, wherein the insertion primer hybridizes to a complementary region of double stranded DNA. Additional cofactors (e.g., single-strand binding protein, ATP, salts, etc.) may also be used to facilitate hybridization. The complex invades the double stranded DNA target region and a strand exchange occurs, forming a D-loop. Once the D-loop forms, the recombinase complex dissociates. A strand-displacing DNA polymerase extends to form a double-stranded product. With the formation of a double-stranded product, the first strand is single stranded and available for capture (e.g., hybridizing to a surface-bound complementary oligonucleotide). FIG. 12 presents an example of such method.

Another method is the use of an insertion primer complementary to a portion of the 5' region of the double stranded portion of a hairpin adapter or Y-adapter within a polynucleotide duplex including a double stranded nucleic acid of interest ligated to a Y-adapter and the hairpin adapter. In embodiments, the method includes generating a blocking strand. In embodiments, generating the blocking strand includes a plurality of extension cycles. In embodiments, generating the blocking strand includes extending the primer by incorporating one or more nucleotides (e.g., dNTPs) using Bst large fragment (Bst LF) polymerase, Bst2.0 polymerase, Bsu polymerase, SD polymerase, Vent exo-polymerase, Phi29 polymerase, or a mutant thereof. With the formation of a double-stranded product, the first strand is single stranded and available for capture (e.g., hybridizing to a surface-bound complementary oligonucleotide) or sequencing.

Figure 13:
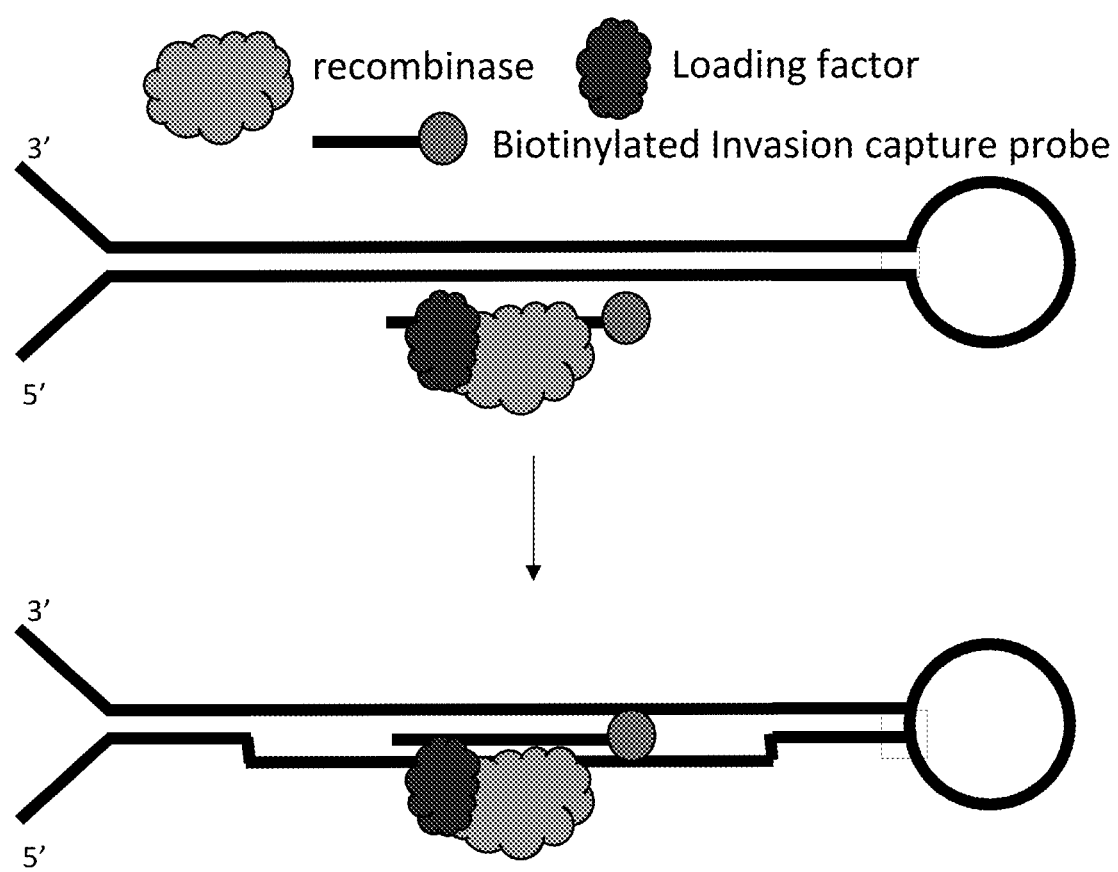
FIG. 13 shows an overview of an embodiment of an affinity capture process of a Y-hairpin construct in which a biotinylated invasion capture probe is bound to a target sequence of the construct via the use of a recombinase and of a loading factor.

Another method is the use of a biotinylated insertion probe (e.g., a biotinylated invasion capture probe) complementary to any region of a polynucleotide duplex including a double stranded nucleic acid of interest ligated to a Y-adapter and a hairpin adapter. In this method, a recombinase (e.g., T4 UvsX protein), assisted by a loading factor (e.g., T4 UvsY), and an invasion capture probe complementary to a target region of a polynucleotide duplex, form a nucleoprotein complex, wherein the insertion primer hybridizes to the complementary region of double stranded DNA of the polynucleotide duplex. Additional cofactors (e.g., single-strand binding protein, ATP, salts, etc.) may be used to facilitate hybridization. The complex invades the double stranded DNA target region and a strand exchange occurs, forming a D-loop. Once the D-loop forms, the recombinase complex may be dissociated. The biotinylated capture probe is therefore then bound to the target sequence, and this biotinylated complex can be pulled down and purified. FIG. 13 presents an example of such method, wherein the biotinylated invasion capture probe is complementary to a region of the second strand of the template nucleic acid of a polynucleotide duplex, including the template nucleic acid of interest ligated to a Y-adapter and a hairpin adapter.

Example 6: De Novo Assembly of Bacterial Genomes

Microbial genome sequencing has revealed how microorganisms adapt, evolve, and contribute to health and disease. With respect to bacterial genomes, the de novo assembly of short reads (100-300 bp) can result in fragmented assemblies, particularly because of the widespread presence of repetitive sequences. These repetitive sequences are often longer than the length of a short read and the span of paired-end reads. For example, antimicrobial resistance regions are often flanked by repetitive insertion sequences; in such a case, from an incomplete short-read assembly, it would be impossible to determine whether resistance regions are present in chromosomes or plasmids (Liao Y C et al. Front. Microbiol. 2019; 10:2068). As such, faithful de novo assembly of bacterial genomes typically requires larger inserts, for example, 1 kbp or larger.

Existing methods for de novo bacterial genome assembly include the use of long-read sequencing technology such as that of Pacific Biosciences and Oxford Nanopore, both of which report higher error rates and lower throughput in comparison to other sequencing methods (e.g., sequencing-by-synthesis technologies). Alternatively, large-scale genome assembly can use mate pair sequencing to generate long-insert paired-end DNA libraries, however the relatively laborious and lengthy protocol that generates long insert sizes needed for mate pair sequencing typically produces a large proportion of duplicates and chimeric variants that reduces true coverage and insight. Still, a major challenge is the higher rate of sequencing errors abundant in these existing methods, in combination with base composition bias and the complexity of repetitive regions in genomes, leading to complicated and unsatisfactory sequence assembly (Liao X et al. Quant. Biol. 2019; 7(2):90-109). The methods described herein address these and other problems. For example, the compositions and sequencing methods described herein will allow for high-accuracy pairwise sequencing of large-insert (e.g., 500-1500 bp) genomic libraries.

Bacterial genomic DNA is purified from isolated cultures using a commercial solution, such as the NEB Monarch® Genomic DNA Purification Kit (Cat. No. T30105). The extracted genomic DNA is fragmented to an average size of approximately 1000 bp by enzymatic fragmentation, or other fragmentation/sizing method known in the art. The fragments are then end repaired, dA-tailed using known methods in the art, and ligated using the two classes of adapters (e.g., S2 and S5 sequences comprise the Y adapter as described in Table 1; and the B2, B10, or B14 hairpin adapter as described in Table 2) as described herein to yield adapter-target-adapter nucleic acids. The resulting adapter-target-adapters are amplified and sequenced as described herein. Following sequencing and acquiring the resulting reads, these reads are then assembled using bioinformatic tools known in the art to generate the complete bacterial genome. These methods could also be applied to other prokaryotic and eukaryotic de novo genome assembly efforts.

Example 7: Alternative Splicing Analysis

Alternative splicing (AS) is a key post-transcriptional regulatory mechanism in which alternative splice sites are selected to generate more than one transcript from heterogenous nuclear RNA (hnRNA) transcripts (Wahl M C Cell 2009; 136:701-718). During AS, intronic sequences are defined by the dinucleotide conserved sequence motifs at the intron/exon junctions, usually GT-AG, which are respectively named as 5' donor site and 3' acceptor site. Other intron/exon junction dinucleotide sequence motifs have also been reported, including AT-AC, GC-AG, and GT-GG (Dubrovina A S et al. Biomed. Res. Int. 2013). Different transcript isoforms may encode proteins with different functions or affect the mRNA stability of translational capacity. For multiexon mRNA, the splicing mode may vary in multiple ways, including intron retention, exon skipping, and alternative donor/acceptor sites, dramatically increasing the complexity of the entire transcriptome and proteome (Li Y et al. The Plant J. 2016; 90(1):164-176).

Accurate detection of AS events remains a challenge due to the limitations of short-read sequences in reconstructing full-length isoforms (Hu H et al. Front. Genet. 2020; 11:48). These disadvantages generally lead to gene prediction without reliable annotation on alternative isoforms and untranslated regions, which can limit their use to characterize the post-transcriptional processes. Therefore, the identification of full-length splice isoforms is essential for a deep understanding of the transcriptome complexity and its potential role in gene regulation. Much like de novo bacterial genome assembly (see Example 6), AS detection will benefit from a longer insert size and reliable capture of AS-related motifs. A comparison between PacBio's SMRT sequencing and Illumina's RNA-seq platforms (Li Y et al. The Plant J. 2016; 90(1):164-176) indicated that SMRT, which utilizes longer read-length technology, was able to identify more genes undergoing AS than standard RNA-seq, although still lacked reliable capture of all known AS events. The sequencing method described herein allows for high-accuracy pairwise RNA sequencing of a large-insert library to enable efficient AS site detection.

Briefly, total RNA is extracted from a sample for AS analysis using a commercial solution such as the RNeasy Mini Kit (Qiagen). Ribosomal RNA (rRNA) is then depleted using a commercial solution such as the NEBNext® rRNA Depletion Kit V2 (Cat. No. E7405S). While polyA+ selection is typically used for RNA-seq protocols, rRNA depletion has been shown to capture significantly more transcriptome features useful for AS analysis (see, for example, Zhao S et al. Scientific Reports 2018; 8: 4781). The RNA is then fragmented to an average size of greater than 200 bases, for example, approximately 200-300 bases, or approximately 300-400 bases, or approximately 400-500 bases, or approximately 500-600 bases, or approximately 600-700 bases, or approximately 700-800 bases, using standard methods for RNA fragmentation such as acoustic shearing or incubation with divalent cations, e.g. $Mg^{2+}$, at elevated temperatures.

The fragmented RNA is then reverse transcribed and converted to double-stranded cDNA using commercial solutions, for example, the Invitrogen™ SuperScript™ Double-Stranded cDNA Synthesis Kit (Cat. No. 11917010). The cDNA is then dA-tailed using known methods in the art, and ligated using the two classes of adapters (e.g., S1 and S4 sequences comprise the Y adapter as described in Table 1; and the B1, B10, or B14 hairpin adapter as described in Table 2) as described herein to yield adapter-target-adapter nucleic acids. The resulting adapter-target-adapters may then be amplified and sequenced as described herein.

Following sequencing of cDNA and acquiring the resulting reads, the identification of major AS events, including exon skipping events, intron retention, alternative 5' donor, and alternative 3' donor usage can be accomplished through bioinformatic analysis, including the use of publicly available tools such as JUM (Wang Q and Rio D C Proc. Natl. Acad. Sci. 2018; 115(35):E8181-E8190) and PASA (Campbell M A et al. BMC Genomics 2006; 7:327). Identified AS events can then be cross-checked with known AS databases and reference genomes.

Example 8: Sequential Ligation on a Solid Support

Figure 14A:
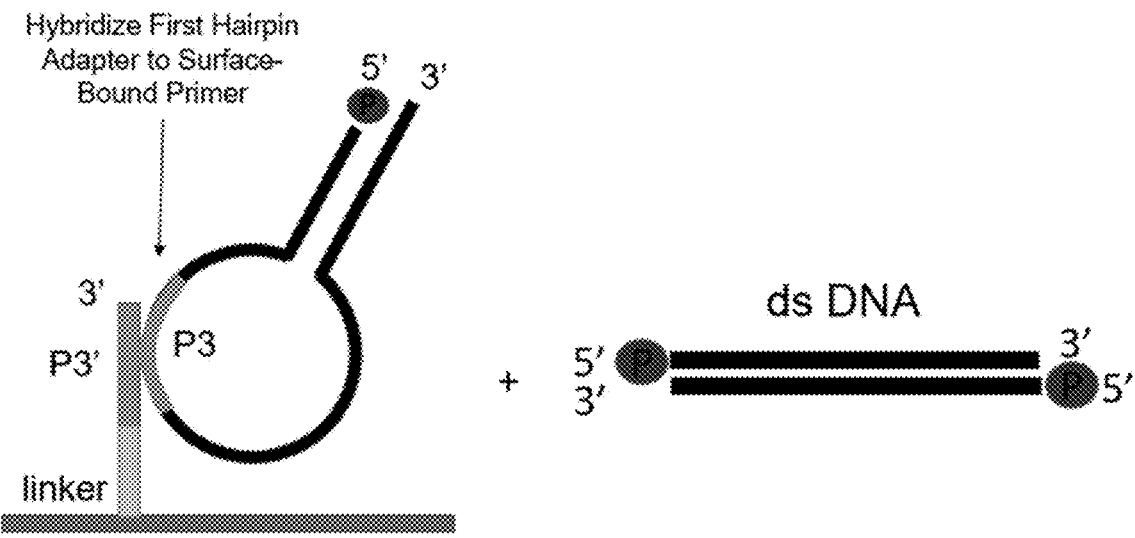
FIGS. 14A-14C show an overview of an embodiment of on-surface sequential ligation of a DNA template for sequencing, as described in Example 8. Depicted in FIG. 14A (right side), the target DNA is double stranded and contains a 5' phosphate for ligation. The loop of the hairpin adapter includes a priming region (PR), depicted in FIG. 14A as P3. The loop of the hairpin adapter may include an optional UMI (unique molecular identifier; barcode). To circularize the ds template DNA, a first hairpin adapter is hybridized to a surface-immobilized oligos, referred to as P3' in FIGS. 14A-14B. The target DNA is ligated to the hairpin adapter to form an adapter duplex. A second hairpin adapter is introduced and ligated to the adapter-duplex to form a circularized product, wherein the second hairpin adapter includes a different PR (i.e., P1 and P2 as illustrated) than the first hairpin adapter (see FIG. 14B). Alternatively, as shown in FIG. 14C, a Y-adapter is introduced, depicted as P1 and P2 in FIG. 14C, and ligated to the adapter-duplex to form an adapter-target-adapter construct resembling a bobby-pin structure.
Figure 14B:
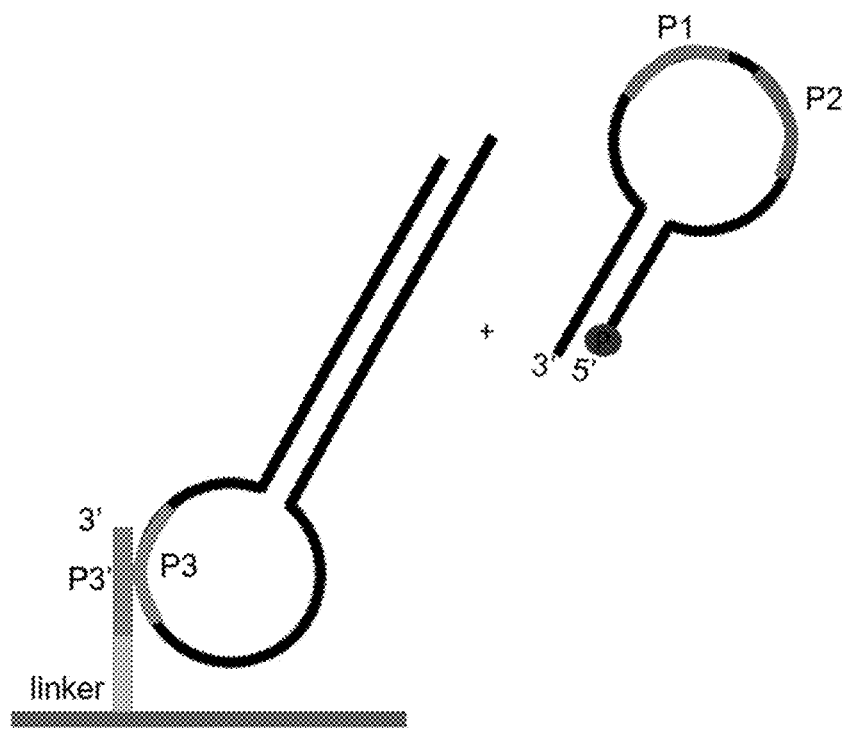
Figure 14C:
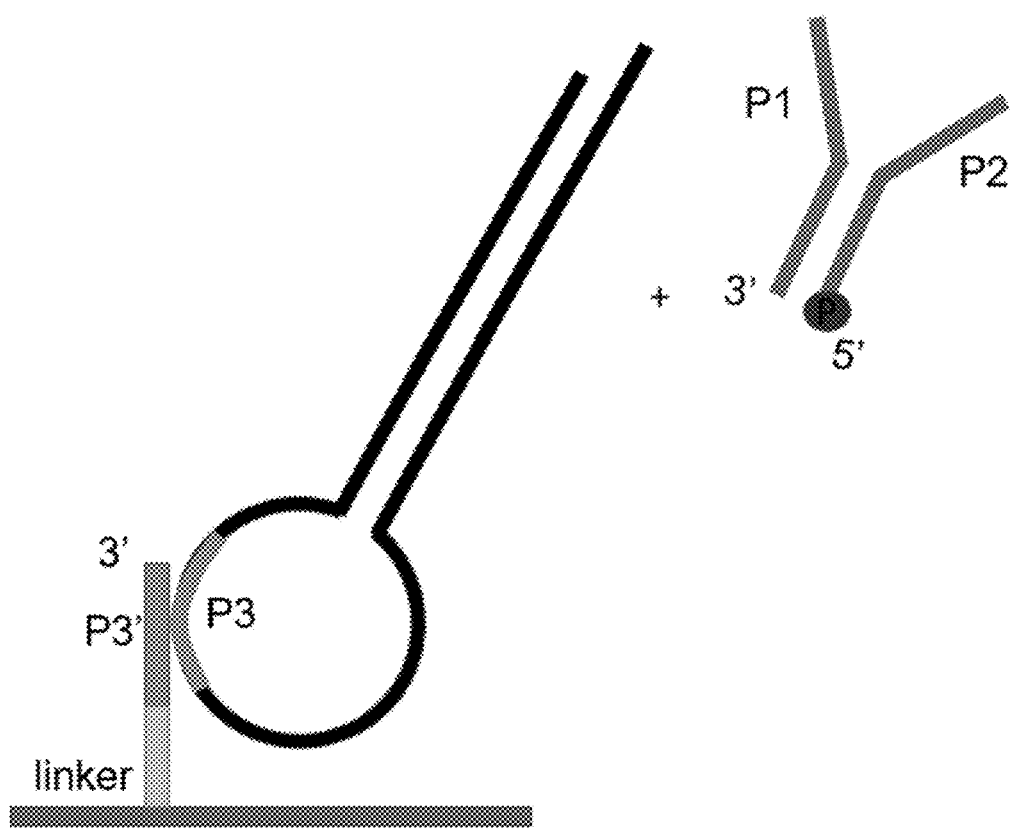

An alternative schematic showing the process for asymmetrical adapter ligation is shown in FIGS. 14A-14C. Depicted in FIG. 14A (right side), the target DNA is double stranded and contains a 5' phosphate for ligation. Embodiments of the hairpin adapters are described throughout the specification, for example in FIG. 4 and FIG. 5. The loop of the hairpin adapter includes a priming region (PR), depicted in FIG. 14 as P3. The loop of the hairpin adapter may include an optional UMI (unique molecular identifier; barcode).

To circularize the ds template DNA, a first hairpin adapter is hybridized to a surface-immobilized oligo, referred to as P3' in FIGS. 14A-14B. Generally, to form a cluster of monoclonal amplicons a plurality of immobilized oligos are present on the surface, however for clarity only one oligo is shown. After the first hairpin adapter is hybridized and excess unhybridized hairpin adapter are removed, the dsDNA is introduced and ligated to the first hairpin adapter to form adapter-duplex (see FIG. 14A). After ligation, any excess dsDNA is removed. A second hairpin adapter is introduced and ligated to the adapter-duplex to form a circularized product, wherein the second hairpin adapter includes a different PR (i.e., P1 and P2 as illustrated) than the first hairpin adapter (see FIG. 14B). The circularized product may then be subjected to circular amplification methods (e.g., RCA or eRCA) to produce a long continuous single stranded product. Alternatively, as shown in FIG. 14C a Y-adapter is introduced, depicted as P1 and P2 in FIG. 14C, and ligated to the adapter-duplex to form an adapter-target-adapter construct resembling a bobby-pin structure.

Surface-conjugation of oligos to flow cell: A plurality of primers, referred to as P3', are chemically attached to a polymer-coated glass slide through a linker via DBCO-azide click chemistry. This polymer-coated glass slide is assembled into a flow cell prior to primer deposition.

Hybridization of hairpin adapter 1 to surface primer: A hairpin adapter which contains a 5' phosphate, a 13 nt stem region (a stem region which is stable below 45° C.) and a loop sequence which is complementary to the P3' surface primer is hybridized to the flow cell at 37° C. for 30 minutes in a DNA hybridization buffer. After hybridization, excess unhybridized hairpin adapter is washed out of the flow cell.

Ligation of Target Sequence: A target sequence (e.g., dsDNA) which has been fragmented, polished, and 5' phosphorylated is introduced to the flow cell in a mixture of buffer and T4 DNA ligase and then incubated at 25-37° C. for 1-3 hours for ligation of target sequence onto adapter 1. After ligation, any excess target sequence is washed out of the flow cell.

Ligation of Adapter 2 onto Target Sequence: A second hairpin adapter which contains a 5' phosphate, a 13 nt stem region (stable below 45° C.) and a loop sequence which contains the P1 sequence and P2 sequence is introduced to the flow cell in a mixture of buffer and T4 DNA ligase and then can be incubated at 25-37° C. for 1-3 hours for ligation of adapter 2 onto target sequence. Alternatively, a Y-shaped adapter is introduced to the flow cell in a mixture of buffer and T4 DNA ligase and then can be incubated at 25-37° C. for 1-3 hours for ligation of adapter 2 onto the target sequence. After ligation, excess adapter is washed out of the flow cell. The adapter-target-adapter constructs are then amplified according to the methods described herein to form monoclonal clusters of amplicons. The resulting clusters can be visualized by staining the amplified product with SYBR-Gold and visualized using fluorescent microscopy.

Example 9: Linked Duplex Methylation Profiling

Somatic mutations alone may not provide adequate information about the tumor site. Epigenetic information, such as biomolecule methylation, and/or additional protein biomarkers combined with cfDNA and ctDNA analyses is useful in determining the tumor origin at an early stage. Biomolecule methylation, such as DNA methylation, is widespread and plays a critical role in the regulation of gene expression in development, differentiation, and disease. Methylation is an epigenetic modification in which a methyl group is added to cytosines and/or adenine nucleobases, and frequently occurs in regions of DNA where a cytosine nucleotide is followed by a guanine nucleotide in the linear sequence of bases along its 5'→3' direction, referred to as a CG or CpG site. In particular regions of genes, for example gene promoter regions, an increase in cytosine methylation at gene promotor regions can inhibit the expression of these genes (Robertson K D Nat. Rev. Genet. 6, 597-610 (2005)). The gene silencing effect of methylated regions is accomplished through the interaction of methylcytosine binding proteins with other structural components of the chromatin, which, in turn, makes the DNA inaccessible to transcription factors through histone deacetylation and chromatin structure changes (Greenberg M V C and Bourc'his D Nat. Rev. Mol. Cell Biol. 20, 590-607 (2019)). Cancers take advantage of this mechanism, and hypermethylate genomic regions associated with DNA repair genes.

Methylation patterns also play an important role in genomic imprinting, in which imprinted genes are preferentially expressed from either the maternal or paternal allele. Patterns of methylation in a genome are heritable because of the semi-conservative nature of DNA replication. During this process, the daughter strand, newly replicated on a methylated template strand is not initially methylated, but the template strand directs methyltransferase enzymes to fully methylate both strands. Deregulation of imprinting has been implicated in several developmental disorders. Moreover, there is abundant evidence that aberrant DNA methylation can preclude normal development.

There are around 25,000 CpG islands in the human genome. CpG islands are usually understood as polynucleotide regions with a length greater than 200 bp having GC content greater than 50%. In various cancers such as leukemia, it has been previously reported that there is a global decrease in DNA methylation and an increase in methylation specifically at CpG islands. It is believed that in a normal cell, the CpG islands are unmethylated and when the cell becomes a tumor cell the CpG island becomes methylated at every CpG. It is suspected that in a normal cell the CpG islands, which are typically located near the promoters of genes, are normally kept hypomethylated. In an unmethylated state, cytosine is converted to uracil after deamination, which is recognized by the cell's repair machinery and is removed, while in a methylated state deamination of cytosine results in the formation of thymine which is not recognized by the repair machinery. Therefore, the presence or absence of hypermethylation at these CpG islands can be used to detect tumor cells. As cancer cells are constantly evolving to avoid treatment regimens, there is a need for a method to detect a tumor cell with high accuracy.

A common method of determining the methylation level and/or pattern of DNA requires methylation status-dependent conversion of cytosine in order to distinguish between methylated and non-methylated CpG dinucleotide sequences. For example, methylation of CpG dinucleotide sequences can be measured by employing cytosine conversion-based technologies, which rely on methylation status-dependent chemical modification of CpG sequences within isolated genomic DNA, or fragments thereof, followed by DNA sequence analysis. Chemical reagents that can be used to distinguish between methylated and non-methylated CpG dinucleotide sequences include for example, hydrazine, which cleaves the nucleic acid, and bisulfite treatment. Bisulfite treatment followed by alkaline hydrolysis specifically converts non-methylated cytosine to uracil, leaving 5-methylcytosine unmodified as described by Olek A., Nucleic Acids Res. 24:5064-6, (1996) or Frommer et al., Proc. Natl. Acad. Sci. USA 89:1827-1831 (1992), each of which is incorporated herein by reference in its entirety. The bisulfite-treated DNA can subsequently be analyzed by conventional molecular techniques, such as PCR amplification, sequencing, and detection comprising oligonucleotide hybridization.

One consequence of bisulfite-mediated deamination of cytosine is that the bisulfite treated cytosine is converted to uracil, which reduces the complexity of the genome. Specifically, a typical 4-base genome (A,T,C,G) is essentially reduced to a 3-base genome (A,T,G) because uracil is read as thymine during downstream analysis techniques such as PCR and sequencing reactions. Thus, the only cytosines present are those that were methylated prior to bisulfite conversion. Because the complexity of the genome is reduced, standard methods for comparing and/or aligning a bisulfite-converted sequence to the pre-conversion genome can be cumbersome and, in some cases, ineffective. For example, problems may arise when aligning converted fragments to the genome, especially when using short sequences. Accordingly, there remains a need for methods which facilitate identification of the genomic context of bisulfite converted DNA.

Provided herein are methods and compositions that relate to sequencing nucleic acids and determining the methylation level and/or pattern of the nucleic acids. Using methods and/or compositions described herein, the complexity of the target nucleic acids is preserved by keeping track of complementary strands after the strands have been subjected to bisulfite conversion of nucleic acids. In order to preserve complexity of the nucleic acid, embodiments of the present invention relate to a pairing of the cytosine-converted sequences of both strands of a double-stranded nucleic acid and using the sequence information from both strands to determine the sequence and/or methylation status of one or both strands prior to conversion.

Linked Duplex Sequencing: Methylated/Unmethylated Cytosine Conversion

Methylation of CpG dinucleotide sequences can be measured by employing cytosine conversion-based technologies. The term "conversion" or "converted" as used herein in reference to 5-methylcytosine and 5-hydroxymethylcytosine means the conversion of an unmethylated cytosine to another nucleotide which will distinguish the unmethylated from the methylated cytosine. Typically, the agent modifies unmethylated cytosine to uracil. A commonly used agent for modifying unmethylated cytosine preferentially to methylated cytosine is sodium bisulfite. However, other agents that similarly modify unmethylated cytosine, but not methylated cytosine, can also be used in the method of the invention. Sodium bisulfite ($NaHSO_3$) reacts readily with the 5,6-double bond of cytosine, but poorly with methylated cytosine, as described by Olek A., Nucleic Acids Res. 24:5064-6, 1996 or Frommer et al., Proc. Natl. Acad. Sci. USA 89:1827-1831 (1992), each of which is incorporated herein by reference. Cytosine reacts with the bisulfite ion to form a sulfonated cytosine reaction intermediate which is susceptible to deamination, giving rise to a sulfonated uracil. The sulfonate group can be removed under alkaline conditions, resulting in the formation of uracil. Uracil is recognized as a thymine by Taq polymerase and other polymerases and therefore upon PCR or during a sequencing reaction, the resultant product contains cytosine only at the position where 5-methylcytosine occurs in the starting template nucleic acid. Alternatively, conversion may be accomplished using restriction enzymes, such as HpaII and MspI, which recognize the sequence CCGG.

Traditionally, the recovery of bisulfite-converted DNA is very poor due to DNA degradation caused by extended-duration sodium bisulfite treatment protocols and subsequent depyrimidation (Grunau C et al. Nucleic Acids Res. 2001, 29(13):E65-5). Optimized bisulfite conversion protocols that include a fast deamination step reduce incubation times from 12 to 16 hours to 40 min by using a highly concentrated bisulfite solution at high temperatures, leading to a more homogenous conversion of cytosine due to the easier process of DNA denaturation at high temperatures and reduced degradation due to shorter incubation times (Shiraishi M and Hayatsu H. DNA Res. 2004, 11(6):409-15). One study has shown that bisulfite treatment of cfDNA for 30 min at 70° C. leads to complete conversion of cytosine to uracil and is achieved with high post-treatment DNA recovery (Yi S et al. BMC Molecular Biol. 2017, 18:24, which is incorporated herein by reference). Such rapid-bisulfite conversion can also be used in the method described herein. For example, 10 M (NH4) $HSO_3$—$NaHSO_3$ bisulfite solution was added to Y-template-hairpin constructs. The mixtures are heated for 30 min at 70° C. or for 10 min at 90° C. and subsequently cooled to 4° C.

While bisulfite conversion is the current standard for performing DNA methylation analysis, it has several drawbacks. As discussed supra, bisulfite treatment is a harsh chemical reaction which can lead to DNA degradation, severely limiting its utility if sample DNA quantities are low, as is often the case with cfDNA. Additionally, the complete conversion of unmodified cytosine to thymine reduces sequencing complexity, potentially leading to poor sequencing quality, low mapping rates, and uneven genome coverage. A method for bisulfite-free direct detection of 5-methylcytosine (5mC) and 5-hydroxymethylcytosine (5hmC) has been described (Liu Y et al. Nat. Biotechnol. 2019, 37(4) 424-429, which is incorporated herein by reference), which combines ten-eleven translocation (TET) oxidation of 5mC and 5hmC to 5-carboxylcytosine (5caC) with pyridine borane reduction of 5caC to dihydrouracil (DHU). Subsequent PCR converts DHU to thymine, enabling a C-to-T transition of 5mC and 5hmC. This TET-assisted pyridine borane sequencing (TAPS) method results in higher mapping rates and more even coverage than bisulfite conversion and may be applied to the methods described herein for linked duplex methylation profiling. Another bisulfite-free approach for methylation analysis is the NEBNext® Enzymatic Methyl-seq product, which first protects 5mC and 5hmC from deamination by TET2 and an oxidation enhancer, followed by APOBEC deamination of unprotected cytosines to uracils.

Converted DNA can subsequently be analyzed by conventional molecular techniques, such as PCR amplification, sequencing, and detection comprising oligonucleotide hybridization. As described below, a variety of techniques are available for sequence-specific analysis (e.g., MSP) of the methylation status of one or more CpG dinucleotides in a particular region of interest. Methods provided herein are particularly useful for creating a reference complimentary copy of the pre-conversion sequence for each of a multitude of genomic fragments. Using these methods, the reference copy may be covalently linked to the converted template. By linking parent strands together using the constructs described herein (e.g., the hairpin adapter depicted in FIG. 4), the sequence can be corrected prior to mapping using the second strand, increasing the fraction of properly mapped reads. Additionally, C to T mutations (SNVs) are distinguishable from converted bases as the "T" mutation will be confirmed by an "A" on the opposite strand enabling both detection of sequencing variants and methylation state in the same assay.

Figure 15A:
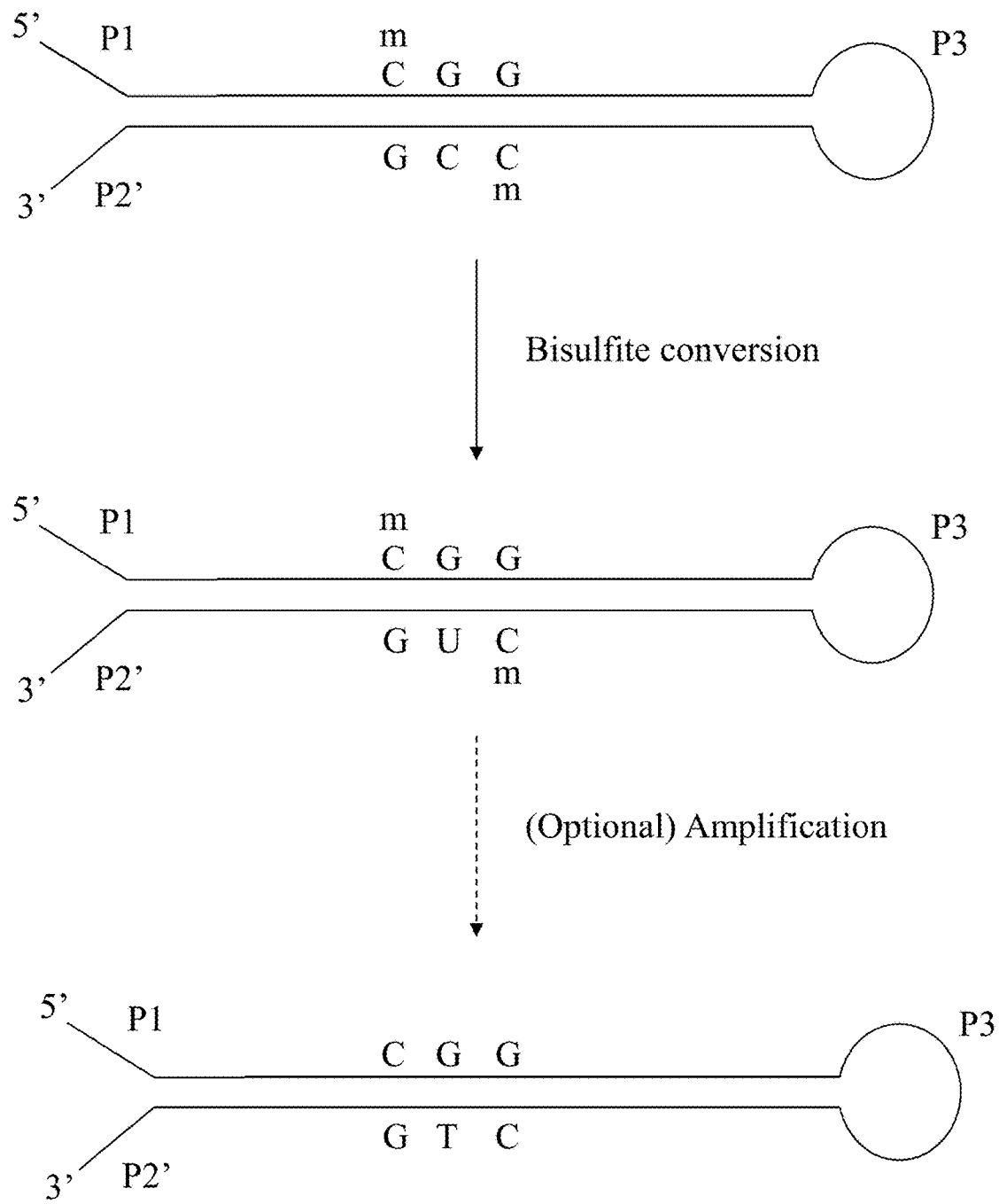
FIGS. 15A-15D show an overview of an embodiment of an amplification method for linked methylation detection of a cytosine-converted adapter-target-adapter construct.

The DNA is fragmented, repaired, and adapters ligated as described in Example 1. As a result of cytosine conversion, unmethylated cytosines in the template nucleic acid are converted to uracil residues, while methylated cytosines are unchanged (see, for example, FIG. 15A). In embodiments, the cytosine-converted construct may be amplified prior to hybridization to increase the amount of material available for cluster amplification, resulting in conversion of the uracil nucleotides (dUTP) to thymine nucleotides (dTTP). In embodiments where the adapter oligonucleotides include a sequence that will be used in later steps (i.e., for capture on a support or for binding of a sequencing primer), the adapter can be synthesized, for example, using a bisulfite-resistant cytosine analog such as 5-methyl dCTP (Me-C, or 5mC) in the positions where maintaining a cytosine at that position is important. Alternatively, a hairpin adapter could be ligated to one side of a linear template, with the hairpin adapter functioning as a primer to fill in the second strand of the template with dNTPs including Me-C. Following cytosine conversion, the second strand remains unconverted due to the incorporated Me-C bases and can serve as a reference for the original converted template strand.

Described herein, the methods use the physical pairing of the complementary strands to identify DNA fragments having an asymmetric methylcytosine profile (e.g., hemimethylated DNA fragments). These can arise from imprinting, but also as a consequence of active demethylation catalyzed by TET family enzymes (Erlich et al 2012, Shen et al 2014, Song et al 2017), which are misregulated in some cancers. During TET mediated active demethylation, the standard methyl cytosine is converted to 5-hydroxymethylcytosine as well as additional intermediates, finally resulting in an unmethylated cytosine. 5-hydroxymethylcytosine and other intermediates are relatively short lived and are found at low frequency in a cell type undergoing active demethylation.

Figure 16:
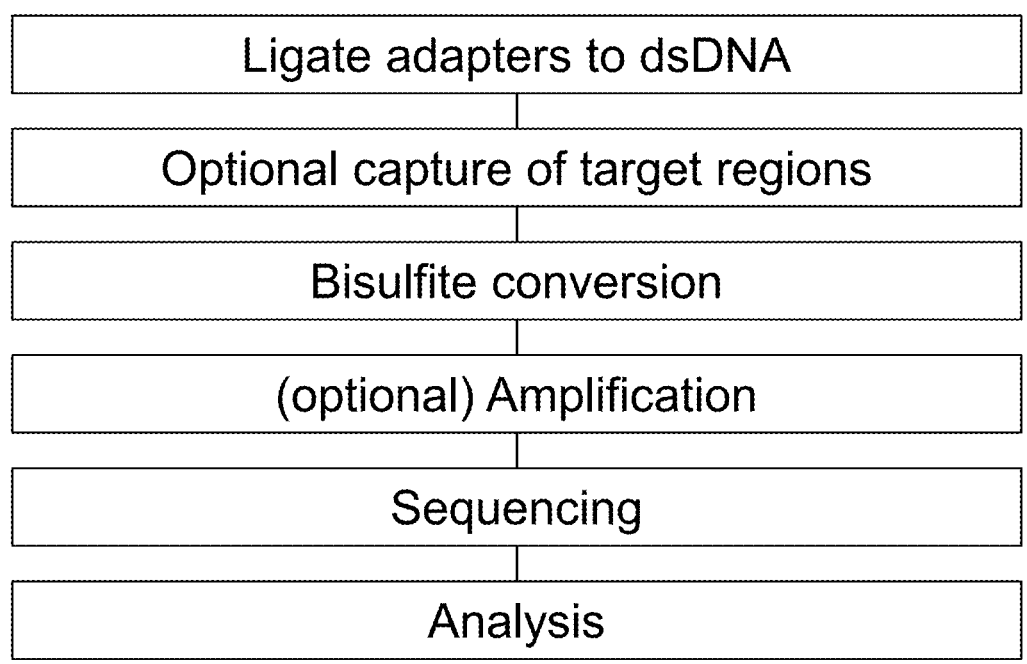
FIG. 16 illustrates an overview of an exemplary workflow for analysis of hemimethylated DNA (e.g., asymmetric methylation methods as described herein). First, to a cfDNA sample, a first adapter is ligated to a first end of the cfDNA molecule, and a second adapter is ligated to a second end of the cfDNA molecule, wherein the second adapter is a hairpin adapter, thereby forming a nucleic acid template. Following ligation the sample may be optionally captured via a target capture (e.g., a hybridization capture panel), subjected to cytosine conversion (e.g., bisulfite conversion or an enzymatic conversion method), amplified, followed by sequencing to identify hemimethylated DNA fragments. Sequencing reads representing hemimethylated fragments are then used for downstream analysis, for example via mapping to a reference genome to identify hemimethylated DNA regions to assess patterns of cytosine methylation on both strands.
Figure 17A:
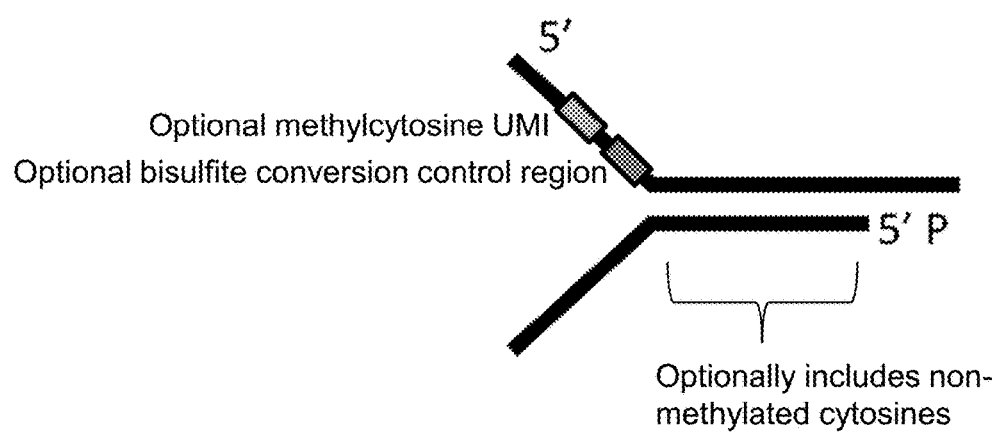
FIGS. 17A-17B.
Figure 17B:
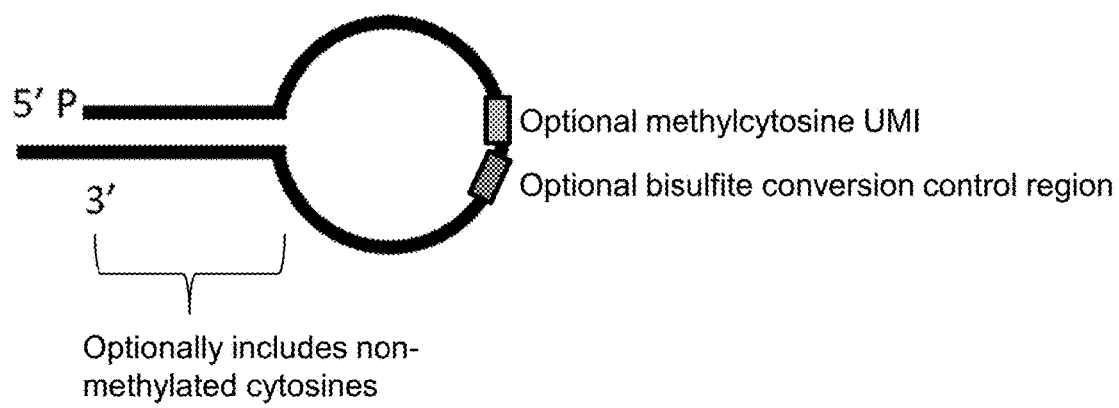

Quantifying 5-hydroxymethylcytosine and these additional intermediates as a liquid biopsy biomarker is helpful at obtaining an epigenetic snapshot of the cancer status. The methyl moiety of methylated cytosines can be lost or eliminated e.g., passively during DNA replication, or actively through enzymatic DNA demethylation. During active DNA demethylation, 5mC is oxidized to produce 5-hydroxymethylcytosine (5hmC), which acts not only as an intermediate during 5mC demethylation, but also plays important roles in many cellular and developmental processes, including the pluripotency of embryonic stem cells, neuron development, and tumorigenesis in mammals. Methods described herein are useful at quantifying 5mC and 5hmC in both strands of a sample and are useful at revealing the extent of methylation symmetry in a double-stranded nucleic acid. For example, using the methods described herein, one method to detect asymmetric methylation profiles consists of (1) ligating a first adapter and a second adapter to a cfDNA sample, wherein the second adapter is a hairpin adapter, wherein some or all of the adapter cytosines of the hairpin adapters are methylated; (2) optionally, capturing fragments using a hybrid capture panel; (3) converting the cytosines (e.g., contacting the sample with bisulfite to treat the fragments, or using an enzymatic conversion methodology); (4) amplifying the converted sample; and (5) sequencing to identify forward and reverse read mismatches indicative of asymmetric methylation (FIG. 16). One useful embodiment of the above approach employs hairpin adapters designed to contain a region consisting of partially methylated cytosines (e.g., during hairpin oligomer synthesis, request that a given position consist of an equal proportion of cytosines and methylcytosines). Bisulfite conversion provides information on the methylation state of individual cytosines by converting cytosine (but not 5-methylcytosine) to uracil, and subsequently to thymine upon PCR amplification. Following bisulfite treatment, a subset of the adapter cytosines would undergo conversion and be read as thymine. The resultant random 2-base code gives rise to a low complexity "methylcytosine UMI" (FIG. 17A-17B) for use in downstream error correction. Hairpin adapters could be further improved, in some embodiments, by inclusion of a "bisulfite conversion control region" consisting of one or more unmethylated cytosines, which undergo bisulfite conversion and are read as thymines. Quantifying the fraction of unconverted cytosines bases in this region provides an indication of the efficiency of bisulfite conversion and may serve as a quality control metric.

Linked Duplex Sequencing: Clustering Amplification

Once formed, the library of adapter-target-adapter templates prepared according to the methods described above can be used for solid-phase nucleic acid amplification. In some embodiments of the invention, the templates used for solid-phase nucleic acid amplification have been treated with bisulfite to convert any unmethylated cytosines to uracils using protocols known in the art. In other embodiments of the invention, the templates used for solid-phase nucleic acid amplification were subjected to TET oxidation of 5mC and 5hmC to 5caC with pyridine borane reduction of 5caC to DHU, as described supra.

Figure 15B:
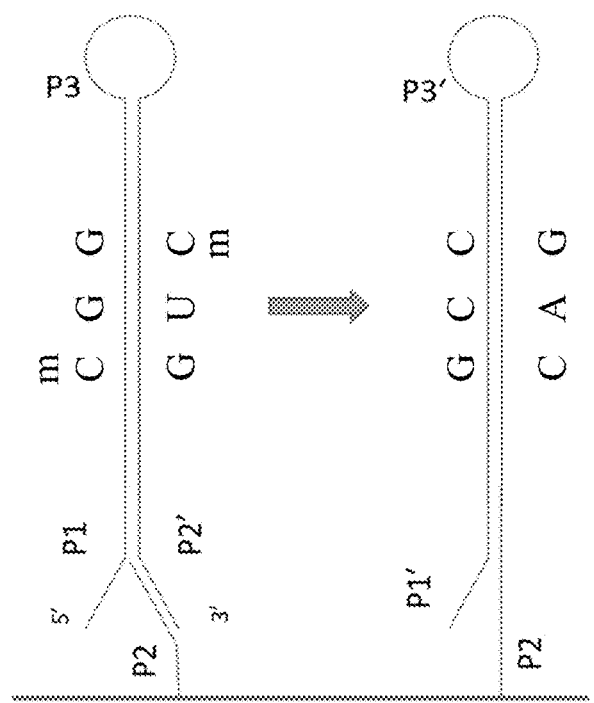

Thus, in another aspect is provided a method of nucleic acid amplification of template polynucleotide molecules which includes preparing a library of template polynucleotide molecules (e.g., adapter-target-adapter templates) and performing an amplification reaction (e.g., a solid-phase nucleic acid amplification reaction) wherein the template polynucleotide molecules are amplified. In embodiments, the method includes providing a plurality of primers (e.g., P1 and P2) that are immobilized on a solid substrate. Note, however, for clarity only a few immobilized primers are depicted in FIG. 15B.

Figure 15C:
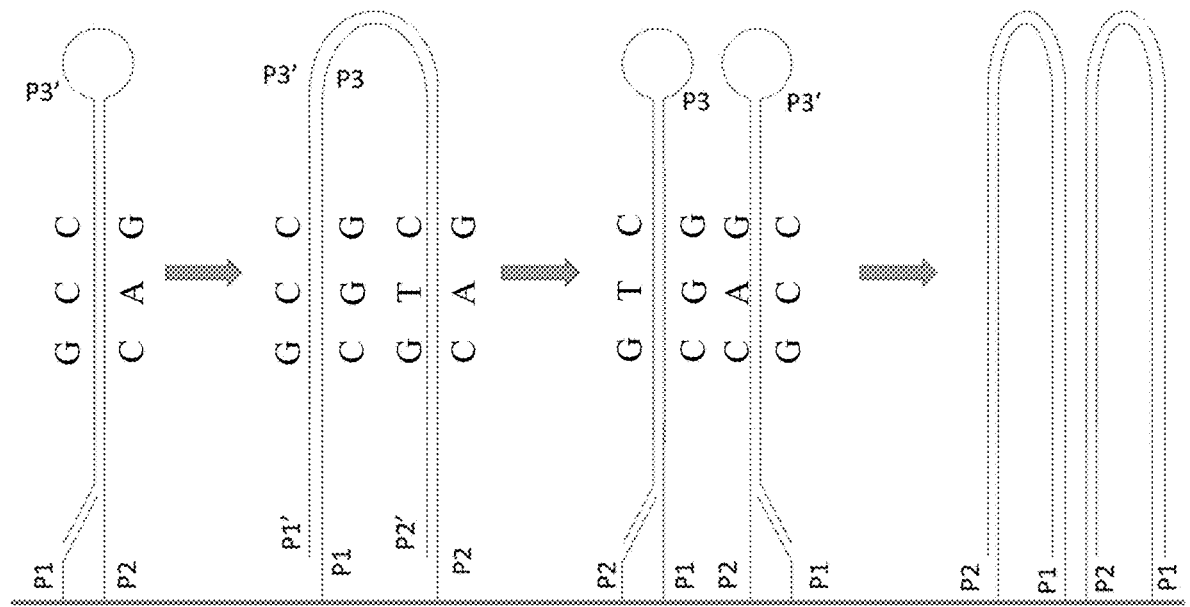
Figure 15D:
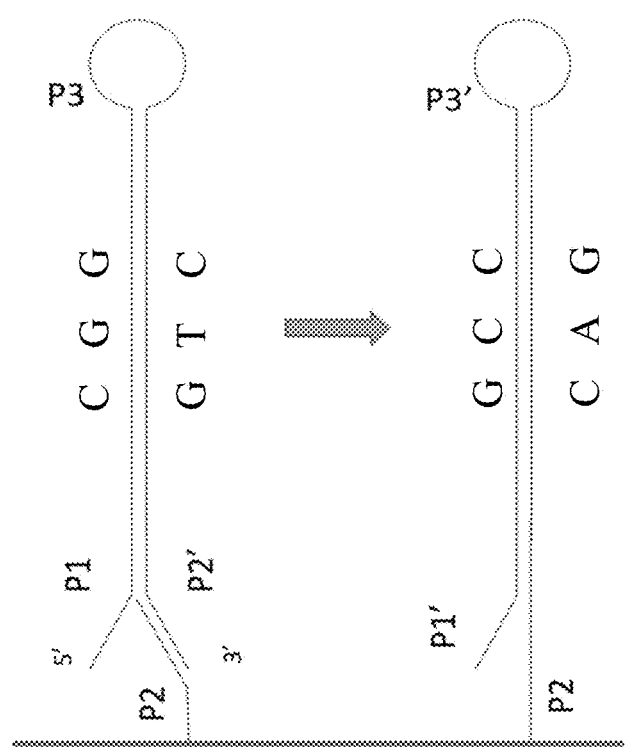

An adapter-target-adapter construct (i.e., the denatured single strand, reading from 5' to 3' having the formula P1-template-P3-template-P2' generated according to methods described herein) is hybridized to a complementary primer (e.g., the complement to P2', referred to as P2) that is immobilized on a solid substrate. In the presence of a polymerase (wherein the polymerase is not shown in FIG. 15B) the P2 strand is extended to generate a complimentary copy, wherein the denatured single strand, reading from the 5' to the 3' has the formula P2-template-P3'-template-P1'. The original adapter-target-adapter may be removed. As shown on the right side of FIG. 15B, the complementary strand of the converted template will contain adenines that are mispaired with cytosines facilitating identification of methylation sites during sequencing analysis. Because of the self-folding of the adapter-target-adapter construct, initially seeding on the solid surface could be done without additional denaturation steps (e.g., as long as the products are in the hairpin state). In some embodiments, an amplified, cytosine-converted Y-template-hairpin construct hybridizes to an immobilized P2 primer (FIG. 15D), wherein the uracil is replaced with a thymine prior to hybridization. In the presence of a polymerase, a copy of the original template is made; this copy then hybridizes to an immobilized P1 primer as shown in FIG. 15C.

Next, the complimentary copy is annealed to a P1 primer that is immobilized on the solid substrate, which in the presence of a DNA polymerase (the polymerase is not shown in FIG. 15C) extends P1 primer to reform the original adapter-target-adapter construct (i.e., the denatured single strand having the formula P1-template-P3-template-P2') which then hybridizes with an immobilized P2 primer. The products of the extension reaction (i.e., the P1-template-P3-template-P2' hybridized to an immobilized P2, and P1'-template-P3'-template-P2 hybridized to P1) may be subjected to standard denaturing conditions in order to separate the extension products from strands of the adapter-target constructs. The adapter-target-adapter constructs may then anneal to a complementary immobilized primer and may be extended in the presence of a polymerase. These steps, depicted in FIGS. 15B-15C, may be repeated one or more times, through rounds of primer annealing, extension and denaturation, in order to form multiple copies of the same extension products containing adapter-target-adapter constructs, or the complements thereof. The A/C and T/G mismatches are carried forward through each round of amplification (not shown for clarity on far-right panel of FIG. 15C). Note, this bridging amplification is typically more efficient than amplifying linear strands, because the adapter-target-adapter products self-fold, thus leaving the primer site accessible.

Sequencing can be carried out using any suitable sequencing-by-synthesis technique, wherein nucleotides are added successively to a free 3' hydroxyl group, resulting in synthesis of a polynucleotide chain in the 5' to 3' direction. In embodiments, the identity of the nucleotide added is determined after each nucleotide addition. In embodiments, detection of a methylated cytosine is determined by the presence of a G-T mismatch following sequencing of the amplified converted template nucleic acid. Using the methods described herein, SNPs are distinguishable from converted G-T base pairs.

Example 10: Differentiating True Variants from Library Prep Errors

Pervasive mutations in somatic cells generate a heterogenous genomic population within an organism and may result in serious medical conditions. Next-generation sequencing (NGS) technologies have been pivotal for the systematic identification and characterization of tumor-associated variants. While the accurate identification of low allelic frequency somatic variants relies on factors including deep sequencing coverage, it has been found that false positive variants can account for more than 70% of identified somatic variations, rendering conventional detection methods inadequate for accurate determination of low allelic variants (Chen L et al. bioRxiv 2016, 070334). Mutagenic DNA damage has been recognized as a major source of sequencing error in specialized samples such as FFPE-treated DNA (Do H and Dobrovic A. Clin. Chem. 2015, 61(1): 64-71). Another study indicated that a common technique used in sample preparation for DNA sequencing (e.g., acoustic shearing in water) induces oxidative damage, including 7,8-dihydro-8-oxoguanine (8-oxo-dG), suggesting that sequencing results may also be affected by mutagenic damage (Costello M et al. Nucleic Acids Res. 2013, 41(6): e67). Furthermore, it has been reported that somatic SNVs cannot be distinguished from sequencing errors, which occur at a much higher frequency than somatic mutations. Such low-abundance SNVs and deletions have been suggested to only be able to be detected using single-cell sequencing, through which a heterozygous mutation will be observed in approximately half of the reads (Zhang L and Vijg J. Annu. Rev. Genet. 2018, 52:397-419), or alternatively requiring extremely deep sequencing (e.g., 80× to up to thousands-fold coverage).

Provided herein are methods and compositions that relate to sequencing nucleic acids and determining the identity of true somatic variants from sequencing errors. Using methods and/or compositions described herein, the complexity of the target nucleic acids is preserved by keeping track of complementary strands after the strands have been intentionally damaged. In order to preserve complexity of the nucleic acid, embodiments of the present disclosure relate to pairing the damaged sequences of both strands of a double-stranded nucleic acid and using the sequence information from both strands to distinguish low-frequency somatic variants from sequencing errors. Briefly, nucleic acid samples were subjected to oxidative damage using, for example, sonication during sample prep to intentionally introduce library prep errors. As described supra, oxidative damage can result in the formation of 8-oxo-dG, an oxidative damage marker introduced, for example, during acoustic shearing. Alternative DNA damaging modalities may be employed, such as ionizing radiation, platinum drugs (cis-platin, oxaliplatin, and carboplatin), cyclophosphamide, chlorambucil, and temozolomide. Following intentional damage procedure, the samples contain a mixture of known variants and shearing-induced errors. Since 8-oxo-dG is known to pair with adenine, this results in a G to T transversion after amplification; this leads to an increase in "G to T" and "C to A" errors. As damage affects only one base of a base-pair in a duplex, acoustic shearing in water leads to an excess of G to T transversion errors when one strand (i.e., read 1) is mapped to a reference genome, whereas, the read of the complementary strand will show an excess of the reverse complement of G to T, i.e. C to A transversion errors, instead. As a consequence, there is an imbalance in the number of G to T variants in the first read compared to the second read sequences; see FIGS. 19A-19D for an illustrative overview. This imbalance is specific to the inflicted damage and can be corrected using the methods described herein.

Two different libraries were prepared: a first library of template nucleic acids containing Y adapters on each end (referred to as the forked library); and a second library of Y-template-hairpin constructs prepared according to the methods described herein, for example in Example 2. Each library was subjected to three different fragmentation methods: enzymatic (enz_frag), acoustic shearing in a TE buffer (shearTE), and acoustic shearing in water (shearWAT). Fragmentation method shearWAT is known to impart oxidative damage. The libraries were amplified (see, FIGS. 19A-19D), and sequenced according to the protocols described herein, see the example workflow provided in Example 2. Sequencing can be carried out using any suitable method (e.g., sequencing-by-synthesis) that provides suitable quality. By comparing the reads of the two strands of the sequenced duplex it is possible to calculate the rate of G to T errors.

The sequencing results of each individual read confirmed that acoustic shearing of both the forked libraries and the Y-template-hairpin libraries result in a greater proportion of G to T errors, relative to each enzymatic fragmentation control. The Y-template-hairpin libraries subjected to acoustic shearing in a TE buffer did not report an increase in G to T errors. Correcting the sequencing read includes bioinformatically combining the information gained from the first read and the second read of the duplex and allows concordant base calls to benefit from higher accuracy and removes discordant base calls. Correcting optionally further includes aligning the reads to a reference sequence. The results are summarized in terms of accuracy and Q-score presented in Table 3 for the Y-template-hairpin libraries sequenced herein. The quality score (Q-score) is a prediction of the probability of an error in base calling increases following correction. A high quality score implies that a base call is more reliable and less likely to be incorrect.

TABLE 3

Accuracy improvement following sequencing read correction

| Sample Name | % Accuracy | Q-Score |
|---|---|---|
| enz_frag | 99.4012 | 22.2 |
| enz_frag (corrected) | 99.9743 | 35.9 |
| shearTE | 99.4886 | 22.9 |
| shearTE (corrected) | 99.9939 | 42.1 |
| shearWAT | 99.1694 | 20.8 |
| shearWAT (corrected) | 99.9862 | 38.6 |

Errors introduced during library prep or during sequencing were identified and can be removed from the sequencing reads (i.e., corrected), leaving only rare variants in the sequencing reads. As reported in Table 3, the accuracy increases approximately 0.8% for the shearWAT condition as the G to T errors are identified and removed. Specifically, the G-T error rate was reduced 50-fold for these libraries after read correction. Sequencing according to methods and constructs described herein improve the accuracy, reduce false positives, and allow one to identify rare variants without increasing the sequencing read depth. Using methods described herein, true somatic variants are thus distinguishable from sequencing errors.

P-EMBODIMENTS

The present disclosure provides the following illustrative embodiments.

Embodiment P1. A method of sequencing a double stranded nucleic acid, the method comprising: (a) ligating a first adapter to a first end of the double stranded nucleic acid, and ligating a second adapter to a second end of the double stranded nucleic acid, wherein the second adapter is a hairpin adapter, thereby forming a nucleic acid template; (b) annealing a first primer to the nucleic acid template, wherein the first primer comprises a sequence that is complementary to a portion of the first adapter, or a complement thereof; (c) sequencing a first portion of the nucleic acid template by extending the first primer, thereby generating a first read comprising a first nucleic acid sequence of at least a first portion of the double stranded nucleic acid; (d) annealing a second primer to the nucleic acid template, wherein the second primer comprising a sequence that is complementary to a sequence within a loop of the hairpin adapter, or a complement thereof; and (e) sequencing a second portion of the nucleic acid template by extending the second primer, thereby generating a second read comprising a nucleic acid sequence of at least a second portion of the double stranded nucleic acid.

Embodiment P2. The method of Embodiment P1, wherein the double stranded nucleic acid comprises a forward strand and a reverse strand.

Embodiment P3. The method of Embodiment P1 or Embodiment P2, wherein the first adapter is a Y-adapter.

Embodiment P4. The method of Embodiment P3, wherein the Y-adapter comprises (i) a first strand having a 5'-arm and a 3'-portion, and (ii) a second strand having a 5'-portion and a 3'-arm, wherein the 3'-portion of the first strand is substantially complementary to the 5'-portion of the second strand, and the 5'-arm of the first strand is not substantially complementary to the 3'-arm of the second strand.

Embodiment P5. The method of Embodiment P4, wherein the ligating of the first adapter comprises ligating a 3'-end of the first strand of the Y-adapter to a 5'-end of the forward strand of the double stranded nucleic acid, and ligating a 5'-end of the second strand of the Y-adapter to a 3'-end of the reverse strand of the double stranded nucleic acid.

Embodiment P6. The method of Embodiment P4 or Embodiment P5, wherein the first primer anneals to the second strand of the Y-adapter.

Embodiment P7. The method of one of Embodiment P4 to Embodiment P6, wherein the 5'-arm of the first strand or the 3'-arm of the second strand of the Y-adapter comprises a GC content of greater than 50% method of claim 4 or 5, wherein the first primer anneals to the second strand of the Y-adapter.

Embodiment P8. The method of one of Embodiment P4 to Embodiment P7, wherein the 5'-arm of the first strand or the 3'-arm of the second strand of the Y-adapter comprises a melting temperature (Tm) in a range of 60-85° C.

Embodiment P9. The method of one of Embodiment P4 to Embodiment P8, wherein the 5'-arm of the first strand or the 3'-arm of the second strand of the Y-adapter comprises locked nucleotides.

Embodiment P10. The method of one of Embodiment P4 to Embodiment P9, wherein the 3'-portion of the first strand or the 5'-portion of second strand of the Y-adapter comprises a Tm in a range of 40-50° C.

Embodiment P11. The method of one of Embodiment P4 to Embodiment P10, wherein a duplex comprising the 3'-portion of the first strand and the 5'-portion of second strand of the Y-adapter comprises a Tm in a range of 40-50° C.

Embodiment P12. The method of one of Embodiment P4 to Embodiment P11, wherein the 3'-end or 3'-arm of the second strand of the Y-adapter comprises a binding motif or a nucleic acid sequence complementary to a first capture nucleic acid.

Embodiment P13. The method of one of Embodiment P4 to Embodiment P12, wherein the 5'-end or 5'-arm of the first strand of the Y-adapter comprises a binding motif or a nucleic acid sequence substantially identical to a second capture nucleic acid.

Embodiment P14. The method of one of Embodiment P4 to Embodiment P13, wherein the nucleic acid template includes sequences of the first strand of the Y-adapter, the forward strand of the double stranded nucleic acid, the second adapter, the reverse strand of the double stranded nucleic acid and the second strand of the Y-adapter arranged in a 5' to 3' direction.

Embodiment P15. The method of one of Embodiment P4 to Embodiment P14, wherein the first primer anneals to the 5'-portion of the second strand of the Y-adapter.

Embodiment P16. The method of Embodiment P1 or Embodiment P2, wherein the first adapter is a hairpin adapter.

Embodiment P17. The method of Embodiment P16, wherein the first primer anneals to a sequence within a loop of the first adapter.

Embodiment P18. The method of one of Embodiment P2 to Embodiment P17, wherein the first read includes a nucleic acid sequence of the reverse strand of the double stranded nucleic acid, or a portion thereof, and the second read comprises a nucleic acid sequence of the forward strand of the double stranded nucleic acid, or a portion thereof.

Embodiment P19. The method of one of Embodiment P2 to Embodiment P17, wherein the first read comprises a nucleic acid sequence of the forward strand of the double stranded nucleic acid, or a portion thereof, and the second read comprises a nucleic acid sequence of the reverse strand of the double stranded nucleic acid, or a portion thereof.

Embodiment P20. The method of one of Embodiment P1 to Embodiment P19, wherein the second adapter comprises a nucleic acid having a 5'-end, a 5'-portion, the loop, a 3'-portion and a 3'-end, and the 5'-portion of the second adapter is substantially complementary to the 3'-portion of the second adapter.

Embodiment P21. The method of Embodiment P20, wherein the ligating of the second adapter comprises ligating the 5'-end of the second adapter to a 3'-end of the forward strand of the double stranded nucleic acid and ligating the 3'-end of the second adapter to a 5'-end of the reverse strand of the double stranded nucleic acid.

Embodiment P22. The method of one of Embodiment P20 to Embodiment P21, wherein a duplex comprising the 5'-portion and the 3'-portion of the second adapter comprise a Tm in a range of 40-50° C.

Embodiment P23. The method of one of Embodiment P1 to Embodiment P22, wherein the first end of the double stranded nucleic acid comprises a blunt end, a 5' overhang, or a 3' overhang.

Embodiment P24. The method of one of Embodiment P1 to Embodiment P23, wherein the second end of the double stranded nucleic acid comprises a blunt end, a 5' overhang, or a 3' overhang.

Embodiment P25. The method of one of Embodiment P1 to Embodiment P24, wherein the method further comprises, after (a) and prior to (b), generating amplicons of the nucleic acid template.

Embodiment P26. The method of Embodiment P25, wherein the method of generating amplicons of the nucleic acid template comprises a polymerase chain reaction.

Embodiment P27. The method of Embodiment P26, wherein the polymerase chain reaction comprises a bridge amplification method.

Embodiment P28. The method of one of Embodiment P25 to Embodiment P27, wherein the generating of amplicons comprises attaching the nucleic acid template to a substrate.

Embodiment P29. The method of Embodiment P28, wherein the substrate is a chip, a wafer, a bead, or a flow cell.

Embodiment P30. The method of Embodiment P28 or Embodiment P29, wherein the substrate comprises a first capture nucleic acid comprising a nucleic acid sequence complementary to at least a portion of the second strand of the Y-adapter, or a complement thereof.

Embodiment P31. The method of one of Embodiment P28 to Embodiment P30, wherein the attaching of the nucleic acid template to the substrate comprises annealing the nucleic acid template to the first capture nucleic acid.

Embodiment P32. The method of one of Embodiment P28 to Embodiment P31, wherein the substrate comprises a second capture nucleic acid comprising a nucleic acid sequence complementary to at least a portion of the first strand of the Y-adapter, or complement thereof.

Embodiment P33. The method of one of Embodiment P25 to Embodiment P32, wherein the amplicons comprise a first copy of the nucleic acid template having a nucleic acid sequence that is substantially identical to the nucleic acid sequence of the nucleic acid template, or a portion thereof, and a second copy of the template having a nucleic acid sequence that is substantially complementary to the nucleic acid sequence of the nucleic acid template.

Embodiment P34. The method of Embodiment P33, wherein after generating the amplicons of the nucleic acid template, and before (b), the first or the second copy of the nucleic acid template is removed from the substrate.

Embodiment P35. The method of one of Embodiment P25 to Embodiment P34, wherein the amplicons that are attached to the substrate are attached at addressable locations on the substrate.

Embodiment P36. The method of Embodiment P25, wherein the generating of amplicons comprises rolling circle amplification, and wherein the first adapter is a hairpin adapter.

Embodiment P37. The method of one of Embodiment P1 to Embodiment P36, wherein the sequencing of (c) and the sequencing of (e) comprise a process comprising sequencing by synthesis.

Embodiment P38. The method of one of Embodiment P1 to Embodiment P37, wherein after step (c), the first sequenced strand is removed or terminated.

Embodiment P39. The method of one of Embodiment P1 to Embodiment P38, wherein the first adapter comprises one or more of a sample barcode sequence or a molecular identifier sequence.

Embodiment P40. The method of one of Embodiment P1 to Embodiment P39, wherein the second adapter comprises one or more of a sample barcode sequence or a molecular identifier sequence.

Embodiment P41. A method of sequencing a double stranded nucleic acid, the method comprising: (a) ligating a first adapter to a first end of the double stranded nucleic acid, and ligating a second adapter to a second end of the double stranded nucleic acid, wherein the second adapter is a hairpin adapter, thereby forming a nucleic acid template; (b) annealing a first primer to the nucleic acid template, wherein the first primer comprises a sequence that is complementary to a portion of the first adapter, or a complement thereof (c) sequencing a first portion and a second portion of the nucleic acid template by extending the first primer, thereby generating a first read comprising a first nucleic acid sequence of at least a first portion of the double stranded nucleic acid, and a second read comprising a nucleic acid sequence of at least a second portion of the double stranded nucleic acid.

Embodiment P42. A multiplex method of sequencing a plurality of double stranded nucleic acids comprising one of the methods of Embodiment P1 to Embodiment P41, comprising performing steps (a) through (e) for each of a plurality of double-stranded nucleic acids in a mixture.

Embodiment P43. A composition for sequencing a double stranded nucleic acid comprising a forward strand and a reverse strand, the composition comprising a template nucleic acid comprising sequences of a first strand of a Y-adapter, the forward strand of the double stranded nucleic acid, a hairpin adapter, the reverse strand of the double stranded nucleic acid and a second strand of the Y-adapter arranged in a 5' to 3' direction, wherein the template is attached to a substrate.

Embodiment P44. The composition of Embodiment P43, further comprising (ii) a primer hybridized to a loop of the hairpin adapter.

Embodiment P45. A kit for sequencing a double stranded nucleic acid, comprising: (i) a first adapter, wherein the first adapter comprises a double-stranded portion and at least one single-stranded portion; (ii) a second adapter, wherein the second adapter is a hairpin adapter comprising a nucleic acid having a 5'-end, a 5'-portion, a loop, a 3'-portion and a 3'-end, and the 5'-portion of the hairpin adapter is substantially complementary to the 3'-portion of the hairpin adapter; (iii) a first primer having a nucleic acid sequence complementary to a portion of the first adapter, or a complement thereof; and (iv) a second primer having a nucleic acid sequence complementary to the loop of the hairpin adapter, or a complement thereof.

Embodiment P46. The kit of Embodiment P45, wherein the first adapter is a Y-adapter, wherein the Y-adapter comprises (i) a first strand having a 5'-portion and a 3'-portion, and (ii) a second strand having a 5'-portion and a 3'-portion, wherein the 3'-portion of the first strand is substantially complementary to the 5'-portion of the second strand, and the 5'-portion of the first strand is not substantially complementary to the 3'-portion of the second strand.

Embodiment P47. The kit of Embodiment P46, wherein the first adapter is a hairpin adapter.

Embodiment P48. A method of selectively sequencing a double-stranded nucleic acid, the method comprising: (a) ligating a first adapter to a first end of the double-stranded nucleic acid, and ligating a second adapter to a second end of the double-stranded nucleic acid, wherein the second adapter is a hairpin adapter; (b) displacing at least a portion of one strand of the double-stranded nucleic acid from step (a); (c) hybridizing a probe oligonucleotide to the displaced portion of the double-stranded nucleic acid; (d) separating the probe-hybridized double-stranded nucleic acid from nucleic acids not hybridized to a probe; and (e) sequencing the probe-hybridized double-stranded nucleic acid of step (d).

Embodiment P49. The method of Embodiment P48, wherein the first adapter is a Y-adapter, and the displacing at least a portion of one strand of the double-stranded nucleic acid comprises: (i) hybridizing a primer to a single-stranded portion of the Y-adapter, and (ii) in a primer extension reaction, extending the primer with a strand-displacing polymerase that terminates extension within a loop of the hairpin adapter at a terminating nucleotide.

Embodiment P50. The method of Embodiment P48, wherein the first adapter is a hairpin adapter, and the displacing at least a portion of one strand of the double-stranded nucleic acid comprises: (i) hybridizing a primer within a loop of the first hairpin adapter, and (ii) in a primer extension reaction, extending the primer with a strand-displacing polymerase that terminates extension within a loop of the second hairpin adapter at a terminating nucleotide.

Embodiment P51. The method of Embodiment P49 or Embodiment P50, wherein the terminating nucleotide comprises a removable group that blocks progression of the strand-displacing polymerase, and further wherein the terminating nucleotide is treated to release the removable group prior to sequencing.

Embodiment P52. The method of Embodiment P51, wherein the removable group is a polymer or a protein joined to the terminating nucleotide by a cleavable linker.

Embodiment P53. The method of Embodiment P51, wherein the removable group is a protein that is non-covalently complexed to the terminating nucleotide, and further wherein releasing the protein comprises a change in reaction conditions to disrupt the complex.

Embodiment P54. The method of Embodiment P53, wherein (i) the protein is a first member of a binding pair complexed with a second member of the binding pair that is linked to the terminating nucleotide, or (ii) the protein is a single-stranded binding protein that recognizes a sequence within the loop of the hairpin adapter.

Embodiment P55. The method of Embodiment P49 or Embodiment P50, wherein (i) the terminating nucleotide is a first nucleotide analog that base pairs with a second nucleotide analog, and (ii) the second nucleotide analog is not present in the primer extension reaction, such that primer extension terminates.

Embodiment P56. The method of Embodiment P49 or Embodiment P50, wherein the terminating nucleotide is an RNA nucleotide.

Embodiment P57. The method of Embodiment P48, wherein the first adapter is a Y-adapter, and the displacing at least a portion of one strand of the double-stranded nucleic acid comprises: (i) hybridizing a primer within a loop of the hairpin adapter, and (ii) in a primer extension reaction, extending the primer with a strand-displacing polymerase.

Embodiment P58. The method of Embodiment P48, wherein the first adapter is a hairpin adapter, and the displacing at least a portion of one strand of the double-stranded nucleic acid comprises: (i) hybridizing a primer within a loop of the hairpin adapter, and (ii) in a primer extension reaction, extending the primer with a strand-displacing polymerase.

Embodiment P59. The method of Embodiment P48, wherein the displacing at least a portion of one strand of the double-stranded nucleic acid comprises (i) forming a complex comprising a portion of the double-stranded nucleic acid, a primer, and a homologous recombination complex comprising a recombinase, (ii) releasing the recombinase, and (iii) in a primer extension reaction, extending the primer with a strand-displacing polymerase.

Embodiment P60. The method of Embodiment P48, wherein (i) the displacing at least a portion of one strand of the double-stranded nucleic acid comprises forming a complex comprising a portion of the double-stranded nucleic acid, the probe oligonucleotide, and a homologous recombination complex comprising a recombinase, and (ii) the step of hybridizing the probe oligonucleotide comprises releasing the recombinase.

Embodiment P61. The method of Embodiment P59 or Embodiment P60, wherein the homologous recombination complex further comprises a loading factor, a single-stranded binding (SSB) protein, or both.

Embodiment P62. The method of one of Embodiment P59 to Embodiment P61, wherein the recombinase is a T4 UvsX, RecA, or Rad51 protein.

Embodiment P63. The method of Embodiment P61 or Embodiment P62, wherein the loading factor comprises a T4 UvsY protein.

Embodiment P64. The method of Embodiment P48, wherein the displacing at least a portion of one strand of the double-stranded nucleic acid comprises exposing the double-stranded nucleic acid to denaturing conditions.

Embodiment P65. The method of one of Embodiment P48 to Embodiment P64, wherein the probe oligonucleotide is covalently attached to a solid substrate.

Embodiment P66. The method of one of Embodiment P48 to Embodiment P64, wherein the probe oligonucleotide is labeled with a first member of a binding pair, and the step of separating the probe-hybridized double-stranded nucleic acid comprises capturing the probe with a second member of the binding pair.

Embodiment P67. The method of Embodiment P66, wherein (i) the first member of the binding pair is biotin and the second member of the binding pair is avidin or streptavidin, or (ii) the second member of the binding pair is biotin and the first member of the binding pair is avidin or streptavidin.

Embodiment P68. The method of one of Embodiment P48 to Embodiment P67, wherein the probe is complementary to 10, 15, 20, 25, 50, 75, 120, or more consecutive nucleotides of the displaced portion of the double-stranded nucleic acid.

Embodiment P69. The method of Embodiment P64, wherein the probe is complementary to 100, 120, or more consecutive nucleotides of the displaced portion of the double-stranded nucleic acid.

Embodiment P70. The method of one of Embodiment P48 to Embodiment P69, wherein the double-stranded nucleic acid is a cell-free DNA (cfDNA) or circulating tumor DNA (ctDNA).

Embodiment P71. A method of selectively sequencing a plurality of different double-stranded nucleic acids in a sample according to a method of one of Embodiment P48 to Embodiment P70, wherein a plurality of different probe oligonucleotides are utilized during the hybridizing step.

Embodiment P72. The method of one of Embodiment P48 to Embodiment P71, wherein the sequencing comprises sequencing according to the method of one of Embodiment P1 to Embodiment P42.

ADDITIONAL EMBODIMENTS

The present disclosure provides the following additional illustrative embodiments.

Embodiment 1. A method of sequencing a double stranded nucleic acid, the method comprising: (a) ligating a first adapter to a first end of the double stranded nucleic acid, and ligating a second adapter to a second end of the double stranded nucleic acid, wherein the second adapter is a hairpin adapter, thereby forming a nucleic acid template; (b) annealing a first primer to the nucleic acid template, wherein the first primer comprises a sequence that is complementary to a portion of the first adapter, or a complement thereof; (c) sequencing a first portion of the nucleic acid template by extending the first primer, thereby generating a first read comprising a first nucleic acid sequence of at least a first portion of the double stranded nucleic acid; (d) annealing a second primer to the nucleic acid template, wherein the second primer comprising a sequence that is complementary to a sequence within a loop of the hairpin adapter, or a complement thereof; and (e) sequencing a second portion of the nucleic acid template by extending the second primer, thereby generating a second read comprising a nucleic acid sequence of at least a second portion of the double stranded nucleic acid.

Embodiment 2. The method of embodiment 1, wherein the double stranded nucleic acid comprises a forward strand and a reverse strand.

Embodiment 3. The method of embodiment 1 or 2, wherein the first adapter is a Y-adapter.

Embodiment 4. The method of embodiment 3, wherein the Y-adapter comprises (i) a first strand having a 5'-arm and a 3'-portion, and (ii) a second strand having a 5'-portion and a 3'-arm, wherein the 3'-portion of the first strand is substantially complementary to the 5'-portion of the second strand, and the 5'-arm of the first strand is not substantially complementary to the 3'-arm of the second strand.

Embodiment 5. The method of embodiment 4, wherein the ligating of the first adapter comprises ligating a 3'-end of the first strand of the Y-adapter to a 5'-end of the forward strand of the double stranded nucleic acid, and ligating a 5'-end of the second strand of the Y-adapter to a 3'-end of the reverse strand of the double stranded nucleic acid.

Embodiment 6. The method of embodiment 4 or 5, wherein the first primer anneals to the second strand of the Y-adapter.

Embodiment 7. The method of any one of embodiments 4 to 6, wherein the 5'-arm of the first strand or the 3'-arm of the second strand of the Y-adapter comprises a GC content of greater than 50%. method of claim 4 or 5, wherein the first primer anneals to the second strand of the Y-adapter.

Embodiment 8. The method of any one of embodiments 4 to 7, wherein the 5'-arm of the first strand or the 3'-arm of the second strand of the Y-adapter comprises a melting temperature (Tm) in a range of 60-85° C.

Embodiment 9. The method of any one of embodiments 4 to 8, wherein the 5'-arm of the first strand or the 3'-arm of the second strand of the Y-adapter comprises locked nucleotides.

Embodiment 10. The method of any one of embodiments 4 to 9, wherein the 3'-portion of the first strand or the 5'-portion of second strand of the Y-adapter comprises a Tm in a range of 40-50° C.

Embodiment 11. The method of any one of embodiments 4 to 10, wherein a duplex comprising the 3'-portion of the first strand and the 5'-portion of second strand of the Y-adapter comprises a Tm in a range of 40-50° C.

Embodiment 12. The method of any one of embodiments 4 to 11, wherein the 3'-end or 3'-arm of the second strand of the Y-adapter comprises a binding motif or a nucleic acid sequence complementary to a first capture nucleic acid.

Embodiment 13. The method of any one of embodiments 4 to 12, wherein the 5'-end or 5'-arm of the first strand of the Y-adapter comprises a binding motif or a nucleic acid sequence substantially identical to a second capture nucleic acid.

Embodiment 14. The method of any one of embodiments 4 to 13, wherein the nucleic acid template includes sequences of the first strand of the Y-adapter, the forward strand of the double stranded nucleic acid, the second adapter, the reverse strand of the double stranded nucleic acid and the second strand of the Y-adapter arranged in a 5' to 3' direction.

Embodiment 15. The method of any one of embodiments 4 to 14, wherein the first primer anneals to the 5'-portion of the second strand of the Y-adapter.

Embodiment 16. The method of embodiment 1 or 2, wherein the first adapter is a hairpin adapter.

Embodiment 17. The method of embodiment 16, wherein the first primer anneals to a sequence within a loop of the first adapter.

Embodiment 18. The method of any one of embodiments 2 to 17, wherein the first read includes a nucleic acid sequence of the reverse strand of the double stranded nucleic acid, or a portion thereof, and the second read comprises a nucleic acid sequence of the forward strand of the double stranded nucleic acid, or a portion thereof.

Embodiment 19. The method of any one of embodiments 2 to 17, wherein the first read comprises a nucleic acid sequence of the forward strand of the double stranded nucleic acid, or a portion thereof, and the second read comprises a nucleic acid sequence of the reverse strand of the double stranded nucleic acid, or a portion thereof.

Embodiment 20. The method of any one of embodiments 1 to 19, wherein the second adapter comprises a nucleic acid having a 5'-end, a 5'-portion, the loop, a 3'-portion and a 3'-end, and the 5'-portion of the second adapter is substantially complementary to the 3'-portion of the second adapter.

Embodiment 21. The method of embodiment 20, wherein the ligating of the second adapter comprises ligating the 5'-end of the second adapter to a 3'-end of the forward strand of the double stranded nucleic acid and ligating the 3'-end of the second adapter to a 5'-end of the reverse strand of the double stranded nucleic acid.

Embodiment 22. The method of any one of embodiments 20 to 21, wherein a duplex comprising the 5'-portion and the 3'-portion of the second adapter comprise a Tm in a range of 40-50° C.

Embodiment 23. The method of any one of embodiments 1 to 22, wherein the first end of the double stranded nucleic acid comprises a blunt end, a 5' overhang, or a 3' overhang.

Embodiment 24. The method of any one of embodiments 1 to 23, wherein the second end of the double stranded nucleic acid comprises a blunt end, a 5' overhang, or a 3' overhang.

Embodiment 25. The method of any one of embodiments 1 to 24, wherein the method further comprises, after (a) and prior to (b), generating amplicons of the nucleic acid template.

Embodiment 26. The method of embodiment 25, wherein the method of generating amplicons of the nucleic acid template comprises a polymerase chain reaction.

Embodiment 27. The method of embodiment 26, wherein the polymerase chain reaction comprises a bridge amplification method.

Embodiment 28. The method of any one of embodiments 25 to 27, wherein the generating of amplicons comprises attaching the nucleic acid template to a substrate.

Embodiment 29. The method of embodiment 28, wherein the substrate is a chip, a wafer, a bead, or a flow cell.

Embodiment 30. The method of embodiment 28 or 29, wherein the substrate comprises a first capture nucleic acid comprising a nucleic acid sequence complementary to at least a portion of the second strand of the Y-adapter, or a complement thereof.

Embodiment 31. The method of any one of embodiments 28 to 30, wherein the attaching of the nucleic acid template to the substrate comprises annealing the nucleic acid template to the first capture nucleic acid.

Embodiment 32. The method of any one of embodiments 28 to 31, wherein the substrate comprises a second capture nucleic acid comprising a nucleic acid sequence complementary to at least a portion of the first strand of the Y-adapter, or complement thereof.

Embodiment 33. The method of any one of embodiments 25 to 32, wherein the amplicons comprise a first copy of the nucleic acid template having a nucleic acid sequence that is substantially identical to the nucleic acid sequence of the nucleic acid template, or a portion thereof, and a second copy of the template having a nucleic acid sequence that is substantially complementary to the nucleic acid sequence of the nucleic acid template.

Embodiment 34. The method of embodiment 33, wherein after generating the amplicons of the nucleic acid template, and before (b), the first or the second copy of the nucleic acid template is removed from the substrate.

Embodiment 35. The method of any one of embodiments 25 to 34, wherein the amplicons that are attached to the substrate are attached at addressable locations on the substrate.

Embodiment 36. The method of embodiment 25, wherein the generating of amplicons comprises rolling circle amplification, and wherein the first adapter is a hairpin adapter.

Embodiment 37. The method of any one of embodiments 1 to 36, wherein the sequencing of (c) and the sequencing of (e) comprise a process comprising sequencing by synthesis.

Embodiment 38. The method of any one of embodiments 1 to 37, wherein after step (c), the first sequenced strand is removed or terminated.

Embodiment 39. The method of any one of embodiments 1 to 38, wherein the first adapter comprises one or more of a sample barcode sequence or a molecular identifier sequence.

Embodiment 40. The method of any one of embodiments 1 to 39, wherein the second adapter comprises one or more of a sample barcode sequence or a molecular identifier sequence.

Embodiment 41. A method of sequencing a double stranded nucleic acid, the method comprising: (a) ligating a first adapter to a first end of the double stranded nucleic acid, and ligating a second adapter to a second end of the double stranded nucleic acid, wherein the second adapter is a hairpin adapter, thereby forming a nucleic acid template; (b) annealing a first primer to the nucleic acid template, wherein the first primer comprises a sequence that is complementary to a portion of the first adapter, or a complement thereof; (c) sequencing a first portion and a second portion of the nucleic acid template by extending the first primer, thereby generating a first read comprising a first nucleic acid sequence of at least a first portion of the double stranded nucleic acid, and a second read comprising a nucleic acid sequence of at least a second portion of the double stranded nucleic acid.

Embodiment 42. A multiplex method of sequencing a plurality of double stranded nucleic acids comprising any one of the methods of embodiments 1 to 41, comprising performing steps (a) through (e) for each of a plurality of double-stranded nucleic acids in a mixture.

Embodiment 43. A composition for sequencing a double stranded nucleic acid comprising a forward strand and a reverse strand, the composition comprising a template nucleic acid comprising sequences of a first strand of a Y-adapter, the forward strand of the double stranded nucleic acid, a hairpin adapter, the reverse strand of the double stranded nucleic acid and a second strand of the Y-adapter arranged in a 5' to 3' direction, wherein the template is attached to a substrate.

Embodiment 44. The composition of embodiment 43, further comprising (ii) a primer hybridized to a loop of the hairpin adapter.

Embodiment 45. A kit for sequencing a double stranded nucleic acid, comprising: (i) a first adapter, wherein the first adapter comprises a double-stranded portion and at least one single-stranded portion; (ii) a second adapter, wherein the second adapter is a hairpin adapter comprising a nucleic acid having a 5'-end, a 5'-portion, a loop, a 3'-portion and a 3'-end, and the 5'-portion of the hairpin adapter is substantially complementary to the 3'-portion of the hairpin adapter; (iii) a first primer having a nucleic acid sequence complementary to a portion of the first adapter, or a complement thereof; and (iv) a second primer having a nucleic acid sequence complementary to the loop of the hairpin adapter, or a complement thereof.

Embodiment 46. The kit of embodiment 45, wherein the first adapter is a Y-adapter, wherein the Y-adapter comprises (i) a first strand having a 5'-portion and a 3'-portion, and (ii) a second strand having a 5'-portion and a 3'-portion, wherein the 3'-portion of the first strand is substantially complementary to the 5'-portion of the second strand, and the 5'-portion of the first strand is not substantially complementary to the 3'-portion of the second strand.

Embodiment 47. The kit of embodiment 46, wherein the first adapter is a hairpin adapter.

Embodiment 48. A method of selectively sequencing a double-stranded nucleic acid, the method comprising: (a) ligating a first adapter to a first end of the double-stranded nucleic acid, and ligating a second adapter to a second end of the double-stranded nucleic acid, wherein the second adapter is a hairpin adapter; (b) displacing at least a portion of one strand of the double-stranded nucleic acid from step (a); (c) hybridizing a probe oligonucleotide to the displaced portion of the double-stranded nucleic acid; (d) separating the probe-hybridized double-stranded nucleic acid from nucleic acids not hybridized to a probe; and (e) sequencing the probe-hybridized double-stranded nucleic acid of step (d).

Embodiment 49. The method of embodiment 48, wherein the first adapter is a Y-adapter, and the displacing at least a portion of one strand of the double-stranded nucleic acid comprises: (i) hybridizing a primer to a single-stranded portion of the Y-adapter, and (ii) in a primer extension reaction, extending the primer with a strand-displacing polymerase that terminates extension within a loop of the hairpin adapter at a terminating nucleotide.

Embodiment 50. The method of embodiment 48, wherein the first adapter is a hairpin adapter, and the displacing at least a portion of one strand of the double-stranded nucleic acid comprises: (i) hybridizing a primer within a loop of the first hairpin adapter, and (ii) in a primer extension reaction, extending the primer with a strand-displacing polymerase that terminates extension within a loop of the second hairpin adapter at a terminating nucleotide.

Embodiment 51. The method of embodiment 49 or 50, wherein the terminating nucleotide comprises a removable group that blocks progression of the strand-displacing polymerase, and further wherein the terminating nucleotide is treated to release the removable group prior to sequencing.

Embodiment 52. The method of embodiment 51, wherein the removable group is a polymer or a protein joined to the terminating nucleotide by a cleavable linker.

Embodiment 53. The method of embodiment 51, wherein the removable group is a protein that is non-covalently complexed to the terminating nucleotide, and further wherein releasing the protein comprises a change in reaction conditions to disrupt the complex.

Embodiment 54. The method of embodiment 53, wherein (i) the protein is a first member of a binding pair complexed with a second member of the binding pair that is linked to the terminating nucleotide, or (ii) the protein is a single-stranded binding protein that recognizes a sequence within the loop of the hairpin adapter.

Embodiment 55. The method of embodiment 49 or 50, wherein (i) the terminating nucleotide is a first nucleotide analog that base pairs with a second nucleotide analog, and (ii) the second nucleotide analog is not present in the primer extension reaction, such that primer extension terminates.

Embodiment 56. The method of embodiment 49 or 50, wherein the terminating nucleotide is an RNA nucleotide.

Embodiment 57. The method of embodiment 48, wherein the first adapter is a Y-adapter, and the displacing at least a portion of one strand of the double-stranded nucleic acid comprises: (i) hybridizing a primer within a loop of the hairpin adapter, and (ii) in a primer extension reaction, extending the primer with a strand-displacing polymerase.

Embodiment 58. The method of embodiment 48, wherein the first adapter is a hairpin adapter, and the displacing at least a portion of one strand of the double-stranded nucleic acid comprises: (i) hybridizing a primer within a loop of the hairpin adapter, and (ii) in a primer extension reaction, extending the primer with a strand-displacing polymerase.

Embodiment 59. The method of embodiment 48, wherein the displacing at least a portion of one strand of the double-stranded nucleic acid comprises (i) forming a complex comprising a portion of the double-stranded nucleic acid, a primer, and a homologous recombination complex comprising a recombinase, (ii) releasing the recombinase, and (iii) in a primer extension reaction, extending the primer with a strand-displacing polymerase.

Embodiment 60. The method of embodiment 48, wherein (i) the displacing at least a portion of one strand of the double-stranded nucleic acid comprises forming a complex comprising a portion of the double-stranded nucleic acid, the probe oligonucleotide, and a homologous recombination complex comprising a recombinase, and (ii) the step of hybridizing the probe oligonucleotide comprises releasing the recombinase.

Embodiment 61. The method of embodiment 59 or 60, wherein the homologous recombination complex further comprises a loading factor, a single-stranded binding (SSB) protein, or both.

Embodiment 62. The method of any one of embodiments 59 to 61, wherein the recombinase is a T4 UvsX, RecA, or Rad51 protein.

Embodiment 63. The method of embodiment 61 or 62, wherein the loading factor comprises a T4 UvsY protein.

Embodiment 64. The method of embodiment 48, wherein the displacing at least a portion of one strand of the double-stranded nucleic acid comprises exposing the double-stranded nucleic acid to denaturing conditions.

Embodiment 65. The method of any one of embodiments 48 to 64, wherein the probe oligonucleotide is covalently attached to a solid substrate.

Embodiment 66. The method of any one of embodiments 48 to 64, wherein the probe oligonucleotide is labeled with a first member of a binding pair, and the step of separating the probe-hybridized double-stranded nucleic acid comprises capturing the probe with a second member of the binding pair.

Embodiment 67. The method of embodiment 66, wherein (i) the first member of the binding pair is biotin and the second member of the binding pair is avidin or streptavidin, or (ii) the second member of the binding pair is biotin and the first member of the binding pair is avidin or streptavidin.

Embodiment 68. The method of any one of embodiments 48 to 67, wherein the probe is complementary to 10, 15, 20, 25, 50, 75, 120, or more consecutive nucleotides of the displaced portion of the double-stranded nucleic acid.

Embodiment 69. The method of embodiment 64, wherein the probe is complementary to 100, 120, or more consecutive nucleotides of the displaced portion of the double-stranded nucleic acid.

Embodiment 70. The method of any one of embodiments 48 to 69, wherein the double-stranded nucleic acid is a cell-free DNA (cfDNA) or circulating tumor DNA (ctDNA).

Embodiment 71. A method of selectively sequencing a plurality of different double-stranded nucleic acids in a sample according to a method of any one of embodiments 48 to 70, wherein a plurality of different probe oligonucleotides are utilized during the hybridizing step.

Embodiment 72. The method of any one of embodiments 48 to 71, wherein the sequencing comprises sequencing according to the method of any one of embodiments 1 to 42.

Embodiment 73. A method of sequencing a double stranded nucleic acid comprising one or more methylated cytosines, the method comprising: (a) ligating a first adapter to a first end of the double stranded nucleic acid, and ligating a second adapter to a second end of the double stranded nucleic acid, wherein the second adapter is a hairpin adapter, thereby forming a nucleic acid template; (b) converting one or more cytosines to uracil; (c) annealing a first primer to the nucleic acid template, wherein the first primer comprises a sequence that is complementary to a portion of the first adapter, or a complement thereof; (d) sequencing a first portion of the nucleic acid template by extending the first primer, thereby generating a first read comprising a first nucleic acid sequence of at least a first portion of the double stranded nucleic acid; (e) annealing a second primer to the nucleic acid template, wherein the second primer comprises a sequence that is complementary to a sequence within a loop of the hairpin adapter, or a complement thereof; and (f) sequencing a second portion of the nucleic acid template by extending the second primer, thereby generating a second read comprising a nucleic acid sequence of at least a second portion of the double stranded nucleic acid.

Embodiment 74. The method of Embodiment 74, wherein the first adapter comprises one or more methylated cytosines.

Embodiment 75. The method of Embodiment 73 or 74, wherein the second adapter comprises one or more methylated cytosines.

Embodiment 76. The method of one of Embodiments 73-75, wherein converting the one or more cytosines to uracil comprises chemical or enzymatic conversion.

Embodiment. 77. A method of amplifying a double stranded nucleic acid comprising a first strand and a second strand, the method comprising: (a) ligating a first adapter to a first end of the double stranded nucleic acid wherein the first adapter is a Y adapter comprising (i) a first strand having a 5'-arm and a 3'-portion, and (ii) a second strand having a 5'-portion and a 3'-arm, wherein the 3'-portion of the first strand is substantially complementary to the 5'-portion of the second strand, and the 5'-arm of the first strand is not substantially complementary to the 3'-arm of the second strand, and ligating a second adapter to a second end of the double stranded nucleic acid, wherein the second adapter is a hairpin adapter, thereby forming a nucleic acid template; (b) annealing a primer to the nucleic acid template, wherein the first primer comprises a sequence that is complementary to a portion of the first adapter, or a complement thereof, and is not substantially complementary to a portion of the second adapter or a complement thereof; (c) amplifying the nucleic acid template by extending the primer using a strand-displacing polymerase, thereby generating a an amplicon comprising a complement of the first and second strand of the double stranded nucleic acid.

Embodiment 78. The method of Embodiment 77, wherein amplifying the nucleic acid template is on a solid support comprising a plurality of primers attached to said solid support, wherein the plurality of primers comprise a plurality of forward primers with complementarity to a complement of the first strand of the Y adapter and a plurality of reverse primers with complementarity to the second strand of the Y adapter, and the amplifying comprises a plurality of cycles of strand denaturation, primer hybridization, and primer extension, thereby generating a plurality of forward amplicons and a plurality of reverse amplicons.

Embodiment 79. The method of Embodiment 78, further comprising removing the plurality of reverse amplicons or forward amplicons, annealing a primer to the first amplicon, wherein the first primer comprises a sequence that is complementary to a portion of the first amplicon, or a complement thereof, and sequencing a portion of the first amplicon by extending the primer, thereby generating a sequencing read comprising a first nucleic acid sequence of at least a first portion of the double stranded nucleic acid.

Embodiment 80. A method of sequencing a first portion and a second portion of a double-stranded nucleic acid, the method comprising: (a) ligating a first adapter to a first end of the double stranded nucleic acid, and ligating a second adapter to a second end of the double stranded nucleic acid, wherein the second adapter is a hairpin adapter, thereby forming a nucleic acid template; (b) displacing at least a portion of one strand of the nucleic acid template by annealing a blocking primer to the nucleic acid template and extending the blocking primer to generate a blocking strand, wherein the blocking primer comprises a sequence within a loop of the hairpin adapter, or a complement thereof (c) annealing a first sequencing primer to the nucleic acid template and sequencing a first portion of the nucleic acid template by extending the first sequencing primer, thereby generating a first read comprising a first nucleic acid sequence of at least a first portion of the double stranded nucleic acid, wherein the first sequencing primer comprises a sequence that is complementary to a portion of the first adapter; (d) annealing a second sequencing primer to the nucleic acid template and sequencing a second portion of the nucleic acid template by extending the second sequencing primer, thereby generating a second read comprising a second nucleic acid sequence of at least a second portion of the double stranded nucleic acid, wherein the second sequencing primer comprises a sequence that is complementary to a sequence within a loop of the hairpin adapter, or a complement thereof.

Embodiment 81. The method of Embodiment 80, wherein the second adapter comprises a cleavable site.

Embodiment 82. The method of Embodiments 80 or 81, wherein the blocking strand is removed prior to step d).
Embodiment 83. The method of any one of Embodiments 80 to 82, wherein the extended sequencing primer from step c) is removed prior to step d).
Embodiment 84. The method of any one of Embodiments 80 to 83, wherein sequencing the first portion and a second portion of a double-stranded nucleic acid is on a solid support comprising a plurality of primers attached to said solid support, wherein the plurality of primers comprise a plurality of forward primers with complementarity to a complement of the first strand of the Y adapter and a plurality of reverse primers with complementarity to the second strand of the Y adapter.

What is claimed:

1. A method of sequencing a double stranded nucleic acid, the method comprising:
   (a) ligating a first adapter to a first end of the double stranded nucleic acid, wherein the first adapter is a Y-adapter comprising a first strand and a second strand, and ligating a second adapter to a second end of the double stranded nucleic acid, wherein the second adapter is a hairpin adapter, thereby forming a nucleic acid template;
   (b) generating amplicons of the nucleic acid template, wherein generating amplicons comprises attaching the nucleic acid template to a substrate, wherein the substrate comprises a plurality of primers with complementarity to the first strand, or a complement thereof, of the Y adapter and a plurality of primers with complementarity to the second strand, or a complement thereof, of the Y adapter;
   (c) displacing at least a portion of one strand of the nucleic acid template by annealing a blocking primer to a loop of the hairpin adapter, or a complement thereof, and extending the blocking primer to generate a blocking strand;
   (d) annealing a first primer to the nucleic acid template, wherein the first primer comprises a sequence that is complementary to a portion of the first adapter, or a complement thereof;
   (e) sequencing a first portion of the nucleic acid template by extending the first primer, thereby generating a first read comprising a first nucleic acid sequence of at least a first portion of the double stranded nucleic acid;
   (f) annealing a second primer to the nucleic acid template, wherein the second primer comprises a sequence that is complementary to a sequence within the loop of the hairpin adapter, or a complement thereof; and
   (g) sequencing a second portion of the nucleic acid template by extending the second primer, thereby generating a second read comprising a nucleic acid sequence of at least a second portion of the double stranded nucleic acid.

2. The method of claim 1, wherein the Y-adapter comprises (i) a first strand having a 5'-arm and a 3'-portion, and (ii) a second strand having a 5'-portion and a 3'-arm, wherein the 3'-portion of the first strand is substantially complementary to the 5'-portion of the second strand, and the 5'-arm of the first strand is not substantially complementary to the 3'-arm of the second strand.

3. The method of claim 2, wherein the ligating of the first adapter comprises ligating a 3'-end of the first strand of the Y-adapter to a 5'-end of the forward strand of the double stranded nucleic acid, and ligating a 5'-end of the second strand of the Y-adapter to a 3'-end of the reverse strand of the double stranded nucleic acid.

4. The method of claim 2, wherein the first primer anneals to the second strand of the Y-adapter.

5. The method of claim 1, wherein the Y adapter is generated by cleaving a hairpin adapter comprising a cleavable site within the loop.

6. The method of claim 1, wherein the second adapter comprises a nucleic acid having a 5'-end, a 5'-portion, the loop, a 3'-portion and a 3'-end, and the 5'-portion of the second adapter is substantially complementary to the 3'-portion of the second adapter.

7. The method of claim 6, wherein the ligating of the second adapter comprises ligating the 5'-end of the second adapter to a 3'-end of the forward strand of the double stranded nucleic acid and ligating the 3'-end of the second adapter to a 5'-end of the reverse strand of the double stranded nucleic acid.

8. The method of claim 1, wherein the method of generating amplicons of the nucleic acid template comprises a polymerase chain reaction.

9. The method of claim 8, wherein the polymerase chain reaction comprises a bridge PCR amplification method.

10. The method of claim 1, wherein the sequencing of (e) and the sequencing of (g) comprise a process comprising sequencing by synthesis.

11. The method of claim 1, wherein the first adapter, second adapter, or both the first adapter and second adapter comprise one or more of a sample barcode sequence, a molecular identifier sequence, or both a sample barcode sequence and a molecular identifier sequence.

12. The method of claim 1, wherein the double stranded nucleic acid is about 50 to 1000 nucleotides in length.

13. The method of claim 2, wherein the nucleic acid template comprises sequences of the first strand of the Y-adapter, the forward strand of the double stranded nucleic acid, the second adapter, the reverse strand of the double stranded nucleic acid and the second strand of the Y-adapter arranged in a 5' to 3' direction.

14. The method of claim 2, wherein the first primer anneals to the 5'-portion of the second strand of the Y-adapter.

15. The method of claim 1, wherein the double stranded nucleic acid comprises a forward strand and a reverse strand.

16. The method of claim 15, wherein the first read comprises a nucleic acid sequence of the reverse strand of the double stranded nucleic acid, or a portion thereof, and the second read comprises a nucleic acid sequence of the forward strand of the double stranded nucleic acid, or a portion thereof.

17. The method of claim 15, wherein the first read comprises a nucleic acid sequence of the forward strand of the double stranded nucleic acid, or a portion thereof, and the second read comprises a nucleic acid sequence of the reverse strand of the double stranded nucleic acid, or a portion thereof.

18. The method of claim 1, wherein the substrate is a polymer coated solid support.

19. The method of claim 1, wherein the amplicons comprise a first copy of the nucleic acid template having a nucleic acid sequence that is substantially identical to the nucleic acid sequence of the nucleic acid template, or a portion thereof, and a second copy of the template having a nucleic acid sequence that is substantially complementary to the nucleic acid sequence of the nucleic acid template.

20. The method of claim 19, wherein after generating the amplicons of the nucleic acid template, and before (d), the first or the second copy of the nucleic acid template is removed from the substrate.

21. The method of claim 1, wherein the amplicons that are attached to the substrate are attached at addressable locations on the substrate.

22. The method of claim 11, wherein the one or more molecular identifier sequence is about or at least about 5, 6, 7, 8, 9, 10, 15, 20, 25, 30, 40, 50, 75 or more nucleotides in length.

23. The method of claim 11, wherein the one or more molecular identifier sequence uniquely distinguishes the nucleic acid template.

24. The method of claim 11, wherein the one or more molecular identifier sequence comprises sample nucleic acid sequence adjacent to the one or more molecular identifier sequence.

25. The method of claim 11, wherein the one or more sample barcode sequence comprises about 3, 4, 5, 6, 7, 8, 9, or about 10 nucleotides.

26. The method of claim 11, wherein each of the one or more sample barcode sequence in a plurality of sample barcode sequences differs from every other sample barcode sequence in the plurality by at least 3, 4, 5, 6, 7, 8, 9, 10, or more nucleotide positions.

27. The method of claim 11, wherein a sequencing read comprises reading a molecular identifier sequence, a sample barcode, or a template nucleic acid sequence, or all of a molecular identifier sequence, a sample barcode, and a template nucleic acid sequence.

28. The method of claim 1, wherein the blocking strand is removed prior to step (f).

29. The method of claim 1, wherein generating the blocking strand comprises a plurality of blocking primer extension cycles.

30. The method of claim 1, wherein the blocking strand remains during the first sequencing read, and is removed prior to starting the second sequencing read.

* * * * *

```
                          SEQUENCE LISTING

<160> NUMBER OF SEQ ID NOS: 19

<210> SEQ ID NO 1
    <211> LENGTH: 41
    <212> TYPE: DNA
    <213> ORGANISM: Artificial Sequence
    <220> FEATURE:
    <223> OTHER INFORMATION: Synthetic construct

<400> SEQUENCE: 1
acaaaggcag ccacgcactc cttccctgaa ggccggaatc t              41

<210> SEQ ID NO 2
    <211> LENGTH: 41
    <212> TYPE: DNA
    <213> ORGANISM: Artificial Sequence
    <220> FEATURE:
    <223> OTHER INFORMATION: Synthetic construct

<400> SEQUENCE: 2
gctgccgcca ctagccatct tactgctgag gactcttcgc t              41

<210> SEQ ID NO 3
    <211> LENGTH: 40
    <212> TYPE: DNA
    <213> ORGANISM: Artificial Sequence
    <220> FEATURE:
    <223> OTHER INFORMATION: Synthetic construct

<400> SEQUENCE: 3
gattccggcc ttgtggttgg tgagggtcat ctcgctggag              40

<210> SEQ ID NO 4
    <211> LENGTH: 40
    <212> TYPE: DNA
    <213> ORGANISM: Artificial Sequence
    <220> FEATURE:
    <223> OTHER INFORMATION: Synthetic construct

<400> SEQUENCE: 4
gcgaagagtc ctggagtgcc gccaatgtat gcgagggtga              40

<210> SEQ ID NO 5
    <211> LENGTH: 71
    <212> TYPE: DNA
    <213> ORGANISM: Artificial Sequence
    <220> FEATURE:
    <223> OTHER INFORMATION: Synthetic construct

<400> SEQUENCE: 5
gcgcgcgttt tttttgcttg cgtctcctgc cagccatatc cggtctacgt gatccttttt    60
tttcgcgcgc t                                                         71

<210> SEQ ID NO 6
    <211> LENGTH: 83
    <212> TYPE: DNA
    <213> ORGANISM: Artificial Sequence
```

```
<220> FEATURE:
<223> OTHER INFORMATION: Synthetic construct

<400> SEQUENCE: 6
gcgcgcgttt ttttttttttt tgcttgcgtc tcctgccagc catatccggt ctacgtgatc     60
cttttttttt ttttttcgcgc gct                                              83

<210> SEQ ID NO 7
<211> LENGTH: 62
<212> TYPE: DNA
<213> ORGANISM: Artificial Sequence
<220> FEATURE:
<223> OTHER INFORMATION: Synthetic construct

<400> SEQUENCE: 7
ggatcacgta gattttgctt gcgtctcctg ccagccatat ccggttttc tacgtgattc       60 ct                                                                      62

<210> SEQ ID NO 8
<211> LENGTH: 81
<212> TYPE: DNA
<213> ORGANISM: Artificial Sequence
<220> FEATURE:
<223> OTHER INFORMATION: Synthetic construct

<400> SEQUENCE: 8
gcgaagagtc ctggagtgcc gccaatgtat gcgagggtga gctgccgcca ctagccatct     60
tactgctgag gactcttcgc t                                                 81

<210> SEQ ID NO 9
<211> LENGTH: 93
<212> TYPE: DNA
<213> ORGANISM: Artificial Sequence
<220> FEATURE:
<223> OTHER INFORMATION: Synthetic construct

<400> SEQUENCE: 9
gcgaagagtc ctttttttgg agtgccgcca atgtatgcga gggtgagctg ccgccactag     60
ccatcttact gctgtttttt aggactcttc gct                                    93

<210> SEQ ID NO 10
<211> LENGTH: 100
<212> TYPE: DNA
<213> ORGANISM: Artificial Sequence
<220> FEATURE:
<223> OTHER INFORMATION: Synthetic construct

<400> SEQUENCE: 10
gcgaagagtc ctttttttgg agtgccgcca atgtatgcga gggtgatttt tttgctgccg     60
ccactagcca tcttactgct gttttttagg actcttcgct                            100

<210> SEQ ID NO 11
<211> LENGTH: 81
<212> TYPE: DNA
<213> ORGANISM: Artificial Sequence
<220> FEATURE:
<223> OTHER INFORMATION: Synthetic construct

<400> SEQUENCE: 11
gattccggcc ttgtggttgg tgagggtcat ctcgctggag acaaaggcag ccacgcactc     60
cttccctgaa ggccggaatc t                                                 81
```

<210> SEQ ID NO 12
<211> LENGTH: 93
<212> TYPE: DNA
<213> ORGANISM: Artificial Sequence
<220> FEATURE:
<223> OTHER INFORMATION: Synthetic construct

<400> SEQUENCE: 12
gattccggcc ttttttttgt ggttggtgag ggtcatctcg ctggagacaa aggcagccac    60
gcactccttc cctgtttttt aaggccggaa tct                                 93

<210> SEQ ID NO 13
<211> LENGTH: 100
<212> TYPE: DNA
<213> ORGANISM: Artificial Sequence
<220> FEATURE:
<223> OTHER INFORMATION: Synthetic construct

<400> SEQUENCE: 13
gattccggcc ttttttttgt ggttggtgag ggtcatctcg ctggagtttt tttacaaagg    60
cagccacgca ctccttccct gttttttaag gccggaatct                         100

<210> SEQ ID NO 14
<211> LENGTH: 61
<212> TYPE: DNA
<213> ORGANISM: Artificial Sequence
<220> FEATURE:
<223> OTHER INFORMATION: Synthetic construct

<400> SEQUENCE: 14
ggatcacgta gattttgctt gcgtctcctg ccagccatat ccggttttc tacgtgatcc     60 t                                                                    61

<210> SEQ ID NO 15
<211> LENGTH: 77
<212> TYPE: DNA
<213> ORGANISM: Artificial Sequence
<220> FEATURE:
<223> OTHER INFORMATION: Synthetic construct

<400> SEQUENCE: 15
ggatcacgta gatttttttt ttttgcttgc gtctcctgcc agccatatcc ggtttttttt    60
tttttctacg tgatcct                                                   77

<210> SEQ ID NO 16
<211> LENGTH: 101
<212> TYPE: DNA
<213> ORGANISM: Artificial Sequence
<220> FEATURE:
<223> OTHER INFORMATION: Synthetic construct

<400> SEQUENCE: 16
ggatcacgta gatttttttt ttttttttttt tttttgctt gcgtctcctg ccagccatat    60
ccggtttttt tttttttttt tttttttttc tacgtgatcc t                       101

<210> SEQ ID NO 17
<211> LENGTH: 103
<212> TYPE: DNA
<213> ORGANISM: Artificial Sequence
<220> FEATURE:
<223> OTHER INFORMATION: Synthetic construct

<400> SEQUENCE: 17

```
ggatcacgta gatttttttt tttttttttt tttttttttt tttttttttt ttgcttgcgt    60
ctcctgccag ccatatccgg tttttttttt tctacgtgat cct                     103
```

<210> SEQ ID NO 18
<211> LENGTH: 67
<212> TYPE: DNA
<213> ORGANISM: Artificial Sequence
<220> FEATURE:
<223> OTHER INFORMATION: Synthetic construct

<400> SEQUENCE: 18

```
ggatcacgta gattttagat ctgcttgcgt ctcctgccag ccatatccgg tttttctacg    60
tgatcct                                                              67
```

<210> SEQ ID NO 19
<211> LENGTH: 82
<212> TYPE: DNA
<213> ORGANISM: Artificial Sequence
<220> FEATURE:
<223> OTHER INFORMATION: Synthetic construct

<400> SEQUENCE: 19

```
ggatcacgta gatttttttt ttttagatct gcttgcgtct cctgccagcc atatccggtt    60
tttttttttt ctacgtgatc ct                                             82
```